US012563967B2

(12) United States Patent
Takada

(10) Patent No.: US 12,563,967 B2
(45) Date of Patent: Feb. 24, 2026

(54) LIGHT EMITTING DEVICE AND AMINE COMPOUND FOR LIGHT EMITTING DEVICE

(71) Applicant: Samsung Display Co., Ltd., Yongin-si (KR)

(72) Inventor: Ichinori Takada, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 833 days.

(21) Appl. No.: 17/932,512

(22) Filed: Sep. 15, 2022

(65) Prior Publication Data

US 2023/0200223 A1 Jun. 22, 2023

(30) Foreign Application Priority Data

Dec. 17, 2021 (KR) ........................ 10-2021-0181765

(51) Int. Cl.
*H10K 85/60* (2023.01)
*C07D 209/86* (2006.01)
(Continued)

(52) U.S. Cl.
CPC ......... *H10K 85/636* (2023.02); *C07D 209/86* (2013.01); *C07D 405/14* (2013.01); (Continued)

(58) Field of Classification Search
CPC .. C07D 209/82; C07D 209/86; H10K 85/636; H10K 85/6572; C09K 11/06
See application file for complete search history.

(56) References Cited

U.S. PATENT DOCUMENTS

| | | | |
|---|---|---|---|
| 9,278,926 | B2 | 3/2016 | Kato |
| 2008/0254318 | A1 | 10/2008 | Nakashima et al. |
| 2017/0317290 | A1 | 11/2017 | Lee et al. |

FOREIGN PATENT DOCUMENTS

| | | | |
|---|---|---|---|
| CN | 108191744 | A | 6/2018 |
| KR | 10-1303894 | B1 | 9/2013 |

(Continued)

*Primary Examiner* — Vu A Nguyen

(74) *Attorney, Agent, or Firm* — Womble Bond Dickinson (US) LLP

(57) ABSTRACT

A light emitting device that includes a first electrode, a second electrode oppositely disposed to the first electrode, and multiple functional layers between the first electrode and the second electrode is provided. At least one functional layer among the multiple functional layers includes an amine compound represented by Formula 1:

Formula 1

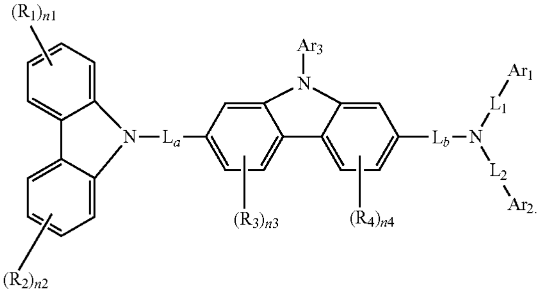

20 Claims, 8 Drawing Sheets

(51) Int. Cl.

| | |
|---|---|
| ***C07D 405/14*** | (2006.01) |
| ***C07D 409/14*** | (2006.01) |
| ***C09K 11/06*** | (2006.01) |
| ***H10K 50/15*** | (2023.01) |

(52) U.S. Cl.

CPC ............ *C07D 409/14* (2013.01); *C09K 11/06* (2013.01); *H10K 85/633* (2023.02); *C09K 2211/1018* (2013.01); *H10K 50/15* (2023.02); *H10K 85/615* (2023.02); *H10K 85/6572* (2023.02); *H10K 85/6574* (2023.02); *H10K 85/6576* (2023.02)

(56) References Cited

FOREIGN PATENT DOCUMENTS

| | | | | | |
|---|---|---|---|---|---|
| KR | 20150007476 | A | * | 1/2015 | ........... H10K 85/656 |
| KR | 10-1580074 | B1 | | 12/2015 | |
| KR | 10-1764911 | B1 | | 8/2017 | |
| KR | 10-2018-0137315 | A | | 12/2018 | |
| KR | 20180137315 | A | * | 12/2018 | ......... H01L 51/0072 |
| KR | 10-2072756 | B1 | | 2/2020 | |
| KR | 10-2073322 | B1 | | 2/2020 | |
| WO | WO 2015/056965 | A1 | | 4/2015 | |
| WO | WO 2016/064111 | A1 | | 4/2016 | |

* cited by examiner

LIGHT EMITTING DEVICE AND AMINE COMPOUND FOR LIGHT EMITTING DEVICE

CROSS-REFERENCE TO RELATED APPLICATION

This application claims priority to and the benefit of Korean Patent Application No. 10-2021-0181765, filed on Dec. 17, 2021, the entire content of which is hereby incorporated by reference.

BACKGROUND

1. Field

Aspects of one or more embodiments of the present disclosure herein relate to an amine compound used in a light emitting device, and for example, to an amine compound used in a hole transport region, and a light emitting device including the same.

2. Description of the Related Art

Recently, the development of an organic electroluminescence display as an image display is being actively conducted. The organic electroluminescence display is different from a liquid crystal display and is a self-luminescent type (kind) display in which holes and electrons injected from a first electrode and a second electrode recombine in an emission layer so that a light emitting material including an organic compound in the emission layer emits light to achieve display.

In the application of an organic electroluminescence device to a display, the decrease of a driving voltage and the increase of emission efficiency and life of the organic electroluminescence device are required, and development on materials for an organic electroluminescence device stably achieving the requirements is being continuously required (sought).

In addition, in order to achieve an organic electroluminescence device with high efficiency, development on a material for a hole transport layer is being conducted.

SUMMARY

Aspects of one or more embodiments of the present disclosure are directed to a light emitting device having improved emission efficiency and device life.

An embodiment of the present disclosure also provides an amine compound which may improve the emission efficiency and device life of a light emitting device.

An embodiment of the present disclosure provides a light emitting device including a first electrode, a second electrode oppositely disposed to the first electrode, and multiple functional layers between the first electrode and the second electrode, wherein at least one functional layer among the multiple functional layers includes an amine compound represented by Formula 1.

Formula 1

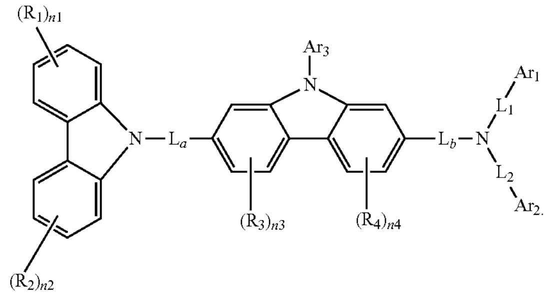

In Formula 1, $Ar_1$ to $Ar_3$ may each independently be a substituted or unsubstituted alkyl group of 1 to 20 carbon atoms, a substituted or unsubstituted silyl group, a substituted or unsubstituted aryl group of 6 to 30 ring-forming carbon atoms, or a substituted or unsubstituted heteroaryl group of 2 to 30 ring-forming carbon atoms, $L_a$, $L_b$, $L_1$, and $L_2$ are each independently a direct linkage, or a substituted or unsubstituted arylene group of 6 to 30 ring-forming carbon atoms, $R_1$ to $R_4$ are each independently a substituted or unsubstituted alkyl group of 1 to 20 carbon atoms, or a substituted or unsubstituted aryl group of 6 to 30 ring-forming carbon atoms, n1 and n2 are each independently an integer from 0 to 4, and n3 and n4 are each independently an integer from 0 to 3, in Formula 1, a sum of n1 and n2 is 1 or more, at least one among $Ar_1$ to $Ar_3$ may be a substituent represented by Formula a, at least one among $Ar_1$ and $Ar_2$ may be a substituted or unsubstituted dibenzofuran group, a substituted or unsubstituted dibenzothiophene group, a substituted or unsubstituted phenanthrene group, a substituted or unsubstituted carbazole group, or a substituent represented by Formula b, or at least one among $L_a$ and $L_b$ may be a substituted or unsubstituted arylene group of 6 to 30 ring-forming carbon atoms.

Formula a

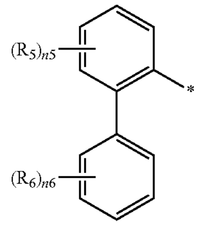

In Formula a, $R_5$ and $R_6$ may each independently be a hydrogen atom, a deuterium atom, a halogen atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, n5 is an integer from 0 to 4, and n6 is an integer from 0 to 5.

Formula b

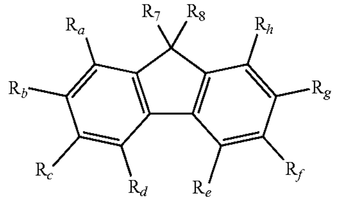

In Formula b, $R_a$ to $R_h$, $R_7$, and $R_8$ may each independently be a hydrogen atom, a deuterium atom, a halogen atom, a substituted or unsubstituted alkyl group of 1 to 20 carbon atoms, or a substituted or unsubstituted aryl group of 6 to 30 ring-forming carbon atoms, and any one among $R_a$, $R_b$, $R_d$, $R_e$, $R_g$, and $R_h$ may be a part (a substituent) connected to $L_1$ or $L_2$.

In an embodiment, the multiple functional layers may include a hole transport region on the first electrode, an emission layer on the hole transport region, and an electron transport region on the emission layer, and the hole transport region may include the amine compound.

In an embodiment, the hole transport region may include a hole injection layer on the first electrode, and a hole transport layer on the hole injection layer, and the hole transport layer may include the amine compound.

In an embodiment, the amine compound represented by Formula 1 may be a monoamine compound.

In an embodiment, the amine compound represented by Formula 1 may be represented by any one among Formula 2-1 to Formula 2-3.

Formula 2-1

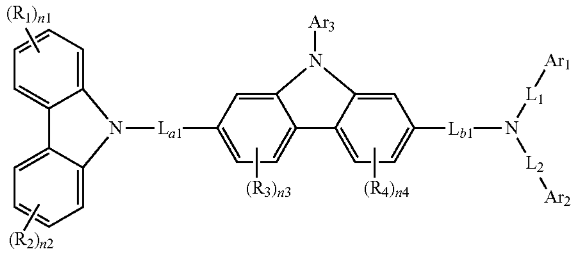

Formula 2-2

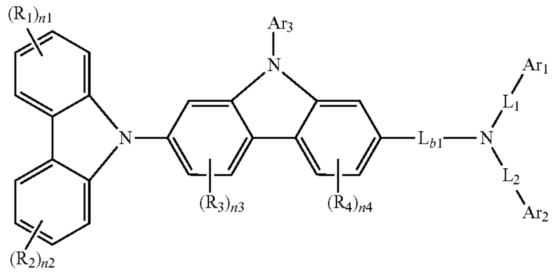

Formula 2-3

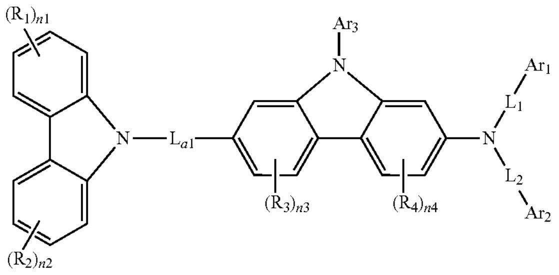

In Formula 2-1 to Formula 2-3, $L_{a1}$ and $L_{b1}$ may each independently be a substituted or unsubstituted arylene group of 6 to 30 ring-forming carbon atoms.

In Formula 2-1 to Formula 2-3, the same explanation on $Ar_1$ to $Ar_3$, $R_1$ to $R_4$, $L_1$, $L_2$, and n1 to n4 defined in Formula 1 may be applied.

In an embodiment, the amine compound represented by Formula 1 may be represented by Formula 3.

Formula 3

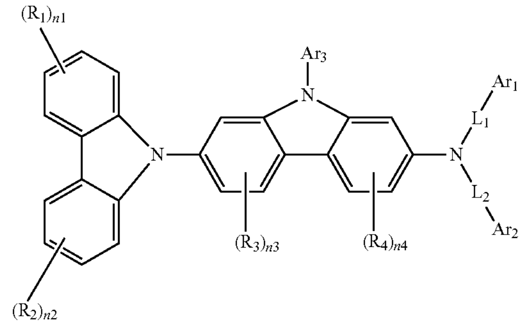

In Formula 3, the same explanation on $Ar_1$ to $Ar_3$, $R_1$ to $R_4$, $L_1$, $L_2$, and n1 to n4 defined in Formula 1 may be applied.

In an embodiment, the amine compound represented by Formula 1 may be represented by any one among Formula 4-1 to Formula 4-3.

Formula 4-1

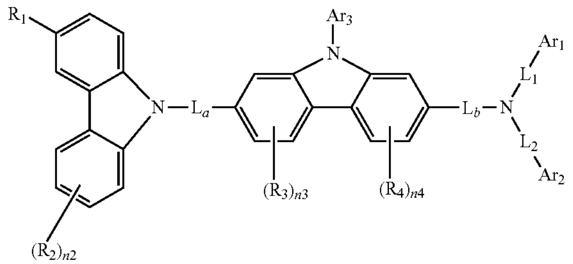

Formula 4-2

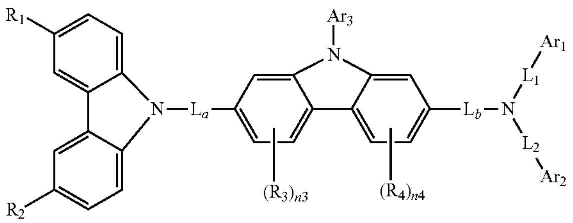

Formula 4-3

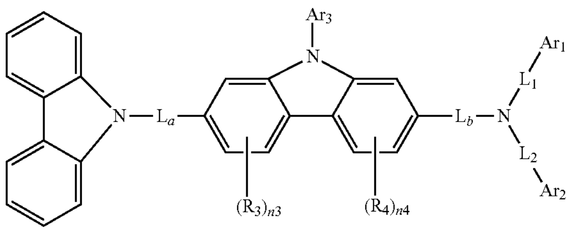

In Formula 4-1 to Formula 4-3, the same explanation on $Ar_1$ to $Ar_3$, $R_1$ to $R_4$, $L_a$, $L_b$, $L_1$, $L_2$, and n2 to n4 defined in Formula 1 may be applied.

In an embodiment, the amine compound represented by Formula 1 may be represented by any one among Formula 5-1 to Formula 5-3.

Formula 5-1

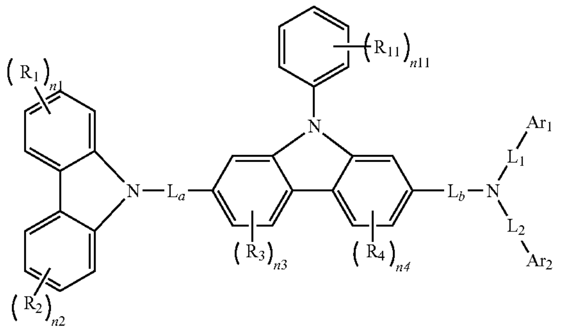

Formula 5-2

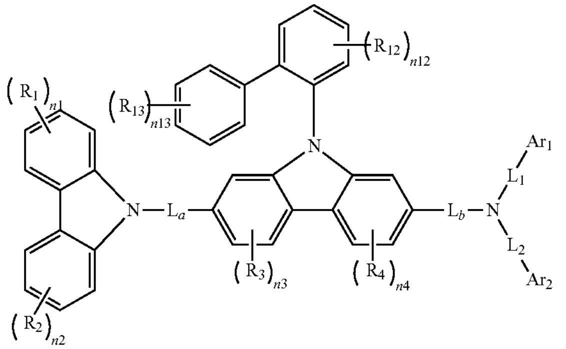

Formula 5-3

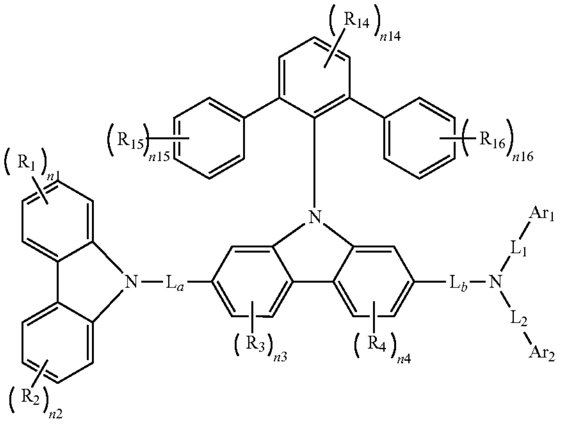

In Formula 5-1 to Formula 5-3, $R_{11}$ to $R_{16}$ may each independently be a hydrogen atom, a deuterium atom, a halogen atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, n11, n13, n15, and n16 are each independently an integer from 0 to 5, n12 is an integer from 0 to 4, and n14 is an integer from 0 to 3.

In Formula 5-1 to Formula 5-3, the same explanation on $Ar_1$, $Ar_2$, $R_1$ to $R_4$, $L_a$, $L_b$, $L_1$, $L_2$, and n1 to n4 defined in Formula 1 may be applied.

In an embodiment, the amine compound represented by Formula 1 may be represented by any one among Formula 6-1 to Formula 6-3.

Formula 6-1

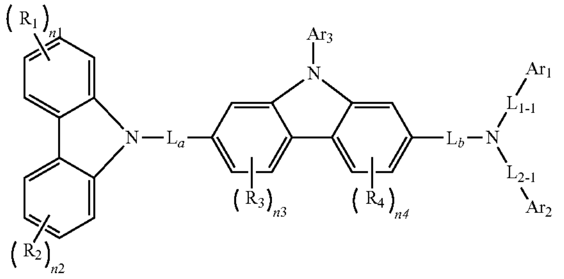

Formula 6-2

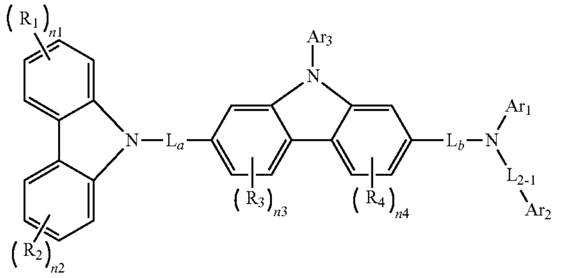

Formula 6-3

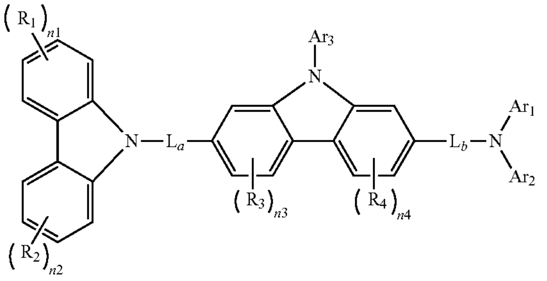

In Formula 6-1 to Formula 6-3, $L_{1\text{-}1}$ and $L_{2\text{-}1}$ may each independently be a substituted or unsubstituted arylene group of 6 to 30 ring-forming carbon atoms.

In Formula 6-1 to Formula 6-3, the same explanation on $Ar_1$ to $Ar_3$, $R_1$ to $R_4$, $L_a$, $L_b$, and n1 to n4 defined in Formula 1 may be applied.

In an embodiment, the amine compound represented by Formula 1 may be represented by any one among Formula 7-1 to Formula 7-3.

Formula 7-1

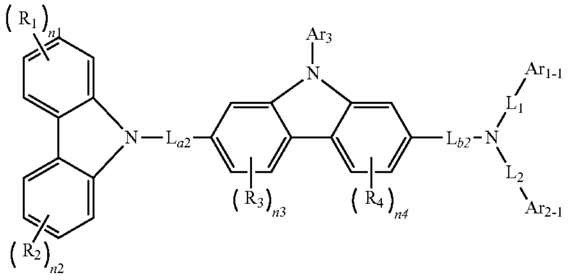

-continued

Formula 7-2

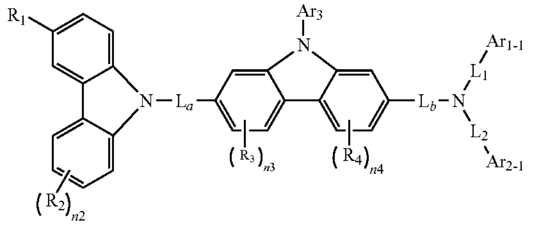

Formula 7-3

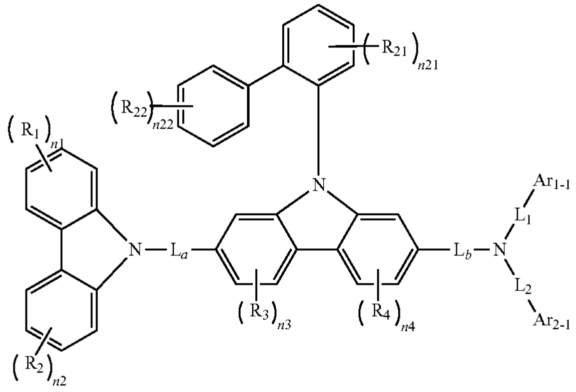

In Formula 7-1, any one among $L_{a2}$ and $L_{b2}$ may be a substituted or unsubstituted arylene group of 6 to 30 ring-forming carbon atoms, and the remainder is a direct linkage or a substituted or unsubstituted arylene group of 6 to 30 ring-forming carbon atoms, in Formula 7-3, $R_{21}$, and $R_{22}$ may each independently be a hydrogen atom, a deuterium atom, a halogen atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, n21 is an integer from 0 to 4, and n22 is an integer from 0 to 5, in Formula 7-1 to Formula 7-3, any one among $Ar_{1-1}$ and $Ar_{2-1}$ may be represented by any one among Formula A1 to Formula A4, and the remainder may be a substituted or unsubstituted alkyl group of 1 to 20 carbon atoms, a substituted or unsubstituted silyl group, a substituted or unsubstituted aryl group of 6 to 30 ring-forming carbon atoms, or a substituted or unsubstituted heteroaryl group of 2 to 30 ring-forming carbon atoms.

Formula A1

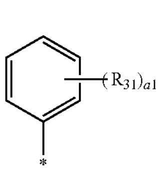

Formula A2

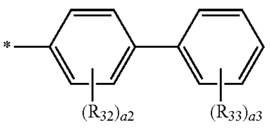

Formula A3

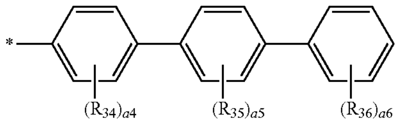

-continued

Formula A4

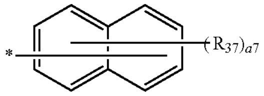

In Formula A1 to Formula A4, $R_{31}$ to $R_{37}$ may each independently be a hydrogen atom, a deuterium atom, a halogen atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, a1, a3, and a6 may each independently be an integer from 0 to 5, a2, a4, and a5 may each independently be an integer from 0 to 4, and a7 may be an integer from 0 to 7.

In some embodiments, in Formula 7-1 to Formula 7-3, the same explanation on $Ar_3$, $R_1$ to $R_4$, $L_a$, $L_b$, $L_1$, $L_2$, and n1 to n4 defined in Formula 1 may be applied.

In an embodiment, $L_a$ and $L_b$ may each independently be represented by any one among Formula L-1 to Formula L-5.

Formula L-1

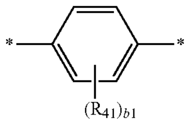

Formula L-2

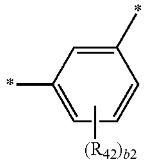

Formula L-3

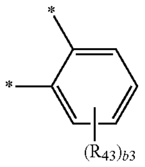

Formula L-4

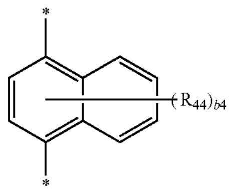

Formula L-5

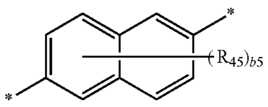

In Formula L-1 to Formula L-5, $R_{41}$ to $R_{45}$ may each independently be a hydrogen atom, a deuterium atom, a halogen atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, b1 to b3 are each independently an integer from 0 to 4, and b4, and b5 are each independently an integer from 0 to 6.

In an embodiment, the amine compound represented by Formula 1 may be represented by Formula 8.

Formula 8

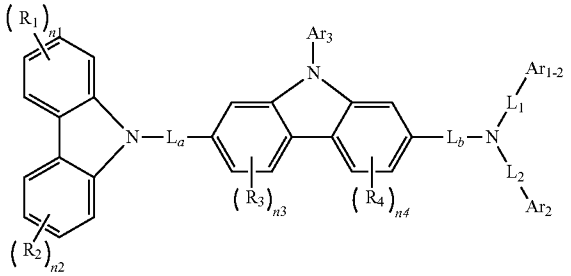

In Formula 8, $Ar_{1-2}$ may be represented by Formula a, or represented by any one among Formula B1 to Formula B3.

Formula B1

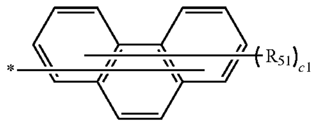

Formula B2

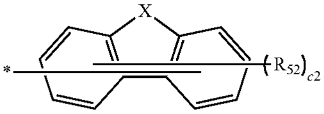

Formula B3

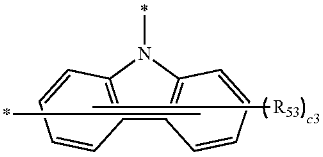

In Formula B1 to Formula B3, X may be O, S, $NR_{54}$, or $CR_{55}R_{56}$, $R_{51}$ to $R_{53}$ may each independently be a hydrogen atom, a deuterium atom, a halogen atom, a substituted or unsubstituted oxy group, a substituted or unsubstituted alkyl group of 1 to 20 carbon atoms, a substituted or unsubstituted alkenyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms, or combined with an adjacent group to form a ring, $R_{54}$ to $R_{56}$ may each independently be a substituted or unsubstituted aryl group of 6 to 30 carbon atoms, c1 may be an integer from 0 to 9, c2 may be an integer from 0 to 7, and c3 may be an integer from 0 to 8.

In Formula 8, the same explanation on $Ar_2$, $Ar_3$, $R_1$ to $R_4$, $L_a$, $L_b$, $L_1$, $L_2$, and n1 to n4 defined in Formula 1 may be applied.

In an embodiment, $Ar_1$ and $Ar_2$ may each independently include at least one among compounds in Compound Group A to Compound Group E.

Compound Group A a1

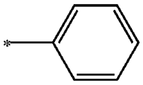

-continued a2

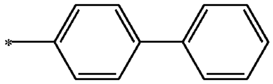

a3

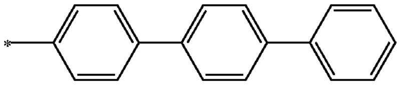

a4

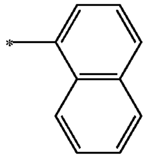

a5

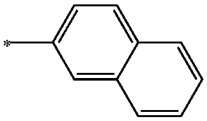

a6

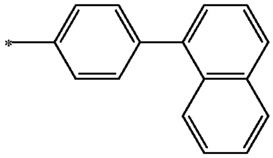

a7

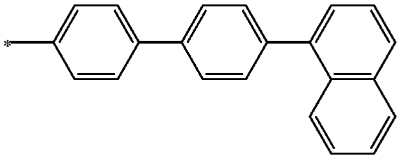

a8

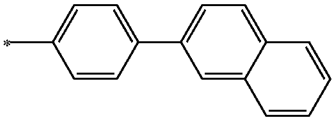

a9

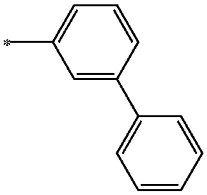

a10

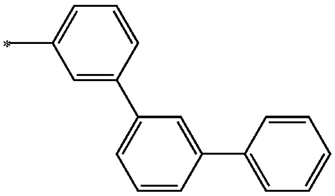

a11

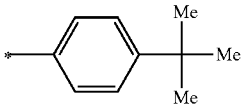

a12

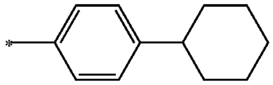

-continued
a14
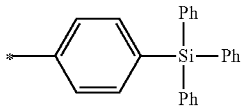
a15
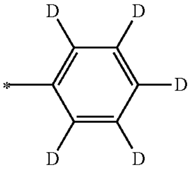
Compound Group B
b1
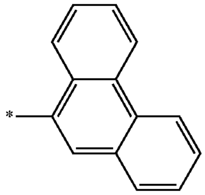
b2
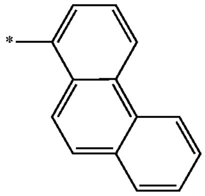
b3
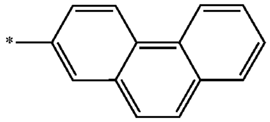
b4
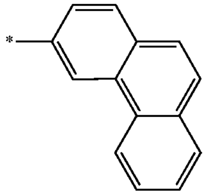
b5
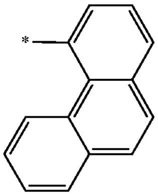
b6
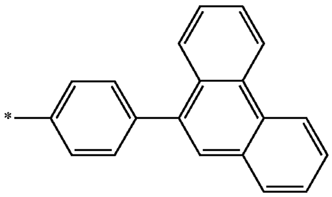
-continued
b7
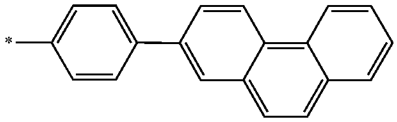
b8
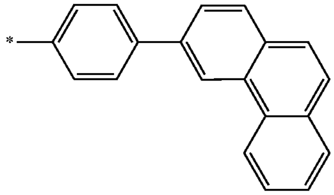
Compound Group C
c1
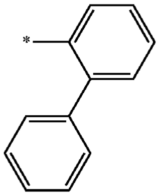
c2
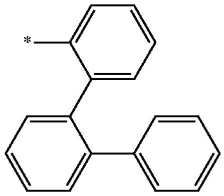
c3
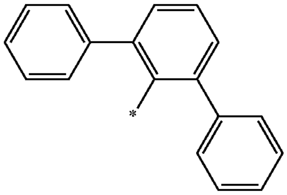
c4
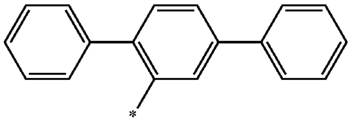
c5
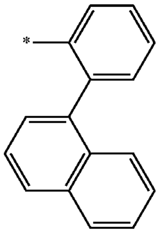

Compound Group D
d1
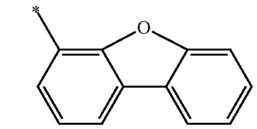
d2
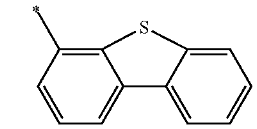
d3
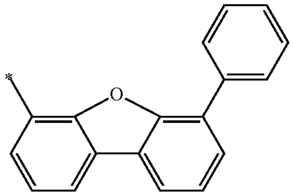
d4
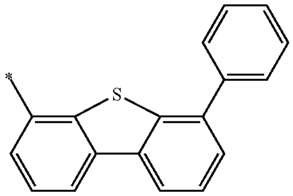
d5
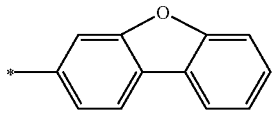
d6
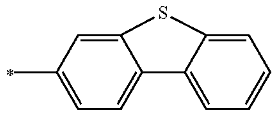
d7
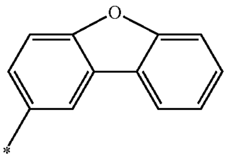
d8
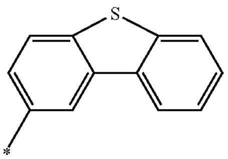
d9
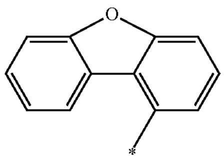
-continued
d10
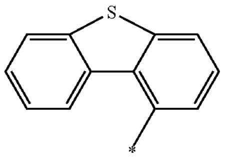
d11
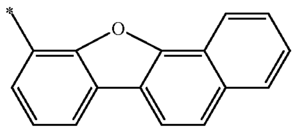
d12
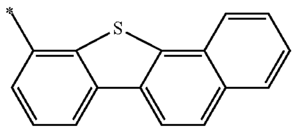
d13
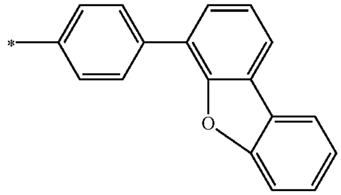
d14
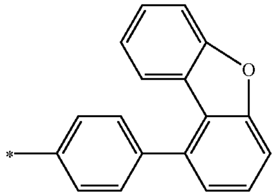
d15
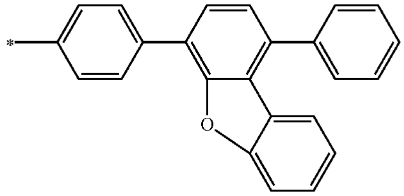
d16
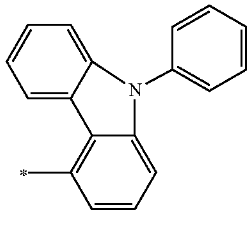
d17
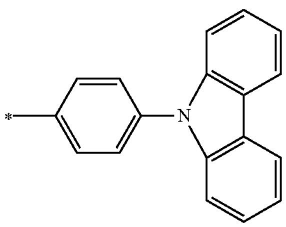

-continued d18

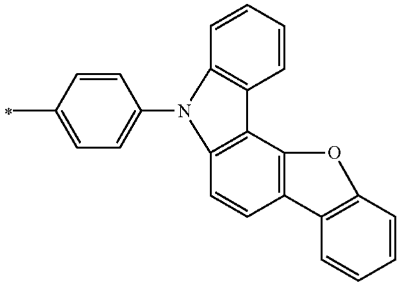

Compound Group E e1

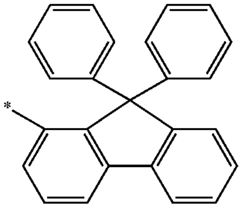

e2

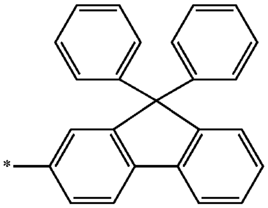

e3

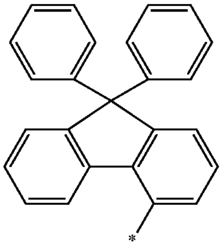

e4

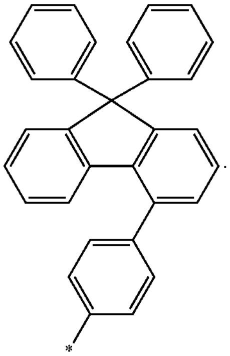

In an embodiment, the amine compound represented by Formula 1 may be represented by Formula 9.

Formula 9

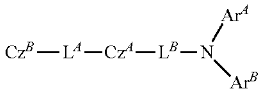

In Formula 9, $Ar^A$ and $Ar^B$ may each independently be selected from Compound Group A to Compound Group E, $Cz^A$ may be selected from Compound Group G, $Cz^B$ may be selected from Compound Group F, and $L^A$, and $L^B$ may be selected from Compound Group H.

Compound Group F f1

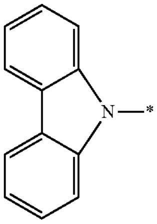

f2

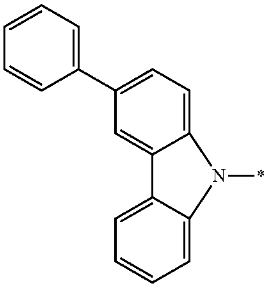

f3

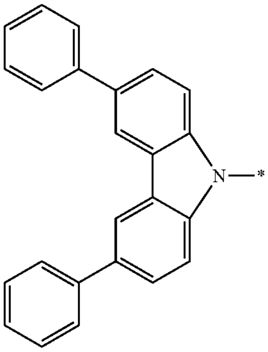

f4

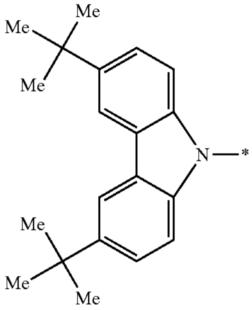

Compound Group G g1

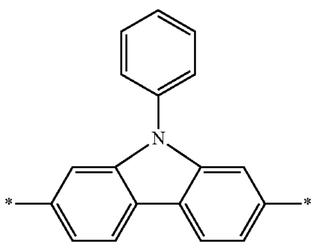

g2

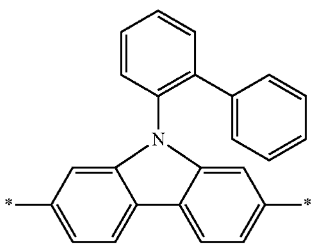

g3

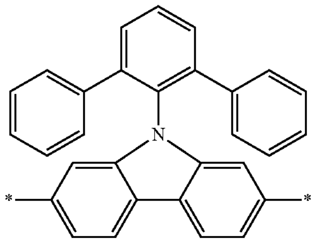

Compound Group H h1 h2

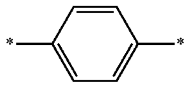

h3

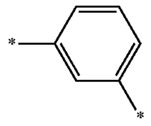

h4

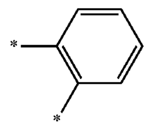

h5

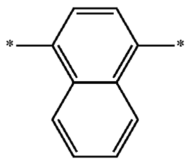

h6

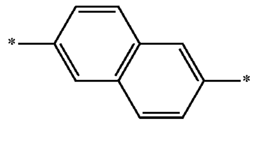

An amine compound according to an embodiment of the present disclosure may be represented by Formula 1.

BRIEF DESCRIPTION OF THE FIGURES

The accompanying drawings are included to provide a further understanding of the present disclosure and are incorporated in and constitute a part of this disclosure. The drawings illustrate embodiments of the present disclosure and, together with the description, serve to explain principles of the present disclosure. In the drawings.

DETAILED DESCRIPTION

Figure 1:
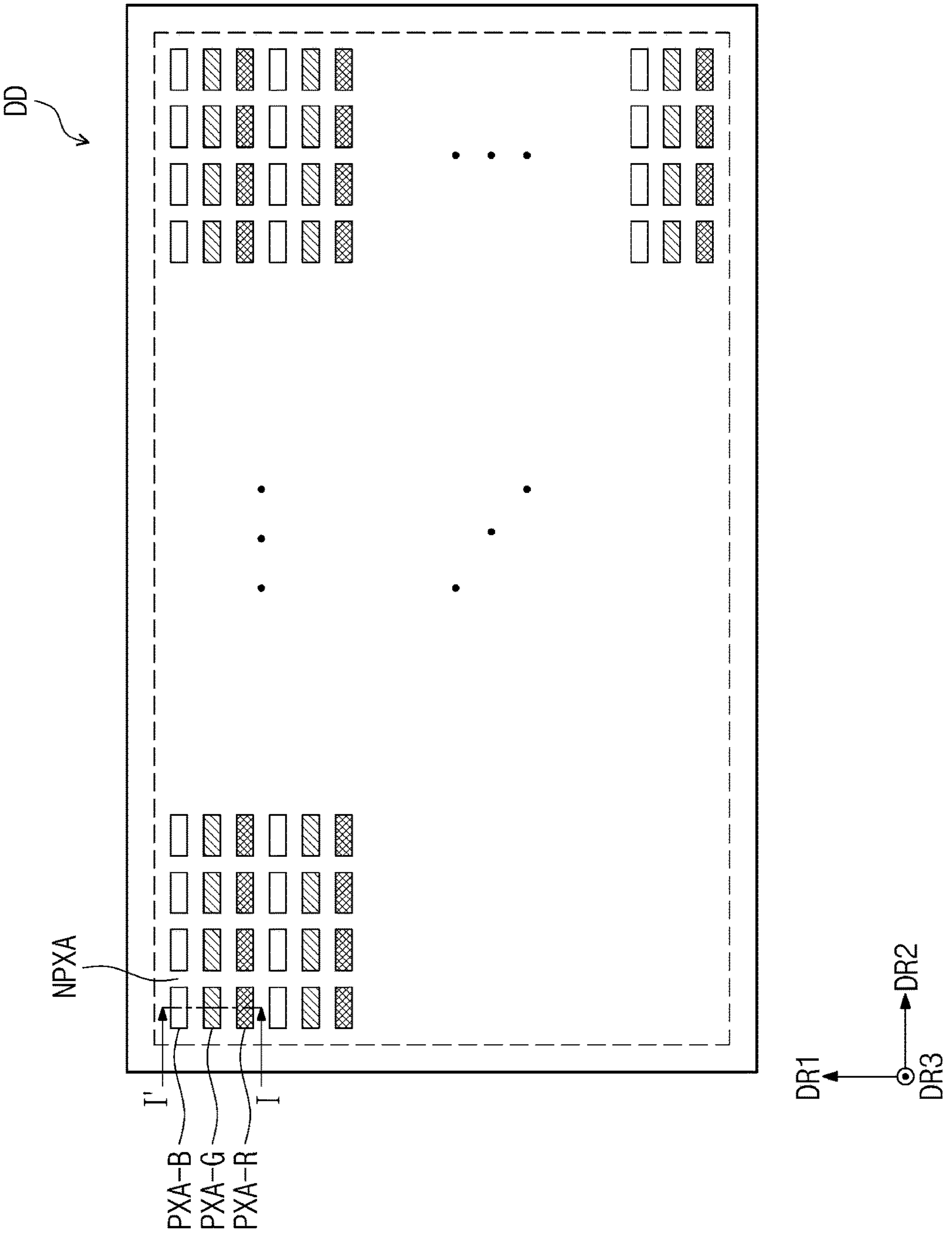
FIG. 1 is a plan view of a display apparatus according to an embodiment.

The present disclosure may have one or more suitable modifications and may be embodied in different forms, and example embodiments will be explained in more detail with reference to the accompany drawings. The present disclosure may, however, be embodied in different forms and should not be construed as limited to the embodiments set forth herein. Rather, all modifications, equivalents, and substituents which are included in the spirit and technical scope of the present disclosure should be included in the present disclosure.

Like reference numerals refer to like elements throughout, and duplicative descriptions thereof may not be provided. In the drawings, the dimensions of structures may be exaggerated for clarity of illustration. It will be understood that, although the terms first, second, etc. may be used herein to describe one or more suitable elements, these elements should not be limited by these terms. These terms are only used to distinguish one element from another element. Thus, a first element could be termed a second element without departing from the teachings of the present disclosure. Similarly, a second element could be termed a first element. As used herein, the singular forms are intended to include the plural forms as well, unless the context clearly indicates otherwise.

In the disclosure, it will be further understood that the terms "comprises" and/or "comprising," when used in this disclosure, specify the presence of stated features, numerals, steps, operations, elements, parts, or the combination thereof, but do not preclude the presence or addition of one or more other features, numerals, steps, operations, elements, parts, or a combination thereof.

In the disclosure, when a layer, a film, a region, a plate, etc. is referred to as being "on" or "above" another part, it can be "directly on" the other part, or intervening layers may also be present. In addition, when a layer, a film, a region, a plate, etc. is referred to as being "under" or "below" another part, it can be "directly under" the other part, or intervening layers may also be present. Also, when an element is referred to as being disposed "on" another element, it can be disposed under the other element.

In the disclosure, the term "substituted or unsubstituted" corresponds to substituted or unsubstituted with at least one substituent selected from the group including (e.g., consisting of) a deuterium atom, a halogen atom, a cyano group, a nitro group, an amine group, a silyl group, an oxy group, a thio group, a sulfinyl group, a sulfonyl group, a carbonyl group, a boron group, a phosphine oxide group, a phosphine sulfide group, an alkyl group, an alkenyl group, an alkynyl group, an alkoxy group, a hydrocarbon ring group, an aryl group, and a heterocyclic group. In addition, each of the exemplified substituents may be substituted or unsubstituted. For example, a biphenyl group may be interpreted as an aryl group or a phenyl group substituted with a phenyl group.

In the disclosure, the term "forming a ring via the combination with an adjacent group" may refer to forming a substituted or unsubstituted hydrocarbon ring, or a substituted or unsubstituted heterocycle via the combination with an adjacent group. The hydrocarbon ring includes an aliphatic hydrocarbon ring and an aromatic hydrocarbon ring. The heterocycle includes an aliphatic heterocycle and an aromatic heterocycle. The hydrocarbon ring and the heterocycle may be monocycles or polycycles. In addition, the ring formed via the combination with an adjacent group may be combined with another ring to form a spiro structure.

In the disclosure, the term "adjacent group" may refer to a substituent substituted for an atom which is directly combined with an atom substituted with a corresponding substituent, another substituent substituted for an atom which is substituted with a corresponding substituent, or a substituent sterically positioned at the nearest position to a corresponding substituent. For example, in 1,2-dimethylbenzene, two methyl groups may be interpreted as "adjacent groups" to each other, and in 1,1-diethylcyclopentene, two ethyl groups may be interpreted as "adjacent groups" to each other. In addition, in 4,5-dimethylphenanthrene, two methyl groups may be interpreted as "adjacent groups" to each other.

In the disclosure, a halogen atom may be a fluorine atom, a chlorine atom, a bromine atom or an iodine atom.

In the disclosure, an alkyl group may be a linear, branched or cyclic type (kind). The carbon number of the alkyl group may be 1 to 50, 1 to 30, 1 to 20, 1 to 10, or 1 to 6. Examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the disclosure, an alkyl group may be a linear, or branched type (kind). The carbon number of the alkyl group may be 1 to 50, 1 to 30, 1 to 20, 1 to 10, or 1 to 6. Examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, 1-methylpentyl, 3-methylpentyl, 2-ethylpentyl, 4-methyl-2-pentyl, n-hexyl, 1-methylhexyl, 2-ethylhexyl, 2-butylhexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the disclosure, an alkenyl group refers to a hydrocarbon group including one or more carbon double bonds in the middle or at the terminal of an alkyl group having a carbon number of 2 or more. The alkenyl group may be a linear chain or a branched chain. The carbon number is not limited, but may be 2 to 30, 2 to 20, or 2 to 10. Examples of the alkenyl group include a vinyl group, a 1-butenyl group, a 1-pentenyl group, a 1,3-butadienyl aryl group, a styrenyl group, a styrylvinyl group, etc., without limitation.

In the disclosure, an aryl group refers to an optional functional group or substituent derived from an aromatic hydrocarbon ring. The aryl group may be a monocyclic aryl group or a polycyclic aryl group. The carbon number for forming rings in the aryl group may be 6 to 30, 6 to 20, or 6 to 15. Examples of the aryl group may include phenyl, naphthyl, fluorenyl, anthracenyl, phenanthryl, biphenyl, terphenyl, quaterphenyl, quinquephenyl, sexiphenyl, triphenylenyl, pyrenyl, benzofluoranthenyl, chrysenyl, etc., without limitation.

In the disclosure, a fluorenyl group may be substituted, and two substituents may be combined with each other to form a spiro structure. Examples of a substituted fluorenyl group are as follows, but an embodiment of the present disclosure is not limited thereto.

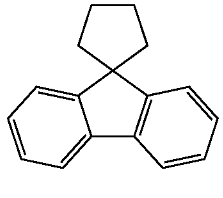

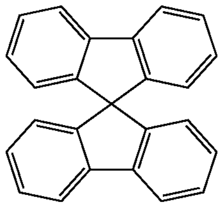

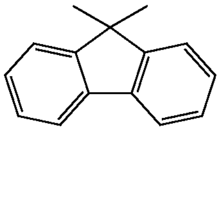

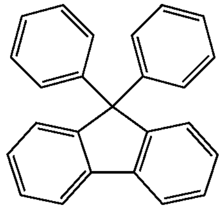

In the disclosure, a heteroaryl group may include one or more selected from among B, O, N, P, Si and S as heteroatoms. When the heteroaryl group includes two or more heteroatoms, two or more heteroatoms may be the same or different. The heteroaryl group may be a monocyclic heterocyclic group or polycyclic heterocyclic group. The carbon number for forming rings of the heteroaryl group may be 2 to 30, 2 to 20, or 2 to 10. Examples of the heteroaryl group may include thiophene, furan, pyrrole, imidazole, triazole, pyridine, bipyridine, pyrimidine, triazine, triazole, acridyl, pyridazine, pyrazinyl, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophene, thienothiophene, benzofuran, phenanthroline, thiazole, isoxazole, oxazole, oxadiazole, thiadiazole, phenothiazine, dibenzosilole, dibenzofuran, etc., without limitation.

In the disclosure, the explanation on the aryl group may be applied to an arylene group except that the arylene group is a divalent group. The explanation on the heteroaryl group may be applied to a heteroarylene group except that the heteroarylene group is a divalent group.

In the disclosure, a silyl group includes an alkyl silyl group and an aryl silyl group. Examples of the silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, etc., without limitation.

In the disclosure, an oxy group may refer to the above-defined alkyl group or aryl group which is combined with an oxygen atom. The oxy group may include an alkoxy group and an aryl oxy group. The alkoxy group may be a linear, branched or cyclic chain. The carbon number of the alkoxy group is not limited but may be, for example, 1 to 20 or 1 to 10. Examples of the oxy group may include methoxy, ethoxy, n-propoxy, isopropoxy, butoxy, pentyloxy, hexyloxy, octyloxy, nonyloxy, decyloxy, benzyloxy, etc. However, an embodiment of the present disclosure is not limited thereto.

In the disclosure, the carbon number of an amine group is not limited, but may be 1 to 30. The amine group may include an alkyl amine group and/or an aryl amine group. Examples of the amine group include a methylamine group, a dimethylamine group, a phenylamine group, a diphenylamine group, a naphthylamine group, a 9-methyl-anthracenylamine group, a triphenylamine group, etc., without limitation.

In the disclosure, a direct linkage may refer to a single bond.

In some embodiments, in the disclosure,

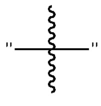
and refer to positions to be connected.

Hereinafter, embodiments of the present disclosure will be explained referring to the drawings.

Figure 2:
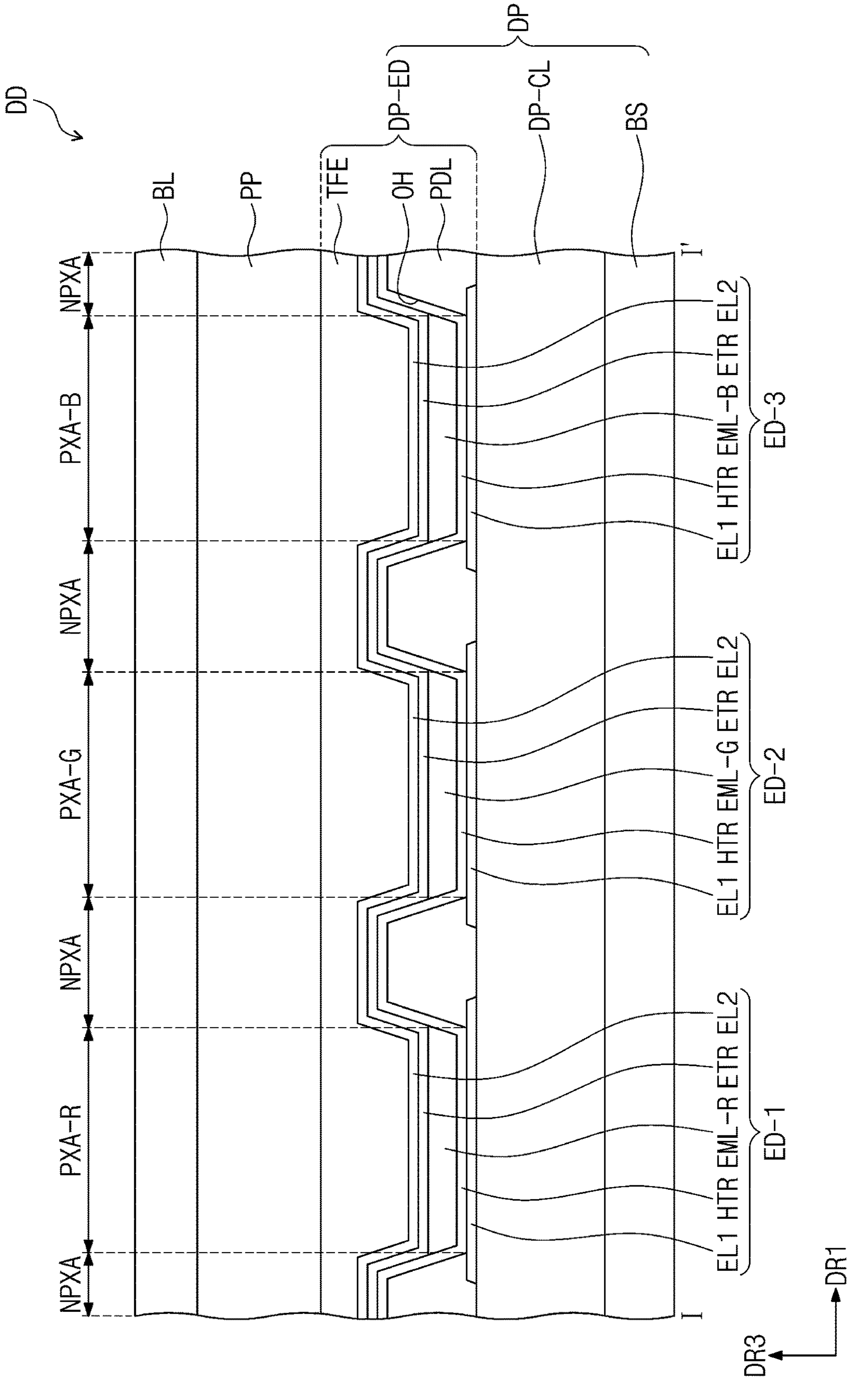
FIG. 2 is a cross-sectional view of a display apparatus according to an embodiment.

FIG. 1 is a plan view showing an embodiment of a display apparatus DD. FIG. 2 is a cross-sectional view of a display apparatus DD of an embodiment. FIG. 2 is a cross-sectional view showing a part corresponding to line I-I' in FIG. 1.

The display apparatus DD may include a display panel DP and an optical layer PP on the display panel DP. The display panel DP includes light emitting devices ED-1, ED-2 and ED-3. The display apparatus DD may include multiple light emitting devices ED-1, ED-2 and ED-3. The optical layer PP may be on the display panel DP and control reflected light by external light at the display panel DP. The optical layer PP may include, for example, a polarization layer or a color filter layer. In some embodiments, the optical layer PP may not be provided in the display apparatus DD.

On the optical layer PP, a base substrate BL may be disposed. The base substrate BL may be a member that provides a base surface on which the optical layer PP is disposed. The base substrate BL may be a glass substrate, a metal substrate, a plastic substrate, etc. However, an embodiment of the present disclosure is not limited thereto, and the base substrate BL may be an inorganic layer, an organic layer or a composite material layer. In some embodiments, the base substrate BL may not be provided.

The display apparatus DD according to an embodiment may further include a plugging layer. The plugging layer may be between a display device layer DP-ED and a base substrate BL. The plugging layer may be an organic layer. The plugging layer may include at least one selected from among an acrylic resin, a silicon-based resin and an epoxy-based resin.

The display panel DP may include a base layer BS, a circuit layer DP-CL provided on the base layer BS and a display device layer DP-ED. The display device layer DP-ED may include a pixel definition layer PDL, light emitting devices ED-1, ED-2 and ED-3 in the pixel definition layer PDL, and an encapsulating layer TFE on the light emitting devices ED-1, ED-2 and ED-3.

The base layer BS may be a member that provides a base surface in which the display device layer DP-ED is disposed. The base layer BS may be a glass substrate, a metal substrate, a plastic substrate, etc. However, an embodiment of the present disclosure is not limited thereto, and the base layer BS may be an inorganic layer, an organic layer or a composite material layer.

In an embodiment, the circuit layer DP-CL is on the base layer BS, and the circuit layer DP-CL may include multiple transistors. Each of the transistors may include a control electrode, an input electrode, and an output electrode. For example, the circuit layer DP-CL may include switching transistors and driving transistors for driving the light emitting devices ED-1, ED-2 and ED-3 of the display device layer DP-ED.

Each of the light emitting devices ED-1, ED-2 and ED-3 may have the structures of light emitting devices ED of embodiments according to FIG. 3 to FIG. 6, described below. Each of the light emitting devices ED-1, ED-2 and ED-3 may include a first electrode EL1, a hole transport region HTR, emission layers EML-R, EML-G and EML-B, an electron transport region ETR, and a second electrode EL2.

In FIG. 2, shown is an embodiment in which the emission layers EML-R, EML-G and EML-B of light emitting devices ED-1, ED-2 and ED-3, which are in opening portions OH defined in a pixel definition layer PDL, are disposed, and a hole transport region HTR, an electron transport region ETR and a second electrode EL2 are provided as common layers in all light emitting devices ED-1, ED-2 and ED-3. However, an embodiment of the present disclosure is not limited thereto. In an embodiment, the hole transport region HTR and the electron transport region ETR may be patterned and provided in the opening portions OH defined in the pixel definition layer PDL. For example, in an embodiment, the hole transport region HTR, the emission layers EML-R, EML-G and EML-B, and the electron transport region ETR of the light emitting devices ED-1, ED-2 and ED-3 may be patterned by an ink jet printing method and provided.

An encapsulating layer TFE may cover the light emitting devices ED-1, ED-2 and ED-3. The encapsulating layer TFE may encapsulate the display device layer DP-ED. The encapsulating layer TFE may be a thin film encapsulating layer. The encapsulating layer TFE may be one layer or a stacked layer of multiple layers. The encapsulating layer TFE includes at least one insulating layer. The encapsulating layer TFE according to an embodiment may include at least one inorganic layer (hereinafter, encapsulating inorganic layer). In some embodiments, the encapsulating layer TFE according to an embodiment may include at least one organic layer (hereinafter, encapsulating organic layer) and at least one encapsulating inorganic layer.

The encapsulating inorganic layer protects the display device layer DP-ED from moisture/oxygen, and the encapsulating organic layer protects (reduces the exposure to foreign materials) the display device layer DP-ED from foreign materials such as dust particles. The encapsulating inorganic layer may include silicon nitride, silicon oxy nitride, silicon oxide, titanium oxide, and/or aluminum oxide, without specific limitation. The encapsulating organic layer may include an acrylic compound, an epoxy-based compound, etc. The encapsulating organic layer may include a photopolymerizable organic material, without specific limitation.

The encapsulating layer TFE may be on the second electrode EL2 and may be disposed while filling the opening portion OH.

Referring to FIG. 1 and FIG. 2, the display apparatus DD may include a non-luminous area NPXA and luminous areas PXA-R, PXA-G and PXA-B. The luminous areas PXA-R, PXA-G and PXA-B may be areas emitting light produced from the light emitting devices ED-1, ED-2 and ED-3, respectively. The luminous areas PXA-R, PXA-G and PXA-B may be separated from each other on a plane (e.g., in a plan view).

The luminous areas PXA-R, PXA-G and PXA-B may be areas separated by the pixel definition layer PDL. The non-luminous areas NPXA may be areas between neighboring luminous areas PXA-R, PXA-G and PXA-B and may be areas corresponding to the pixel definition layer PDL. In some embodiments, in the disclosure, each of the luminous areas PXA-R, PXA-G and PXA-B may correspond to each pixel. The pixel definition layer PDL may divide the light emitting devices ED-1, ED-2 and ED-3. The emission layers EML-R, EML-G and EML-B of the light emitting devices ED-1, ED-2 and ED-3 may be disposed and divided in the opening portions OH defined in the pixel definition layer PDL.

The luminous areas PXA-R, PXA-G and PXA-B may be divided into multiple groups according to the color of light produced from the light emitting devices ED-1, ED-2 and ED-3. In the display apparatus DD of an embodiment, shown in FIG. 1 and FIG. 2, three luminous areas PXA-R, PXA-G and PXA-B emitting red light, green light and blue light are illustrated as an embodiment. For example, the display apparatus DD of an embodiment may include a red luminous area PXA-R, a green luminous area PXA-G and a blue luminous area PXA-B, which are separated from each other.

In the display apparatus DD according to an embodiment, multiple light emitting devices ED-1, ED-2 and ED-3 may emit light having different wavelength regions. For example, in an embodiment, the display apparatus DD may include a first light emitting device ED-1 emitting red light, a second light emitting device ED-2 emitting green light, and a third light emitting device ED-3 emitting blue light. For example, each of the red luminous area PXA-R, the green luminous area PXA-G, and the blue luminous area PXA-B of the display apparatus DD may correspond to the first light emitting device ED-1, the second light emitting device ED-2, and the third light emitting device ED-3, respectively.

However, an embodiment of the present disclosure is not limited thereto, and the first to third light emitting devices ED-1, ED-2 and ED-3 may emit light in the same wavelength region, or at least one thereof may emit light in a different wavelength region. For example, all the first to third light emitting devices ED-1, ED-2 and ED-3 may emit blue light.

The luminous areas PXA-R, PXA-G and PXA-B in the display apparatus DD according to an embodiment may be arranged in a stripe shape. Referring to FIG. 1, multiple red luminous areas PXA-R may be arranged with each other along a second direction axis DR2, multiple green luminous areas PXA-G may be arranged with each other along the second direction axis DR2, and multiple blue luminous areas PXA-B may be arranged with each other along the second direction axis DR2. In addition, the red luminous area PXA-R, the green luminous area PXA-G and the blue luminous area PXA-B may be arranged by turns along a first direction axis DR1. (DR3 is a third direction which is normal or perpendicular to the plane defined by the first direction DR1 and the second direction DR2).

In FIG. 1 and FIG. 2, the areas of the luminous areas PXA-R, PXA-G and PXA-B are shown to be substantially similar, but an embodiment of the present disclosure is not limited thereto. The areas of the luminous areas PXA-R, PXA-G and PXA-B may be different from each other according to the wavelength region of light emitted. In some embodiments, the areas of the luminous areas PXA-R, PXA-G and PXA-B may refer to areas on a plane defined by the first direction axis DR1 and the second direction axis DR2.

In some embodiments, the arrangement type (kind) of the luminous areas PXA-R, PXA-G and PXA-B is not limited to the configuration shown in FIG. 1, and the arrangement order of the red luminous areas PXA-R, the green luminous areas PXA-G and the blue luminous areas PXA-B may be provided in one or more suitable combinations according to the properties of display quality required for the display apparatus DD. For example, the arrangement type (kind) of the luminous areas PXA-R, PXA-G and PXA-B may be a pentile (PENTILE®) arrangement type (PENTILE® arrangement form, for example, an RGBG matrix, an RGBG structure, or RGBG matrix structure), or a diamond arrangement type (Diamond Pixel™ arrangement form). PENTILE® is a duly registered trademark of Samsung Display Co., Ltd. Diamond Pixel™ is a trademark of Samsung Display Co., Ltd.

In some embodiments, the areas (i.e., sizes) of the luminous areas PXA-R, PXA-G and PXA-B may be different from each other. For example, in an embodiment, the area of the green luminous area PXA-G may be smaller than the area of the blue luminous area PXA-B, but an embodiment of the present disclosure is not limited thereto.

Hereinafter, FIG. 3 to FIG. 6 are cross-sectional views schematically showing light emitting devices according to embodiments. The light emitting device ED according to an embodiment may include a first electrode EL1, a hole transport region HTR, an emission layer EML, an electron transport region ETR, and a second electrode EL2 stacked in order.

Figure 3:
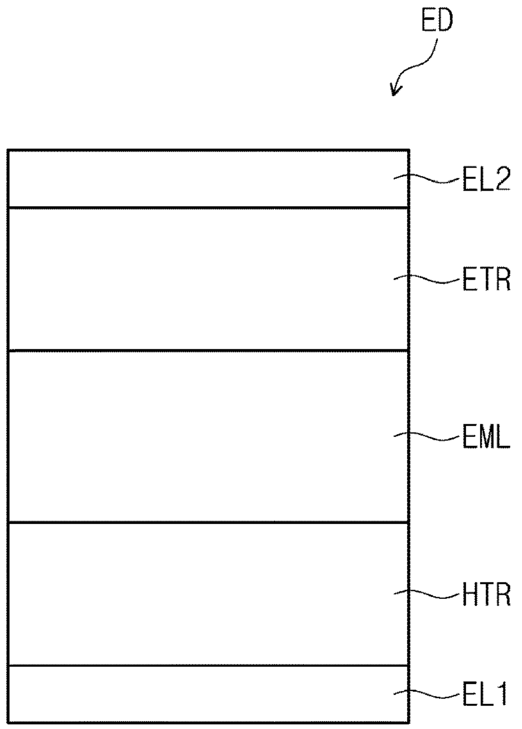
FIG. 3 is a cross-sectional view schematically showing a light emitting device according to an embodiment.
Figure 4:
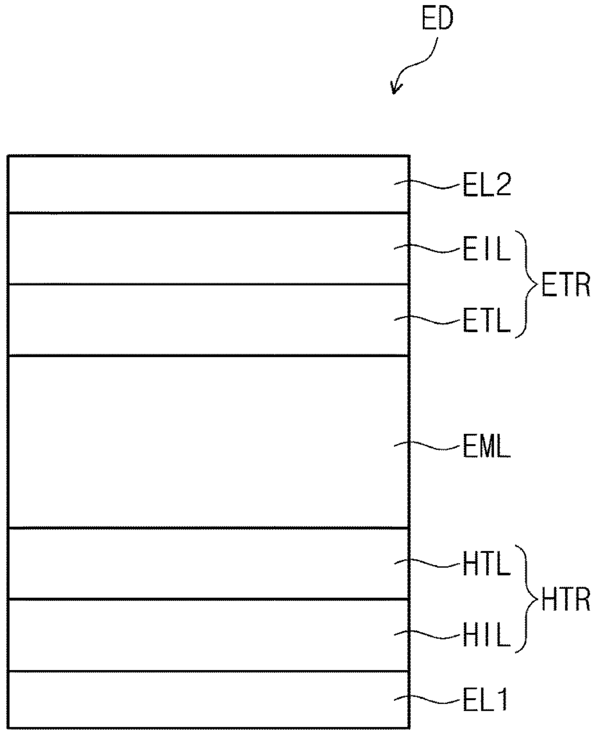
FIG. 4 is a cross-sectional view schematically showing a light emitting device according to an embodiment.
Figure 5:
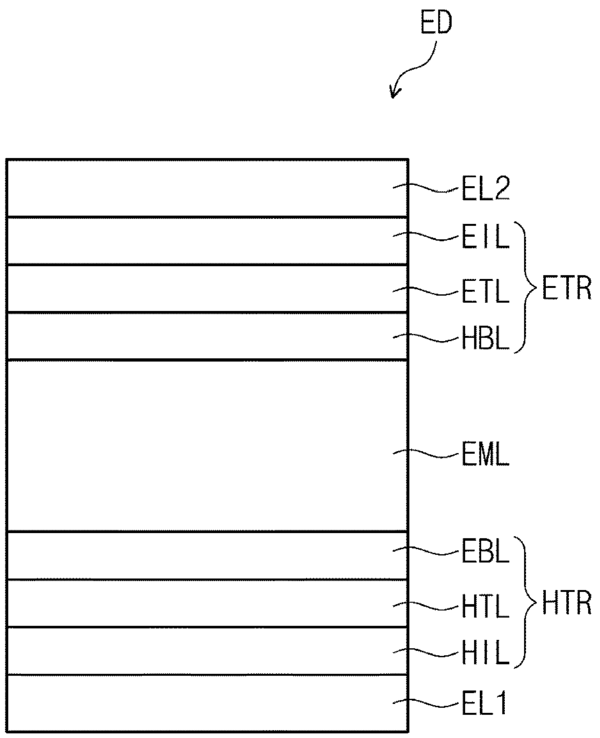
FIG. 5 is a cross-sectional view schematically showing a light emitting device according to an embodiment.
Figure 6:
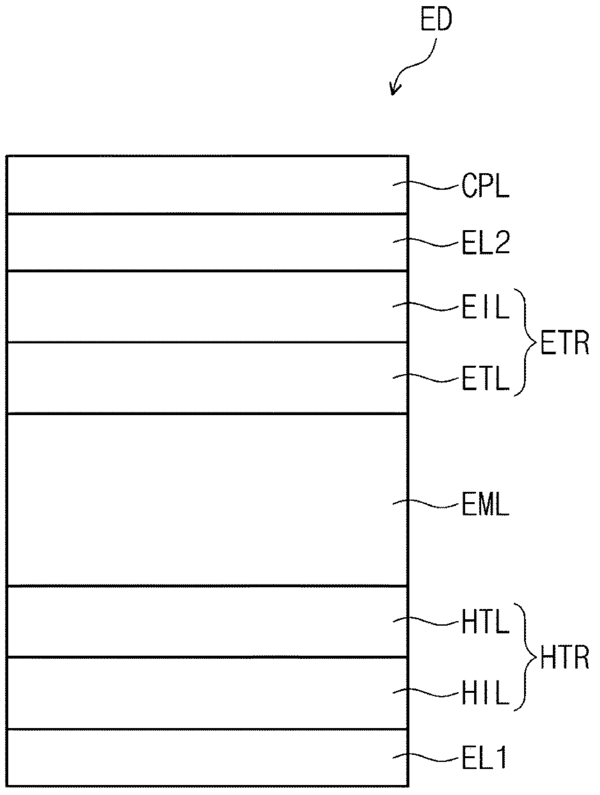
FIG. 6 is a cross-sectional view schematically showing a light emitting device according to an embodiment.

When compared with FIG. 3, FIG. 4 shows the cross-sectional view of a light emitting device ED of an embodiment, wherein a hole transport region HTR includes a hole injection layer HIL and a hole transport layer HTL, and an electron transport region ETR includes an electron injection layer EIL and an electron transport layer ETL. In some embodiments, when compared with FIG. 3, FIG. 5 shows the cross-sectional view of a light emitting device ED of an embodiment, wherein a hole transport region HTR includes a hole injection layer HIL, a hole transport layer HTL, and an electron blocking layer EBL, and an electron transport region ETR includes an electron injection layer EIL, an electron transport layer ETL, and a hole blocking layer HBL. When compared with FIG. 4, FIG. 6 shows the cross-sectional view of a light emitting device ED of an embodiment, including a capping layer CPL on the second electrode EL2.

The first electrode EL1 has conductivity. The first electrode EL1 may be formed using a metal material, a metal alloy and/or a conductive compound. The first electrode EL1 may be an anode or a cathode. However, an embodiment of the present disclosure is not limited thereto. In some embodiments, the first electrode EL1 may be a pixel electrode. The first electrode EL1 may be a transmissive electrode, a transflective electrode, or a reflective electrode. The first electrode EL1 may include at least one selected from among Ag, Mg, Cu, Al, Pt, Pd, Au, Ni, Nd, Ir, Cr, Li, Ca, LiF, Mo, Ti, W, In, Sn, Zn, compounds comprising one or more of the foregoing elements, combinations of two or more of the foregoing elements or compounds, mixtures of two or more of the foregoing elements or compounds, and oxides thereof.

When the first electrode EL1 is the transmissive electrode, the first electrode EL1 may include a transparent metal oxide such as indium tin oxide (ITO), indium zinc oxide (IZO), zinc oxide (ZnO), and/or indium tin zinc oxide (ITZO). When the first electrode EL1 is the transflective electrode or the reflective electrode, the first electrode EL1 may include Ag, Mg, Cu, Al, Pt, Pd, Au, Ni, Nd, Ir, Cr, Li, Ca, LiF/Ca (a stacked structure of LiF and Ca), LiF/Al (a stacked structure of LiF and Al), Mo, Ti, W, compounds thereof, or mixtures thereof (for example, a mixture of Ag and Mg). Also, the first electrode EL1 may have a structure including multiple layers including a reflective layer or a transflective layer formed using the above materials, and a transmissive conductive layer formed using ITO, IZO, ZnO, or ITZO. For example, the first electrode EL1 may include a three-layer structure of ITO/Ag/ITO. However, an embodiment of the present disclosure is not limited thereto. The first electrode EL1 may include the above-described metal materials, combinations of two or more metal materials selected from the above-described metal materials, or oxides of the above-described metal materials. The thickness of the first electrode EL1 may be from about 700 Å to about 10,000 Å. For example, the thickness of the first electrode EL1 may be from about 1,000 Å to about 3,000 Å.

The hole transport region HTR is provided on the first electrode EL1. The hole transport region HTR may include at least one of a hole injection layer HIL, a hole transport layer HTL, a buffer layer or an emission auxiliary layer (not shown), or an electron blocking layer EBL. The thickness of the hole transport region HTR may be, for example, about 50 Å to about 15,000 Å.

The hole transport region HTR may have a single layer formed using a single material, a single layer formed using multiple different materials, or a multilayer structure including multiple layers formed using multiple different materials.

For example, the hole transport region HTR may have the structure of a single layer of a hole injection layer HIL or a hole transport layer HTL, and may have a structure of a single layer formed using a hole injection material and a hole transport material. In some embodiments, the hole transport region HTR may have a structure of a single layer formed using multiple different materials, or a structure stacked from the first electrode EL1 of hole injection layer HIL/hole transport layer HTL, hole injection layer HIL/hole transport layer HTL/buffer layer, hole injection layer HIL/buffer layer, hole transport layer HTL/buffer layer, or hole injection layer HIL/hole transport layer HTL/electron blocking layer EBL, without limitation.

The hole transport region HTR may be formed by one or more suitable methods such as a vacuum deposition method, a spin coating method, a cast method, a Langmuir-Blodgett (LB) method, an ink jet printing method, a laser printing method, and/or a laser induced thermal imaging (LITI) method.

In the light emitting device ED of an embodiment, the hole transport region HTR may include the amine compound of an embodiment.

The amine compound of an embodiment includes an amine group and may have a structure in which the nitrogen atom of the amine group is connected with a carbazole moiety. The carbazole moiety may include a first carbazole group and a second carbazole group. The second carbazole group is connected with the first carbazole group, and the first carbazole group may be connected with the nitrogen atom of the amine group. Accordingly, the amine compound of an embodiment may include a conjugated system from the second carbazole group via the first carbazole group to the nitrogen atom of the amine group. In some embodiments, in the disclosure, the second carbazole group-substituted, and the first carbazole group-substituted amine group may refer to a "central skeleton".

In the amine compound of an embodiment, any one among the benzene rings composing the first carbazole group may be connected with the second carbazole group, and the remaining one may be connected with the nitrogen atom of the amine group. For example, the first carbazole group may be connected with the nitrogen atom of the amine group at any one selected from among carbon at position 2 and carbon at position 7, and the remainder may be connected with the second carbazole group. The first carbazole group may be directly connected with the nitrogen atom of the amine group or connected via a linker. In some embodiments, the first carbazole group may be connected with the nitrogen atom at position 9 of the second carbazole group, and the first carbazole group and the second carbazole group may be directly linked or connected via a linker. In some embodiments, the number of the carbon atoms and the nitrogen atom of the carbazole group are shown in Formula c.

Formula c

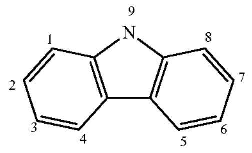

In some embodiments, the amine compound of an embodiment may have a structure in which two substituents other than the first carbazole group are connected. For example, the amine compound may include the second carbazole group-substituted first carbazole group, a first substituent, and a second substituent. The first substituent and the second substituent may each independently be substituted through a direct linkage with the nitrogen atom of the amine group or through the connection via a linker. In an embodiment, the linker may be a substituted or unsubstituted arylene group of 6 to 30 ring-forming carbon atoms.

The amine compound of an embodiment may be a mono-amine compound. The amine compound may include one amine group in the compound structure.

The amine compound of an embodiment may be represented by Formula 1.

Formula 1

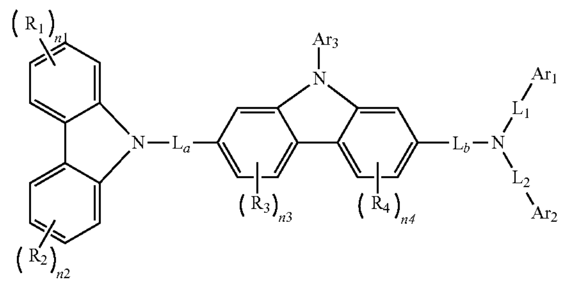

In Formula 1, $Ar_1$ to $Ar_3$ may each independently be a substituted or unsubstituted alkyl group of 1 to 20 carbon atoms, a substituted or unsubstituted silyl group, a substituted or unsubstituted aryl group of 6 to 30 ring-forming carbon atoms, or a substituted or unsubstituted heteroaryl group of 2 to 30 ring-forming carbon atoms. For example, $Ar_1$ to $Ar_3$ may each independently be a substituted or unsubstituted t-butyl group, a substituted or unsubstituted cyclohexyl group, a substituted or unsubstituted triphenylsilyl group, a substituted or unsubstituted phenyl group, a substituted or unsubstituted biphenyl group, a substituted or unsubstituted terphenyl group, a substituted or unsubstituted naphthyl group, a substituted or unsubstituted phenanthrene group, a substituted or unsubstituted dibenzofuran group, a substituted or unsubstituted dibenzothiophene group, a substituted or unsubstituted fluorenyl group, a substituted or unsubstituted carbazole group, a substituted or unsubstituted benzonaphthofuran group, a substituted or unsubstituted benzonaphthothiophene group, or a substituted or unsubstituted benzofurocarbazole group. $Ar_3$ may be a substituted or unsubstituted phenyl group, a substituted or unsubstituted biphenyl group, or a substituted or unsubstituted terphenyl group. In some embodiments, when $Ar_1$ and $Ar_2$ are substituted or unsubstituted fluorenyl groups, each of $Ar_1$ and $Ar_2$ may be represented by Formula b.

In Formula 1, $L_a$, $L_b$, $L_1$, and $L_2$ may each independently be a direct linkage, or a substituted or unsubstituted arylene group of 6 to 30 ring-forming carbon atoms. For example, $L_a$, $L_b$, $L_1$, and $L_2$ may each independently be a direct linkage, a substituted or unsubstituted phenylene group, a substituted or unsubstituted divalent biphenyl group, or a substituted or unsubstituted divalent naphthyl group.

In Formula 1, $R_1$ to $R_4$ may each independently be a substituted or unsubstituted alkyl group of 1 to 20 carbon atoms, or a substituted or unsubstituted aryl group of 6 to 30 ring-forming carbon atoms. For example, $R_1$ to $R_4$ may each independently be a substituted or unsubstituted t-butyl group, or a substituted or unsubstituted phenyl group.

In Formula 1, n1 refers to the number of $R_1$, and n1 is an integer from 0 to 4. n2 refers to the number of $R_2$ and is an integer from 0 to 4. When n1 and n2 are 0, the amine compound of an embodiment may be unsubstituted with $R_1$ and $R_2$, respectively. When n1 and n2 are integers of 2 or more, each of multiple $R_1$ and $R_2$ may be all the same, or at least one among each of multiple $R_1$ and $R_2$ may be different.

In Formula 1, n3 refers to the number of $R_3$, and n3 is an integer from 0 to 3. n4 refers to the number of $R_4$, and n4 is an integer from 0 to 3. When n3 and n4 are 0, the amine compound of an embodiment may be unsubstituted with $R_3$ and $R_4$, respectively. When n3 and n4 are integers of 2 or more, each of multiple $R_3$ and $R_4$ may be all the same, or at least one among each of multiple $R_3$ and $R_4$ may be different.

In Formula 1, i) the sum of n1 and n2 is 1 or more, ii) at least one among $Ar_1$ to $Ar_3$ is a substituent represented by Formula a, iii) at least one among $Ar_1$ and $Ar_2$ is a substituted or unsubstituted dibenzofuran group, a substituted or unsubstituted dibenzothiophene group, a substituted or unsubstituted phenanthrene group, a substituted or unsubstituted carbazole group, or a substituent represented by Formula b, or iv) at least one among $L_a$ and $L_b$ is a substituted or unsubstituted arylene group of 6 to 30 ring-forming carbon atoms. The amine compound of an embodiment, represented by Formula 1 may satisfy at least one among i) to iv) above.

Formula a

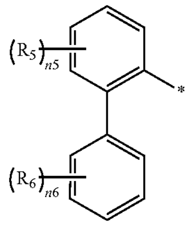

In Formula a, $R_5$ and $R_6$ may each independently be a hydrogen atom, a deuterium atom, a halogen atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms. For example, $R_5$ and $R_6$ may each independently be a hydrogen atom, a substituted or unsubstituted phenyl group, or a substituted or unsubstituted naphthyl group.

In Formula a, n5 may be an integer from 0 to 4. When n5 is 0, the amine compound of an embodiment may be unsubstituted with $R_5$. An embodiment of Formula a in which n5 is 4, and all $R_5$ are hydrogen atoms, may be the same as an embodiment of Formula a in which n5 is 0. When n5 is an integer of 2 or more, multiple $R_5$ may be all the same, or at least one among multiple $R_5$ may be different.

In Formula a, n6 may be an integer from 0 to 5. When n6 is 0, the amine compound of an embodiment may be unsubstituted with $R_6$. An embodiment of Formula a in which n6 is 5, and all $R_6$ are hydrogen atoms, may be the same as an embodiment of Formula a in which n6 is 0. When n6 is an integer of 2 or more, multiple $R_6$ may be all the same, or at least one among multiple $R_6$ may be different.

Formula b

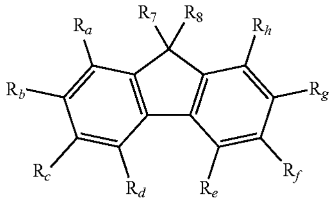

In Formula b, $R_a$ to $R_h$, $R_7$, and $R_8$ may each independently be a hydrogen atom, a deuterium atom, a halogen atom, a substituted or unsubstituted alkyl group of 1 to 20 carbon atoms, or a substituted or unsubstituted aryl group of 6 to 30 ring-forming carbon atoms. For example, $R_a$ to $R_h$ may each independently be a hydrogen atom. $R_7$ and $R_8$ may each independently be a substituted or unsubstituted phenyl group.

In Formula b, any one among $R_a$, $R_b$, $R_d$, $R_e$, $R_g$, and $R_h$ may be a part (a substituent) connected to $L_1$ or $L_2$. For example, a fluorenyl moiety represented by Formula b may be connected with $L_1$ or $L_2$ of Formula 1 at carbon position other than carbon at position 3 or 6. In some embodiments, the number of carbon atoms of the fluorenyl group is shown as in Formula F.

Formula F

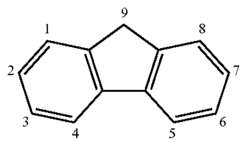

The amine compound of an embodiment may satisfy at least one among i) to iv) above. Accordingly, the central skeleton of the amine compound may be sterically protected and electronically stabilized. Accordingly, a light emitting device including the amine compound of an embodiment as a hole transport material may show high emission efficiency and long-life characteristics. In some embodiments, the amine compound of an embodiment satisfies at least one among i) to iv), and the highest occupied molecular orbital (HOMO) energy level of the compound changes, and due to the change of the HOMO energy level, energy balance in an emission layer may be improved even further to improve emission efficiency. Further, by introducing a specific substituent or a linker to the central skeleton of the amine compound of an embodiment, properties such as the HOMO energy level of the compound change, and at the same time (concurrently), the packing density in the device changes to improve device-life characteristics.

In an embodiment, the amine compound represented by Formula 1 may be represented by any one among Formula 2-1 to Formula 2-3.

Formula 2-1

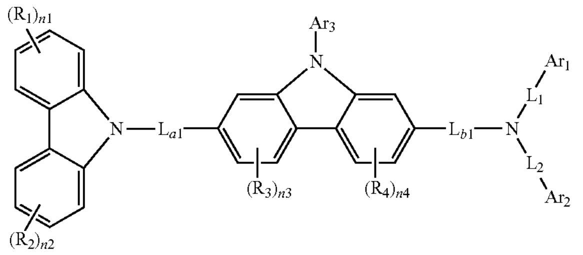

Formula 2-2

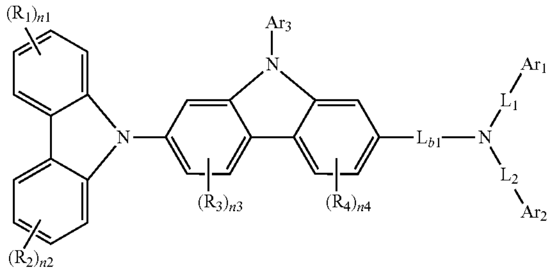

Formula 2-3

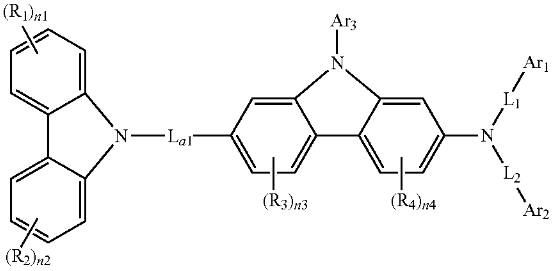

Formula 2-1 to Formula 2-3 represent Formula 1 in which the types (kinds) of $L_a$ and $L_b$ are specified. Formula 2-1 represents Formula 1 in which $L_a$ and $L_b$ may be substituted or unsubstituted arylene groups of 6 to 30 ring-forming carbon atoms. Formula 2-2 represents Formula 1 in which $L_a$ may be a direct linkage, and $L_b$ may be a substituted or unsubstituted arylene group of 6 to 30 ring-forming carbon atoms. Formula 2-3 represents Formula 1 in which $L_a$ may be a substituted or unsubstituted arylene group of 6 to 30 ring-forming carbon atoms, and $L_b$ may be a direct linkage.

In Formula 2-1 to Formula 2-3, $L_{a1}$ and $L_{b1}$ may each independently be a substituted or unsubstituted arylene group. For example, $L_{a1}$ and $L_{b1}$ may each independently be a substituted or unsubstituted p-phenylene group, a substituted or unsubstituted m-phenylene group, a substituted or unsubstituted o-phenylene group, or a substituted or unsubstituted divalent naphthyl group.

In Formula 2-1 to Formula 2-3, the same explanation on $Ar_1$ to $Ar_3$, $R_1$ to $R_4$, $L_1$, $L_2$, and n1 to n4 referring to Formula 1 may be applied.

In an embodiment, the amine compound represented by Formula 1 may be represented by Formula 3.

Formula 3

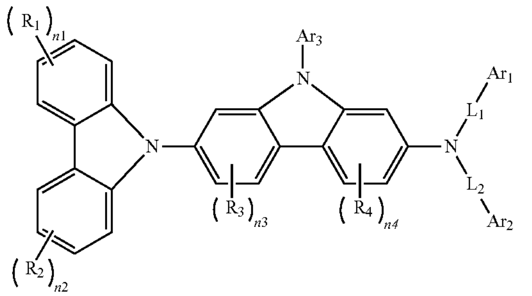

Formula 3 represents Formula 1 in which both $L_a$ and $L_b$ are direct linkages.

In Formula 3, the same explanation on $Ar_1$ to $Ar_3$, $R_1$ to $R_4$, and n1 to n4 referring to Formula 1 may be applied.

In an embodiment, the amine compound represented by Formula 1 may be represented by any one among Formula 4-1 to Formula 4-3.

Formula 4-1

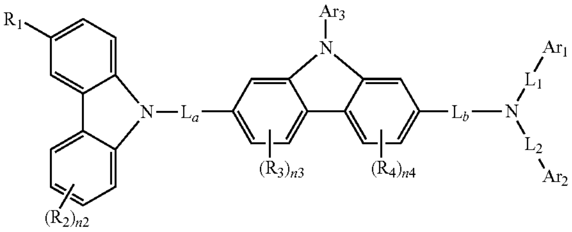

Formula 4-2

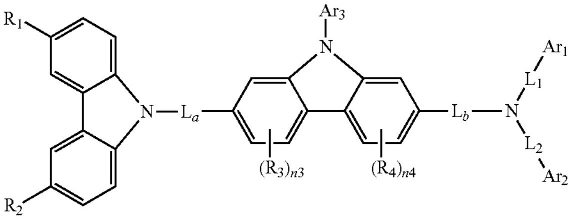

Formula 4-3

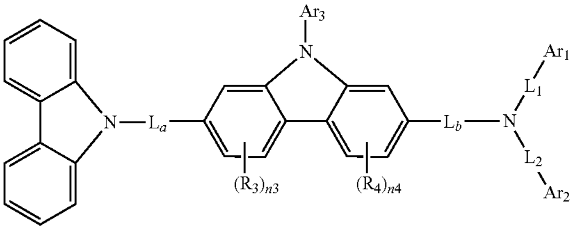

Formula 4-1 to Formula 4-3 represent Formula 1 in which the substitution positions of $R_1$ or $R_2$ are specified. Formula 4-1 represents Formula 1 in which $R_1$ is substituted at the para position to the nitrogen atom of the carbazole group. Formula 4-2 represents Formula 1 in which $R_1$ is connected with any one among two benzene rings composing the carbazole group, $R_2$ is connected with the remaining benzene ring, and $R_1$ and $R_2$ are substituted at para positions to the nitrogen atom of the carbazole group. Formula 4-3 represents Formula 1 in which both n1 and n2 are 0. For example, Formula 4-3 represents the amine compound of Formula 1, which is unsubstituted with $R_1$ and $R_2$.

In Formula 4-1 to Formula 4-3, the same explanation on $Ar_1$ to $Ar_3$, $R_1$ to $R_4$, $L_a$, $L_b$, $L_1$, $L_2$, and n2 to n4 referring to Formula 1 may be applied.

In an embodiment, the amine compound represented by Formula 1 may be represented by any one among Formula 5-1 to Formula 5-3.

Formula 5-1

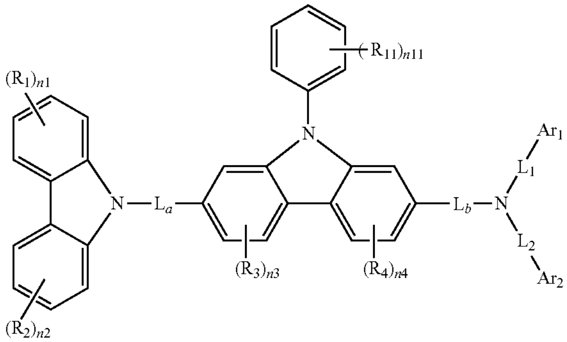

Formula 5-2

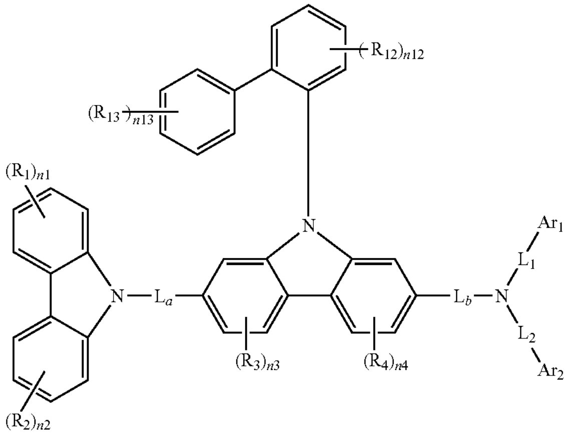

Formula 5-3

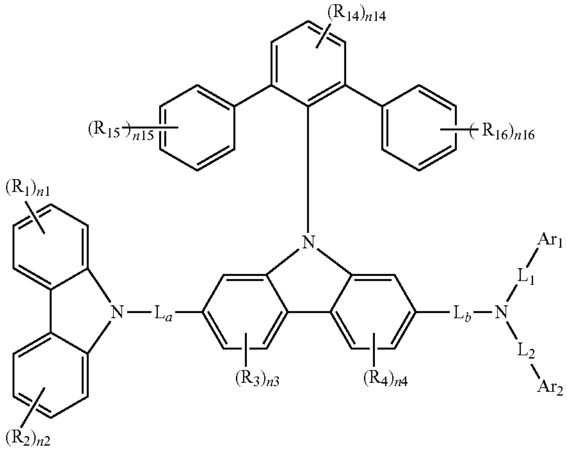

Formula 5-1 to Formula 5-3 represent Formula 1 in which the type (kind) of the substituent of $Ar_3$ is specified. Formula 5-1 represents Formula 1 in which $Ar_3$ is a substituted or unsubstituted phenyl group. Formula 5-2 represents Formula 1 in which $Ar_3$ is a substituted or unsubstituted biphenyl group. Formula 5-3 represents Formula 1 in which $Ar_3$ is a substituted or unsubstituted terphenyl group.

In Formula 5-1 to Formula 5-3, $R_{11}$ to $R_{16}$ may each independently be a hydrogen atom, a deuterium atom, a halogen atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms. For example, $R_{11}$ to $R_{16}$ may each independently be a hydrogen atom.

In Formula 5-1 to Formula 5-3, n11, n13, n15, and n16 may each independently be an integer from 0 to 5. When n11, n13, n15, and n16 are 0, the amine compound of an embodiment may be unsubstituted with $R_{11}$, $R_{13}$, $R_{15}$, and $R_{16}$, respectively. An embodiment in which n11, n13, n15, and n16 are 5, and $R_{11}$, $R_{13}$, $R_{15}$, and $R_{16}$ are all hydrogen atoms, may be the same as an embodiment in which n11, n13, n15, and n16 are 0. When n11, n13, n15, and n16 are integers of 2 or more, each of multiple $R_{11}$, $R_{13}$, $R_{15}$, and $R_{16}$ may be the same, or at least one among multiple $R_{11}$, $R_{13}$, $R_{15}$, and $R_{16}$ may be different.

In Formula 5-2, n12 may be an integer from 0 to 4. When n12 is 0, the amine compound of an embodiment may be unsubstituted with $R_{12}$. An embodiment of Formula 5-2 in which n12 is 4, and all $R_{12}$ are hydrogen atoms, may be the same as an embodiment of Formula 5-2 in which n12 is 0. When n12 is an integer of 2 or more, multiple $R_{12}$ may be all the same, or at least one among multiple $R_{12}$ may be different.

In Formula 5-3, n14 may be an integer from 0 to 3. When n14 is 0, the amine compound of an embodiment may be unsubstituted with $R_{14}$. An embodiment of Formula 5-3 in which n14 is 3, and all $R_{14}$ are hydrogen atoms, may be the same as an embodiment of Formula 5-3 in which n14 is 0. When n14 is an integer of 2 or more, multiple $R_{14}$ may be all the same, or at least one among multiple $R_{14}$ may be different.

In Formula 5-1 to Formula 5-3, the same explanation on $Ar_1$, $Ar_2$, $R_1$ to $R_4$, $L_a$, $L_b$, $L_1$, $L_2$, and n1 to n4 referring to Formula 1 may be applied.

In an embodiment, the amine compound represented by Formula 1 may be represented by any one among Formula 6-1 to Formula 6-3.

Formula 6-1

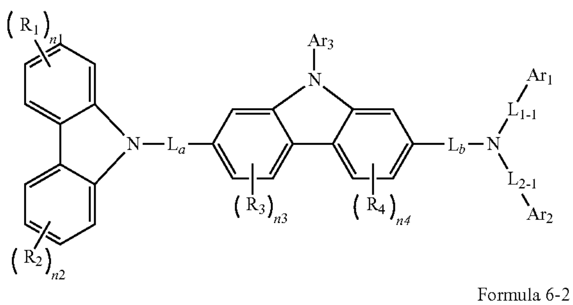

Formula 6-2

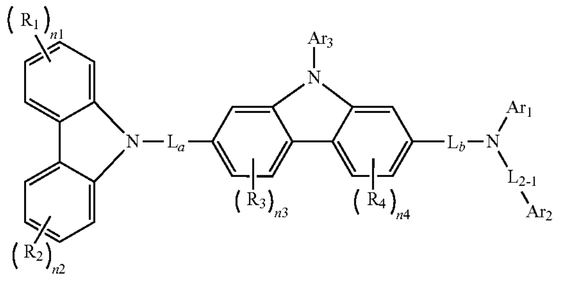

-continued

Formula 6-3

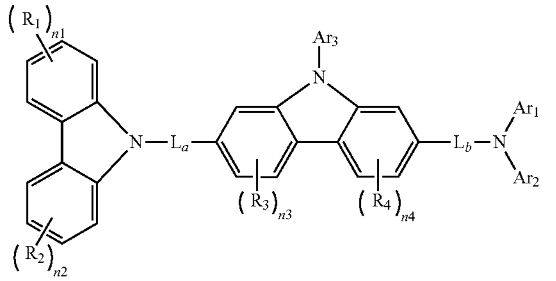

Formula 6-1 to Formula 6-3 represent Formula 1 in which the types (kinds) of $L_1$ and $L_2$ are specified. Formula 6-1 represents Formula 1 in which $L_1$ and $L_2$ are substituted or unsubstituted arylene groups of 6 to 30 ring-forming carbon atoms. Formula 6-2 represents Formula 1 in which $L_1$ is a direct linkage, and $L_2$ is a substituted or unsubstituted arylene group of 6 to 30 ring-forming carbon atoms. Formula 6-3 represents Formula 1 where $L_1$ and $L_2$ are direct linkages.

In Formula 6-1 to Formula 6-3, $L_{1-1}$ and $L_{2-1}$ may each independently be a substituted or unsubstituted arylene group of 6 to 30 ring-forming carbon atoms. For example, $L_{1-1}$ and $L_{2-1}$ may each independently be a substituted or unsubstituted phenylene group, a substituted or unsubstituted divalent biphenyl group, or a substituted or unsubstituted divalent naphthyl group.

In Formula 6-1 to Formula 6-3, the same explanation on $Ar_1$ to $Ar_3$, $R_1$ to $R_4$, $L_a$, $L_b$, and n1 to n4 referring to Formula 1 may be applied.

In an embodiment, the amine compound represented by Formula 1 may be represented by any one among Formula 7-1 to Formula 7-3.

Formula 7-1

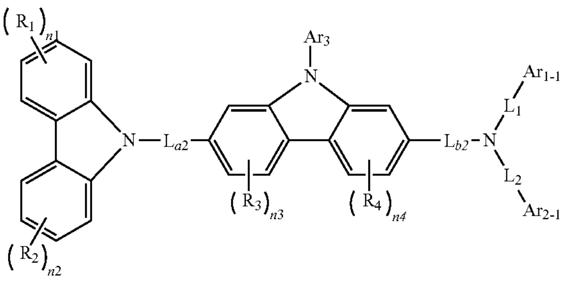

Formula 7-2

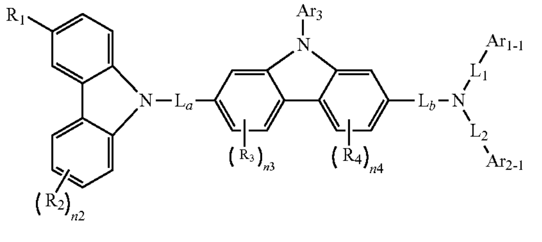

-continued

Formula 7-3

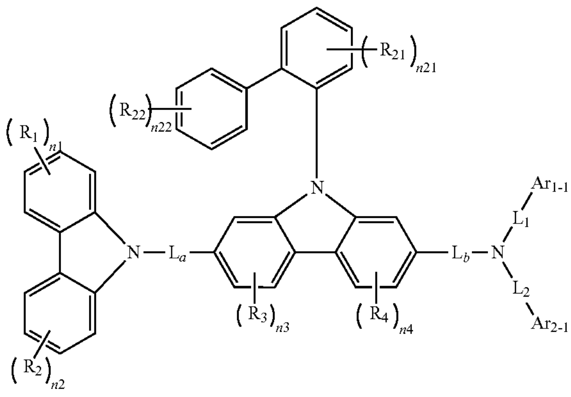

Formula 7-1 to Formula 7-3 represent Formula 1 in which the types (kinds) of the substituents represented by $Ar_1$ and $Ar_2$ are specified, and any one among i), ii), and iv) is substantially satisfied.

In Formula 7-1, any one among $L_{a2}$ and $L_{b2}$ may be a substituted or unsubstituted arylene group of 6 to 30 ring-forming carbon atoms, and the remainder may be a direct linkage or a substituted or unsubstituted arylene group of 6 to 30 ring-forming carbon atoms.

In Formula 7-3, $R_{21}$, and $R_{22}$ may each independently be a hydrogen atom, a deuterium atom, a halogen atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms. For example, $R_{21}$, and $R_{22}$ may each independently be a hydrogen atom, or a substituted or unsubstituted phenyl group.

In Formula 7-3, n21 may be an integer from 0 to 4. When n21 is 0, the amine compound of an embodiment may be unsubstituted with $R_{21}$. An embodiment of Formula 7-3 in which n21 is 4, and all $R_{21}$ are hydrogen atoms, may be the same as an embodiment of Formula 7-3 in which n21 is 0. When n21 is an integer of 2 or more, multiple $R_{21}$ may be all the same, or at least one among multiple $R_{21}$ may be different.

In Formula 7-3, n22 may be an integer from 0 to 5. When n22 is 0, the amine compound of an embodiment may be unsubstituted with $R_{22}$. An embodiment of Formula 7-3 in which n22 is 5, and all $R_{22}$ are hydrogen atoms, may be the same as a case of Formula 7-3 where n22 is 0. When n22 is an integer of 2 or more, multiple $R_{22}$ may be all the same, or at least one among multiple $R_{22}$ may be different.

In Formula 7-1 to Formula 7-3, any one among $Ar_{1-1}$ and $Ar_{2-1}$ may be represented by any one among Formula A1 to Formula A4, and the remainder may be a substituted or unsubstituted alkyl group of 1 to 20 carbon atoms, a substituted or unsubstituted silyl group, a substituted or unsubstituted aryl group of 6 to 30 ring-forming carbon atoms, or a substituted or unsubstituted heteroaryl group of 2 to 30 ring-forming carbon atoms. For example, any one among $Ar_{1-1}$ and $Ar_{2-1}$ may be represented by any one among Formula A1 to Formula A4, and the remainder may be a substituted or unsubstituted t-butyl group, a substituted or unsubstituted cyclohexyl group, a substituted or unsubstituted triphenylsilyl group, a substituted or unsubstituted phenyl group, a substituted or unsubstituted biphenyl group, a substituted or unsubstituted terphenyl group, a substituted or unsubstituted naphthyl group, a substituted or unsubstituted phenanthrene group, a substituted or unsubstituted dibenzofuran group, a substituted or unsubstituted dibenzothiophene group, a substituted or unsubstituted fluorenyl group, a substituted or unsubstituted carbazole group, a substituted or unsubstituted benzonaphthofuran group, a substituted or unsubstituted benzonaphthothiophene group, or a substituted or unsubstituted benzofurocarbazole group.

Formula A1

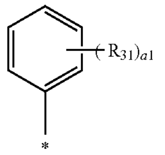

Formula A2

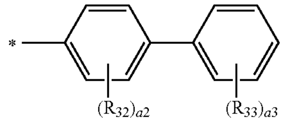

Formula A3

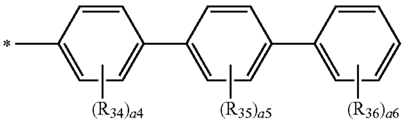

Formula A4

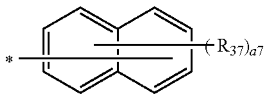

In Formula A1 to Formula A4, $R_{31}$ to $R_{37}$ may each independently be a hydrogen atom, a deuterium atom, a halogen atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms. For example, $R_{31}$ to $R_{37}$ may each independently be a hydrogen atom, a deuterium atom, a substituted or unsubstituted t-butyl group, a substituted or unsubstituted cyclohexyl group, a substituted or unsubstituted triphenylsilyl group, or a substituted or unsubstituted phenyl group.

In Formula A1 to Formula A3, a1, a3, and a6 may each independently be an integer from 0 to 5. When a1, a3, and a6 are 0, the amine compound of an embodiment may be unsubstituted with $R_{31}$, $R_{33}$, and $R_{36}$, respectively. An embodiment in which a1, a3, and a6 are 5, and $R_{31}$, $R_{33}$, and $R_{36}$ are hydrogen atoms, may be the same as an embodiment in which a1, a3, and a6 are 0. When a1, a3, and a6 are integers of 2 or more, multiple $R_{31}$, $R_{33}$, and $R_{36}$ may be all the same, respectively, or at least one among multiple $R_{31}$, $R_{33}$, and $R_{36}$ may be different.

In Formula A2 and Formula A3, a2, a4, and a5 may each independently be an integer from 0 to 4. When a2, a4, and a5 are 0, the amine compound of an embodiment may be unsubstituted with $R_{32}$, $R_{34}$, and $R_{35}$, respectively. An embodiment in which a2, a4, and a5 are 4, and $R_{32}$, $R_{34}$, and $R_{35}$ are hydrogen atoms, may be the same as an embodiment in which a2, a4, and a5 are 0. When a2, a4, and a5 are integers of 2 or more, multiple $R_{32}$, $R_{34}$, and $R_{35}$ may be all the same, respectively, or at least one among multiple $R_{32}$, $R_{34}$, and $R_{35}$ may be different.

In Formula A4, a7 may be an integer from 0 to 7. When a7 is 0, the amine compound of an embodiment may be unsubstituted with $R_{37}$. An embodiment in which a7 is 7, and all $R_{37}$ are hydrogen atoms, may be the same as an embodiment in which a7 is 0. When a7 is an integer of 2 or more, multiple $R_{37}$ may be all the same, or at least one among multiple $R_{37}$ may be different.

In Formula 7-1 to Formula 7-3, the same explanation on $Ar_1$ to $Ar_3$, $R_1$ to $R_4$, $L_a$, $L_b$, $L_1$, $L_2$, and n1 to n4 referring to Formula 1 may be applied.

In an embodiment, $L_a$ and $L_b$ may each independently be represented by any one among Formula L-1 to Formula L-5.

Formula L-1

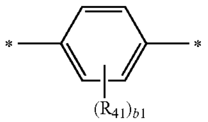

Formula L-2

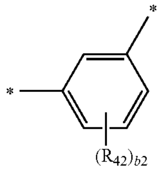

Formula L-3

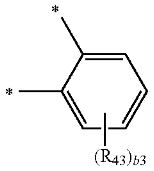

Formula L-4

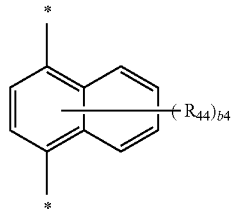

Formula L-5

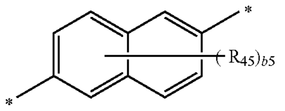

In Formula L-1 to Formula L-5, $R_{41}$ to $R_{45}$ may each independently be a hydrogen atom, a deuterium atom, a halogen atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms. For example, $R_{41}$ to $R_{45}$ may each independently be a hydrogen atom.

In Formula L-1 to Formula L-3, b1 to b3 may each independently be an integer from 0 to 4. When b1 to b3 are 0, the amine compound of an embodiment may be unsubstituted with $R_{41}$ to $R_{43}$, respectively. Embodiments in which b1 to b3 are 4, and $R_{41}$ to $R_{43}$ are hydrogen atoms, may be the same as embodiments of Formula L-1 to Formula L-3 in which b1 to b3 are 0, respectively. When b1 to b3 are integers of 2 or more, each of multiple $R_{41}$ to $R_{43}$ may be all the same, or at least one among multiple $R_{41}$ to $R_{43}$ may be different.

In Formula L-4 and Formula L-5, b4 and b5 may each independently be an integer from 0 to 6. When b4 and b5 are 0, the amine compound of an embodiment may be unsubstituted with $R_{44}$ and $R_{45}$, respectively. Embodiments in which b4 and b5 are 6, and $R_{44}$ and $R_{45}$ are hydrogen atoms, may be the same as embodiments of Formula 1-4 and Formula L-5 in which b4 and b5 are 0, respectively. When b4 and b5 are integers of 2 or more, each of multiple $R_{44}$ and $R_{45}$ may be all the same, or at least one among multiple $R_{44}$ and $R_{45}$ may be different.

In an embodiment, the amine compound represented by Formula 1 may be represented by Formula 8.

Formula 8

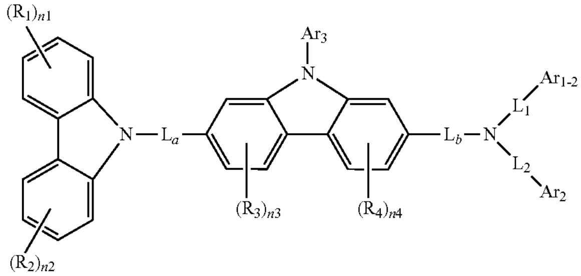

Formula 8 represents Formula 1 in which the types (kinds) of substituents represented by $Ar_1$ and $Ar_2$ are specified. Formula 8 represents the amine compound represented by Formula 1 where iii) above is substantially satisfied.

In Formula 8, $Ar_{1-2}$ may be represented by Formula a, or represented by any one among Formula B1 to Formula B3.

Formula B1

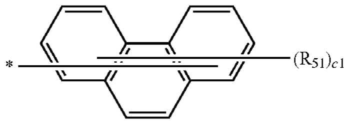

Formula B2

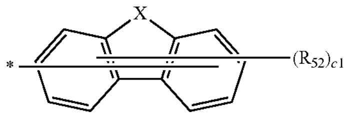

Formula B3

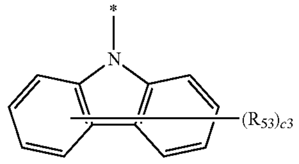

In Formula B2, X may be O, S, $NR_{54}$, or $CR_{55}R_{56}$.

In Formula B1 to Formula B3, $R_{51}$ to $R_{53}$ may each independently be a hydrogen atom, a deuterium atom, a halogen atom, a substituted or unsubstituted oxy group, a substituted or unsubstituted alkyl group of 1 to 20 carbon atoms, a substituted or unsubstituted alkenyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms. Otherwise, $R_{51}$ to $R_{53}$ may be combined with an adjacent group to form a ring. For example, $R_{51}$ to $R_{53}$ may be each independently a hydrogen atom, or a substituted or unsubstituted phenyl group.

In Formula B2, $R_{54}$ to $R_{56}$ may each independently be a substituted or unsubstituted aryl group of 6 to 30 carbon atoms. For example, $R_{54}$ to $R_{56}$ may each independently be a substituted or unsubstituted phenyl group.

In Formula B1, c1 is an integer from 0 to 9. When c1 is 0, the amine compound of an embodiment may be unsubstituted with $R_{51}$. An embodiment of Formula B1 in which c1 is 9, and all $R_{51}$ are hydrogen atoms, may be the same as an embodiment of Formula B1 in which c1 is 0. When c1 is an integer of 2 or more, multiple $R_{51}$ may be all the same, or at least one among multiple $R_{51}$ may be different.

In Formula B2, c2 may be an integer from 0 to 7. When c2 is 0, the amine compound of an embodiment may be unsubstituted with $R_{52}$. An embodiment of Formula B2 in which c2 is 7, and all $R_{52}$ are hydrogen atoms, may be the same as an embodiment of Formula B2 in which c2 is 0. When c2 is an integer of 2 or more, multiple $R_{52}$ may be all the same, or at least one among multiple $R_{52}$ may be different.

In Formula B3, c3 may be an integer from 0 to 8. When c3 is 0, the amine compound of an embodiment may be unsubstituted with $R_{53}$. An embodiment of Formula B3 in which c3 is 8, and all $R_{53}$ are hydrogen atoms, may be the same as an embodiment of Formula B3 in which c3 is 0. When c3 is an integer of 2 or more, multiple $R_{53}$ may be all the same, or at least one among multiple $R_{53}$ may be different.

In Formula 8, the same explanation on $Ar_2$, $Ar_3$, $R_1$ to $R_4$, $L_a$, $L_b$, $L_1$, $L_2$, and n1 to n4 referring to Formula 1 may be applied.

In an embodiment, $Ar_1$ and $Ar_2$ may be each independently include at least one among the compounds in Compound Group A to Compound Group E.

Compound Group A a1

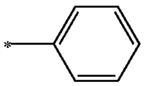

a2

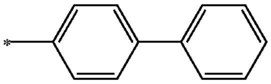

a3

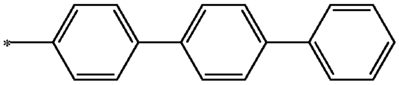

a4

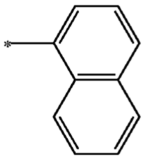

a5

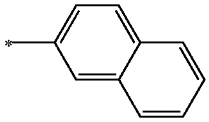

a6

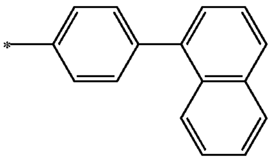

-continued a7

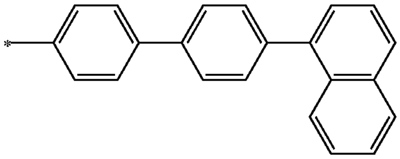

a8

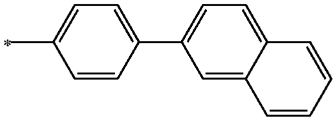

a9

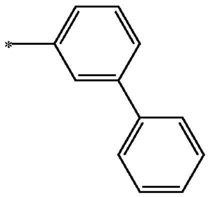

a10

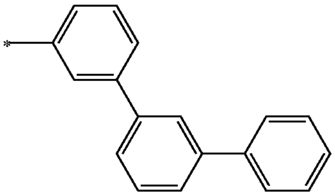

a11

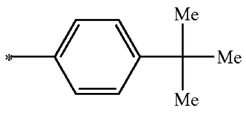

a12

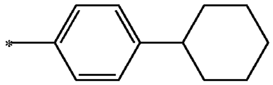

a14

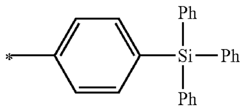

a15

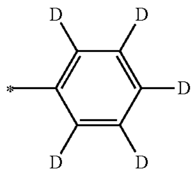

Compound Group B b1

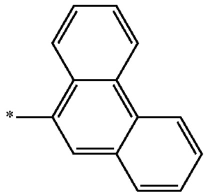

-continued
b2
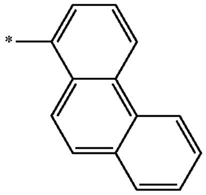
b3
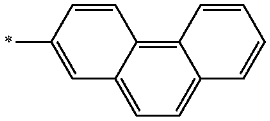
b4
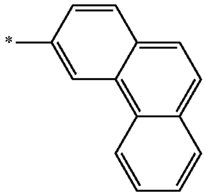
b5
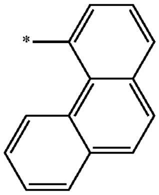
b6
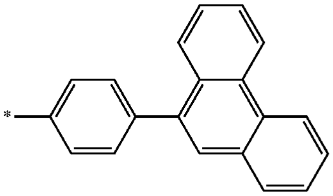
b7
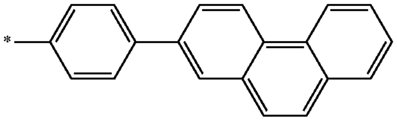
b8
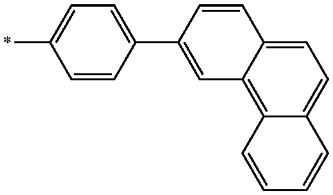
Compound Group C
c1
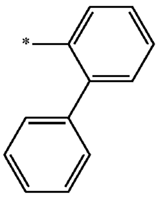
-continued
c2
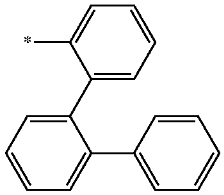
c3
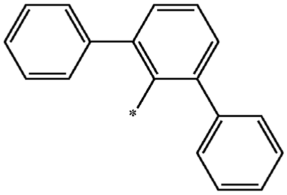
c4
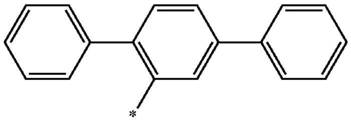
c5
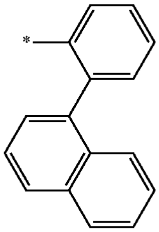
Compound Group D
d1
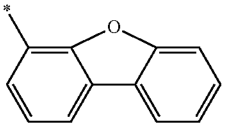
d2
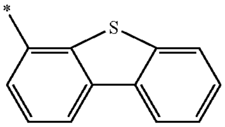
d3
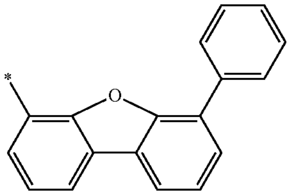
d4
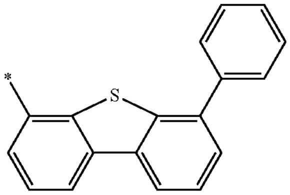

-continued
d5
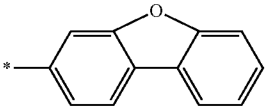
d6
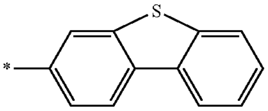
d7
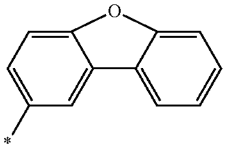
d8
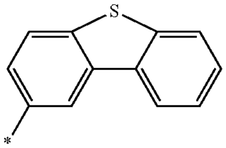
d9
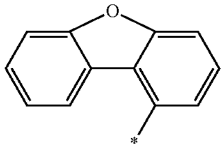
d10
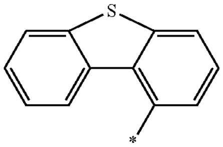
d11
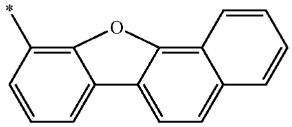
d12
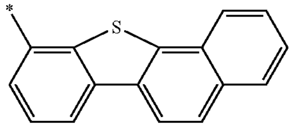
d13
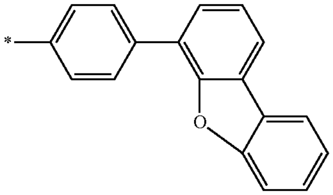
d14
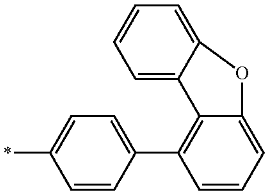
-continued
d15
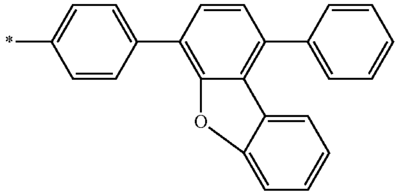
d16
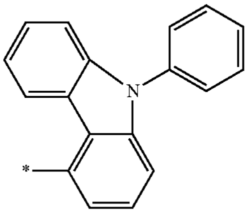
d17
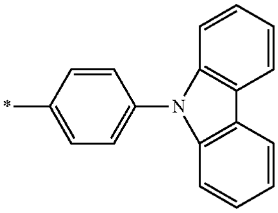
d18
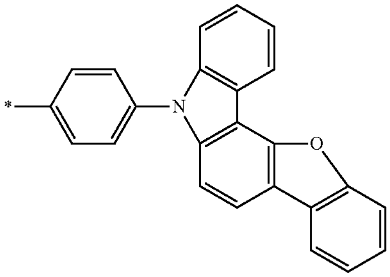
Compound Group E
e1
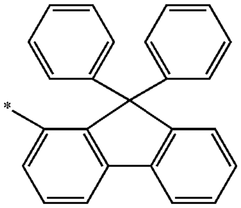
e2
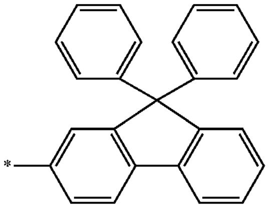

-continued e3

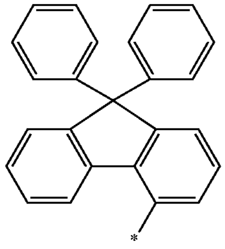

e4

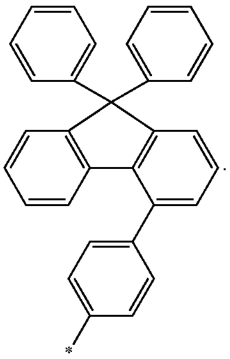

In the structure of the compounds in Compound Group A, “D” refers to a deuterium atom, “Me” refers to a substituted or unsubstituted methyl group, and “Ph” refers to a substituted or unsubstituted phenyl group. For example, in the structure of the compounds in Compound Group A, “Me” may be an unsubstituted methyl group, and “Ph” may be an unsubstituted phenyl group.

In an embodiment, the amine compound represented by Formula 1 may be represented by Formula 9, and the amine compound may be a compound satisfying any one among the combinations represented in Compound Combination Table 1.

Formula 9

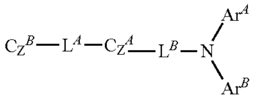

In Formula 9, $Ar^A$ and $Ar^B$ may each independently be selected from Compound Group A to Compound Group E, $Cz^A$ may be selected from Compound Group G, $Cz^B$ may be selected from Compound Group F, and $L^A$, and $L^B$ may be selected from Compound Group H.

Compound Group A a1

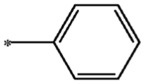

a2

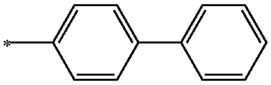

a3

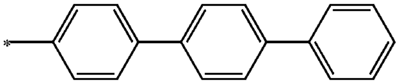

-continued a4

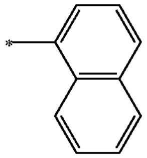

a5

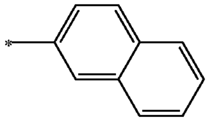

a6

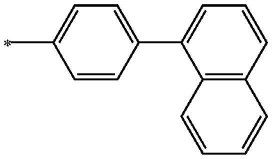

a7

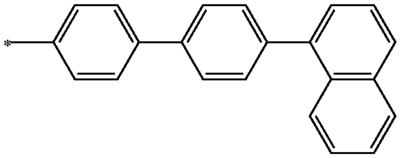

a8

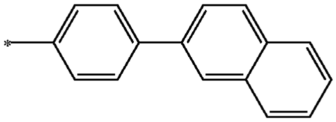

a9

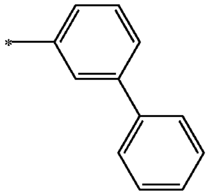

a10

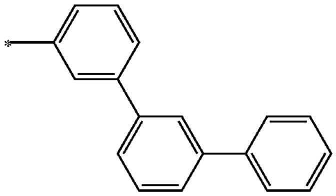

a11

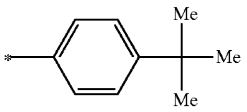

a12

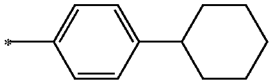

a14

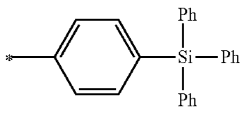

-continued
a15
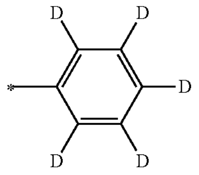
Compound Group B
b1
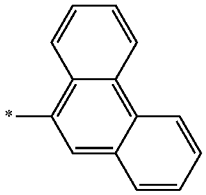
b2
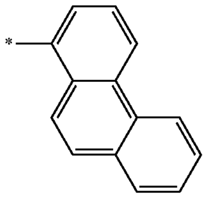
b3
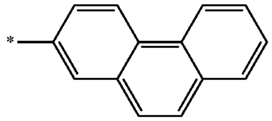
b4
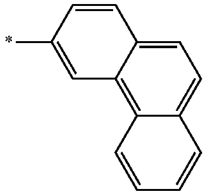
b5
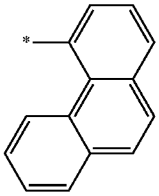
b6
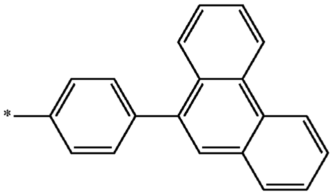
b7
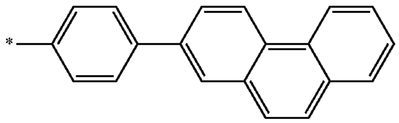
-continued
b8
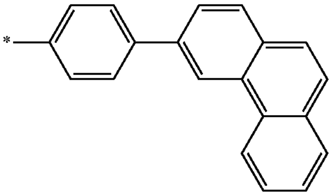
Compound Group C
c1
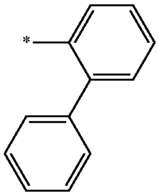
c2
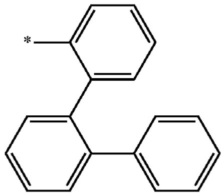
c3
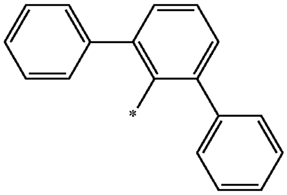
c4
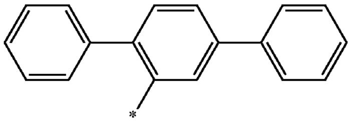
c5
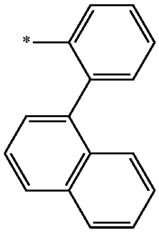
Compound Group D
d1
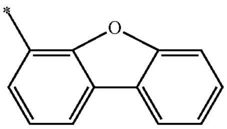

-continued
d2
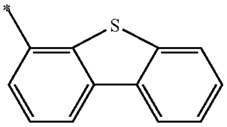
d3
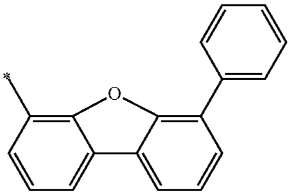
d4
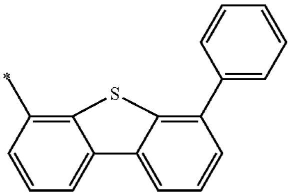
d5
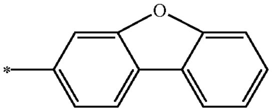
d6
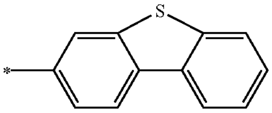
d7
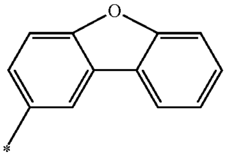
d8
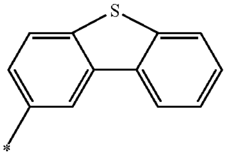
d9
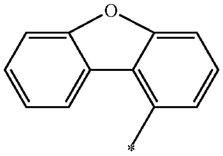
d10
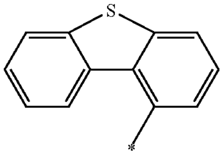
-continued
d11
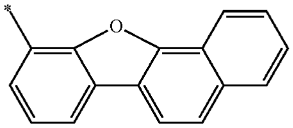
d12
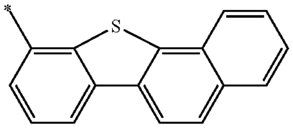
d13
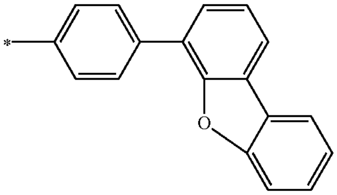
d14
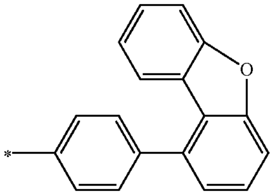
d15
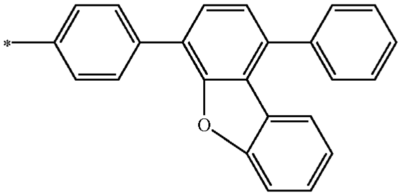
d16
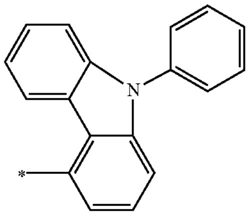
d17
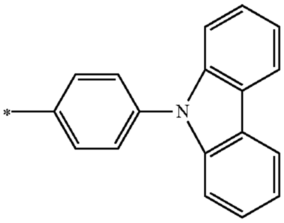

-continued
d18
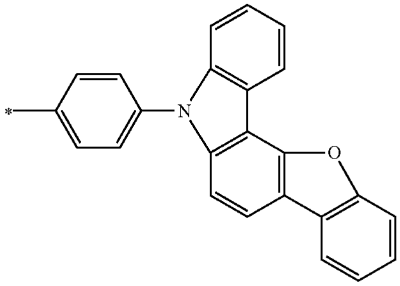
Compound Group E
e1
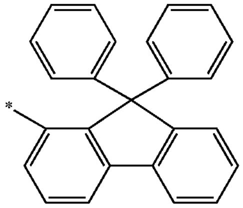
e2
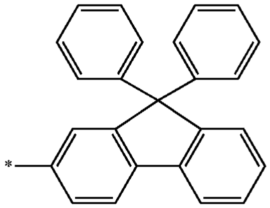
e3
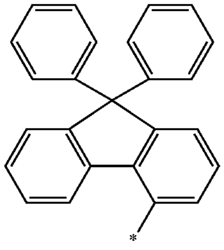
e4
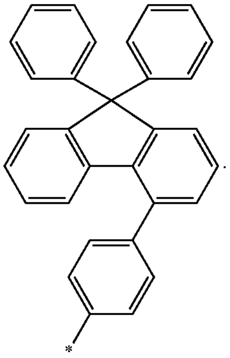
Compound Group F
f1
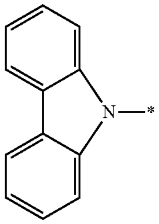
f2
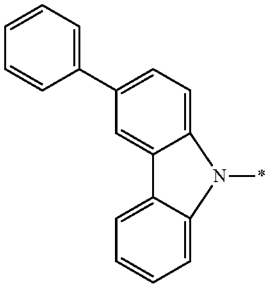
f3
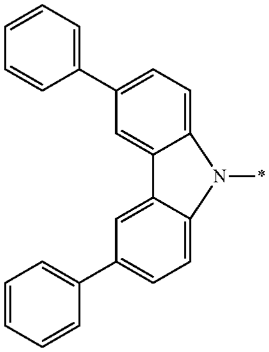
f4
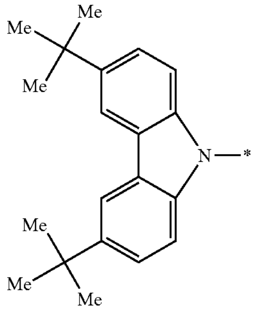
Compound Group G
g1
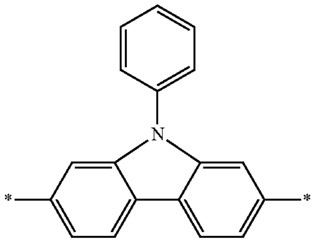

-continued g2

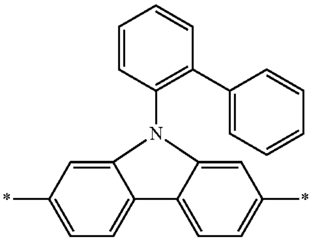

g3

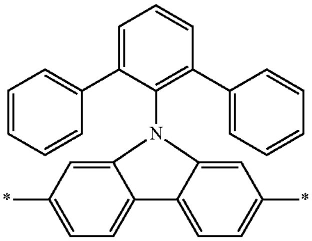

Compound Group H h1 h2

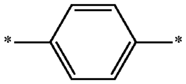

h3

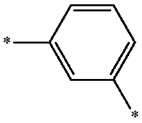

h4

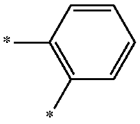

h5

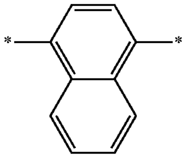

h6

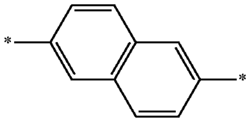

Compound Combination Table 1

| No. | $Cz^b$ | $L^A$ | $Cz^A$ | $L^B$ | $Ar^A$ | $Ar^B$ |
|---|---|---|---|---|---|---|
| 1 | f1 | h2 | g1 | h2 | a1 | a1 |
| 2 | f1 | h2 | g1 | h1 | a1 | a1 |
| 3 | f1 | h3 | g1 | h1 | a1 | a1 |
| 4 | f1 | h4 | g1 | h1 | a1 | a1 |
| 5 | f1 | h5 | g1 | h1 | a1 | a1 |
| 6 | f1 | h6 | g1 | h1 | a1 | a1 |
| 7 | f1 | h1 | g1 | h2 | a1 | a1 |
| 8 | f1 | h1 | g1 | h2 | a1 | a2 |
| 9 | f1 | h1 | g1 | h2 | a1 | a4 |
| 10 | f1 | h1 | g1 | h2 | a1 | a5 |
| 11 | f1 | h1 | g1 | h2 | a1 | a6 |
| 12 | f1 | h1 | g1 | h2 | a1 | a11 |
| 13 | f1 | h1 | g1 | h2 | a1 | a15 |
| 14 | f1 | h1 | g1 | h2 | a1 | b1 |
| 15 | f1 | h1 | g1 | h2 | a1 | b3 |
| 16 | f1 | h1 | g1 | h2 | a1 | b4 |
| 17 | f1 | h1 | g1 | h2 | a1 | b6 |
| 18 | f1 | h1 | g1 | h2 | a1 | c1 |
| 19 | f1 | h1 | g1 | h2 | a1 | d1 |
| 20 | f1 | h1 | g1 | h2 | a1 | d2 |
| 21 | f1 | h1 | g1 | h2 | a1 | d3 |
| 22 | f1 | h1 | g1 | h2 | a1 | d5 |
| 23 | f1 | h1 | g1 | h2 | a1 | d7 |
| 24 | f1 | h1 | g1 | h2 | a1 | d9 |
| 25 | f1 | h1 | g1 | h2 | a1 | d11 |
| 26 | f1 | h1 | g1 | h2 | a1 | d13 |
| 27 | f1 | h1 | g1 | h2 | a1 | d17 |
| 28 | f1 | h1 | g1 | h2 | a1 | e3 |
| 29 | f1 | h1 | g1 | h2 | a2 | a2 |
| 30 | f1 | h1 | g1 | h2 | a2 | a4 |
| 31 | f1 | h1 | g1 | h2 | a2 | a5 |
| 32 | f1 | h1 | g1 | h2 | a2 | a6 |
| 33 | f1 | h1 | g1 | h2 | a2 | a11 |
| 34 | f1 | h1 | g1 | h2 | a2 | a15 |
| 35 | f1 | h1 | g1 | h2 | a2 | b1 |
| 36 | f1 | h1 | g1 | h2 | a2 | b3 |
| 37 | f1 | h1 | g1 | h2 | a2 | b4 |
| 38 | f1 | h1 | g1 | h2 | a2 | b6 |
| 39 | f1 | h1 | g1 | h2 | a2 | c1 |
| 40 | f1 | h1 | g1 | h2 | a2 | d1 |
| 41 | f1 | h1 | g1 | h2 | a2 | d2 |
| 42 | f1 | h1 | g1 | h2 | a2 | d3 |
| 43 | f1 | h1 | g1 | h2 | a2 | d5 |
| 44 | f1 | h1 | g1 | h2 | a2 | d7 |
| 45 | f1 | h1 | g1 | h2 | a2 | d9 |
| 46 | f1 | h1 | g1 | h2 | a2 | d11 |
| 47 | f1 | h1 | g1 | h2 | a2 | d13 |
| 48 | f1 | h1 | g1 | h2 | a2 | d17 |
| 49 | f1 | h1 | g1 | h2 | a2 | e3 |
| 50 | f1 | h1 | g1 | h2 | a4 | a4 |
| 51 | f1 | h1 | g1 | h2 | a4 | a5 |
| 52 | f1 | h1 | g1 | h2 | a4 | a6 |
| 53 | f1 | h1 | g1 | h2 | a4 | a11 |
| 54 | f1 | h1 | g1 | h2 | a4 | a15 |
| 55 | f1 | h1 | g1 | h2 | a4 | b1 |
| 56 | f1 | h1 | g1 | h2 | a4 | b3 |
| 57 | f1 | h1 | g1 | h2 | a4 | b4 |
| 58 | f1 | h1 | g1 | h2 | a4 | b6 |
| 59 | f1 | h1 | g1 | h2 | a4 | c1 |
| 60 | f1 | h1 | g1 | h2 | a4 | d1 |
| 61 | f1 | h1 | g1 | h2 | a4 | d2 |
| 62 | f1 | h1 | g1 | h2 | a4 | d3 |
| 63 | f1 | h1 | g1 | h2 | a4 | d5 |
| 64 | f1 | h1 | g1 | h2 | a4 | d7 |
| 65 | f1 | h1 | g1 | h2 | a4 | d9 |
| 66 | f1 | h1 | g1 | h2 | a4 | d11 |
| 67 | f1 | h1 | g1 | h2 | a4 | d13 |
| 68 | f1 | h1 | g1 | h2 | a4 | d17 |
| 69 | f1 | h1 | g1 | h2 | a4 | e3 |
| 70 | f1 | h1 | g1 | h2 | a5 | a5 |
| 71 | f1 | h1 | g1 | h2 | a5 | a6 |
| 72 | f1 | h1 | g1 | h2 | a5 | a11 |
| 73 | f1 | h1 | g1 | h2 | a5 | a15 |
| 74 | f1 | h1 | g1 | h2 | a5 | b1 |
| 75 | f1 | h1 | g1 | h2 | a5 | b3 |
| 76 | f1 | h1 | g1 | h2 | a5 | b4 |
| 77 | f1 | h1 | g1 | h2 | a5 | b6 |
| 78 | f1 | h1 | g1 | h2 | a5 | c1 |
| 79 | f1 | h1 | g1 | h2 | a5 | d1 |
| 80 | f1 | h1 | g1 | h2 | a5 | d2 |
| 81 | f1 | h1 | g1 | h2 | a5 | d3 |
| 82 | f1 | h1 | g1 | h2 | a5 | d5 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 83 | f1 | h1 | g1 | h2 | a5 | d7 |
| 84 | f1 | h1 | g1 | h2 | a5 | d9 |
| 85 | f1 | h1 | g1 | h2 | a5 | d11 |
| 86 | f1 | h1 | g1 | h2 | a5 | d13 |
| 87 | f1 | h1 | g1 | h2 | a5 | d17 |
| 88 | f1 | h1 | g1 | h2 | a5 | e3 |
| 89 | f1 | h1 | g1 | h2 | a6 | a6 |
| 90 | f1 | h1 | g1 | h2 | a6 | a11 |
| 91 | f1 | h1 | g1 | h2 | a6 | a15 |
| 92 | f1 | h1 | g1 | h2 | a6 | b1 |
| 93 | f1 | h1 | g1 | h2 | a6 | b3 |
| 94 | f1 | h1 | g1 | h2 | a6 | b4 |
| 95 | f1 | h1 | g1 | h2 | a6 | b6 |
| 96 | f1 | h1 | g1 | h2 | a6 | c1 |
| 97 | f1 | h1 | g1 | h2 | a6 | d1 |
| 98 | f1 | h1 | g1 | h2 | a6 | d2 |
| 99 | f1 | h1 | g1 | h2 | a6 | d3 |
| 100 | f1 | h1 | g1 | h2 | a6 | d5 |
| 101 | f1 | h1 | g1 | h2 | a6 | d7 |
| 102 | f1 | h1 | g1 | h2 | a6 | d9 |
| 103 | f1 | h1 | g1 | h2 | a6 | d11 |
| 104 | f1 | h1 | g1 | h2 | a6 | d13 |
| 105 | f1 | h1 | g1 | h2 | a6 | d17 |
| 106 | f1 | h1 | g1 | h2 | a6 | e3 |
| 107 | f1 | h1 | g1 | h2 | a11 | a11 |
| 108 | f1 | h1 | g1 | h2 | a11 | a15 |
| 109 | f1 | h1 | g1 | h2 | a11 | b1 |
| 110 | f1 | h1 | g1 | h2 | a11 | b3 |
| 111 | f1 | h1 | g1 | h2 | a11 | b4 |
| 112 | f1 | h1 | g1 | h2 | a11 | b6 |
| 113 | f1 | h1 | g1 | h2 | a11 | c1 |
| 114 | f1 | h1 | g1 | h2 | a11 | d1 |
| 115 | f1 | h1 | g1 | h2 | a11 | d2 |
| 116 | f1 | h1 | g1 | h2 | a11 | d3 |
| 117 | f1 | h1 | g1 | h2 | a11 | d5 |
| 118 | f1 | h1 | g1 | h2 | a11 | d7 |
| 119 | f1 | h1 | g1 | h2 | a11 | d9 |
| 120 | f1 | h1 | g1 | h2 | a11 | d11 |
| 121 | f1 | h1 | g1 | h2 | a11 | d13 |
| 122 | f1 | h1 | g1 | h2 | a11 | d17 |
| 123 | f1 | h1 | g1 | h2 | a11 | e3 |
| 124 | f1 | h1 | g1 | h2 | a15 | a15 |
| 125 | f1 | h1 | g1 | h2 | a15 | b1 |
| 126 | f1 | h1 | g1 | h2 | a15 | b3 |
| 127 | f1 | h1 | g1 | h2 | a15 | b4 |
| 128 | f1 | h1 | g1 | h2 | a15 | b6 |
| 129 | f1 | h1 | g1 | h2 | a15 | c1 |
| 130 | f1 | h1 | g1 | h2 | a15 | d1 |
| 131 | f1 | h1 | g1 | h2 | a15 | d2 |
| 132 | f1 | h1 | g1 | h2 | a15 | d3 |
| 133 | f1 | h1 | g1 | h2 | a15 | d5 |
| 134 | f1 | h1 | g1 | h2 | a15 | d7 |
| 135 | f1 | h1 | g1 | h2 | a15 | d9 |
| 136 | f1 | h1 | g1 | h2 | a15 | d11 |
| 137 | f1 | h1 | g1 | h2 | a15 | d13 |
| 138 | f1 | h1 | g1 | h2 | a15 | d17 |
| 139 | f1 | h1 | g1 | h2 | a15 | e3 |
| 140 | f1 | h1 | g1 | h2 | b1 | b1 |
| 141 | f1 | h1 | g1 | h2 | b1 | b3 |
| 142 | f1 | h1 | g1 | h2 | b1 | b4 |
| 143 | f1 | h1 | g1 | h2 | b1 | b6 |
| 144 | f1 | h1 | g1 | h2 | b1 | c1 |
| 145 | f1 | h1 | g1 | h2 | b1 | d1 |
| 146 | f1 | h1 | g1 | h2 | b1 | d2 |
| 147 | f1 | h1 | g1 | h2 | b1 | d3 |
| 148 | f1 | h1 | g1 | h2 | b1 | d5 |
| 149 | f1 | h1 | g1 | h2 | b1 | d7 |
| 150 | f1 | h1 | g1 | h2 | b1 | d9 |
| 151 | f1 | h1 | g1 | h2 | b1 | d11 |
| 152 | f1 | h1 | g1 | h2 | b1 | d13 |
| 153 | f1 | h1 | g1 | h2 | b1 | d17 |
| 154 | f1 | h1 | g1 | h2 | b1 | e3 |
| 155 | f1 | h1 | g1 | h2 | b3 | b3 |
| 156 | f1 | h1 | g1 | h2 | b3 | b4 |
| 157 | f1 | h1 | g1 | h2 | b3 | b6 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 158 | f1 | h1 | g1 | h2 | b3 | c1 |
| 159 | f1 | h1 | g1 | h2 | b3 | d1 |
| 160 | f1 | h1 | g1 | h2 | b3 | d2 |
| 161 | f1 | h1 | g1 | h2 | b3 | d3 |
| 162 | f1 | h1 | g1 | h2 | b3 | d5 |
| 163 | f1 | h1 | g1 | h2 | b3 | d7 |
| 164 | f1 | h1 | g1 | h2 | b3 | d9 |
| 165 | f1 | h1 | g1 | h2 | b3 | d11 |
| 166 | f1 | h1 | g1 | h2 | b3 | d13 |
| 167 | f1 | h1 | g1 | h2 | b3 | d17 |
| 168 | f1 | h1 | g1 | h2 | b3 | e3 |
| 169 | f1 | h1 | g1 | h2 | b4 | b4 |
| 170 | f1 | h1 | g1 | h2 | b4 | b6 |
| 171 | f1 | h1 | g1 | h2 | b4 | c1 |
| 172 | f1 | h1 | g1 | h2 | b4 | d1 |
| 173 | f1 | h1 | g1 | h2 | b4 | d2 |
| 174 | f1 | h1 | g1 | h2 | b4 | d3 |
| 175 | f1 | h1 | g1 | h2 | b4 | d5 |
| 176 | f1 | h1 | g1 | h2 | b4 | d7 |
| 177 | f1 | h1 | g1 | h2 | b4 | d9 |
| 178 | f1 | h1 | g1 | h2 | b4 | d11 |
| 179 | f1 | h1 | g1 | h2 | b4 | d13 |
| 180 | f1 | h1 | g1 | h2 | b4 | d17 |
| 181 | f1 | h1 | g1 | h2 | b4 | e3 |
| 182 | f1 | h1 | g1 | h2 | b6 | b6 |
| 183 | f1 | h1 | g1 | h2 | b6 | c1 |
| 184 | f1 | h1 | g1 | h2 | b6 | d1 |
| 185 | f1 | h1 | g1 | h2 | b6 | d2 |
| 186 | f1 | h1 | g1 | h2 | b6 | d3 |
| 187 | f1 | h1 | g1 | h2 | b6 | d5 |
| 188 | f1 | h1 | g1 | h2 | b6 | d7 |
| 189 | f1 | h1 | g1 | h2 | b6 | d9 |
| 190 | f1 | h1 | g1 | h2 | b6 | d11 |
| 191 | f1 | h1 | g1 | h2 | b6 | d13 |
| 192 | f1 | h1 | g1 | h2 | b6 | d17 |
| 193 | f1 | h1 | g1 | h2 | b6 | e3 |
| 194 | f1 | h1 | g1 | h2 | c1 | c1 |
| 195 | f1 | h1 | g1 | h2 | c1 | d1 |
| 196 | f1 | h1 | g1 | h2 | c1 | d2 |
| 197 | f1 | h1 | g1 | h2 | c1 | d3 |
| 198 | f1 | h1 | g1 | h2 | c1 | d5 |
| 199 | f1 | h1 | g1 | h2 | c1 | d7 |
| 200 | f1 | h1 | g1 | h2 | c1 | d9 |
| 201 | f1 | h1 | g1 | h2 | c1 | d11 |
| 202 | f1 | h1 | g1 | h2 | c1 | d13 |
| 203 | f1 | h1 | g1 | h2 | c1 | d17 |
| 204 | f1 | h1 | g1 | h2 | c1 | e3 |
| 205 | f1 | h1 | g1 | h2 | d1 | d1 |
| 206 | f1 | h1 | g1 | h2 | d1 | d2 |
| 207 | f1 | h1 | g1 | h2 | d1 | d3 |
| 208 | f1 | h1 | g1 | h2 | d1 | d5 |
| 209 | f1 | h1 | g1 | h2 | d1 | d7 |
| 210 | f1 | h1 | g1 | h2 | d1 | d9 |
| 211 | f1 | h1 | g1 | h2 | d1 | d11 |
| 212 | f1 | h1 | g1 | h2 | d1 | d13 |
| 213 | f1 | h1 | g1 | h2 | d1 | d17 |
| 214 | f1 | h1 | g1 | h2 | d1 | e3 |
| 215 | f1 | h1 | g1 | h2 | d2 | d2 |
| 216 | f1 | h1 | g1 | h2 | d2 | d3 |
| 217 | f1 | h1 | g1 | h2 | d2 | d5 |
| 218 | f1 | h1 | g1 | h2 | d2 | d7 |
| 219 | f1 | h1 | g1 | h2 | d2 | d9 |
| 220 | f1 | h1 | g1 | h2 | d2 | d11 |
| 221 | f1 | h1 | g1 | h2 | d2 | d13 |
| 222 | f1 | h1 | g1 | h2 | d2 | d17 |
| 223 | f1 | h1 | g1 | h2 | d2 | e3 |
| 224 | f1 | h1 | g1 | h2 | d3 | d3 |
| 225 | f1 | h1 | g1 | h2 | d3 | d5 |
| 226 | f1 | h1 | g1 | h2 | d3 | d7 |
| 227 | f1 | h1 | g1 | h2 | d3 | d9 |
| 228 | f1 | h1 | g1 | h2 | d3 | d11 |
| 229 | f1 | h1 | g1 | h2 | d3 | d13 |
| 230 | f1 | h1 | g1 | h2 | d3 | d17 |
| 231 | f1 | h1 | g1 | h2 | d3 | e3 |
| 232 | f1 | h1 | g1 | h2 | d5 | d5 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 233 | f1 | h1 | g1 | h2 | d5 | d7 |
| 234 | f1 | h1 | g1 | h2 | d5 | d9 |
| 235 | f1 | h1 | g1 | h2 | d5 | d11 |
| 236 | f1 | h1 | g1 | h2 | d5 | d13 |
| 237 | f1 | h1 | g1 | h2 | d5 | d17 |
| 238 | f1 | h1 | g1 | h2 | d5 | e3 |
| 239 | f1 | h1 | g1 | h2 | d7 | d7 |
| 240 | f1 | h1 | g1 | h2 | d7 | d9 |
| 241 | f1 | h1 | g1 | h2 | d7 | d11 |
| 242 | f1 | h1 | g1 | h2 | d7 | d13 |
| 243 | f1 | h1 | g1 | h2 | d7 | d17 |
| 244 | f1 | h1 | g1 | h2 | d7 | e3 |
| 245 | f1 | h1 | g1 | h2 | d9 | d9 |
| 246 | f1 | h1 | g1 | h2 | d9 | d11 |
| 247 | f1 | h1 | g1 | h2 | d9 | d13 |
| 248 | f1 | h1 | g1 | h2 | d9 | d17 |
| 249 | f1 | h1 | g1 | h2 | d9 | e3 |
| 250 | f1 | h1 | g1 | h2 | d11 | d11 |
| 251 | f1 | h1 | g1 | h2 | d11 | d13 |
| 252 | f1 | h1 | g1 | h2 | d11 | d17 |
| 253 | f1 | h1 | g1 | h2 | d11 | e3 |
| 254 | f1 | h1 | g1 | h2 | d13 | d13 |
| 255 | f1 | h1 | g1 | h2 | d13 | d17 |
| 256 | f1 | h1 | g1 | h2 | d13 | e3 |
| 257 | f1 | h1 | g1 | h2 | d17 | d17 |
| 258 | f1 | h1 | g1 | h2 | e3 | e3 |
| 259 | f2 | h1 | g1 | h1 | a1 | a1 |
| 260 | f2 | h1 | g1 | h1 | a1 | a2 |
| 261 | f2 | h1 | g1 | h1 | a1 | a4 |
| 262 | f2 | h1 | g1 | h1 | a1 | a5 |
| 263 | f2 | h1 | g1 | h1 | a1 | a6 |
| 264 | f2 | h1 | g1 | h1 | a1 | a11 |
| 265 | f2 | h1 | g1 | h1 | a1 | a15 |
| 266 | f2 | h1 | g1 | h1 | a1 | b1 |
| 267 | f2 | h1 | g1 | h1 | a1 | b3 |
| 268 | f2 | h1 | g1 | h1 | a1 | b4 |
| 269 | f2 | h1 | g1 | h1 | a1 | b6 |
| 270 | f2 | h1 | g1 | h1 | a1 | c1 |
| 271 | f2 | h1 | g1 | h1 | a1 | d1 |
| 272 | f2 | h1 | g1 | h1 | a1 | d2 |
| 273 | f2 | h1 | g1 | h1 | a1 | d3 |
| 274 | f2 | h1 | g1 | h1 | a1 | d5 |
| 275 | f2 | h1 | g1 | h1 | a1 | d7 |
| 276 | f2 | h1 | g1 | h1 | a1 | d9 |
| 277 | f2 | h1 | g1 | h1 | a1 | d11 |
| 278 | f2 | h1 | g1 | h1 | a1 | d13 |
| 279 | f2 | h1 | g1 | h1 | a1 | d17 |
| 280 | f2 | h1 | g1 | h1 | a1 | e3 |
| 281 | f2 | h1 | g1 | h1 | a2 | a2 |
| 282 | f2 | h1 | g1 | h1 | a2 | a4 |
| 283 | f2 | h1 | g1 | h1 | a2 | a5 |
| 284 | f2 | h1 | g1 | h1 | a2 | a6 |
| 285 | f2 | h1 | g1 | h1 | a2 | a11 |
| 286 | f2 | h1 | g1 | h1 | a2 | a15 |
| 287 | f2 | h1 | g1 | h1 | a2 | b1 |
| 288 | f2 | h1 | g1 | h1 | a2 | b3 |
| 289 | f2 | h1 | g1 | h1 | a2 | b4 |
| 290 | f2 | h1 | g1 | h1 | a2 | b6 |
| 291 | f2 | h1 | g1 | h1 | a2 | c1 |
| 292 | f2 | h1 | g1 | h1 | a2 | d1 |
| 293 | f2 | h1 | g1 | h1 | a2 | d2 |
| 294 | f2 | h1 | g1 | h1 | a2 | d3 |
| 295 | f2 | h1 | g1 | h1 | a2 | d5 |
| 296 | f2 | h1 | g1 | h1 | a2 | d7 |
| 297 | f2 | h1 | g1 | h1 | a2 | d9 |
| 298 | f2 | h1 | g1 | h1 | a2 | d11 |
| 299 | f2 | h1 | g1 | h1 | a2 | d13 |
| 300 | f2 | h1 | g1 | h1 | a2 | d17 |
| 301 | f2 | h1 | g1 | h1 | a2 | e3 |
| 302 | f2 | h1 | g1 | h1 | a4 | a4 |
| 303 | f2 | h1 | g1 | h1 | a4 | a5 |
| 304 | f2 | h1 | g1 | h1 | a4 | a6 |
| 305 | f2 | h1 | g1 | h1 | a4 | a11 |
| 306 | f2 | h1 | g1 | h1 | a4 | a15 |
| 307 | f2 | h1 | g1 | h1 | a4 | b1 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 308 | f2 | h1 | g1 | h1 | a4 | b3 |
| 309 | f2 | h1 | g1 | h1 | a4 | b4 |
| 310 | f2 | h1 | g1 | h1 | a4 | b6 |
| 311 | f2 | h1 | g1 | h1 | a4 | c1 |
| 312 | f2 | h1 | g1 | h1 | a4 | d1 |
| 313 | f2 | h1 | g1 | h1 | a4 | d2 |
| 314 | f2 | h1 | g1 | h1 | a4 | d3 |
| 315 | f2 | h1 | g1 | h1 | a4 | d5 |
| 316 | f2 | h1 | g1 | h1 | a4 | d7 |
| 317 | f2 | h1 | g1 | h1 | a4 | d9 |
| 318 | f2 | h1 | g1 | h1 | a4 | d11 |
| 319 | f2 | h1 | g1 | h1 | a4 | d13 |
| 320 | f2 | h1 | g1 | h1 | a4 | d17 |
| 321 | f2 | h1 | g1 | h1 | a4 | e3 |
| 322 | f2 | h1 | g1 | h1 | a5 | a5 |
| 323 | f2 | h1 | g1 | h1 | a5 | a6 |
| 324 | f2 | h1 | g1 | h1 | a5 | a11 |
| 325 | f2 | h1 | g1 | h1 | a5 | a15 |
| 326 | f2 | h1 | g1 | h1 | a5 | b1 |
| 327 | f2 | h1 | g1 | h1 | a5 | b3 |
| 328 | f2 | h1 | g1 | h1 | a5 | b4 |
| 329 | f2 | h1 | g1 | h1 | a5 | b6 |
| 330 | f2 | h1 | g1 | h1 | a5 | c1 |
| 331 | f2 | h1 | g1 | h1 | a5 | d1 |
| 332 | f2 | h1 | g1 | h1 | a5 | d2 |
| 333 | f2 | h1 | g1 | h1 | a5 | d3 |
| 334 | f2 | h1 | g1 | h1 | a5 | d5 |
| 335 | f2 | h1 | g1 | h1 | a5 | d7 |
| 336 | f2 | h1 | g1 | h1 | a5 | d9 |
| 337 | f2 | h1 | g1 | h1 | a5 | d11 |
| 338 | f2 | h1 | g1 | h1 | a5 | d13 |
| 339 | f2 | h1 | g1 | h1 | a5 | d17 |
| 340 | f2 | h1 | g1 | h1 | a5 | e3 |
| 341 | f2 | h1 | g1 | h1 | a6 | a6 |
| 342 | f2 | h1 | g1 | h1 | a6 | a11 |
| 343 | f2 | h1 | g1 | h1 | a6 | a15 |
| 344 | f2 | h1 | g1 | h1 | a6 | b1 |
| 345 | f2 | h1 | g1 | h1 | a6 | b3 |
| 346 | f2 | h1 | g1 | h1 | a6 | b4 |
| 347 | f2 | h1 | g1 | h1 | a6 | b6 |
| 348 | f2 | h1 | g1 | h1 | a6 | c1 |
| 349 | f2 | h1 | g1 | h1 | a6 | d1 |
| 350 | f2 | h1 | g1 | h1 | a6 | d2 |
| 351 | f2 | h1 | g1 | h1 | a6 | d3 |
| 352 | f2 | h1 | g1 | h1 | a6 | d5 |
| 353 | f2 | h1 | g1 | h1 | a6 | d7 |
| 354 | f2 | h1 | g1 | h1 | a6 | d9 |
| 355 | f2 | h1 | g1 | h1 | a6 | d11 |
| 356 | f2 | h1 | g1 | h1 | a6 | d13 |
| 357 | f2 | h1 | g1 | h1 | a6 | d17 |
| 358 | f2 | h1 | g1 | h1 | a6 | e3 |
| 359 | f2 | h1 | g1 | h1 | a11 | a11 |
| 360 | f2 | h1 | g1 | h1 | a11 | a15 |
| 361 | f2 | h1 | g1 | h1 | a11 | b1 |
| 362 | f2 | h1 | g1 | h1 | a11 | b3 |
| 363 | f2 | h1 | g1 | h1 | a11 | b4 |
| 364 | f2 | h1 | g1 | h1 | a11 | b6 |
| 365 | f2 | h1 | g1 | h1 | a11 | c1 |
| 366 | f2 | h1 | g1 | h1 | a11 | d1 |
| 367 | f2 | h1 | g1 | h1 | a11 | d2 |
| 368 | f2 | h1 | g1 | h1 | a11 | d3 |
| 369 | f2 | h1 | g1 | h1 | a11 | d5 |
| 370 | f2 | h1 | g1 | h1 | a11 | d7 |
| 371 | f2 | h1 | g1 | h1 | a11 | d9 |
| 372 | f2 | h1 | g1 | h1 | a11 | d11 |
| 373 | f2 | h1 | g1 | h1 | a11 | d13 |
| 374 | f2 | h1 | g1 | h1 | a11 | d17 |
| 375 | f2 | h1 | g1 | h1 | a11 | e3 |
| 376 | f2 | h1 | g1 | h1 | a15 | a15 |
| 377 | f2 | h1 | g1 | h1 | a15 | b1 |
| 378 | f2 | h1 | g1 | h1 | a15 | b3 |
| 379 | f2 | h1 | g1 | h1 | a15 | b4 |
| 380 | f2 | h1 | g1 | h1 | a15 | b6 |
| 381 | f2 | h1 | g1 | h1 | a15 | c1 |
| 382 | f2 | h1 | g1 | h1 | a15 | d1 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 383 | f2 | h1 | g1 | h1 | a15 | d2 |
| 384 | f2 | h1 | g1 | h1 | a15 | d3 |
| 385 | f2 | h1 | g1 | h1 | a15 | d5 |
| 386 | f2 | h1 | g1 | h1 | a15 | d7 |
| 387 | f2 | h1 | g1 | h1 | a15 | d9 |
| 388 | f2 | h1 | g1 | h1 | a15 | d11 |
| 389 | f2 | h1 | g1 | h1 | a15 | d13 |
| 390 | f2 | h1 | g1 | h1 | a15 | d17 |
| 391 | f2 | h1 | g1 | h1 | a15 | e3 |
| 392 | f2 | h1 | g1 | h1 | b1 | b1 |
| 393 | f2 | h1 | g1 | h1 | b1 | b3 |
| 394 | f2 | h1 | g1 | h1 | b1 | b4 |
| 395 | f2 | h1 | g1 | h1 | b1 | b6 |
| 396 | f2 | h1 | g1 | h1 | b1 | c1 |
| 397 | f2 | h1 | g1 | h1 | b1 | d1 |
| 398 | f2 | h1 | g1 | h1 | b1 | d2 |
| 399 | f2 | h1 | g1 | h1 | b1 | d3 |
| 400 | f2 | h1 | g1 | h1 | b1 | d5 |
| 401 | f2 | h1 | g1 | h1 | b1 | d7 |
| 402 | f2 | h1 | g1 | h1 | b1 | d9 |
| 403 | f2 | h1 | g1 | h1 | b1 | d11 |
| 404 | f2 | h1 | g1 | h1 | b1 | d13 |
| 405 | f2 | h1 | g1 | h1 | b1 | d17 |
| 406 | f2 | h1 | g1 | h1 | b1 | e3 |
| 407 | f2 | h1 | g1 | h1 | b3 | b3 |
| 408 | f2 | h1 | g1 | h1 | b3 | b4 |
| 409 | f2 | h1 | g1 | h1 | b3 | b6 |
| 410 | f2 | h1 | g1 | h1 | b3 | c1 |
| 411 | f2 | h1 | g1 | h1 | b3 | d1 |
| 412 | f2 | h1 | g1 | h1 | b3 | d2 |
| 413 | f2 | h1 | g1 | h1 | b3 | d3 |
| 414 | f2 | h1 | g1 | h1 | b3 | d5 |
| 415 | f2 | h1 | g1 | h1 | b3 | d7 |
| 416 | f2 | h1 | g1 | h1 | b3 | d9 |
| 417 | f2 | h1 | g1 | h1 | b3 | d11 |
| 418 | f2 | h1 | g1 | h1 | b3 | d13 |
| 419 | f2 | h1 | g1 | h1 | b3 | d17 |
| 420 | f2 | h1 | g1 | h1 | b3 | e3 |
| 421 | f2 | h1 | g1 | h1 | b4 | b4 |
| 422 | f2 | h1 | g1 | h1 | b4 | b6 |
| 423 | f2 | h1 | g1 | h1 | b4 | c1 |
| 424 | f2 | h1 | g1 | h1 | b4 | d1 |
| 425 | f2 | h1 | g1 | h1 | b4 | d2 |
| 426 | f2 | h1 | g1 | h1 | b4 | d3 |
| 427 | f2 | h1 | g1 | h1 | b4 | d5 |
| 428 | f2 | h1 | g1 | h1 | b4 | d7 |
| 429 | f2 | h1 | g1 | h1 | b4 | d9 |
| 430 | f2 | h1 | g1 | h1 | b4 | d11 |
| 431 | f2 | h1 | g1 | h1 | b4 | d13 |
| 432 | f2 | h1 | g1 | h1 | b4 | d17 |
| 433 | f2 | h1 | g1 | h1 | b4 | e3 |
| 434 | f2 | h1 | g1 | h1 | b6 | b6 |
| 435 | f2 | h1 | g1 | h1 | b6 | c1 |
| 436 | f2 | h1 | g1 | h1 | b6 | d1 |
| 437 | f2 | h1 | g1 | h1 | b6 | d2 |
| 438 | f2 | h1 | g1 | h1 | b6 | d3 |
| 439 | f2 | h1 | g1 | h1 | b6 | d5 |
| 440 | f2 | h1 | g1 | h1 | b6 | d7 |
| 441 | f2 | h1 | g1 | h1 | b6 | d9 |
| 442 | f2 | h1 | g1 | h1 | b6 | d11 |
| 443 | f2 | h1 | g1 | h1 | b6 | d13 |
| 444 | f2 | h1 | g1 | h1 | b6 | d17 |
| 445 | f2 | h1 | g1 | h1 | b6 | e3 |
| 446 | f2 | h1 | g1 | h1 | c1 | c1 |
| 447 | f2 | h1 | g1 | h1 | c1 | d1 |
| 448 | f2 | h1 | g1 | h1 | c1 | d2 |
| 449 | f2 | h1 | g1 | h1 | c1 | d3 |
| 450 | f2 | h1 | g1 | h1 | c1 | d5 |
| 451 | f2 | h1 | g1 | h1 | c1 | d7 |
| 452 | f2 | h1 | g1 | h1 | c1 | d9 |
| 453 | f2 | h1 | g1 | h1 | c1 | d11 |
| 454 | f2 | h1 | g1 | h1 | c1 | d13 |
| 455 | f2 | h1 | g1 | h1 | c1 | d17 |
| 456 | f2 | h1 | g1 | h1 | c1 | e3 |
| 457 | f2 | h1 | g1 | h1 | d1 | d1 |
| 458 | f2 | h1 | g1 | h1 | d1 | d2 |
| 459 | f2 | h1 | g1 | h1 | d1 | d3 |
| 460 | f2 | h1 | g1 | h1 | d1 | d5 |
| 461 | f2 | h1 | g1 | h1 | d1 | d7 |
| 462 | f2 | h1 | g1 | h1 | d1 | d9 |
| 463 | f2 | h1 | g1 | h1 | d1 | d11 |
| 464 | f2 | h1 | g1 | h1 | d1 | d13 |
| 465 | f2 | h1 | g1 | h1 | d1 | d17 |
| 466 | f2 | h1 | g1 | h1 | d1 | e3 |
| 467 | f2 | h1 | g1 | h1 | d2 | d2 |
| 468 | f2 | h1 | g1 | h1 | d2 | d3 |
| 469 | f2 | h1 | g1 | h1 | d2 | d5 |
| 470 | f2 | h1 | g1 | h1 | d2 | d7 |
| 471 | f2 | h1 | g1 | h1 | d2 | d9 |
| 472 | f2 | h1 | g1 | h1 | d2 | d11 |
| 473 | f2 | h1 | g1 | h1 | d2 | d13 |
| 474 | f2 | h1 | g1 | h1 | d2 | d17 |
| 475 | f2 | h1 | g1 | h1 | d2 | e3 |
| 476 | f2 | h1 | g1 | h1 | d3 | d3 |
| 477 | f2 | h1 | g1 | h1 | d3 | d5 |
| 478 | f2 | h1 | g1 | h1 | d3 | d7 |
| 479 | f2 | h1 | g1 | h1 | d3 | d9 |
| 480 | f2 | h1 | g1 | h1 | d3 | d11 |
| 481 | f2 | h1 | g1 | h1 | d3 | d13 |
| 482 | f2 | h1 | g1 | h1 | d3 | d17 |
| 483 | f2 | h1 | g1 | h1 | d3 | e3 |
| 484 | f2 | h1 | g1 | h1 | d5 | d5 |
| 485 | f2 | h1 | g1 | h1 | d5 | d7 |
| 486 | f2 | h1 | g1 | h1 | d5 | d9 |
| 487 | f2 | h1 | g1 | h1 | d5 | d11 |
| 488 | f2 | h1 | g1 | h1 | d5 | d13 |
| 489 | f2 | h1 | g1 | h1 | d5 | d17 |
| 490 | f2 | h1 | g1 | h1 | d5 | e3 |
| 491 | f2 | h1 | g1 | h1 | d7 | d7 |
| 492 | f2 | h1 | g1 | h1 | d7 | d9 |
| 493 | f2 | h1 | g1 | h1 | d7 | d11 |
| 494 | f2 | h1 | g1 | h1 | d7 | d13 |
| 495 | f2 | h1 | g1 | h1 | d7 | d17 |
| 496 | f2 | h1 | g1 | h1 | d7 | e3 |
| 497 | f2 | h1 | g1 | h1 | d9 | d9 |
| 498 | f2 | h1 | g1 | h1 | d9 | d11 |
| 499 | f2 | h1 | g1 | h1 | d9 | d13 |
| 500 | f2 | h1 | g1 | h1 | d9 | d17 |
| 501 | f2 | h1 | g1 | h1 | d9 | e3 |
| 502 | f2 | h1 | g1 | h1 | d11 | d11 |
| 503 | f2 | h1 | g1 | h1 | d11 | d13 |
| 504 | f2 | h1 | g1 | h1 | d11 | d17 |
| 505 | f2 | h1 | g1 | h1 | d11 | e3 |
| 506 | f2 | h1 | g1 | h1 | d13 | d13 |
| 507 | f2 | h1 | g1 | h1 | d13 | d17 |
| 508 | f2 | h1 | g1 | h1 | d13 | e3 |
| 509 | f2 | h1 | g1 | h1 | d17 | d17 |
| 510 | f2 | h1 | g1 | h1 | e3 | e3 |
| 511 | f3 | h1 | g1 | h1 | a1 | a1 |
| 512 | f4 | h1 | g1 | h1 | a1 | a1 |
| 513 | f5 | h1 | g1 | h1 | a1 | a1 |
| 514 | f1 | h1 | g1 | h1 | b1 | a1 |
| 515 | f1 | h1 | g1 | h1 | b1 | a2 |
| 516 | f1 | h1 | g1 | h1 | b1 | a3 |
| 517 | f1 | h1 | g1 | h1 | b1 | a4 |
| 518 | f1 | h1 | g1 | h1 | b1 | a5 |
| 519 | f1 | h1 | g1 | h1 | b1 | a6 |
| 520 | f1 | h1 | g1 | h1 | b1 | a7 |
| 521 | f1 | h1 | g1 | h1 | b1 | a8 |
| 522 | f1 | h1 | g1 | h1 | b1 | a9 |
| 523 | f1 | h1 | g1 | h1 | b1 | a10 |
| 524 | f1 | h1 | g1 | h1 | b1 | a11 |
| 525 | f1 | h1 | g1 | h1 | b1 | a12 |
| 526 | f1 | h1 | g1 | h1 | b1 | a13 |
| 527 | f1 | h1 | g1 | h1 | b1 | a14 |
| 528 | f1 | h1 | g1 | h1 | b1 | a15 |
| 529 | f1 | h1 | g1 | h1 | b1 | b1 |
| 530 | f1 | h1 | g1 | h1 | b1 | b2 |
| 531 | f1 | h1 | g1 | h1 | b1 | b3 |
| 532 | f1 | h1 | g1 | h1 | b1 | b4 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 533 | f1 | h1 | g1 | h1 | b1 | b5 |
| 534 | f1 | h1 | g1 | h1 | b1 | b6 |
| 535 | f1 | h1 | g1 | h1 | b1 | b7 |
| 536 | f1 | h1 | g1 | h1 | b1 | b8 |
| 537 | f1 | h1 | g1 | h1 | b1 | c1 |
| 538 | f1 | h1 | g1 | h1 | b1 | c2 |
| 539 | f1 | h1 | g1 | h1 | b1 | c3 |
| 540 | f1 | h1 | g1 | h1 | b1 | c4 |
| 541 | f1 | h1 | g1 | h1 | b1 | c6 |
| 542 | f1 | h1 | g1 | h1 | b1 | d1 |
| 543 | f1 | h1 | g1 | h1 | b1 | d2 |
| 544 | f1 | h1 | g1 | h1 | b1 | d3 |
| 545 | f1 | h1 | g1 | h1 | b1 | d4 |
| 546 | f1 | h1 | g1 | h1 | b1 | d5 |
| 547 | f1 | h1 | g1 | h1 | b1 | d6 |
| 548 | f1 | h1 | g1 | h1 | b1 | d7 |
| 549 | f1 | h1 | g1 | h1 | b1 | d8 |
| 550 | f1 | h1 | g1 | h1 | b1 | d9 |
| 551 | f1 | h1 | g1 | h1 | b1 | d10 |
| 552 | f1 | h1 | g1 | h1 | b1 | d11 |
| 553 | f1 | h1 | g1 | h1 | b1 | d12 |
| 554 | f1 | h1 | g1 | h1 | b1 | d13 |
| 555 | f1 | h1 | g1 | h1 | b1 | d14 |
| 556 | f1 | h1 | g1 | h1 | b1 | d15 |
| 557 | f1 | h1 | g1 | h1 | b1 | d16 |
| 558 | f1 | h1 | g1 | h1 | b1 | d17 |
| 559 | f1 | h1 | g1 | h1 | b1 | d18 |
| 560 | f1 | h1 | g1 | h1 | b1 | e1 |
| 561 | f1 | h1 | g1 | h1 | b1 | e2 |
| 562 | f1 | h1 | g1 | h1 | b1 | e3 |
| 563 | f1 | h1 | g1 | h1 | b1 | e4 |
| 564 | f1 | h1 | g1 | h1 | b2 | a1 |
| 565 | f1 | h1 | g1 | h1 | b2 | a2 |
| 566 | f1 | h1 | g1 | h1 | b2 | a3 |
| 567 | f1 | h1 | g1 | h1 | b2 | a4 |
| 568 | f1 | h1 | g1 | h1 | b2 | a5 |
| 569 | f1 | h1 | g1 | h1 | b2 | a6 |
| 570 | f1 | h1 | g1 | h1 | b2 | a7 |
| 571 | f1 | h1 | g1 | h1 | b2 | a8 |
| 572 | f1 | h1 | g1 | h1 | b2 | a9 |
| 573 | f1 | h1 | g1 | h1 | b2 | a10 |
| 574 | f1 | h1 | g1 | h1 | b2 | a11 |
| 575 | f1 | h1 | g1 | h1 | b2 | a12 |
| 576 | f1 | h1 | g1 | h1 | b2 | a13 |
| 577 | f1 | h1 | g1 | h1 | b2 | a14 |
| 578 | f1 | h1 | g1 | h1 | b2 | a15 |
| 579 | f1 | h1 | g1 | h1 | b2 | b2 |
| 580 | f1 | h1 | g1 | h1 | b2 | b3 |
| 581 | f1 | h1 | g1 | h1 | b2 | b4 |
| 582 | f1 | h1 | g1 | h1 | b2 | b5 |
| 583 | f1 | h1 | g1 | h1 | b2 | b6 |
| 584 | f1 | h1 | g1 | h1 | b2 | b7 |
| 585 | f1 | h1 | g1 | h1 | b2 | b8 |
| 586 | f1 | h1 | g1 | h1 | b2 | c1 |
| 587 | f1 | h1 | g1 | h1 | b2 | c2 |
| 588 | f1 | h1 | g1 | h1 | b2 | c3 |
| 589 | f1 | h1 | g1 | h1 | b2 | c4 |
| 590 | f1 | h1 | g1 | h1 | b2 | c6 |
| 591 | f1 | h1 | g1 | h1 | b2 | d1 |
| 592 | f1 | h1 | g1 | h1 | b2 | d2 |
| 593 | f1 | h1 | g1 | h1 | b2 | d3 |
| 594 | f1 | h1 | g1 | h1 | b2 | d4 |
| 595 | f1 | h1 | g1 | h1 | b2 | d5 |
| 596 | f1 | h1 | g1 | h1 | b2 | d6 |
| 597 | f1 | h1 | g1 | h1 | b2 | d7 |
| 598 | f1 | h1 | g1 | h1 | b2 | d8 |
| 599 | f1 | h1 | g1 | h1 | b2 | d9 |
| 600 | f1 | h1 | g1 | h1 | b2 | d10 |
| 601 | f1 | h1 | g1 | h1 | b2 | d11 |
| 602 | f1 | h1 | g1 | h1 | b2 | d12 |
| 603 | f1 | h1 | g1 | h1 | b2 | d13 |
| 604 | f1 | h1 | g1 | h1 | b2 | d14 |
| 605 | f1 | h1 | g1 | h1 | b2 | d15 |
| 606 | f1 | h1 | g1 | h1 | b2 | d16 |
| 607 | f1 | h1 | g1 | h1 | b2 | d17 |
| 608 | f1 | h1 | g1 | h1 | b2 | d18 |
| 609 | f1 | h1 | g1 | h1 | b2 | e1 |
| 610 | f1 | h1 | g1 | h1 | b2 | e2 |
| 611 | f1 | h1 | g1 | h1 | b2 | e3 |
| 612 | f1 | h1 | g1 | h1 | b2 | e4 |
| 613 | f1 | h1 | g1 | h1 | b3 | a1 |
| 614 | f1 | h1 | g1 | h1 | b3 | a2 |
| 615 | f1 | h1 | g1 | h1 | b3 | a3 |
| 616 | f1 | h1 | g1 | h1 | b3 | a4 |
| 617 | f1 | h1 | g1 | h1 | b3 | a5 |
| 618 | f1 | h1 | g1 | h1 | b3 | a6 |
| 619 | f1 | h1 | g1 | h1 | b3 | a7 |
| 620 | f1 | h1 | g1 | h1 | b3 | a8 |
| 621 | f1 | h1 | g1 | h1 | b3 | a9 |
| 622 | f1 | h1 | g1 | h1 | b3 | a10 |
| 623 | f1 | h1 | g1 | h1 | b3 | a11 |
| 624 | f1 | h1 | g1 | h1 | b3 | a12 |
| 625 | f1 | h1 | g1 | h1 | b3 | a13 |
| 626 | f1 | h1 | g1 | h1 | b3 | a14 |
| 627 | f1 | h1 | g1 | h1 | b3 | a15 |
| 628 | f1 | h1 | g1 | h1 | b3 | b3 |
| 629 | f1 | h1 | g1 | h1 | b3 | b4 |
| 630 | f1 | h1 | g1 | h1 | b3 | b5 |
| 631 | f1 | h1 | g1 | h1 | b3 | b6 |
| 632 | f1 | h1 | g1 | h1 | b3 | b7 |
| 633 | f1 | h1 | g1 | h1 | b3 | b8 |
| 634 | f1 | h1 | g1 | h1 | b3 | c1 |
| 635 | f1 | h1 | g1 | h1 | b3 | c2 |
| 636 | f1 | h1 | g1 | h1 | b3 | c3 |
| 637 | f1 | h1 | g1 | h1 | b3 | c4 |
| 638 | f1 | h1 | g1 | h1 | b3 | c6 |
| 639 | f1 | h1 | g1 | h1 | b3 | d1 |
| 640 | f1 | h1 | g1 | h1 | b3 | d2 |
| 641 | f1 | h1 | g1 | h1 | b3 | d3 |
| 642 | f1 | h1 | g1 | h1 | b3 | d4 |
| 643 | f1 | h1 | g1 | h1 | b3 | d5 |
| 644 | f1 | h1 | g1 | h1 | b3 | d6 |
| 645 | f1 | h1 | g1 | h1 | b3 | d7 |
| 646 | f1 | h1 | g1 | h1 | b3 | d8 |
| 647 | f1 | h1 | g1 | h1 | b3 | d9 |
| 648 | f1 | h1 | g1 | h1 | b3 | d10 |
| 649 | f1 | h1 | g1 | h1 | b3 | d11 |
| 650 | f1 | h1 | g1 | h1 | b3 | d12 |
| 651 | f1 | h1 | g1 | h1 | b3 | d13 |
| 652 | f1 | h1 | g1 | h1 | b3 | d14 |
| 653 | f1 | h1 | g1 | h1 | b3 | d15 |
| 654 | f1 | h1 | g1 | h1 | b3 | d16 |
| 655 | f1 | h1 | g1 | h1 | b3 | d17 |
| 656 | f1 | h1 | g1 | h1 | b3 | d18 |
| 657 | f1 | h1 | g1 | h1 | b3 | e1 |
| 658 | f1 | h1 | g1 | h1 | b3 | e2 |
| 659 | f1 | h1 | g1 | h1 | b3 | e3 |
| 660 | f1 | h1 | g1 | h1 | b3 | e4 |
| 661 | f1 | h1 | g1 | h1 | b4 | a1 |
| 662 | f1 | h1 | g1 | h1 | b4 | a2 |
| 663 | f1 | h1 | g1 | h1 | b4 | a3 |
| 664 | f1 | h1 | g1 | h1 | b4 | a4 |
| 665 | f1 | h1 | g1 | h1 | b4 | a5 |
| 666 | f1 | h1 | g1 | h1 | b4 | a6 |
| 667 | f1 | h1 | g1 | h1 | b4 | a7 |
| 668 | f1 | h1 | g1 | h1 | b4 | a8 |
| 669 | f1 | h1 | g1 | h1 | b4 | a9 |
| 670 | f1 | h1 | g1 | h1 | b4 | a10 |
| 671 | f1 | h1 | g1 | h1 | b4 | a11 |
| 672 | f1 | h1 | g1 | h1 | b4 | a12 |
| 673 | f1 | h1 | g1 | h1 | b4 | a13 |
| 674 | f1 | h1 | g1 | h1 | b4 | a14 |
| 675 | f1 | h1 | g1 | h1 | b4 | a15 |
| 676 | f1 | h1 | g1 | h1 | b4 | b4 |
| 677 | f1 | h1 | g1 | h1 | b4 | b5 |
| 678 | f1 | h1 | g1 | h1 | b4 | b6 |
| 679 | f1 | h1 | g1 | h1 | b4 | b7 |
| 680 | f1 | h1 | g1 | h1 | b4 | b8 |
| 681 | f1 | h1 | g1 | h1 | b4 | c1 |
| 682 | f1 | h1 | g1 | h1 | b4 | c2 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 683 | f1 | h1 | g1 | h1 | b4 | c3 |
| 684 | f1 | h1 | g1 | h1 | b4 | c4 |
| 685 | f1 | h1 | g1 | h1 | b4 | c6 |
| 686 | f1 | h1 | g1 | h1 | b4 | d1 |
| 687 | f1 | h1 | g1 | h1 | b4 | d2 |
| 688 | f1 | h1 | g1 | h1 | b4 | d3 |
| 689 | f1 | h1 | g1 | h1 | b4 | d4 |
| 690 | f1 | h1 | g1 | h1 | b4 | d5 |
| 691 | f1 | h1 | g1 | h1 | b4 | d6 |
| 692 | f1 | h1 | g1 | h1 | b4 | d7 |
| 693 | f1 | h1 | g1 | h1 | b4 | d8 |
| 694 | f1 | h1 | g1 | h1 | b4 | d9 |
| 695 | f1 | h1 | g1 | h1 | b4 | d10 |
| 696 | f1 | h1 | g1 | h1 | b4 | d11 |
| 697 | f1 | h1 | g1 | h1 | b4 | d12 |
| 698 | f1 | h1 | g1 | h1 | b4 | d13 |
| 699 | f1 | h1 | g1 | h1 | b4 | d14 |
| 700 | f1 | h1 | g1 | h1 | b4 | d15 |
| 701 | f1 | h1 | g1 | h1 | b4 | d16 |
| 702 | f1 | h1 | g1 | h1 | b4 | d17 |
| 703 | f1 | h1 | g1 | h1 | b4 | d18 |
| 704 | f1 | h1 | g1 | h1 | b4 | e1 |
| 705 | f1 | h1 | g1 | h1 | b4 | e2 |
| 706 | f1 | h1 | g1 | h1 | b4 | e3 |
| 707 | f1 | h1 | g1 | h1 | b4 | e4 |
| 708 | f1 | h1 | g1 | h1 | b5 | a1 |
| 709 | f1 | h1 | g1 | h1 | b5 | a2 |
| 710 | f1 | h1 | g1 | h1 | b5 | a3 |
| 711 | f1 | h1 | g1 | h1 | b5 | a4 |
| 712 | f1 | h1 | g1 | h1 | b5 | a5 |
| 713 | f1 | h1 | g1 | h1 | b5 | a6 |
| 714 | f1 | h1 | g1 | h1 | b5 | a7 |
| 715 | f1 | h1 | g1 | h1 | b5 | a8 |
| 716 | f1 | h1 | g1 | h1 | b5 | a9 |
| 717 | f1 | h1 | g1 | h1 | b5 | a10 |
| 718 | f1 | h1 | g1 | h1 | b5 | a11 |
| 719 | f1 | h1 | g1 | h1 | b5 | a12 |
| 720 | f1 | h1 | g1 | h1 | b5 | a13 |
| 721 | f1 | h1 | g1 | h1 | b5 | a14 |
| 722 | f1 | h1 | g1 | h1 | b5 | a15 |
| 723 | f1 | h1 | g1 | h1 | b5 | b5 |
| 724 | f1 | h1 | g1 | h1 | b5 | b6 |
| 725 | f1 | h1 | g1 | h1 | b5 | b7 |
| 726 | f1 | h1 | g1 | h1 | b5 | b8 |
| 727 | f1 | h1 | g1 | h1 | b5 | c1 |
| 728 | f1 | h1 | g1 | h1 | b5 | c2 |
| 729 | f1 | h1 | g1 | h1 | b5 | c3 |
| 730 | f1 | h1 | g1 | h1 | b5 | c4 |
| 731 | f1 | h1 | g1 | h1 | b5 | c6 |
| 732 | f1 | h1 | g1 | h1 | b5 | d1 |
| 733 | f1 | h1 | g1 | h1 | b5 | d2 |
| 734 | f1 | h1 | g1 | h1 | b5 | d3 |
| 735 | f1 | h1 | g1 | h1 | b5 | d4 |
| 736 | f1 | h1 | g1 | h1 | b5 | d5 |
| 737 | f1 | h1 | g1 | h1 | b5 | d6 |
| 738 | f1 | h1 | g1 | h1 | b5 | d7 |
| 739 | f1 | h1 | g1 | h1 | b5 | d8 |
| 740 | f1 | h1 | g1 | h1 | b5 | d9 |
| 741 | f1 | h1 | g1 | h1 | b5 | d10 |
| 742 | f1 | h1 | g1 | h1 | b5 | d11 |
| 743 | f1 | h1 | g1 | h1 | b5 | d12 |
| 744 | f1 | h1 | g1 | h1 | b5 | d13 |
| 745 | f1 | h1 | g1 | h1 | b5 | d14 |
| 746 | f1 | h1 | g1 | h1 | b5 | d15 |
| 747 | f1 | h1 | g1 | h1 | b5 | d16 |
| 748 | f1 | h1 | g1 | h1 | b5 | d17 |
| 749 | f1 | h1 | g1 | h1 | b5 | d18 |
| 750 | f1 | h1 | g1 | h1 | b5 | e1 |
| 751 | f1 | h1 | g1 | h1 | b5 | e2 |
| 752 | f1 | h1 | g1 | h1 | b5 | e3 |
| 753 | f1 | h1 | g1 | h1 | b5 | e4 |
| 754 | f1 | h1 | g1 | h1 | b6 | a1 |
| 755 | f1 | h1 | g1 | h1 | b6 | a2 |
| 756 | f1 | h1 | g1 | h1 | b6 | a3 |
| 757 | f1 | h1 | g1 | h1 | b6 | a4 |
| 758 | f1 | h1 | g1 | h1 | b6 | a5 |
| 759 | f1 | h1 | g1 | h1 | b6 | a6 |
| 760 | f1 | h1 | g1 | h1 | b6 | a7 |
| 761 | f1 | h1 | g1 | h1 | b6 | a8 |
| 762 | f1 | h1 | g1 | h1 | b6 | a9 |
| 763 | f1 | h1 | g1 | h1 | b6 | a10 |
| 764 | f1 | h1 | g1 | h1 | b6 | a11 |
| 765 | f1 | h1 | g1 | h1 | b6 | a12 |
| 766 | f1 | h1 | g1 | h1 | b6 | a13 |
| 767 | f1 | h1 | g1 | h1 | b6 | a14 |
| 768 | f1 | h1 | g1 | h1 | b6 | a15 |
| 769 | f1 | h1 | g1 | h1 | b6 | b6 |
| 770 | f1 | h1 | g1 | h1 | b6 | b7 |
| 771 | f1 | h1 | g1 | h1 | b6 | b8 |
| 772 | f1 | h1 | g1 | h1 | b6 | c1 |
| 773 | f1 | h1 | g1 | h1 | b6 | c2 |
| 774 | f1 | h1 | g1 | h1 | b6 | c3 |
| 775 | f1 | h1 | g1 | h1 | b6 | c4 |
| 776 | f1 | h1 | g1 | h1 | b6 | c6 |
| 777 | f1 | h1 | g1 | h1 | b6 | d1 |
| 778 | f1 | h1 | g1 | h1 | b6 | d2 |
| 779 | f1 | h1 | g1 | h1 | b6 | d3 |
| 780 | f1 | h1 | g1 | h1 | b6 | d4 |
| 781 | f1 | h1 | g1 | h1 | b6 | d5 |
| 782 | f1 | h1 | g1 | h1 | b6 | d6 |
| 783 | f1 | h1 | g1 | h1 | b6 | d7 |
| 784 | f1 | h1 | g1 | h1 | b6 | d8 |
| 785 | f1 | h1 | g1 | h1 | b6 | d9 |
| 786 | f1 | h1 | g1 | h1 | b6 | d10 |
| 787 | f1 | h1 | g1 | h1 | b6 | d11 |
| 788 | f1 | h1 | g1 | h1 | b6 | d12 |
| 789 | f1 | h1 | g1 | h1 | b6 | d13 |
| 790 | f1 | h1 | g1 | h1 | b6 | d14 |
| 791 | f1 | h1 | g1 | h1 | b6 | d15 |
| 792 | f1 | h1 | g1 | h1 | b6 | d16 |
| 793 | f1 | h1 | g1 | h1 | b6 | d17 |
| 794 | f1 | h1 | g1 | h1 | b6 | d18 |
| 795 | f1 | h1 | g1 | h1 | b6 | e1 |
| 796 | f1 | h1 | g1 | h1 | b6 | e2 |
| 797 | f1 | h1 | g1 | h1 | b6 | e3 |
| 798 | f1 | h1 | g1 | h1 | b6 | e4 |
| 799 | f1 | h1 | g1 | h1 | b7 | a1 |
| 800 | f1 | h1 | g1 | h1 | b7 | a2 |
| 801 | f1 | h1 | g1 | h1 | b7 | a3 |
| 802 | f1 | h1 | g1 | h1 | b7 | a4 |
| 803 | f1 | h1 | g1 | h1 | b7 | a5 |
| 804 | f1 | h1 | g1 | h1 | b7 | a6 |
| 805 | f1 | h1 | g1 | h1 | b7 | a7 |
| 806 | f1 | h1 | g1 | h1 | b7 | a8 |
| 807 | f1 | h1 | g1 | h1 | b7 | a9 |
| 808 | f1 | h1 | g1 | h1 | b7 | a10 |
| 809 | f1 | h1 | g1 | h1 | b7 | a11 |
| 810 | f1 | h1 | g1 | h1 | b7 | a12 |
| 811 | f1 | h1 | g1 | h1 | b7 | a13 |
| 812 | f1 | h1 | g1 | h1 | b7 | a14 |
| 813 | f1 | h1 | g1 | h1 | b7 | a15 |
| 814 | f1 | h1 | g1 | h1 | b7 | b7 |
| 815 | f1 | h1 | g1 | h1 | b7 | b8 |
| 816 | f1 | h1 | g1 | h1 | b7 | c1 |
| 817 | f1 | h1 | g1 | h1 | b7 | c2 |
| 818 | f1 | h1 | g1 | h1 | b7 | c3 |
| 819 | f1 | h1 | g1 | h1 | b7 | c4 |
| 820 | f1 | h1 | g1 | h1 | b7 | c6 |
| 821 | f1 | h1 | g1 | h1 | b7 | d1 |
| 822 | f1 | h1 | g1 | h1 | b7 | d2 |
| 823 | f1 | h1 | g1 | h1 | b7 | d3 |
| 824 | f1 | h1 | g1 | h1 | b7 | d4 |
| 825 | f1 | h1 | g1 | h1 | b7 | d5 |
| 826 | f1 | h1 | g1 | h1 | b7 | d6 |
| 827 | f1 | h1 | g1 | h1 | b7 | d7 |
| 828 | f1 | h1 | g1 | h1 | b7 | d8 |
| 829 | f1 | h1 | g1 | h1 | b7 | d9 |
| 830 | f1 | h1 | g1 | h1 | b7 | d10 |
| 831 | f1 | h1 | g1 | h1 | b7 | d11 |
| 832 | f1 | h1 | g1 | h1 | b7 | d12 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 833 | f1 | h1 | g1 | h1 | b7 | d13 |
| 834 | f1 | h1 | g1 | h1 | b7 | d14 |
| 835 | f1 | h1 | g1 | h1 | b7 | d15 |
| 836 | f1 | h1 | g1 | h1 | b7 | d16 |
| 837 | f1 | h1 | g1 | h1 | b7 | d17 |
| 838 | f1 | h1 | g1 | h1 | b7 | d18 |
| 839 | f1 | h1 | g1 | h1 | b7 | e1 |
| 840 | f1 | h1 | g1 | h1 | b7 | e2 |
| 841 | f1 | h1 | g1 | h1 | b7 | e3 |
| 842 | f1 | h1 | g1 | h1 | b7 | e4 |
| 843 | f1 | h1 | g1 | h1 | b8 | a1 |
| 844 | f1 | h1 | g1 | h1 | b8 | a2 |
| 845 | f1 | h1 | g1 | h1 | b8 | a3 |
| 846 | f1 | h1 | g1 | h1 | b8 | a4 |
| 847 | f1 | h1 | g1 | h1 | b8 | a5 |
| 848 | f1 | h1 | g1 | h1 | b8 | a6 |
| 849 | f1 | h1 | g1 | h1 | b8 | a7 |
| 850 | f1 | h1 | g1 | h1 | b8 | a8 |
| 851 | f1 | h1 | g1 | h1 | b8 | a9 |
| 852 | f1 | h1 | g1 | h1 | b8 | a10 |
| 853 | f1 | h1 | g1 | h1 | b8 | a11 |
| 854 | f1 | h1 | g1 | h1 | b8 | a12 |
| 855 | f1 | h1 | g1 | h1 | b8 | a13 |
| 856 | f1 | h1 | g1 | h1 | b8 | a14 |
| 857 | f1 | h1 | g1 | h1 | b8 | a15 |
| 858 | f1 | h1 | g1 | h1 | b8 | b8 |
| 859 | f1 | h1 | g1 | h1 | b8 | c1 |
| 860 | f1 | h1 | g1 | h1 | b8 | c2 |
| 861 | f1 | h1 | g1 | h1 | b8 | c3 |
| 862 | f1 | h1 | g1 | h1 | b8 | c4 |
| 863 | f1 | h1 | g1 | h1 | b8 | c6 |
| 864 | f1 | h1 | g1 | h1 | b8 | d1 |
| 865 | f1 | h1 | g1 | h1 | b8 | d2 |
| 866 | f1 | h1 | g1 | h1 | b8 | d3 |
| 867 | f1 | h1 | g1 | h1 | b8 | d4 |
| 868 | f1 | h1 | g1 | h1 | b8 | d5 |
| 869 | f1 | h1 | g1 | h1 | b8 | d6 |
| 870 | f1 | h1 | g1 | h1 | b8 | d7 |
| 871 | f1 | h1 | g1 | h1 | b8 | d8 |
| 872 | f1 | h1 | g1 | h1 | b8 | d9 |
| 873 | f1 | h1 | g1 | h1 | b8 | d10 |
| 874 | f1 | h1 | g1 | h1 | b8 | d11 |
| 875 | f1 | h1 | g1 | h1 | b8 | d12 |
| 876 | f1 | h1 | g1 | h1 | b8 | d13 |
| 877 | f1 | h1 | g1 | h1 | b8 | d14 |
| 878 | f1 | h1 | g1 | h1 | b8 | d15 |
| 879 | f1 | h1 | g1 | h1 | b8 | d16 |
| 880 | f1 | h1 | g1 | h1 | b8 | d17 |
| 881 | f1 | h1 | g1 | h1 | b8 | d18 |
| 882 | f1 | h1 | g1 | h1 | b8 | e1 |
| 883 | f1 | h1 | g1 | h1 | b8 | e2 |
| 884 | f1 | h1 | g1 | h1 | b8 | e3 |
| 885 | f1 | h1 | g1 | h1 | b8 | e4 |
| 886 | f1 | h1 | g1 | h1 | c1 | a1 |
| 887 | f1 | h1 | g1 | h1 | c1 | a2 |
| 888 | f1 | h1 | g1 | h1 | c1 | a3 |
| 889 | f1 | h1 | g1 | h1 | c1 | a4 |
| 890 | f1 | h1 | g1 | h1 | c1 | a5 |
| 891 | f1 | h1 | g1 | h1 | c1 | a6 |
| 892 | f1 | h1 | g1 | h1 | c1 | a7 |
| 893 | f1 | h1 | g1 | h1 | c1 | a8 |
| 894 | f1 | h1 | g1 | h1 | c1 | a9 |
| 895 | f1 | h1 | g1 | h1 | c1 | a10 |
| 896 | f1 | h1 | g1 | h1 | c1 | a11 |
| 897 | f1 | h1 | g1 | h1 | c1 | a12 |
| 898 | f1 | h1 | g1 | h1 | c1 | a13 |
| 899 | f1 | h1 | g1 | h1 | c1 | a14 |
| 900 | f1 | h1 | g1 | h1 | c1 | a15 |
| 901 | f1 | h1 | g1 | h1 | c1 | b1 |
| 902 | f1 | h1 | g1 | h1 | c1 | b2 |
| 903 | f1 | h1 | g1 | h1 | c1 | b3 |
| 904 | f1 | h1 | g1 | h1 | c1 | b4 |
| 905 | f1 | h1 | g1 | h1 | c1 | b5 |
| 906 | f1 | h1 | g1 | h1 | c1 | b6 |
| 907 | f1 | h1 | g1 | h1 | c1 | b7 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 908 | f1 | h1 | g1 | h1 | c1 | b8 |
| 909 | f1 | h1 | g1 | h1 | c1 | c1 |
| 910 | f1 | h1 | g1 | h1 | c1 | d1 |
| 911 | f1 | h1 | g1 | h1 | c1 | d2 |
| 912 | f1 | h1 | g1 | h1 | c1 | d3 |
| 913 | f1 | h1 | g1 | h1 | c1 | d4 |
| 914 | f1 | h1 | g1 | h1 | c1 | d5 |
| 915 | f1 | h1 | g1 | h1 | c1 | d6 |
| 916 | f1 | h1 | g1 | h1 | c1 | d7 |
| 917 | f1 | h1 | g1 | h1 | c1 | d8 |
| 918 | f1 | h1 | g1 | h1 | c1 | d9 |
| 919 | f1 | h1 | g1 | h1 | c1 | d10 |
| 920 | f1 | h1 | g1 | h1 | c1 | d11 |
| 921 | f1 | h1 | g1 | h1 | c1 | d12 |
| 922 | f1 | h1 | g1 | h1 | c1 | d13 |
| 923 | f1 | h1 | g1 | h1 | c1 | d14 |
| 924 | f1 | h1 | g1 | h1 | c1 | d15 |
| 925 | f1 | h1 | g1 | h1 | c1 | d16 |
| 926 | f1 | h1 | g1 | h1 | c1 | d17 |
| 927 | f1 | h1 | g1 | h1 | c1 | d18 |
| 928 | f1 | h1 | g1 | h1 | c1 | e1 |
| 929 | f1 | h1 | g1 | h1 | c1 | e2 |
| 930 | f1 | h1 | g1 | h1 | c1 | e3 |
| 931 | f1 | h1 | g1 | h1 | c1 | e4 |
| 932 | f1 | h1 | g1 | h1 | c2 | a1 |
| 933 | f1 | h1 | g1 | h1 | c2 | a2 |
| 934 | f1 | h1 | g1 | h1 | c2 | a3 |
| 935 | f1 | h1 | g1 | h1 | c2 | a4 |
| 936 | f1 | h1 | g1 | h1 | c2 | a5 |
| 937 | f1 | h1 | g1 | h1 | c2 | a6 |
| 938 | f1 | h1 | g1 | h1 | c2 | a7 |
| 939 | f1 | h1 | g1 | h1 | c2 | a8 |
| 940 | f1 | h1 | g1 | h1 | c2 | a9 |
| 941 | f1 | h1 | g1 | h1 | c2 | a10 |
| 942 | f1 | h1 | g1 | h1 | c2 | a11 |
| 943 | f1 | h1 | g1 | h1 | c2 | a12 |
| 944 | f1 | h1 | g1 | h1 | c2 | a13 |
| 945 | f1 | h1 | g1 | h1 | c2 | a14 |
| 946 | f1 | h1 | g1 | h1 | c2 | a15 |
| 947 | f1 | h1 | g1 | h1 | c2 | b1 |
| 948 | f1 | h1 | g1 | h1 | c2 | b2 |
| 949 | f1 | h1 | g1 | h1 | c2 | b3 |
| 950 | f1 | h1 | g1 | h1 | c2 | b4 |
| 951 | f1 | h1 | g1 | h1 | c2 | b5 |
| 952 | f1 | h1 | g1 | h1 | c2 | b6 |
| 953 | f1 | h1 | g1 | h1 | c2 | b7 |
| 954 | f1 | h1 | g1 | h1 | c2 | b8 |
| 955 | f1 | h1 | g1 | h1 | c2 | c1 |
| 956 | f1 | h1 | g1 | h1 | c2 | d1 |
| 957 | f1 | h1 | g1 | h1 | c2 | d2 |
| 958 | f1 | h1 | g1 | h1 | c2 | d3 |
| 959 | f1 | h1 | g1 | h1 | c2 | d4 |
| 960 | f1 | h1 | g1 | h1 | c2 | d5 |
| 961 | f1 | h1 | g1 | h1 | c2 | d6 |
| 962 | f1 | h1 | g1 | h1 | c2 | d7 |
| 963 | f1 | h1 | g1 | h1 | c2 | d8 |
| 964 | f1 | h1 | g1 | h1 | c2 | d9 |
| 965 | f1 | h1 | g1 | h1 | c2 | d10 |
| 966 | f1 | h1 | g1 | h1 | c2 | d11 |
| 967 | f1 | h1 | g1 | h1 | c2 | d12 |
| 968 | f1 | h1 | g1 | h1 | c2 | d13 |
| 969 | f1 | h1 | g1 | h1 | c2 | d14 |
| 970 | f1 | h1 | g1 | h1 | c2 | d15 |
| 971 | f1 | h1 | g1 | h1 | c2 | d16 |
| 972 | f1 | h1 | g1 | h1 | c2 | d17 |
| 973 | f1 | h1 | g1 | h1 | c2 | d18 |
| 974 | f1 | h1 | g1 | h1 | c2 | e1 |
| 975 | f1 | h1 | g1 | h1 | c2 | e2 |
| 976 | f1 | h1 | g1 | h1 | c2 | e3 |
| 977 | f1 | h1 | g1 | h1 | c2 | e4 |
| 978 | f1 | h1 | g1 | h1 | c5 | a1 |
| 979 | f1 | h1 | g1 | h1 | c5 | a2 |
| 980 | f1 | h1 | g1 | h1 | c5 | a3 |
| 981 | f1 | h1 | g1 | h1 | c5 | a4 |
| 982 | f1 | h1 | g1 | h1 | c5 | a5 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 983 | f1 | h1 | g1 | h1 | c5 | a6 |
| 984 | f1 | h1 | g1 | h1 | c5 | a7 |
| 985 | f1 | h1 | g1 | h1 | c5 | a8 |
| 986 | f1 | h1 | g1 | h1 | c5 | a9 |
| 987 | f1 | h1 | g1 | h1 | c5 | a10 |
| 988 | f1 | h1 | g1 | h1 | c5 | a11 |
| 989 | f1 | h1 | g1 | h1 | c5 | a12 |
| 990 | f1 | h1 | g1 | h1 | c5 | a13 |
| 991 | f1 | h1 | g1 | h1 | c5 | a14 |
| 992 | f1 | h1 | g1 | h1 | c5 | a15 |
| 993 | f1 | h1 | g1 | h1 | c5 | b1 |
| 994 | f1 | h1 | g1 | h1 | c5 | b2 |
| 995 | f1 | h1 | g1 | h1 | c5 | b3 |
| 996 | f1 | h1 | g1 | h1 | c5 | b4 |
| 997 | f1 | h1 | g1 | h1 | c5 | b5 |
| 998 | f1 | h1 | g1 | h1 | c5 | b6 |
| 999 | f1 | h1 | g1 | h1 | c5 | b7 |
| 1000 | f1 | h1 | g1 | h1 | c5 | b8 |
| 1001 | f1 | h1 | g1 | h1 | c5 | c1 |
| 1002 | f1 | h1 | g1 | h1 | c5 | d1 |
| 1003 | f1 | h1 | g1 | h1 | c5 | d2 |
| 1004 | f1 | h1 | g1 | h1 | c5 | d3 |
| 1005 | f1 | h1 | g1 | h1 | c5 | d4 |
| 1006 | f1 | h1 | g1 | h1 | c5 | d5 |
| 1007 | f1 | h1 | g1 | h1 | c5 | d6 |
| 1008 | f1 | h1 | g1 | h1 | c5 | d7 |
| 1009 | f1 | h1 | g1 | h1 | c5 | d8 |
| 1010 | f1 | h1 | g1 | h1 | c5 | d9 |
| 1011 | f1 | h1 | g1 | h1 | c5 | d10 |
| 1012 | f1 | h1 | g1 | h1 | c5 | d11 |
| 1013 | f1 | h1 | g1 | h1 | c5 | d12 |
| 1014 | f1 | h1 | g1 | h1 | c5 | d13 |
| 1015 | f1 | h1 | g1 | h1 | c5 | d14 |
| 1016 | f1 | h1 | g1 | h1 | c5 | d15 |
| 1017 | f1 | h1 | g1 | h1 | c5 | d16 |
| 1018 | f1 | h1 | g1 | h1 | c5 | d17 |
| 1019 | f1 | h1 | g1 | h1 | c5 | d18 |
| 1020 | f1 | h1 | g1 | h1 | c5 | e1 |
| 1021 | f1 | h1 | g1 | h1 | c5 | e2 |
| 1022 | f1 | h1 | g1 | h1 | c5 | e3 |
| 1023 | f1 | h1 | g1 | h1 | c5 | e4 |
| 1024 | f1 | h1 | g2 | h1 | a1 | a1 |
| 1025 | f1 | h1 | g2 | h1 | a1 | a2 |
| 1026 | f1 | h1 | g2 | h1 | a1 | a4 |
| 1027 | f1 | h1 | g2 | h1 | a1 | a5 |
| 1028 | f1 | h1 | g2 | h1 | a1 | a6 |
| 1029 | f1 | h1 | g2 | h1 | a1 | a11 |
| 1030 | f1 | h1 | g2 | h1 | a1 | a15 |
| 1031 | f1 | h1 | g2 | h1 | a1 | b1 |
| 1032 | f1 | h1 | g2 | h1 | a1 | b3 |
| 1033 | f1 | h1 | g2 | h1 | a1 | b4 |
| 1034 | f1 | h1 | g2 | h1 | a1 | b6 |
| 1035 | f1 | h1 | g2 | h1 | a1 | c1 |
| 1036 | f1 | h1 | g2 | h1 | a1 | d1 |
| 1037 | f1 | h1 | g2 | h1 | a1 | d2 |
| 1038 | f1 | h1 | g2 | h1 | a1 | d3 |
| 1039 | f1 | h1 | g2 | h1 | a1 | d5 |
| 1040 | f1 | h1 | g2 | h1 | a1 | d7 |
| 1041 | f1 | h1 | g2 | h1 | a1 | d9 |
| 1042 | f1 | h1 | g2 | h1 | a1 | d11 |
| 1043 | f1 | h1 | g2 | h1 | a1 | d13 |
| 1044 | f1 | h1 | g2 | h1 | a1 | d17 |
| 1045 | f1 | h1 | g2 | h1 | a1 | e3 |
| 1046 | f1 | h1 | g2 | h1 | a2 | a2 |
| 1047 | f1 | h1 | g2 | h1 | a2 | a4 |
| 1048 | f1 | h1 | g2 | h1 | a2 | a5 |
| 1049 | f1 | h1 | g2 | h1 | a2 | a6 |
| 1050 | f1 | h1 | g2 | h1 | a2 | a11 |
| 1051 | f1 | h1 | g2 | h1 | a2 | a15 |
| 1052 | f1 | h1 | g2 | h1 | a2 | b1 |
| 1053 | f1 | h1 | g2 | h1 | a2 | b3 |
| 1054 | f1 | h1 | g2 | h1 | a2 | b4 |
| 1055 | f1 | h1 | g2 | h1 | a2 | b6 |
| 1056 | f1 | h1 | g2 | h1 | a2 | c1 |
| 1057 | f1 | h1 | g2 | h1 | a2 | d1 |
| 1058 | f1 | h1 | g2 | h1 | a2 | d2 |
| 1059 | f1 | h1 | g2 | h1 | a2 | d3 |
| 1060 | f1 | h1 | g2 | h1 | a2 | d5 |
| 1061 | f1 | h1 | g2 | h1 | a2 | d7 |
| 1062 | f1 | h1 | g2 | h1 | a2 | d9 |
| 1063 | f1 | h1 | g2 | h1 | a2 | d11 |
| 1064 | f1 | h1 | g2 | h1 | a2 | d13 |
| 1065 | f1 | h1 | g2 | h1 | a2 | d17 |
| 1066 | f1 | h1 | g2 | h1 | a2 | e3 |
| 1067 | f1 | h1 | g2 | h1 | a4 | a4 |
| 1068 | f1 | h1 | g2 | h1 | a4 | a5 |
| 1069 | f1 | h1 | g2 | h1 | a4 | a6 |
| 1070 | f1 | h1 | g2 | h1 | a4 | a11 |
| 1071 | f1 | h1 | g2 | h1 | a4 | a15 |
| 1072 | f1 | h1 | g2 | h1 | a4 | b1 |
| 1073 | f1 | h1 | g2 | h1 | a4 | b3 |
| 1074 | f1 | h1 | g2 | h1 | a4 | b4 |
| 1075 | f1 | h1 | g2 | h1 | a4 | b6 |
| 1076 | f1 | h1 | g2 | h1 | a4 | c1 |
| 1077 | f1 | h1 | g2 | h1 | a4 | d1 |
| 1078 | f1 | h1 | g2 | h1 | a4 | d2 |
| 1079 | f1 | h1 | g2 | h1 | a4 | d3 |
| 1080 | f1 | h1 | g2 | h1 | a4 | d5 |
| 1081 | f1 | h1 | g2 | h1 | a4 | d7 |
| 1082 | f1 | h1 | g2 | h1 | a4 | d9 |
| 1083 | f1 | h1 | g2 | h1 | a4 | d11 |
| 1084 | f1 | h1 | g2 | h1 | a4 | d13 |
| 1085 | f1 | h1 | g2 | h1 | a4 | d17 |
| 1086 | f1 | h1 | g2 | h1 | a4 | e3 |
| 1087 | f1 | h1 | g2 | h1 | a5 | a5 |
| 1088 | f1 | h1 | g2 | h1 | a5 | a6 |
| 1089 | f1 | h1 | g2 | h1 | a5 | a11 |
| 1090 | f1 | h1 | g2 | h1 | a5 | a15 |
| 1091 | f1 | h1 | g2 | h1 | a5 | b1 |
| 1092 | f1 | h1 | g2 | h1 | a5 | b3 |
| 1093 | f1 | h1 | g2 | h1 | a5 | b4 |
| 1094 | f1 | h1 | g2 | h1 | a5 | b6 |
| 1095 | f1 | h1 | g2 | h1 | a5 | c1 |
| 1096 | f1 | h1 | g2 | h1 | a5 | d1 |
| 1097 | f1 | h1 | g2 | h1 | a5 | d2 |
| 1098 | f1 | h1 | g2 | h1 | a5 | d3 |
| 1099 | f1 | h1 | g2 | h1 | a5 | d5 |
| 1100 | f1 | h1 | g2 | h1 | a5 | d7 |
| 1101 | f1 | h1 | g2 | h1 | a5 | d9 |
| 1102 | f1 | h1 | g2 | h1 | a5 | d11 |
| 1103 | f1 | h1 | g2 | h1 | a5 | d13 |
| 1104 | f1 | h1 | g2 | h1 | a5 | d17 |
| 1105 | f1 | h1 | g2 | h1 | a5 | e3 |
| 1106 | f1 | h1 | g2 | h1 | a6 | a6 |
| 1107 | f1 | h1 | g2 | h1 | a6 | a11 |
| 1108 | f1 | h1 | g2 | h1 | a6 | a15 |
| 1109 | f1 | h1 | g2 | h1 | a6 | b1 |
| 1110 | f1 | h1 | g2 | h1 | a6 | b3 |
| 1111 | f1 | h1 | g2 | h1 | a6 | b4 |
| 1112 | f1 | h1 | g2 | h1 | a6 | b6 |
| 1113 | f1 | h1 | g2 | h1 | a6 | c1 |
| 1114 | f1 | h1 | g2 | h1 | a6 | d1 |
| 1115 | f1 | h1 | g2 | h1 | a6 | d2 |
| 1116 | f1 | h1 | g2 | h1 | a6 | d3 |
| 1117 | f1 | h1 | g2 | h1 | a6 | d5 |
| 1118 | f1 | h1 | g2 | h1 | a6 | d7 |
| 1119 | f1 | h1 | g2 | h1 | a6 | d9 |
| 1120 | f1 | h1 | g2 | h1 | a6 | d11 |
| 1121 | f1 | h1 | g2 | h1 | a6 | d13 |
| 1122 | f1 | h1 | g2 | h1 | a6 | d17 |
| 1123 | f1 | h1 | g2 | h1 | a6 | e3 |
| 1124 | f1 | h1 | g2 | h1 | a11 | a11 |
| 1125 | f1 | h1 | g2 | h1 | a11 | a15 |
| 1126 | f1 | h1 | g2 | h1 | a11 | b1 |
| 1127 | f1 | h1 | g2 | h1 | a11 | b3 |
| 1128 | f1 | h1 | g2 | h1 | a11 | b4 |
| 1129 | f1 | h1 | g2 | h1 | a11 | b6 |
| 1130 | f1 | h1 | g2 | h1 | a11 | c1 |
| 1131 | f1 | h1 | g2 | h1 | a11 | d1 |
| 1132 | f1 | h1 | g2 | h1 | a11 | d2 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 1133 | f1 | h1 | g2 | h1 | a11 | d3 |
| 1134 | f1 | h1 | g2 | h1 | a11 | d5 |
| 1135 | f1 | h1 | g2 | h1 | a11 | d7 |
| 1136 | f1 | h1 | g2 | h1 | a11 | d9 |
| 1137 | f1 | h1 | g2 | h1 | a11 | d11 |
| 1138 | f1 | h1 | g2 | h1 | a11 | d13 |
| 1139 | f1 | h1 | g2 | h1 | a11 | d17 |
| 1140 | f1 | h1 | g2 | h1 | a11 | e3 |
| 1141 | f1 | h1 | g2 | h1 | a15 | a15 |
| 1142 | f1 | h1 | g2 | h1 | a15 | b1 |
| 1143 | f1 | h1 | g2 | h1 | a15 | b3 |
| 1144 | f1 | h1 | g2 | h1 | a15 | b4 |
| 1145 | f1 | h1 | g2 | h1 | a15 | b6 |
| 1146 | f1 | h1 | g2 | h1 | a15 | c1 |
| 1147 | f1 | h1 | g2 | h1 | a15 | d1 |
| 1148 | f1 | h1 | g2 | h1 | a15 | d2 |
| 1149 | f1 | h1 | g2 | h1 | a15 | d3 |
| 1150 | f1 | h1 | g2 | h1 | a15 | d5 |
| 1151 | f1 | h1 | g2 | h1 | a15 | d7 |
| 1152 | f1 | h1 | g2 | h1 | a15 | d9 |
| 1153 | f1 | h1 | g2 | h1 | a15 | d11 |
| 1154 | f1 | h1 | g2 | h1 | a15 | d13 |
| 1155 | f1 | h1 | g2 | h1 | a15 | d17 |
| 1156 | f1 | h1 | g2 | h1 | a15 | e3 |
| 1157 | f1 | h1 | g2 | h1 | b1 | b1 |
| 1158 | f1 | h1 | g2 | h1 | b1 | b3 |
| 1159 | f1 | h1 | g2 | h1 | b1 | b4 |
| 1160 | f1 | h1 | g2 | h1 | b1 | b6 |
| 1161 | f1 | h1 | g2 | h1 | b1 | c1 |
| 1162 | f1 | h1 | g2 | h1 | b1 | d1 |
| 1163 | f1 | h1 | g2 | h1 | b1 | d2 |
| 1164 | f1 | h1 | g2 | h1 | b1 | d3 |
| 1165 | f1 | h1 | g2 | h1 | b1 | d5 |
| 1166 | f1 | h1 | g2 | h1 | b1 | d7 |
| 1167 | f1 | h1 | g2 | h1 | b1 | d9 |
| 1168 | f1 | h1 | g2 | h1 | b1 | d11 |
| 1169 | f1 | h1 | g2 | h1 | b1 | d13 |
| 1170 | f1 | h1 | g2 | h1 | b1 | d17 |
| 1171 | f1 | h1 | g2 | h1 | b1 | e3 |
| 1172 | f1 | h1 | g2 | h1 | b3 | b3 |
| 1173 | f1 | h1 | g2 | h1 | b3 | b4 |
| 1174 | f1 | h1 | g2 | h1 | b3 | b6 |
| 1175 | f1 | h1 | g2 | h1 | b3 | c1 |
| 1176 | f1 | h1 | g2 | h1 | b3 | d1 |
| 1177 | f1 | h1 | g2 | h1 | b3 | d2 |
| 1178 | f1 | h1 | g2 | h1 | b3 | d3 |
| 1179 | f1 | h1 | g2 | h1 | b3 | d5 |
| 1180 | f1 | h1 | g2 | h1 | b3 | d7 |
| 1181 | f1 | h1 | g2 | h1 | b3 | d9 |
| 1182 | f1 | h1 | g2 | h1 | b3 | d11 |
| 1183 | f1 | h1 | g2 | h1 | b3 | d13 |
| 1184 | f1 | h1 | g2 | h1 | b3 | d17 |
| 1185 | f1 | h1 | g2 | h1 | b3 | e3 |
| 1186 | f1 | h1 | g2 | h1 | b4 | b4 |
| 1187 | f1 | h1 | g2 | h1 | b4 | b6 |
| 1188 | f1 | h1 | g2 | h1 | b4 | c1 |
| 1189 | f1 | h1 | g2 | h1 | b4 | d1 |
| 1190 | f1 | h1 | g2 | h1 | b4 | d2 |
| 1191 | f1 | h1 | g2 | h1 | b4 | d3 |
| 1192 | f1 | h1 | g2 | h1 | b4 | d5 |
| 1193 | f1 | h1 | g2 | h1 | b4 | d7 |
| 1194 | f1 | h1 | g2 | h1 | b4 | d9 |
| 1195 | f1 | h1 | g2 | h1 | b4 | d11 |
| 1196 | f1 | h1 | g2 | h1 | b4 | d13 |
| 1197 | f1 | h1 | g2 | h1 | b4 | d17 |
| 1198 | f1 | h1 | g2 | h1 | b4 | e3 |
| 1199 | f1 | h1 | g2 | h1 | b6 | b6 |
| 1200 | f1 | h1 | g2 | h1 | b6 | c1 |
| 1201 | f1 | h1 | g2 | h1 | b6 | d1 |
| 1202 | f1 | h1 | g2 | h1 | b6 | d2 |
| 1203 | f1 | h1 | g2 | h1 | b6 | d3 |
| 1204 | f1 | h1 | g2 | h1 | b6 | d5 |
| 1205 | f1 | h1 | g2 | h1 | b6 | d7 |
| 1206 | f1 | h1 | g2 | h1 | b6 | d9 |
| 1207 | f1 | h1 | g2 | h1 | b6 | d11 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 1208 | f1 | h1 | g2 | h1 | b6 | d13 |
| 1209 | f1 | h1 | g2 | h1 | b6 | d17 |
| 1210 | f1 | h1 | g2 | h1 | b6 | e3 |
| 1211 | f1 | h1 | g2 | h1 | c1 | c1 |
| 1212 | f1 | h1 | g2 | h1 | c1 | d1 |
| 1213 | f1 | h1 | g2 | h1 | c1 | d2 |
| 1214 | f1 | h1 | g2 | h1 | c1 | d3 |
| 1215 | f1 | h1 | g2 | h1 | c1 | d5 |
| 1216 | f1 | h1 | g2 | h1 | c1 | d7 |
| 1217 | f1 | h1 | g2 | h1 | c1 | d9 |
| 1218 | f1 | h1 | g2 | h1 | c1 | d11 |
| 1219 | f1 | h1 | g2 | h1 | c1 | d13 |
| 1220 | f1 | h1 | g2 | h1 | c1 | d17 |
| 1221 | f1 | h1 | g2 | h1 | c1 | e3 |
| 1222 | f1 | h1 | g2 | h1 | d1 | d1 |
| 1223 | f1 | h1 | g2 | h1 | d1 | d2 |
| 1224 | f1 | h1 | g2 | h1 | d1 | d3 |
| 1225 | f1 | h1 | g2 | h1 | d1 | d5 |
| 1226 | f1 | h1 | g2 | h1 | d1 | d7 |
| 1227 | f1 | h1 | g2 | h1 | d1 | d9 |
| 1228 | f1 | h1 | g2 | h1 | d1 | d11 |
| 1229 | f1 | h1 | g2 | h1 | d1 | d13 |
| 1230 | f1 | h1 | g2 | h1 | d1 | d17 |
| 1231 | f1 | h1 | g2 | h1 | d1 | e3 |
| 1232 | f1 | h1 | g2 | h1 | d2 | d2 |
| 1233 | f1 | h1 | g2 | h1 | d2 | d3 |
| 1234 | f1 | h1 | g2 | h1 | d2 | d5 |
| 1235 | f1 | h1 | g2 | h1 | d2 | d7 |
| 1236 | f1 | h1 | g2 | h1 | d2 | d9 |
| 1237 | f1 | h1 | g2 | h1 | d2 | d11 |
| 1238 | f1 | h1 | g2 | h1 | d2 | d13 |
| 1239 | f1 | h1 | g2 | h1 | d2 | d17 |
| 1240 | f1 | h1 | g2 | h1 | d2 | e3 |
| 1241 | f1 | h1 | g2 | h1 | d3 | d3 |
| 1242 | f1 | h1 | g2 | h1 | d3 | d5 |
| 1243 | f1 | h1 | g2 | h1 | d3 | d7 |
| 1244 | f1 | h1 | g2 | h1 | d3 | d9 |
| 1245 | f1 | h1 | g2 | h1 | d3 | d11 |
| 1246 | f1 | h1 | g2 | h1 | d3 | d13 |
| 1247 | f1 | h1 | g2 | h1 | d3 | d17 |
| 1248 | f1 | h1 | g2 | h1 | d3 | e3 |
| 1249 | f1 | h1 | g2 | h1 | d5 | d5 |
| 1250 | f1 | h1 | g2 | h1 | d5 | d7 |
| 1251 | f1 | h1 | g2 | h1 | d5 | d9 |
| 1252 | f1 | h1 | g2 | h1 | d5 | d11 |
| 1253 | f1 | h1 | g2 | h1 | d5 | d13 |
| 1254 | f1 | h1 | g2 | h1 | d5 | d17 |
| 1255 | f1 | h1 | g2 | h1 | d5 | e3 |
| 1256 | f1 | h1 | g2 | h1 | d7 | d7 |
| 1257 | f1 | h1 | g2 | h1 | d7 | d9 |
| 1258 | f1 | h1 | g2 | h1 | d7 | d11 |
| 1259 | f1 | h1 | g2 | h1 | d7 | d13 |
| 1260 | f1 | h1 | g2 | h1 | d7 | d17 |
| 1261 | f1 | h1 | g2 | h1 | d7 | e3 |
| 1262 | f1 | h1 | g2 | h1 | d9 | d9 |
| 1263 | f1 | h1 | g2 | h1 | d9 | d11 |
| 1264 | f1 | h1 | g2 | h1 | d9 | d13 |
| 1265 | f1 | h1 | g2 | h1 | d9 | d17 |
| 1266 | f1 | h1 | g2 | h1 | d9 | e3 |
| 1267 | f1 | h1 | g2 | h1 | d11 | d11 |
| 1268 | f1 | h1 | g2 | h1 | d11 | d13 |
| 1269 | f1 | h1 | g2 | h1 | d11 | d17 |
| 1270 | f1 | h1 | g2 | h1 | d11 | e3 |
| 1271 | f1 | h1 | g2 | h1 | d13 | d13 |
| 1272 | f1 | h1 | g2 | h1 | d13 | d17 |
| 1273 | f1 | h1 | g2 | h1 | d13 | e3 |
| 1274 | f1 | h1 | g2 | h1 | d17 | d17 |
| 1275 | f1 | h1 | g2 | h1 | e3 | e3 |
| 1276 | f1 | h1 | g3 | h1 | a1 | a1 |
| 1277 | f1 | h1 | g4 | h1 | a1 | a1 |
| 1278 | f1 | h1 | g1 | h1 | d1 | a1 |
| 1279 | f1 | h1 | g1 | h1 | d1 | a2 |
| 1280 | f1 | h1 | g1 | h1 | d1 | a4 |
| 1281 | f1 | h1 | g1 | h1 | d1 | a5 |
| 1282 | f1 | h1 | g1 | h1 | d1 | a6 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 1283 | f1 | h1 | g1 | h1 | d1 | a11 |
| 1284 | f1 | h1 | g1 | h1 | d1 | a15 |
| 1285 | f1 | h1 | g1 | h1 | d1 | b1 |
| 1286 | f1 | h1 | g1 | h1 | d1 | b3 |
| 1287 | f1 | h1 | g1 | h1 | d1 | b4 |
| 1288 | f1 | h1 | g1 | h1 | d1 | b6 |
| 1289 | f1 | h1 | g1 | h1 | d1 | c1 |
| 1290 | f1 | h1 | g1 | h1 | d1 | d1 |
| 1291 | f1 | h1 | g1 | h1 | d1 | d2 |
| 1292 | f1 | h1 | g1 | h1 | d1 | d3 |
| 1293 | f1 | h1 | g1 | h1 | d1 | d5 |
| 1294 | f1 | h1 | g1 | h1 | d1 | d7 |
| 1295 | f1 | h1 | g1 | h1 | d1 | d9 |
| 1296 | f1 | h1 | g1 | h1 | d1 | d11 |
| 1297 | f1 | h1 | g1 | h1 | d1 | d13 |
| 1298 | f1 | h1 | g1 | h1 | d1 | e3 |
| 1299 | f1 | h1 | g1 | h1 | d2 | a1 |
| 1300 | f1 | h1 | g1 | h1 | d2 | a2 |
| 1301 | f1 | h1 | g1 | h1 | d2 | a4 |
| 1302 | f1 | h1 | g1 | h1 | d2 | a5 |
| 1303 | f1 | h1 | g1 | h1 | d2 | a6 |
| 1304 | f1 | h1 | g1 | h1 | d2 | a11 |
| 1305 | f1 | h1 | g1 | h1 | d2 | a15 |
| 1306 | f1 | h1 | g1 | h1 | d2 | b1 |
| 1307 | f1 | h1 | g1 | h1 | d2 | b3 |
| 1308 | f1 | h1 | g1 | h1 | d2 | b4 |
| 1309 | f1 | h1 | g1 | h1 | d2 | b6 |
| 1310 | f1 | h1 | g1 | h1 | d2 | c1 |
| 1311 | f1 | h1 | g1 | h1 | d2 | d2 |
| 1312 | f1 | h1 | g1 | h1 | d2 | d3 |
| 1313 | f1 | h1 | g1 | h1 | d2 | d5 |
| 1314 | f1 | h1 | g1 | h1 | d2 | d7 |
| 1315 | f1 | h1 | g1 | h1 | d2 | d9 |
| 1316 | f1 | h1 | g1 | h1 | d2 | d11 |
| 1317 | f1 | h1 | g1 | h1 | d2 | d13 |
| 1318 | f1 | h1 | g1 | h1 | d2 | e3 |
| 1319 | f1 | h1 | g1 | h1 | d3 | a1 |
| 1320 | f1 | h1 | g1 | h1 | d3 | a2 |
| 1321 | f1 | h1 | g1 | h1 | d3 | a4 |
| 1322 | f1 | h1 | g1 | h1 | d3 | a5 |
| 1323 | f1 | h1 | g1 | h1 | d3 | a6 |
| 1324 | f1 | h1 | g1 | h1 | d3 | a11 |
| 1325 | f1 | h1 | g1 | h1 | d3 | a15 |
| 1326 | f1 | h1 | g1 | h1 | d3 | b1 |
| 1327 | f1 | h1 | g1 | h1 | d3 | b3 |
| 1328 | f1 | h1 | g1 | h1 | d3 | b4 |
| 1329 | f1 | h1 | g1 | h1 | d3 | b6 |
| 1330 | f1 | h1 | g1 | h1 | d3 | c1 |
| 1331 | f1 | h1 | g1 | h1 | d3 | d3 |
| 1332 | f1 | h1 | g1 | h1 | d3 | d5 |
| 1333 | f1 | h1 | g1 | h1 | d3 | d7 |
| 1334 | f1 | h1 | g1 | h1 | d3 | d9 |
| 1335 | f1 | h1 | g1 | h1 | d3 | d11 |
| 1336 | f1 | h1 | g1 | h1 | d3 | d13 |
| 1337 | f1 | h1 | g1 | h1 | d3 | e3 |
| 1338 | f1 | h1 | g1 | h1 | d4 | a1 |
| 1339 | f1 | h1 | g1 | h1 | d4 | a2 |
| 1340 | f1 | h1 | g1 | h1 | d4 | a4 |
| 1341 | f1 | h1 | g1 | h1 | d4 | a5 |
| 1342 | f1 | h1 | g1 | h1 | d4 | a6 |
| 1343 | f1 | h1 | g1 | h1 | d4 | a11 |
| 1344 | f1 | h1 | g1 | h1 | d4 | a15 |
| 1345 | f1 | h1 | g1 | h1 | d4 | b1 |
| 1346 | f1 | h1 | g1 | h1 | d4 | b3 |
| 1347 | f1 | h1 | g1 | h1 | d4 | b4 |
| 1348 | f1 | h1 | g1 | h1 | d4 | b6 |
| 1349 | f1 | h1 | g1 | h1 | d4 | c1 |
| 1350 | f1 | h1 | g1 | h1 | d4 | d1 |
| 1351 | f1 | h1 | g1 | h1 | d4 | d2 |
| 1352 | f1 | h1 | g1 | h1 | d4 | d3 |
| 1353 | f1 | h1 | g1 | h1 | d4 | d5 |
| 1354 | f1 | h1 | g1 | h1 | d4 | d7 |
| 1355 | f1 | h1 | g1 | h1 | d4 | d9 |
| 1356 | f1 | h1 | g1 | h1 | d4 | d11 |
| 1357 | f1 | h1 | g1 | h1 | d4 | d13 |
| 1358 | f1 | h1 | g1 | h1 | d4 | e3 |
| 1359 | f1 | h1 | g1 | h1 | d5 | a1 |
| 1360 | f1 | h1 | g1 | h1 | d5 | a2 |
| 1361 | f1 | h1 | g1 | h1 | d5 | a4 |
| 1362 | f1 | h1 | g1 | h1 | d5 | a5 |
| 1363 | f1 | h1 | g1 | h1 | d5 | a6 |
| 1364 | f1 | h1 | g1 | h1 | d5 | a11 |
| 1365 | f1 | h1 | g1 | h1 | d5 | a15 |
| 1366 | f1 | h1 | g1 | h1 | d5 | b1 |
| 1367 | f1 | h1 | g1 | h1 | d5 | b3 |
| 1368 | f1 | h1 | g1 | h1 | d5 | b4 |
| 1369 | f1 | h1 | g1 | h1 | d5 | b6 |
| 1370 | f1 | h1 | g1 | h1 | d5 | c1 |
| 1371 | f1 | h1 | g1 | h1 | d5 | d5 |
| 1372 | f1 | h1 | g1 | h1 | d5 | d7 |
| 1373 | f1 | h1 | g1 | h1 | d5 | d9 |
| 1374 | f1 | h1 | g1 | h1 | d5 | d11 |
| 1375 | f1 | h1 | g1 | h1 | d5 | d13 |
| 1376 | f1 | h1 | g1 | h1 | d5 | e3 |
| 1377 | f1 | h1 | g1 | h1 | d6 | a1 |
| 1378 | f1 | h1 | g1 | h1 | d6 | a2 |
| 1379 | f1 | h1 | g1 | h1 | d6 | a4 |
| 1380 | f1 | h1 | g1 | h1 | d6 | a5 |
| 1381 | f1 | h1 | g1 | h1 | d6 | a6 |
| 1382 | f1 | h1 | g1 | h1 | d6 | a11 |
| 1383 | f1 | h1 | g1 | h1 | d6 | a15 |
| 1384 | f1 | h1 | g1 | h1 | d6 | b1 |
| 1385 | f1 | h1 | g1 | h1 | d6 | b3 |
| 1386 | f1 | h1 | g1 | h1 | d6 | b4 |
| 1387 | f1 | h1 | g1 | h1 | d6 | b6 |
| 1388 | f1 | h1 | g1 | h1 | d6 | c1 |
| 1389 | f1 | h1 | g1 | h1 | d6 | d1 |
| 1390 | f1 | h1 | g1 | h1 | d6 | d2 |
| 1391 | f1 | h1 | g1 | h1 | d6 | d3 |
| 1392 | f1 | h1 | g1 | h1 | d6 | d5 |
| 1393 | f1 | h1 | g1 | h1 | d6 | d7 |
| 1394 | f1 | h1 | g1 | h1 | d6 | d9 |
| 1395 | f1 | h1 | g1 | h1 | d6 | d11 |
| 1396 | f1 | h1 | g1 | h1 | d6 | d13 |
| 1397 | f1 | h1 | g1 | h1 | d6 | e3 |
| 1398 | f1 | h1 | g1 | h1 | d7 | a1 |
| 1399 | f1 | h1 | g1 | h1 | d7 | a2 |
| 1400 | f1 | h1 | g1 | h1 | d7 | a4 |
| 1401 | f1 | h1 | g1 | h1 | d7 | a5 |
| 1402 | f1 | h1 | g1 | h1 | d7 | a6 |
| 1403 | f1 | h1 | g1 | h1 | d7 | a11 |
| 1404 | f1 | h1 | g1 | h1 | d7 | a15 |
| 1405 | f1 | h1 | g1 | h1 | d7 | b1 |
| 1406 | f1 | h1 | g1 | h1 | d7 | b3 |
| 1407 | f1 | h1 | g1 | h1 | d7 | b4 |
| 1408 | f1 | h1 | g1 | h1 | d7 | b6 |
| 1409 | f1 | h1 | g1 | h1 | d7 | c1 |
| 1410 | f1 | h1 | g1 | h1 | d7 | d7 |
| 1411 | f1 | h1 | g1 | h1 | d7 | d9 |
| 1412 | f1 | h1 | g1 | h1 | d7 | d11 |
| 1413 | f1 | h1 | g1 | h1 | d7 | d13 |
| 1414 | f1 | h1 | g1 | h1 | d7 | e3 |
| 1415 | f1 | h1 | g1 | h1 | d8 | a1 |
| 1416 | f1 | h1 | g1 | h1 | d8 | a2 |
| 1417 | f1 | h1 | g1 | h1 | d8 | a4 |
| 1418 | f1 | h1 | g1 | h1 | d8 | a5 |
| 1419 | f1 | h1 | g1 | h1 | d8 | a6 |
| 1420 | f1 | h1 | g1 | h1 | d8 | a11 |
| 1421 | f1 | h1 | g1 | h1 | d8 | a15 |
| 1422 | f1 | h1 | g1 | h1 | d8 | b1 |
| 1423 | f1 | h1 | g1 | h1 | d8 | b3 |
| 1424 | f1 | h1 | g1 | h1 | d8 | b4 |
| 1425 | f1 | h1 | g1 | h1 | d8 | b6 |
| 1426 | f1 | h1 | g1 | h1 | d8 | c1 |
| 1427 | f1 | h1 | g1 | h1 | d8 | d1 |
| 1428 | f1 | h1 | g1 | h1 | d8 | d2 |
| 1429 | f1 | h1 | g1 | h1 | d8 | d3 |
| 1430 | f1 | h1 | g1 | h1 | d8 | d5 |
| 1431 | f1 | h1 | g1 | h1 | d8 | d7 |
| 1432 | f1 | h1 | g1 | h1 | d8 | d9 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 1433 | f1 | h1 | g1 | h1 | d8 | d11 |
| 1434 | f1 | h1 | g1 | h1 | d8 | d13 |
| 1435 | f1 | h1 | g1 | h1 | d8 | e3 |
| 1436 | f1 | h1 | g1 | h1 | d9 | a1 |
| 1437 | f1 | h1 | g1 | h1 | d9 | a2 |
| 1438 | f1 | h1 | g1 | h1 | d9 | a4 |
| 1439 | f1 | h1 | g1 | h1 | d9 | a5 |
| 1440 | f1 | h1 | g1 | h1 | d9 | a6 |
| 1441 | f1 | h1 | g1 | h1 | d9 | a11 |
| 1442 | f1 | h1 | g1 | h1 | d9 | a15 |
| 1443 | f1 | h1 | g1 | h1 | d9 | b1 |
| 1444 | f1 | h1 | g1 | h1 | d9 | b3 |
| 1445 | f1 | h1 | g1 | h1 | d9 | b4 |
| 1446 | f1 | h1 | g1 | h1 | d9 | b6 |
| 1447 | f1 | h1 | g1 | h1 | d9 | c1 |
| 1448 | f1 | h1 | g1 | h1 | d9 | d9 |
| 1449 | f1 | h1 | g1 | h1 | d9 | d11 |
| 1450 | f1 | h1 | g1 | h1 | d9 | d13 |
| 1451 | f1 | h1 | g1 | h1 | d9 | e3 |
| 1452 | f1 | h1 | g1 | h1 | d10 | a1 |
| 1453 | f1 | h1 | g1 | h1 | d10 | a2 |
| 1454 | f1 | h1 | g1 | h1 | d10 | a4 |
| 1455 | f1 | h1 | g1 | h1 | d10 | a5 |
| 1456 | f1 | h1 | g1 | h1 | d10 | a6 |
| 1457 | f1 | h1 | g1 | h1 | d10 | a11 |
| 1458 | f1 | h1 | g1 | h1 | d10 | a15 |
| 1459 | f1 | h1 | g1 | h1 | d10 | b1 |
| 1460 | f1 | h1 | g1 | h1 | d10 | b3 |
| 1461 | f1 | h1 | g1 | h1 | d10 | b4 |
| 1462 | f1 | h1 | g1 | h1 | d10 | b6 |
| 1463 | f1 | h1 | g1 | h1 | d10 | c1 |
| 1464 | f1 | h1 | g1 | h1 | d10 | d1 |
| 1465 | f1 | h1 | g1 | h1 | d10 | d2 |
| 1466 | f1 | h1 | g1 | h1 | d10 | d3 |
| 1467 | f1 | h1 | g1 | h1 | d10 | d5 |
| 1468 | f1 | h1 | g1 | h1 | d10 | d7 |
| 1469 | f1 | h1 | g1 | h1 | d10 | d9 |
| 1470 | f1 | h1 | g1 | h1 | d10 | d11 |
| 1471 | f1 | h1 | g1 | h1 | d10 | d13 |
| 1472 | f1 | h1 | g1 | h1 | d10 | e3 |
| 1473 | f1 | h1 | g1 | h1 | d11 | a1 |
| 1474 | f1 | h1 | g1 | h1 | d11 | a2 |
| 1475 | f1 | h1 | g1 | h1 | d11 | a4 |
| 1476 | f1 | h1 | g1 | h1 | d11 | a5 |
| 1477 | f1 | h1 | g1 | h1 | d11 | a6 |
| 1478 | f1 | h1 | g1 | h1 | d11 | a11 |
| 1479 | f1 | h1 | g1 | h1 | d11 | a15 |
| 1480 | f1 | h1 | g1 | h1 | d11 | b1 |
| 1481 | f1 | h1 | g1 | h1 | d11 | b3 |
| 1482 | f1 | h1 | g1 | h1 | d11 | b4 |
| 1483 | f1 | h1 | g1 | h1 | d11 | b6 |
| 1484 | f1 | h1 | g1 | h1 | d11 | c1 |
| 1485 | f1 | h1 | g1 | h1 | d11 | d11 |
| 1486 | f1 | h1 | g1 | h1 | d11 | d13 |
| 1487 | f1 | h1 | g1 | h1 | d11 | e3 |
| 1488 | f1 | h1 | g1 | h1 | d12 | a1 |
| 1489 | f1 | h1 | g1 | h1 | d12 | a2 |
| 1490 | f1 | h1 | g1 | h1 | d12 | a4 |
| 1491 | f1 | h1 | g1 | h1 | d12 | a5 |
| 1492 | f1 | h1 | g1 | h1 | d12 | a6 |
| 1493 | f1 | h1 | g1 | h1 | d12 | a11 |
| 1494 | f1 | h1 | g1 | h1 | d12 | a15 |
| 1495 | f1 | h1 | g1 | h1 | d12 | b1 |
| 1496 | f1 | h1 | g1 | h1 | d12 | b3 |
| 1497 | f1 | h1 | g1 | h1 | d12 | b4 |
| 1498 | f1 | h1 | g1 | h1 | d12 | b6 |
| 1499 | f1 | h1 | g1 | h1 | d12 | c1 |
| 1500 | f1 | h1 | g1 | h1 | d12 | d1 |
| 1501 | f1 | h1 | g1 | h1 | d12 | d2 |
| 1502 | f1 | h1 | g1 | h1 | d12 | d3 |
| 1503 | f1 | h1 | g1 | h1 | d12 | d5 |
| 1504 | f1 | h1 | g1 | h1 | d12 | d7 |
| 1505 | f1 | h1 | g1 | h1 | d12 | d9 |
| 1506 | f1 | h1 | g1 | h1 | d12 | d11 |
| 1507 | f1 | h1 | g1 | h1 | d12 | d13 |
| 1508 | f1 | h1 | g1 | h1 | d12 | e3 |
| 1509 | f1 | h1 | g1 | h1 | d13 | a1 |
| 1510 | f1 | h1 | g1 | h1 | d13 | a2 |
| 1511 | f1 | h1 | g1 | h1 | d13 | a4 |
| 1512 | f1 | h1 | g1 | h1 | d13 | a5 |
| 1513 | f1 | h1 | g1 | h1 | d13 | a6 |
| 1514 | f1 | h1 | g1 | h1 | d13 | a11 |
| 1515 | f1 | h1 | g1 | h1 | d13 | a15 |
| 1516 | f1 | h1 | g1 | h1 | d13 | b1 |
| 1517 | f1 | h1 | g1 | h1 | d13 | b3 |
| 1518 | f1 | h1 | g1 | h1 | d13 | b4 |
| 1519 | f1 | h1 | g1 | h1 | d13 | b6 |
| 1520 | f1 | h1 | g1 | h1 | d13 | c1 |
| 1521 | f1 | h1 | g1 | h1 | d13 | d13 |
| 1522 | f1 | h1 | g1 | h1 | d13 | e3 |
| 1523 | f1 | h1 | g1 | h1 | d14 | a1 |
| 1524 | f1 | h1 | g1 | h1 | d14 | a2 |
| 1525 | f1 | h1 | g1 | h1 | d14 | a4 |
| 1526 | f1 | h1 | g1 | h1 | d14 | a5 |
| 1527 | f1 | h1 | g1 | h1 | d14 | a6 |
| 1528 | f1 | h1 | g1 | h1 | d14 | a11 |
| 1529 | f1 | h1 | g1 | h1 | d14 | a15 |
| 1530 | f1 | h1 | g1 | h1 | d14 | b1 |
| 1531 | f1 | h1 | g1 | h1 | d14 | b3 |
| 1532 | f1 | h1 | g1 | h1 | d14 | b4 |
| 1533 | f1 | h1 | g1 | h1 | d14 | b6 |
| 1534 | f1 | h1 | g1 | h1 | d14 | c1 |
| 1535 | f1 | h1 | g1 | h1 | d14 | d1 |
| 1536 | f1 | h1 | g1 | h1 | d14 | d2 |
| 1537 | f1 | h1 | g1 | h1 | d14 | d3 |
| 1538 | f1 | h1 | g1 | h1 | d14 | d5 |
| 1539 | f1 | h1 | g1 | h1 | d14 | d7 |
| 1540 | f1 | h1 | g1 | h1 | d14 | d9 |
| 1541 | f1 | h1 | g1 | h1 | d14 | d11 |
| 1542 | f1 | h1 | g1 | h1 | d14 | d13 |
| 1543 | f1 | h1 | g1 | h1 | d14 | e3 |
| 1544 | f1 | h1 | g1 | h1 | d15 | a1 |
| 1545 | f1 | h1 | g1 | h1 | d15 | a2 |
| 1546 | f1 | h1 | g1 | h1 | d15 | a4 |
| 1547 | f1 | h1 | g1 | h1 | d15 | a5 |
| 1548 | f1 | h1 | g1 | h1 | d15 | a6 |
| 1549 | f1 | h1 | g1 | h1 | d15 | a11 |
| 1550 | f1 | h1 | g1 | h1 | d15 | a15 |
| 1551 | f1 | h1 | g1 | h1 | d15 | b1 |
| 1552 | f1 | h1 | g1 | h1 | d15 | b3 |
| 1553 | f1 | h1 | g1 | h1 | d15 | b4 |
| 1554 | f1 | h1 | g1 | h1 | d15 | b6 |
| 1555 | f1 | h1 | g1 | h1 | d15 | c1 |
| 1556 | f1 | h1 | g1 | h1 | d15 | d1 |
| 1557 | f1 | h1 | g1 | h1 | d15 | d2 |
| 1558 | f1 | h1 | g1 | h1 | d15 | d3 |
| 1559 | f1 | h1 | g1 | h1 | d15 | d5 |
| 1560 | f1 | h1 | g1 | h1 | d15 | d7 |
| 1561 | f1 | h1 | g1 | h1 | d15 | d9 |
| 1562 | f1 | h1 | g1 | h1 | d15 | d11 |
| 1563 | f1 | h1 | g1 | h1 | d15 | d13 |
| 1564 | f1 | h1 | g1 | h1 | d15 | e3 |
| 1565 | f1 | h1 | g1 | h1 | d16 | a1 |
| 1566 | f1 | h1 | g1 | h1 | d16 | a2 |
| 1567 | f1 | h1 | g1 | h1 | d16 | a4 |
| 1568 | f1 | h1 | g1 | h1 | d16 | a5 |
| 1569 | f1 | h1 | g1 | h1 | d16 | a6 |
| 1570 | f1 | h1 | g1 | h1 | d16 | a11 |
| 1571 | f1 | h1 | g1 | h1 | d16 | a15 |
| 1572 | f1 | h1 | g1 | h1 | d16 | d1 |
| 1573 | f1 | h1 | g1 | h1 | d16 | b3 |
| 1574 | f1 | h1 | g1 | h1 | d16 | b4 |
| 1575 | f1 | h1 | g1 | h1 | d16 | b6 |
| 1576 | f1 | h1 | g1 | h1 | d16 | c1 |
| 1577 | f1 | h1 | g1 | h1 | d16 | d1 |
| 1578 | f1 | h1 | g1 | h1 | d16 | d2 |
| 1579 | f1 | h1 | g1 | h1 | d16 | d3 |
| 1580 | f1 | h1 | g1 | h1 | d16 | d5 |
| 1581 | f1 | h1 | g1 | h1 | d16 | d7 |
| 1582 | f1 | h1 | g1 | h1 | d16 | d9 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 1583 | f1 | h1 | g1 | h1 | d16 | d11 |
| 1584 | f1 | h1 | g1 | h1 | d16 | d13 |
| 1585 | f1 | h1 | g1 | h1 | d16 | e3 |
| 1586 | f1 | h1 | g1 | h1 | d17 | a1 |
| 1587 | f1 | h1 | g1 | h1 | d17 | a2 |
| 1588 | f1 | h1 | g1 | h1 | d17 | a4 |
| 1589 | f1 | h1 | g1 | h1 | d17 | a5 |
| 1590 | f1 | h1 | g1 | h1 | d17 | a6 |
| 1591 | f1 | h1 | g1 | h1 | d17 | a11 |
| 1592 | f1 | h1 | g1 | h1 | d17 | a15 |
| 1593 | f1 | h1 | g1 | h1 | d17 | b1 |
| 1594 | f1 | h1 | g1 | h1 | d17 | b3 |
| 1595 | f1 | h1 | g1 | h1 | d17 | b4 |
| 1596 | f1 | h1 | g1 | h1 | d17 | b6 |
| 1597 | f1 | h1 | g1 | h1 | d17 | c1 |
| 1598 | f1 | h1 | g1 | h1 | d17 | d1 |
| 1599 | f1 | h1 | g1 | h1 | d17 | d2 |
| 1600 | f1 | h1 | g1 | h1 | d17 | d3 |
| 1601 | f1 | h1 | g1 | h1 | d17 | d5 |
| 1602 | f1 | h1 | g1 | h1 | d17 | d7 |
| 1603 | f1 | h1 | g1 | h1 | d17 | d9 |
| 1604 | f1 | h1 | g1 | h1 | d17 | d11 |
| 1605 | f1 | h1 | g1 | h1 | d17 | d13 |
| 1606 | f1 | h1 | g1 | h1 | d17 | e3 |
| 1607 | f1 | h1 | g1 | h1 | d18 | a1 |
| 1608 | f1 | h1 | g1 | h1 | d18 | a2 |
| 1609 | f1 | h1 | g1 | h1 | d18 | a4 |
| 1610 | f1 | h1 | g1 | h1 | d18 | a5 |
| 1611 | f1 | h1 | g1 | h1 | d18 | a6 |
| 1612 | f1 | h1 | g1 | h1 | d18 | a11 |
| 1613 | f1 | h1 | g1 | h1 | d18 | a15 |
| 1614 | f1 | h1 | g1 | h1 | d18 | b1 |
| 1615 | f1 | h1 | g1 | h1 | d18 | b3 |
| 1616 | f1 | h1 | g1 | h1 | d18 | b4 |
| 1617 | f1 | h1 | g1 | h1 | d18 | b6 |
| 1618 | f1 | h1 | g1 | h1 | d18 | c1 |
| 1619 | f1 | h1 | g1 | h1 | d18 | d1 |
| 1620 | f1 | h1 | g1 | h1 | d18 | d2 |
| 1621 | f1 | h1 | g1 | h1 | d18 | d3 |
| 1622 | f1 | h1 | g1 | h1 | d18 | d5 |
| 1623 | f1 | h1 | g1 | h1 | d18 | d7 |
| 1624 | f1 | h1 | g1 | h1 | d18 | d9 |
| 1625 | f1 | h1 | g1 | h1 | d18 | d11 |
| 1626 | f1 | h1 | g1 | h1 | d18 | d13 |
| 1627 | f1 | h1 | g1 | h1 | e1 | a1 |
| 1628 | f1 | h1 | g1 | h1 | e1 | a2 |
| 1629 | f1 | h1 | g1 | h1 | e1 | a3 |
| 1630 | f1 | h1 | g1 | h1 | e1 | a4 |
| 1631 | f1 | h1 | g1 | h1 | e1 | a5 |
| 1632 | f1 | h1 | g1 | h1 | e1 | a6 |
| 1633 | f1 | h1 | g1 | h1 | e1 | a7 |
| 1634 | f1 | h1 | g1 | h1 | e1 | a8 |
| 1635 | f1 | h1 | g1 | h1 | e1 | a9 |
| 1636 | f1 | h1 | g1 | h1 | e1 | a10 |
| 1637 | f1 | h1 | g1 | h1 | e1 | a11 |
| 1638 | f1 | h1 | g1 | h1 | e1 | a12 |
| 1639 | f1 | h1 | g1 | h1 | e1 | a13 |
| 1640 | f1 | h1 | g1 | h1 | e1 | a14 |
| 1641 | f1 | h1 | g1 | h1 | e1 | a15 |
| 1642 | f1 | h1 | g1 | h1 | e1 | b1 |
| 1643 | f1 | h1 | g1 | h1 | e1 | b2 |
| 1644 | f1 | h1 | g1 | h1 | e1 | b3 |
| 1645 | f1 | h1 | g1 | h1 | e1 | b4 |
| 1646 | f1 | h1 | g1 | h1 | e1 | b5 |
| 1647 | f1 | h1 | g1 | h1 | e1 | b6 |
| 1648 | f1 | h1 | g1 | h1 | e1 | b7 |
| 1649 | f1 | h1 | g1 | h1 | e1 | b8 |
| 1650 | f1 | h1 | g1 | h1 | e1 | c1 |
| 1651 | f1 | h1 | g1 | h1 | e1 | c2 |
| 1652 | f1 | h1 | g1 | h1 | e1 | c3 |
| 1653 | f1 | h1 | g1 | h1 | e1 | c4 |
| 1654 | f1 | h1 | g1 | h1 | e1 | c5 |
| 1655 | f1 | h1 | g1 | h1 | e1 | d1 |
| 1656 | f1 | h1 | g1 | h1 | e1 | d2 |
| 1657 | f1 | h1 | g1 | h1 | e1 | d3 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 1658 | f1 | h1 | g1 | h1 | e1 | d4 |
| 1659 | f1 | h1 | g1 | h1 | e1 | d5 |
| 1660 | f1 | h1 | g1 | h1 | e1 | d6 |
| 1661 | f1 | h1 | g1 | h1 | e1 | d7 |
| 1662 | f1 | h1 | g1 | h1 | e1 | d8 |
| 1663 | f1 | h1 | g1 | h1 | e1 | d9 |
| 1664 | f1 | h1 | g1 | h1 | e1 | d10 |
| 1665 | f1 | h1 | g1 | h1 | e1 | d11 |
| 1666 | f1 | h1 | g1 | h1 | e1 | d12 |
| 1667 | f1 | h1 | g1 | h1 | e1 | d13 |
| 1668 | f1 | h1 | g1 | h1 | e1 | d14 |
| 1669 | f1 | h1 | g1 | h1 | e1 | d15 |
| 1670 | f1 | h1 | g1 | h1 | e1 | d16 |
| 1671 | f1 | h1 | g1 | h1 | e1 | d17 |
| 1672 | f1 | h1 | g1 | h1 | e1 | d18 |
| 1673 | f1 | h1 | g1 | h1 | e1 | e1 |
| 1674 | f1 | h1 | g1 | h1 | e1 | e2 |
| 1675 | f1 | h1 | g1 | h1 | e1 | e3 |
| 1676 | f1 | h1 | g1 | h1 | e1 | e4 |
| 1677 | f1 | h1 | g1 | h1 | e2 | a1 |
| 1678 | f1 | h1 | g1 | h1 | e2 | a2 |
| 1679 | f1 | h1 | g1 | h1 | e2 | a3 |
| 1680 | f1 | h1 | g1 | h1 | e2 | a4 |
| 1681 | f1 | h1 | g1 | h1 | e2 | a5 |
| 1682 | f1 | h1 | g1 | h1 | e2 | a6 |
| 1683 | f1 | h1 | g1 | h1 | e2 | a7 |
| 1684 | f1 | h1 | g1 | h1 | e2 | a8 |
| 1685 | f1 | h1 | g1 | h1 | e2 | a9 |
| 1686 | f1 | h1 | g1 | h1 | e2 | a10 |
| 1687 | f1 | h1 | g1 | h1 | e2 | a11 |
| 1688 | f1 | h1 | g1 | h1 | e2 | a12 |
| 1689 | f1 | h1 | g1 | h1 | e2 | a13 |
| 1690 | f1 | h1 | g1 | h1 | e2 | a14 |
| 1691 | f1 | h1 | g1 | h1 | e2 | a15 |
| 1692 | f1 | h1 | g1 | h1 | e2 | b1 |
| 1693 | f1 | h1 | g1 | h1 | e2 | b2 |
| 1694 | f1 | h1 | g1 | h1 | e2 | b3 |
| 1695 | f1 | h1 | g1 | h1 | e2 | b4 |
| 1696 | f1 | h1 | g1 | h1 | e2 | b5 |
| 1697 | f1 | h1 | g1 | h1 | e2 | b6 |
| 1698 | f1 | h1 | g1 | h1 | e2 | b7 |
| 1699 | f1 | h1 | g1 | h1 | e2 | b8 |
| 1700 | f1 | h1 | g1 | h1 | e2 | c1 |
| 1701 | f1 | h1 | g1 | h1 | e2 | c2 |
| 1702 | f1 | h1 | g1 | h1 | e2 | c3 |
| 1703 | f1 | h1 | g1 | h1 | e2 | c4 |
| 1704 | f1 | h1 | g1 | h1 | e2 | c5 |
| 1705 | f1 | h1 | g1 | h1 | e2 | d1 |
| 1706 | f1 | h1 | g1 | h1 | e2 | d2 |
| 1707 | f1 | h1 | g1 | h1 | e2 | d3 |
| 1708 | f1 | h1 | g1 | h1 | e2 | d4 |
| 1709 | f1 | h1 | g1 | h1 | e2 | d5 |
| 1710 | f1 | h1 | g1 | h1 | e2 | d6 |
| 1711 | f1 | h1 | g1 | h1 | e2 | d7 |
| 1712 | f1 | h1 | g1 | h1 | e2 | d8 |
| 1713 | f1 | h1 | g1 | h1 | e2 | d9 |
| 1714 | f1 | h1 | g1 | h1 | e2 | d10 |
| 1715 | f1 | h1 | g1 | h1 | e2 | d11 |
| 1716 | f1 | h1 | g1 | h1 | e2 | d12 |
| 1717 | f1 | h1 | g1 | h1 | e2 | d13 |
| 1718 | f1 | h1 | g1 | h1 | e2 | d14 |
| 1719 | f1 | h1 | g1 | h1 | e2 | d15 |
| 1720 | f1 | h1 | g1 | h1 | e2 | d16 |
| 1721 | f1 | h1 | g1 | h1 | e2 | d17 |
| 1722 | f1 | h1 | g1 | h1 | e2 | d18 |
| 1723 | f1 | h1 | g1 | h1 | e2 | e2 |
| 1724 | f1 | h1 | g1 | h1 | e2 | e3 |
| 1725 | f1 | h1 | g1 | h1 | e2 | e4 |
| 1726 | f1 | h1 | g1 | h1 | e3 | a1 |
| 1727 | f1 | h1 | g1 | h1 | e3 | a2 |
| 1728 | f1 | h1 | g1 | h1 | e3 | a3 |
| 1729 | f1 | h1 | g1 | h1 | e3 | a4 |
| 1730 | f1 | h1 | g1 | h1 | e3 | a5 |
| 1731 | f1 | h1 | g1 | h1 | e3 | a6 |
| 1732 | f1 | h1 | g1 | h1 | e3 | a7 |

-continued

Compound Combination Table 1

| No. | $Cz^b$ | $L^A$ | $Cz^A$ | $L^B$ | $Ar^A$ | $Ar^B$ |
| --- | --- | --- | --- | --- | --- | --- |
| 1733 | f1 | h1 | g1 | h1 | e3 | a8 |
| 1734 | f1 | h1 | g1 | h1 | e3 | a9 |
| 1735 | f1 | h1 | g1 | h1 | e3 | a10 |
| 1736 | f1 | h1 | g1 | h1 | e3 | a11 |
| 1737 | f1 | h1 | g1 | h1 | e3 | a12 |
| 1738 | f1 | h1 | g1 | h1 | e3 | a13 |
| 1739 | f1 | h1 | g1 | h1 | e3 | a14 |
| 1740 | f1 | h1 | g1 | h1 | e3 | a15 |
| 1741 | f1 | h1 | g1 | h1 | e3 | b1 |
| 1742 | f1 | h1 | g1 | h1 | e3 | b2 |
| 1743 | f1 | h1 | g1 | h1 | e3 | b3 |
| 1744 | f1 | h1 | g1 | h1 | e3 | b4 |
| 1745 | f1 | h1 | g1 | h1 | e3 | b5 |
| 1746 | f1 | h1 | g1 | h1 | e3 | b6 |
| 1747 | f1 | h1 | g1 | h1 | e3 | b7 |
| 1748 | f1 | h1 | g1 | h1 | e3 | b8 |
| 1749 | f1 | h1 | g1 | h1 | e3 | c1 |
| 1750 | f1 | h1 | g1 | h1 | e3 | c2 |
| 1751 | f1 | h1 | g1 | h1 | e3 | c3 |
| 1752 | f1 | h1 | g1 | h1 | e3 | c3 |
| 1753 | f1 | h1 | g1 | h1 | e3 | c5 |
| 1754 | f1 | h1 | g1 | h1 | e3 | d1 |
| 1755 | f1 | h1 | g1 | h1 | e3 | d2 |
| 1756 | f1 | h1 | g1 | h1 | e3 | d3 |
| 1757 | f1 | h1 | g1 | h1 | e3 | d4 |
| 1758 | f1 | h1 | g1 | h1 | e3 | d5 |
| 1759 | f1 | h1 | g1 | h1 | e3 | d6 |
| 1760 | f1 | h1 | g1 | h1 | e3 | d7 |
| 1761 | f1 | h1 | g1 | h1 | e3 | d8 |
| 1762 | f1 | h1 | g1 | h1 | e3 | d9 |
| 1763 | f1 | h1 | g1 | h1 | e3 | d10 |
| 1764 | f1 | h1 | g1 | h1 | e3 | d11 |
| 1765 | f1 | h1 | g1 | h1 | e3 | d12 |
| 1766 | f1 | h1 | g1 | h1 | e3 | d13 |
| 1767 | f1 | h1 | g1 | h1 | e3 | d14 |
| 1768 | f1 | h1 | g1 | h1 | e3 | d15 |
| 1769 | f1 | h1 | g1 | h1 | e3 | d16 |
| 1770 | f1 | h1 | g1 | h1 | e3 | d17 |
| 1771 | f1 | h1 | g1 | h1 | e3 | d18 |
| 1772 | f1 | h1 | g1 | h1 | e3 | e3 |
| 1773 | f1 | h1 | g1 | h1 | e3 | e4 |
| 1774 | f1 | h1 | g1 | h1 | e4 | a1 |
| 1775 | f1 | h1 | g1 | h1 | e4 | a2 |
| 1776 | f1 | h1 | g1 | h1 | e4 | a3 |
| 1777 | f1 | h1 | g1 | h1 | e4 | a4 |
| 1778 | f1 | h1 | g1 | h1 | e4 | a5 |
| 1779 | f1 | h1 | g1 | h1 | e4 | a6 |
| 1780 | f1 | h1 | g1 | h1 | e4 | a7 |
| 1781 | f1 | h1 | g1 | h1 | e4 | a8 |
| 1782 | f1 | h1 | g1 | h1 | e4 | a9 |
| 1783 | f1 | h1 | g1 | h1 | e4 | a10 |
| 1784 | f1 | h1 | g1 | h1 | e4 | a11 |
| 1785 | f1 | h1 | g1 | h1 | e4 | a12 |
| 1786 | f1 | h1 | g1 | h1 | e4 | a13 |
| 1787 | f1 | h1 | g1 | h1 | e4 | a14 |
| 1788 | f1 | h1 | g1 | h1 | e4 | a15 |
| 1789 | f1 | h1 | g1 | h1 | e4 | b1 |
| 1790 | f1 | h1 | g1 | h1 | e4 | b2 |
| 1791 | f1 | h1 | g1 | h1 | e4 | b3 |
| 1792 | f1 | h1 | g1 | h1 | e4 | b4 |
| 1793 | f1 | h1 | g1 | h1 | e4 | b5 |
| 1794 | f1 | h1 | g1 | h1 | e4 | b6 |
| 1795 | f1 | h1 | g1 | h1 | e4 | b7 |
| 1796 | f1 | h1 | g1 | h1 | e4 | b8 |
| 1797 | f1 | h1 | g1 | h1 | e4 | c1 |
| 1798 | f1 | h1 | g1 | h1 | e4 | c2 |
| 1799 | f1 | h1 | g1 | h1 | e4 | c3 |
| 1800 | f1 | h1 | g1 | h1 | e4 | c4 |
| 1801 | f1 | h1 | g1 | h1 | e4 | c5 |
| 1802 | f1 | h1 | g1 | h1 | e4 | d1 |
| 1803 | f1 | h1 | g1 | h1 | e4 | d2 |
| 1804 | f1 | h1 | g1 | h1 | e4 | d3 |
| 1805 | f1 | h1 | g1 | h1 | e4 | d4 |
| 1806 | f1 | h1 | g1 | h1 | e4 | d5 |
| 1807 | f1 | h1 | g1 | h1 | e4 | d6 |
| 1808 | f1 | h1 | g1 | h1 | e4 | d7 |
| 1809 | f1 | h1 | g1 | h1 | e4 | d8 |
| 1810 | f1 | h1 | g1 | h1 | e4 | d9 |
| 1811 | f1 | h1 | g1 | h1 | e4 | d10 |
| 1812 | f1 | h1 | g1 | h1 | e4 | d11 |
| 1813 | f1 | h1 | g1 | h1 | e4 | d12 |
| 1814 | f1 | h1 | g1 | h1 | e4 | d13 |
| 1815 | f1 | h1 | g1 | h1 | e4 | d14 |
| 1816 | f1 | h1 | g1 | h1 | e4 | d15 |
| 1817 | f1 | h1 | g1 | h1 | e4 | d16 |
| 1818 | f1 | h1 | g1 | h1 | e4 | d17 |
| 1819 | f1 | h1 | g1 | h1 | e4 | d18 |
| 1820 | f1 | h1 | g1 | h1 | e4 | e4. |

In the structure of the compounds in Compound Group A and Compound Group F, "D" refers to a deuterium atom, "Me" refers to a substituted or unsubstituted methyl group, and "Ph" refers to a substituted or unsubstituted phenyl group. For example, in the structure of the compounds in Compound Group A and Compound Group F, "Me" may be an unsubstituted methyl group, and "Ph" may be an unsubstituted phenyl group.

In some embodiments, the light emitting device ED may further include a material of a hole transport region in the hole transport region HTR in addition to the amine compound of an embodiment.

The hole transport region HTR may include a compound represented by Formula H-1.

Formula H-1

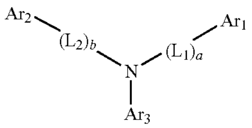

In Formula H-1, $L_1$ and $L_2$ may each independently be a direct linkage, a substituted or unsubstituted arylene group of 6 to 30 ring-forming carbon atoms, or a substituted or unsubstituted heteroarylene group of 2 to 30 ring-forming carbon atoms. "a" and "b" may each independently be an integer from 0 to 10. In some embodiments, when "a" or "b" is an integer of 2 or more, multiple $L_1$ and $L_2$ may each independently be a substituted or unsubstituted arylene group of 6 to 30 ring-forming carbon atoms, or a substituted or unsubstituted heteroarylene group of 2 to 30 ring-forming carbon atoms.

In Formula H-1, $Ar_1$ and $Ar_2$ may each independently be a substituted or unsubstituted aryl group of 6 to 30 ring-forming carbon atoms, or a substituted or unsubstituted heteroaryl group of 2 to 30 ring-forming carbon atoms. In some embodiments, in Formula H-1, $Ar_3$ may be a substituted or unsubstituted aryl group of 6 to 30 ring-forming carbon atoms, or a substituted or unsubstituted heteroaryl group of 2 to 30 ring-forming carbon atoms.

The compound represented by Formula H-1 may be a monoamine compound. Or, the compound represented by Formula H-1 may be a diamine compound in which at least one among $Ar_1$ to $Ar_3$ includes an amine group as a substituent. In some embodiments, the compound represented by Formula H-1 may be a carbazole-based compound in which at least one among $Ar_1$ and $Ar_2$ includes a substituted or unsubstituted carbazole group, or a fluorene-based compound in which at least one among $Ar_1$ and $Ar_2$ includes a substituted or unsubstituted fluorene group.

The compound represented by Formula H-1 may be represented by any one among the compounds in Compound Group H. However, the compounds shown in Compound Group H are merely examples, and the compound represented by Formula H-1 is not limited to the compounds represented in Compound Group H.

Compound Group H

H-1-1

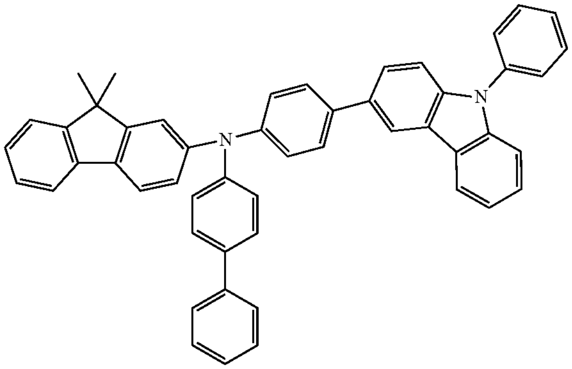

H-1-2

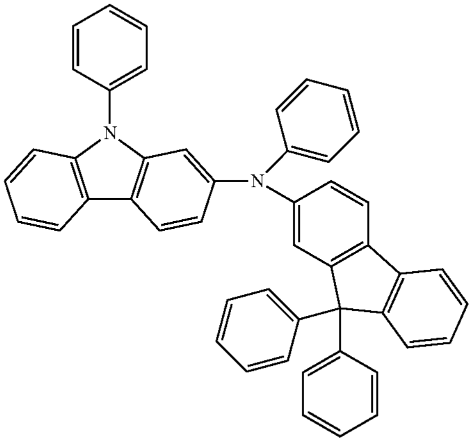

H-1-3

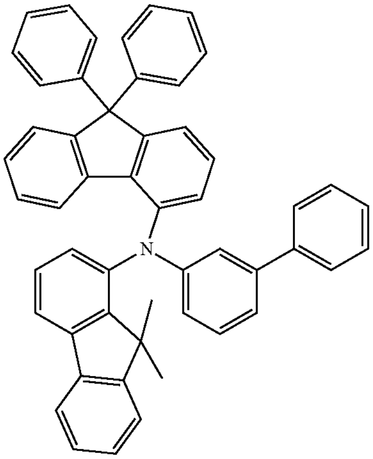

-continued

H-1-4

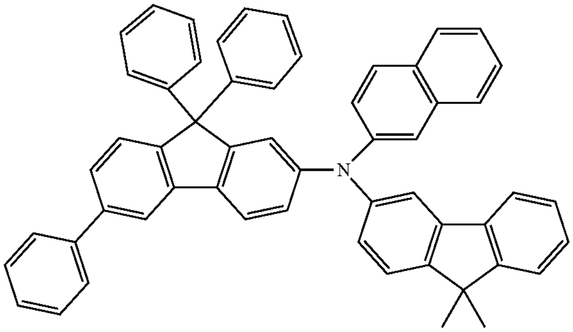

H-1-5

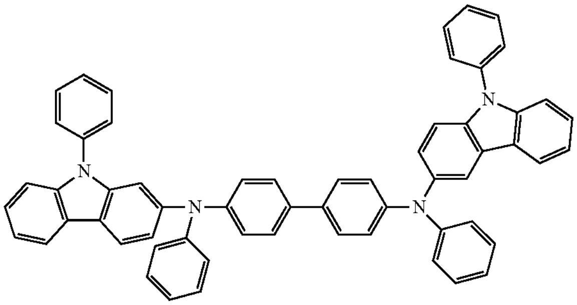

H-1-6

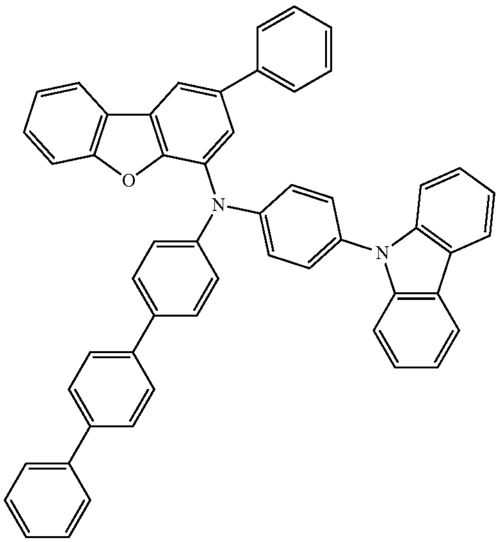

-continued
H-1-7
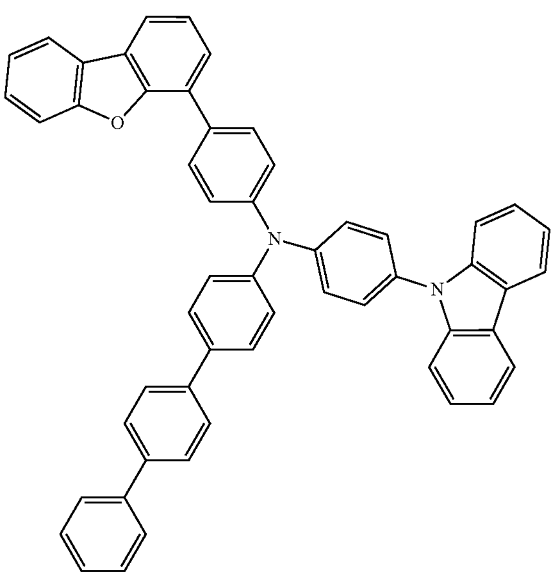
H-1-8
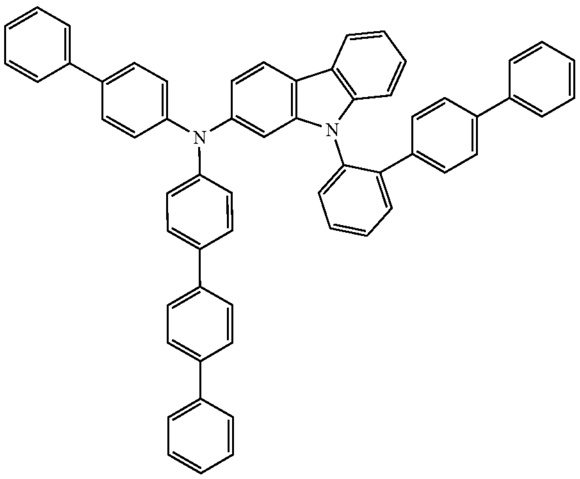
H-1-9
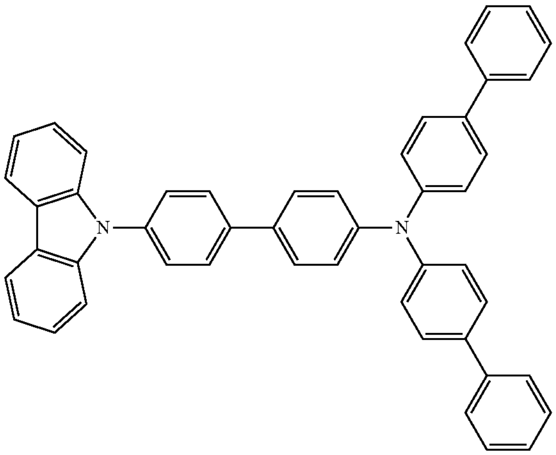
-continued
H-1-10
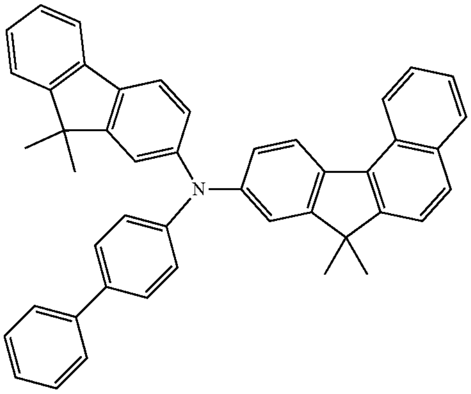
H-1-11
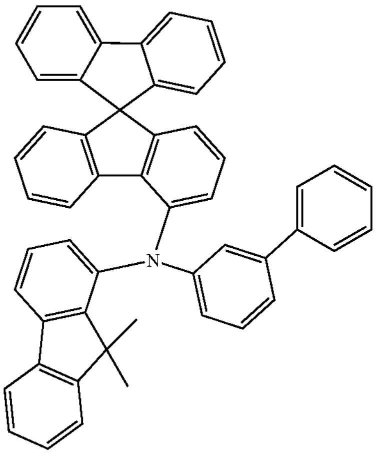
H-1-12
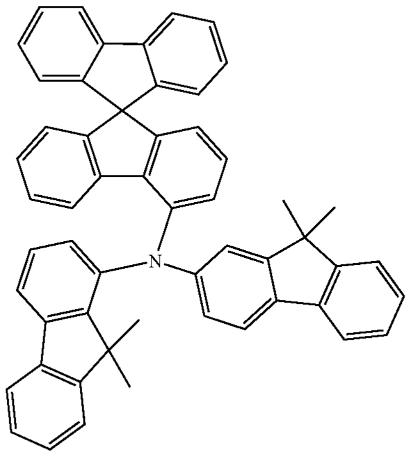
H-1-13
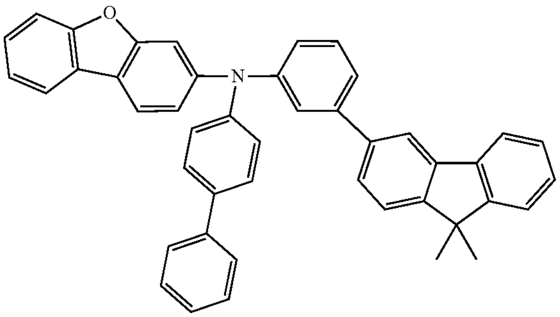

-continued

H-1-14

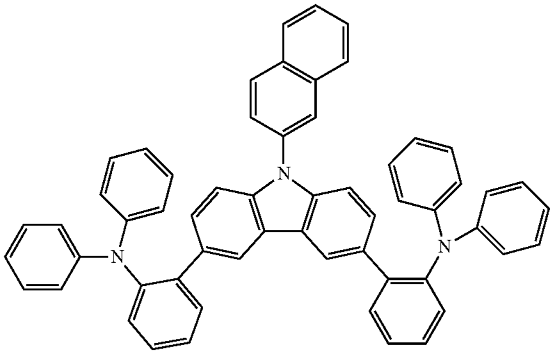

H-1-15

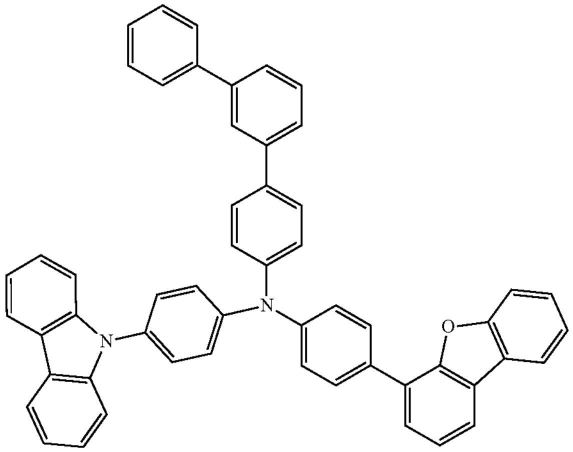

H-1-16

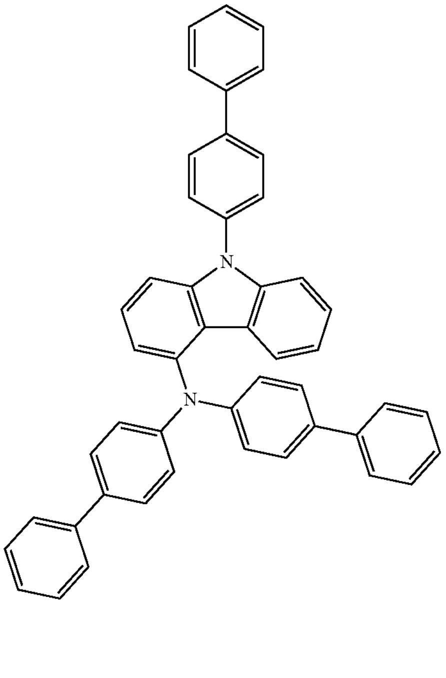

-continued

H-1-17

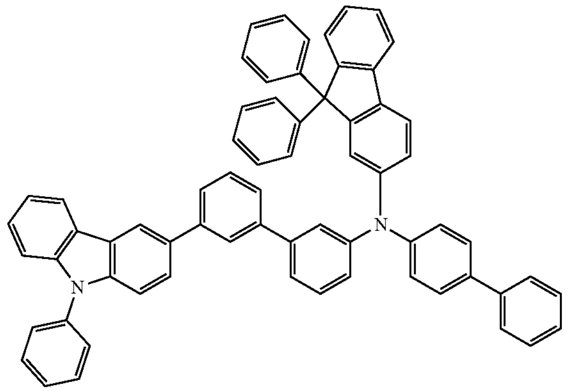

H-1-18

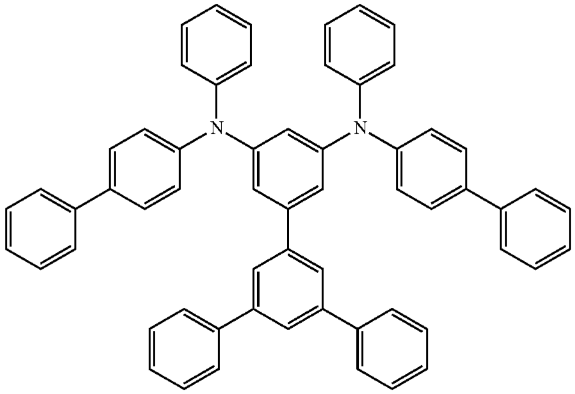

H-1-19

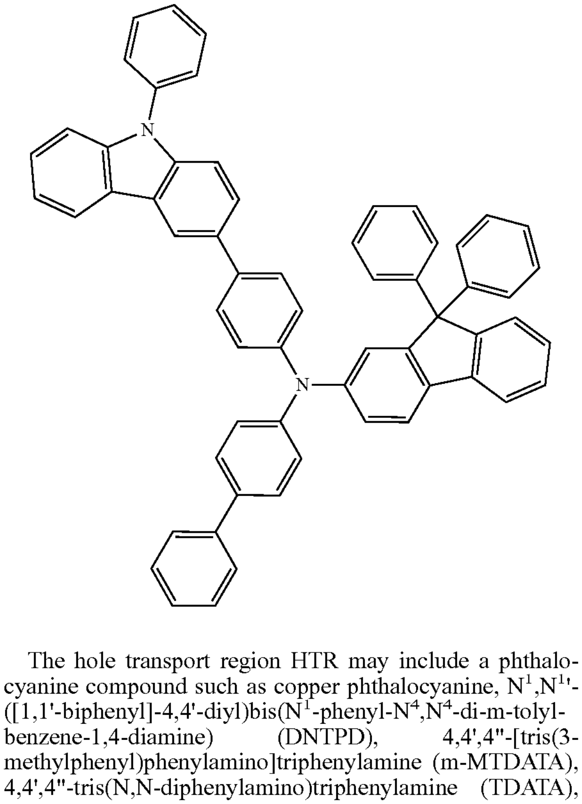

The hole transport region HTR may include a phthalocyanine compound such as copper phthalocyanine, $N^1$,$N^{1'}$-([1,1'-biphenyl]-4,4'-diyl)bis($N^1$-phenyl-$N^4$,$N^4$-di-m-tolylbenzene-1,4-diamine) (DNTPD), 4,4',4"-[tris(3-methylphenyl)phenylamino]triphenylamine (m-MTDATA), 4,4',4"-tris(N,N-diphenylamino)triphenylamine (TDATA), 4,4',4"-tris[N(2-naphthyl)-N-phenylamino]-triphenylamine (2-TNATA), poly(3,4-ethylenedioxythiophene)/poly(4-styrenesulfonate) (PEDOT/PSS), polyaniline/dodecylbenzene-sulfonic acid (PANI/DBSA), polyaniline/camphor sulfonic acid (PANI/CSA), polyaniline/poly(4-styrenesulfonate) (PANI/PSS), N,N'-di(1-naphthalene-1-yl)-N,N'-diphenyl-benzidine (NPB), triphenylamine-containing polyetherketone (TPAPEK), 4-isopropyl-4'-methyldiphenyliodonium [tetrakis(pentafluorophenyl)borate], and dipyrazino[2,3-f:2',3'-h]quinoxaline-2,3,6,7,10,11-hexacarbonitrile (HAT-CN).

The hole transport region HTR may include carbazole derivatives such as N-phenyl carbazole and polyvinyl carbazole, fluorene-based derivatives, N,N'-bis(3-methylphenyl)-N,N'-diphenyl-[1,1'-biphenyl]-4,4'-diamine (TPD), triphenylamine-based derivatives such as 4,4',4"-tris(N-carbazolyl)triphenylamine (TCTA), N,N'-di(1-naphthalene-1-yl)-N,N'-diphenyl-benzidine (NPB), 4,4'-cyclohexylidene bis[N,N-bis(4-methylphenyl)benzeneamine](TAPC), 4,4'-bis[N,N'-(3-tolyl)amino]-3,3'-dimethylbiphenyl (HMTPD), 1,3-bis(N-carbazolyl)benzene (mCP), etc.

In some embodiments, the hole transport region HTR may include 9-(4-tert-butylphenyl)-3,6-bis(triphenylsilyl)-9H-carbazole (CzSi), 9-phenyl-9H-3,9'-bicarbazole (CCP), 1,3-bis(1,8-dimethyl-9H-carbazol-9-yl)benzene (mDCP), etc.

The hole transport region HTR may include the compounds of the hole transport region in at least one selected from among the hole injection layer HIL, hole transport layer HTL, and electron blocking layer EBL.

The thickness of the hole transport region HTR may be from about 100 Å to about 10,000 Å, for example, from about 100 Å to about 5,000 Å. When the hole transport region HTR includes a hole injection layer HIL, the thickness of the hole injection region HIL may be, for example, from about 30 Å to about 1,000 Å. When the hole transport region HTR includes a hole transport layer HTL, the thickness of the hole transport layer HTL may be from about 30 Å to about 1,000 Å. For example, when the hole transport region HTR includes an electron blocking layer, the thickness of the electron blocking layer EBL may be from about 10 Å to about 1,000 Å. When the thicknesses of the hole transport region HTR, the hole injection layer HIL, the hole transport layer HTL and the electron blocking layer EBL satisfy the above-described ranges, satisfactory (suitable) hole transport properties may be achieved without a substantial increase of a driving voltage.

The hole transport region HTR may further include a charge generating material to increase conductivity in addition to the above-described materials. The charge generating material may be dispersed substantially uniformly or non-uniformly in the hole transport region HTR. The charge generating material may be, for example, a p-dopant. The p-dopant may include at least one selected from metal halide compounds, quinone derivatives, metal oxides, and cyano group-containing compounds, without limitation. For example, the p-dopant may include metal halide compounds such as CuI and RbI, quinone derivatives such as tetracyanoquinodimethane (TCNQ) and 2,3,5,6-tetrafluoro-7,7',8,8-tetracyanoquinodimethane (F4-TCNQ), metal oxides such as tungsten oxide and molybdenum oxide, cyano group-containing compounds such as dipyrazino[2,3-f: 2',3'-h] quinoxaline-2,3,6,7,10,11-hexacarbonitrile (HATCN) and 4-[[2,3-bis[cyano-(4-cyano-2,3,5,6-tetrafluorophenyl)methylidene]cyclopropylidene]-cyanomethyl]-2,3,5,6-tetrafluorobenzonitrile (NDP9), etc., without limitation.

As described above, the hole transport region HTR may further include at least one among a buffer layer and an electron blocking layer EBL in addition to the hole injection layer HIL and the hole transport layer HTL. The buffer layer may compensate resonance distance according to the wavelength of light emitted from an emission layer EML and may increase emission efficiency. As materials included in the buffer layer, materials which may be included in the hole transport region HTR may be used. The electron blocking layer EBL is a layer playing the role of blocking the injection of electrons from the electron transport region ETR to the hole transport region HTR.

The emission layer EML is provided on the hole transport region HTR. The emission layer EML may have a thickness of, for example, about 100 Å to about 1,000 Å or about 100 Å to about 300 Å. The emission layer EML may have a single layer formed using a single material, a single layer formed using multiple different materials, or a multilayer structure having multiple layers formed using multiple different materials.

In the light emitting device ED of an embodiment, the emission layer EML may include anthracene derivatives, pyrene derivatives, fluoranthene derivatives, chrysene derivatives, dihydrobenzanthracene derivatives, or triphenylene derivatives. For example, the emission layer EML may include anthracene derivatives or pyrene derivatives.

In the light emitting devices ED of embodiments, shown in FIG. 3 to FIG. 6, the emission layer EML may include a host and a dopant, and the emission layer EML may include a compound represented by Formula E-1. The compound represented by Formula E-1 may be used as a fluorescence host material.

Formula E-1

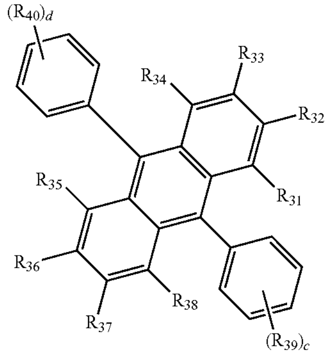

In Formula E-1, $R_{31}$ to $R_{40}$ may each independently be a hydrogen atom, a deuterium atom, a halogen atom, a substituted or unsubstituted silyl group, a substituted or unsubstituted thio group, a substituted or unsubstituted oxy group, a substituted or unsubstituted alkyl group of 1 to 10 carbon atoms, a substituted or unsubstituted alkenyl group of 2 to 10 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring. In some embodiments, $R_{31}$ to $R_{40}$ may be combined with adjacent groups to form saturated hydrocarbon rings, unsaturated hydrocarbon rings, saturated heterocycles, or unsaturated heterocycles.

In Formula E-1, "c" and "d" may each independently be an integer from 0 to 5.

Formula E-1 may be represented by any one among Compound E1 to Compound E19.

E1
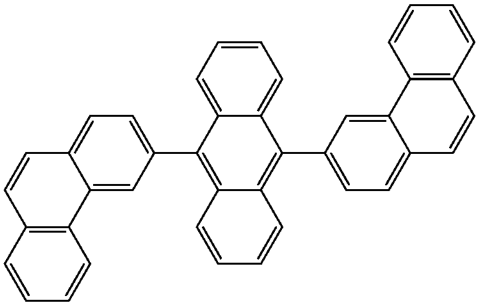
E2
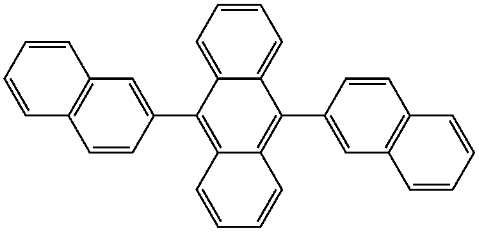
E3
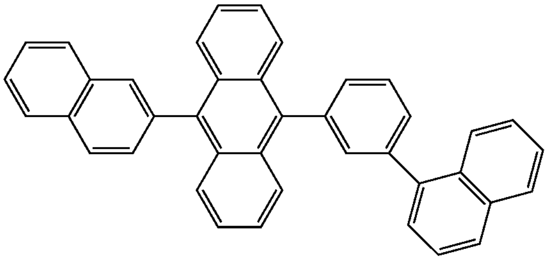
E4
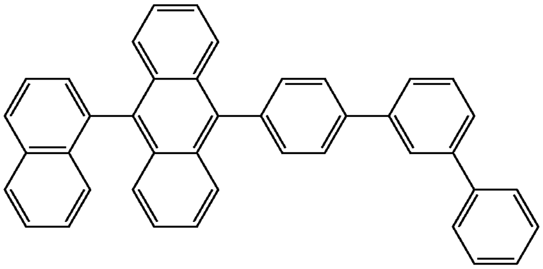
E5
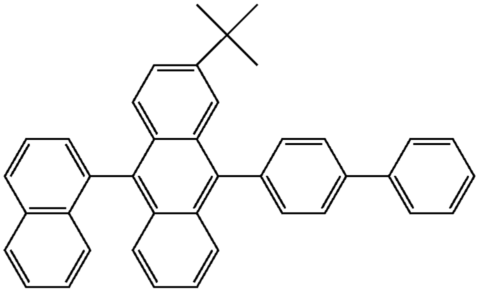
-continued
E6
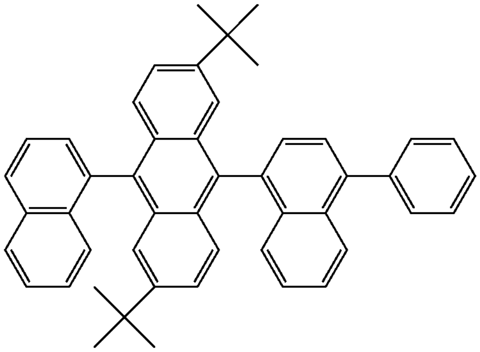
E7
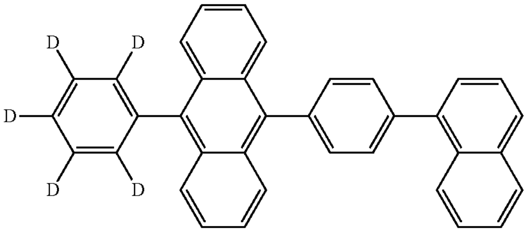
E8
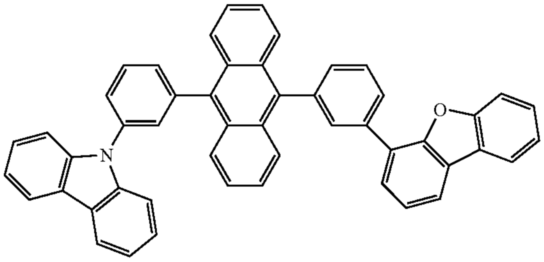
E9
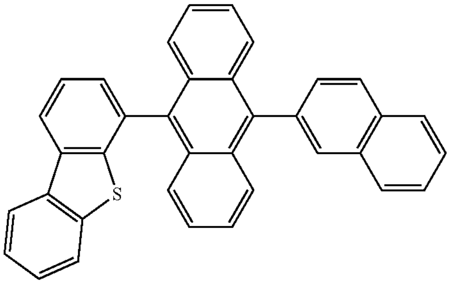
E10
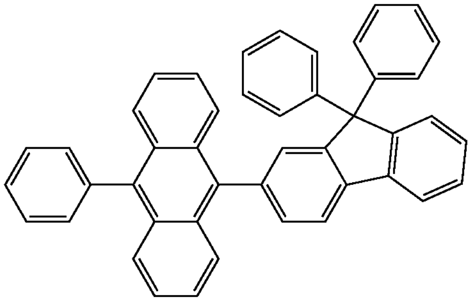

-continued
E11
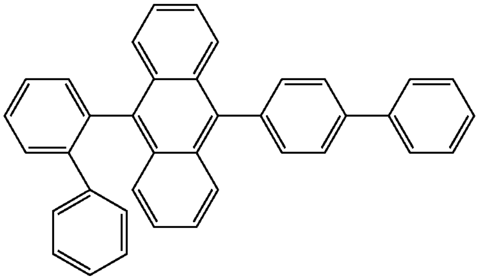
E12
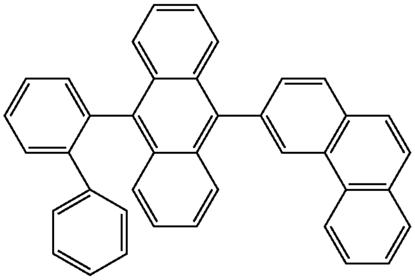
E13
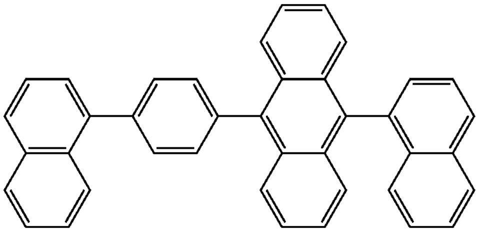
E14
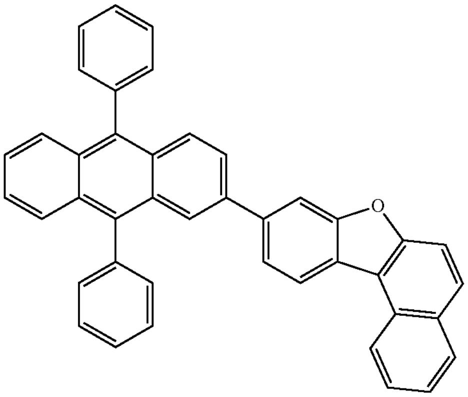
-continued
E15
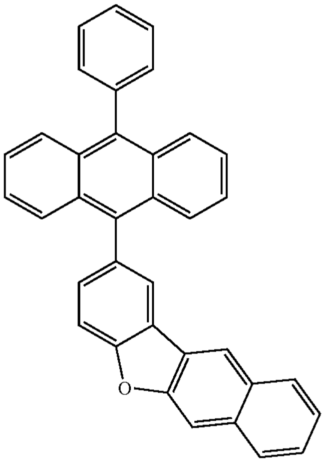
E16
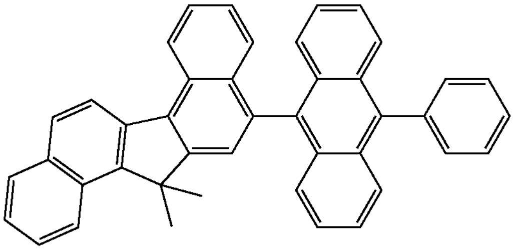
E17
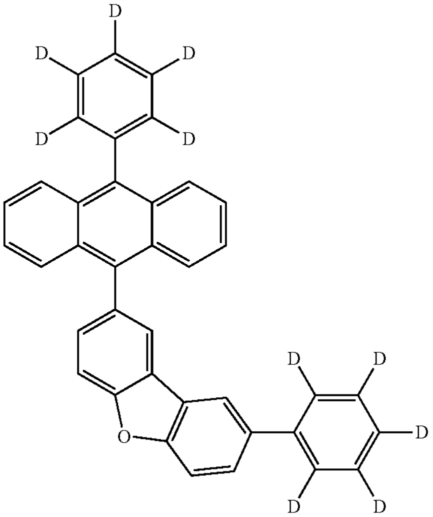
E18
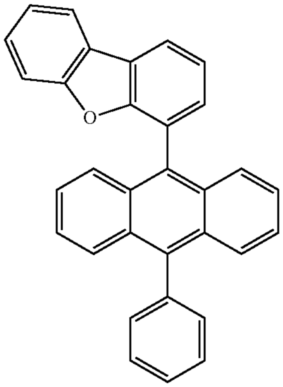

-continued

E19

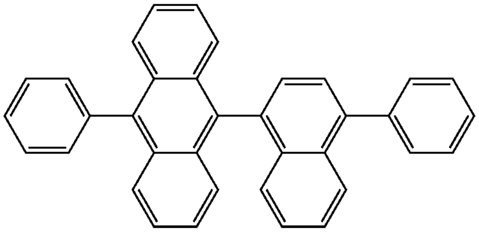

In an embodiment, the emission layer EML may include a compound represented by Formula E-2a or Formula E-2b. The compound represented by Formula E-2a or Formula E-2b may be used as a phosphorescence host material.

Formula E-2a

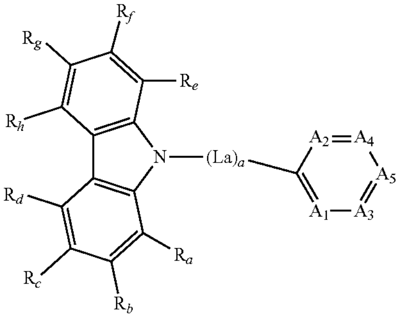

In Formula E-2a, "a" may be an integer of 0 to 10, $L_a$ may be a direct linkage, a substituted or unsubstituted arylene group of 6 to 30 ring-forming carbon atoms, or a substituted or unsubstituted heteroarylene group of 2 to 30 ring-forming carbon atoms. When "a" is an integer of 2 or more, multiple $L_a$ may each independently be a substituted or unsubstituted arylene group of 6 to 30 ring-forming carbon atoms, or a substituted or unsubstituted heteroarylene group of 2 to 30 ring-forming carbon atoms.

In some embodiments, in Formula E-2a, $A_1$ to $A_5$ may each independently be N or CRi. $R_a$ to $R_i$ may each independently be a hydrogen atom, a deuterium atom, a substituted or unsubstituted amine group, a substituted or unsubstituted thio group, a substituted or unsubstituted oxy group, a substituted or unsubstituted alkyl group of 1 to 20 carbon atoms, a substituted or unsubstituted alkenyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring. $R_a$ to $R_i$ may be combined with an adjacent group to form a hydrocarbon ring or a heterocycle including N, O, S, etc. as a ring-forming atom.

In some embodiments, in Formula E-2a, two or three selected from $A_1$ to $A_5$ may be N, and the remainder may be $CR_i$.

Formula E-2b $$(Cbz1) - (L_b)_b - (Cbz2)$$

In Formula E-2b, Cbz1 and Cbz2 may each independently be an unsubstituted carbazole group, or a carbazole group substituted with an aryl group of 6 to 30 ring-forming carbon atoms. $L_b$ may be a direct linkage, a substituted or unsubstituted arylene group of 6 to 30 ring-forming carbon atoms, or a substituted or unsubstituted heteroarylene group of 2 to 30 ring-forming carbon atoms. "b" may be an integer from 0 to 10, and when "b" is an integer of 2 or more, multiple $L_b$ may each independently be a substituted or unsubstituted arylene group of 6 to 30 ring-forming carbon atoms, or a substituted or unsubstituted heteroarylene group of 2 to 30 ring-forming carbon atoms.

The compound represented by Formula E-2a or Formula E-2b may be represented by any one among the compounds in Compound Group E-2. However, the compounds shown in Compound Group E-2 are merely examples, and the compound represented by Formula E-2a or Formula E-2b is not limited to the compounds represented in Compound Group E-2.

Compound Group E-2

E-2-1

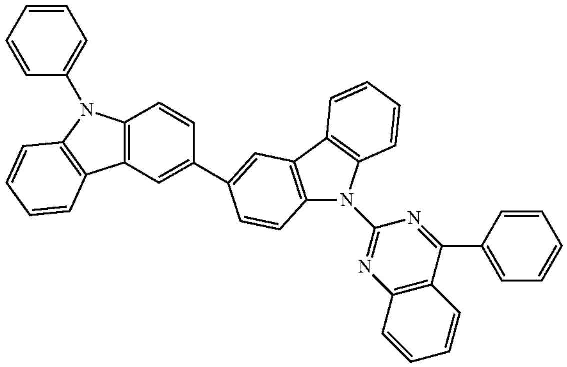

E-2-2

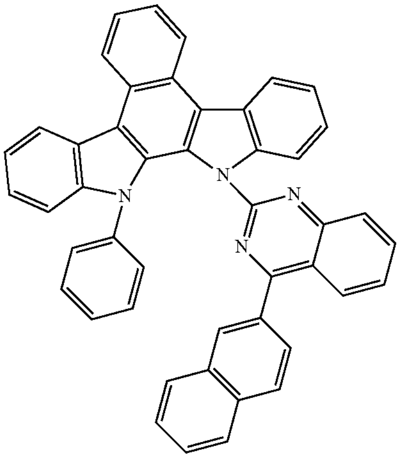

-continued
E-2-3
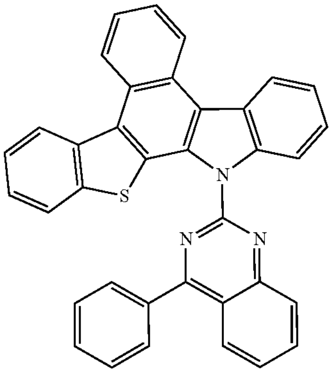
E-2-4
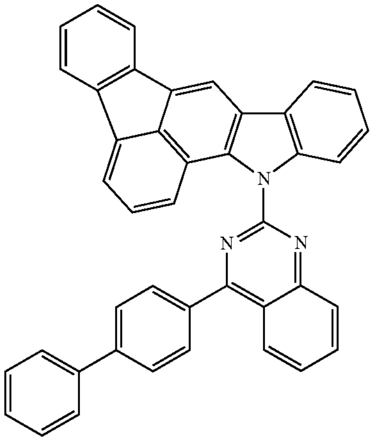
E-2-5
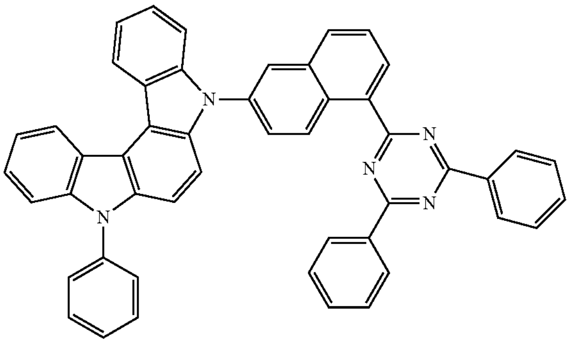
E-2-6
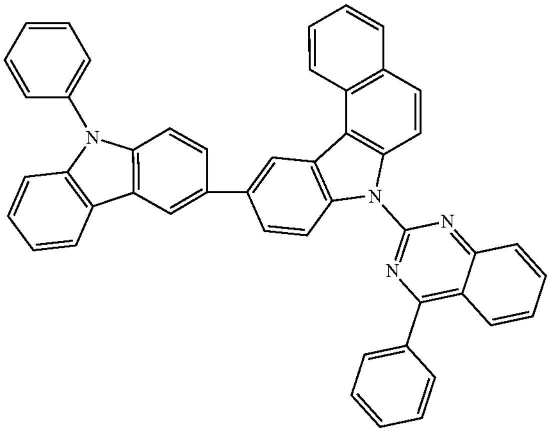
-continued
E-2-7
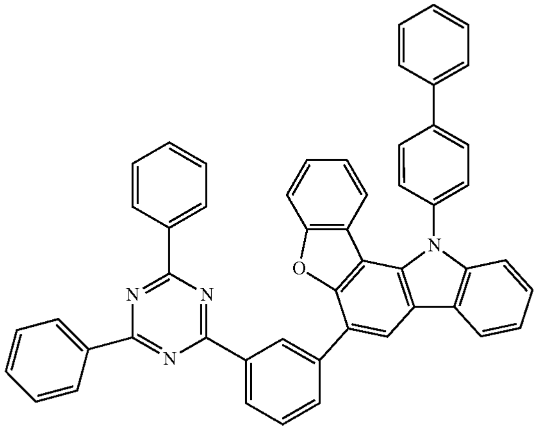
E-2-8
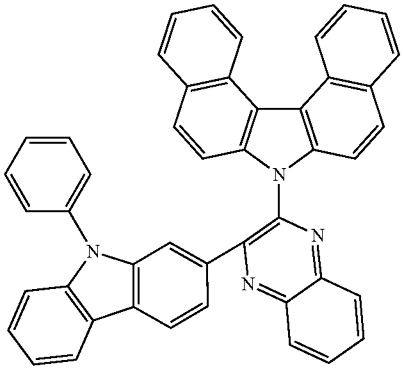
E-2-9
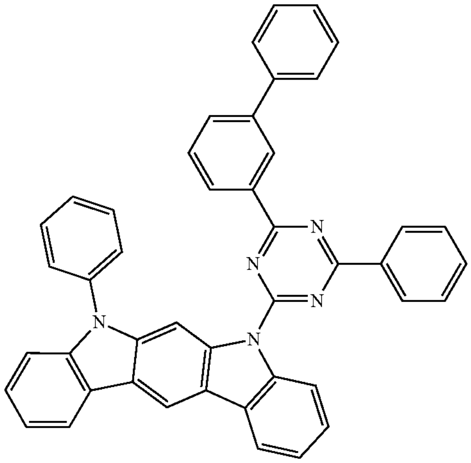

-continued
E-2-10
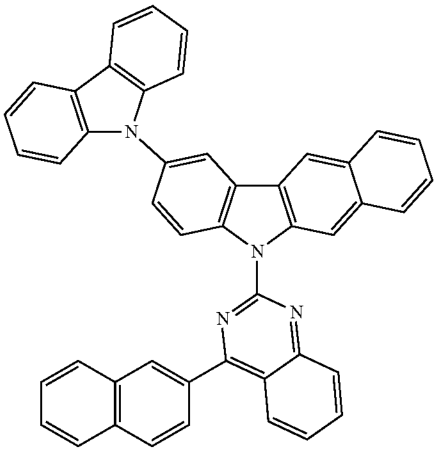
E-2-11
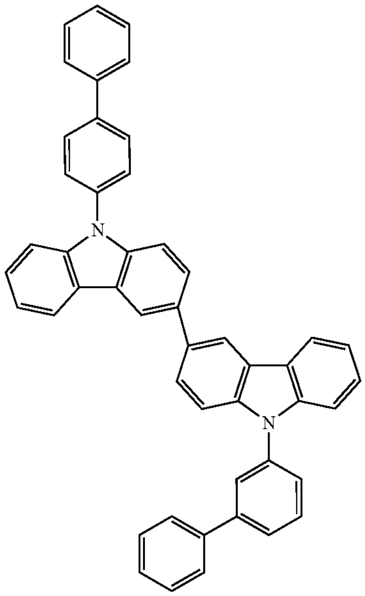
E-2-12
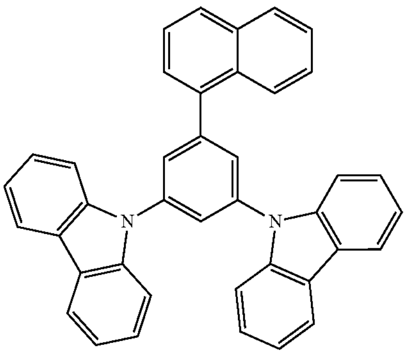
-continued
E-2-13
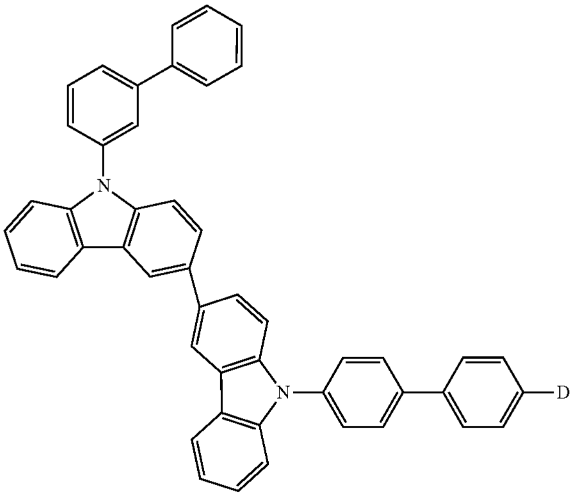
E-2-14
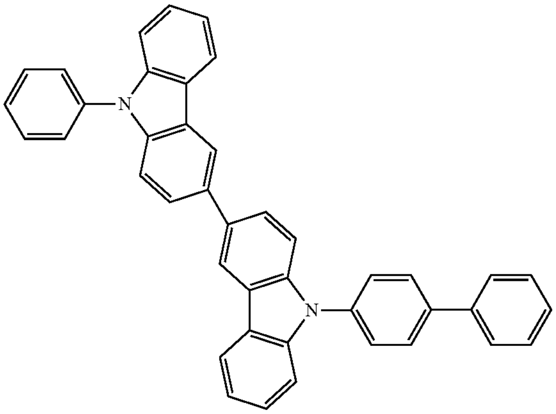
E-2-15
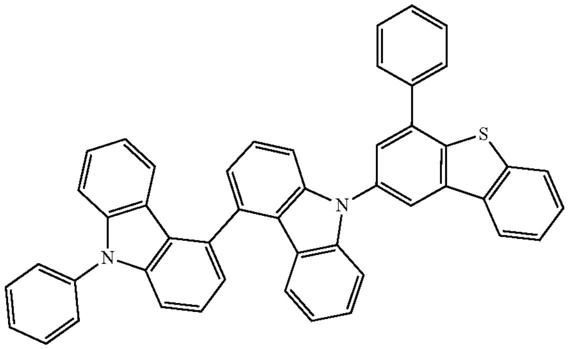

-continued
E-2-16
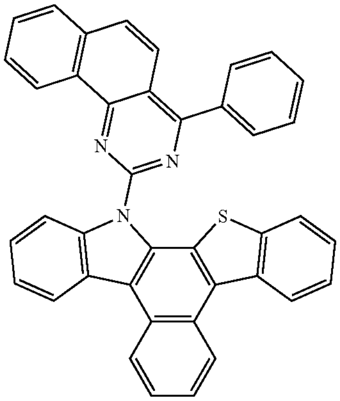
E-2-17
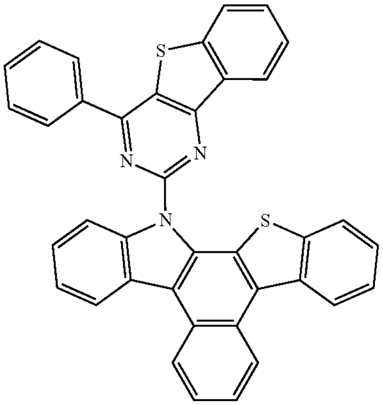
E-2-18
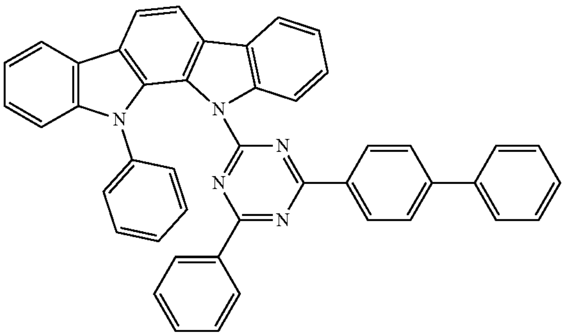
E-2-19
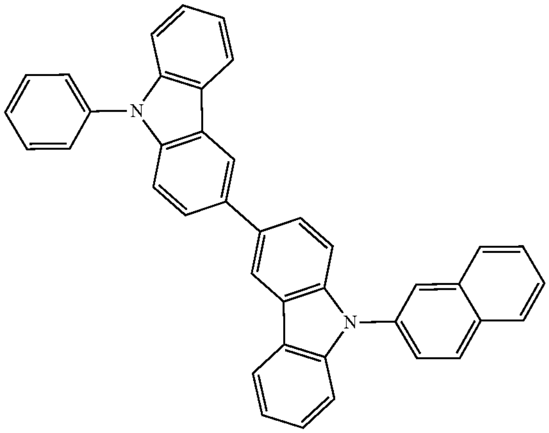
-continued
E-2-20
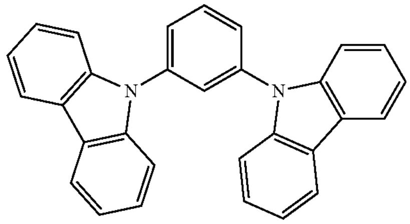
E-2-21
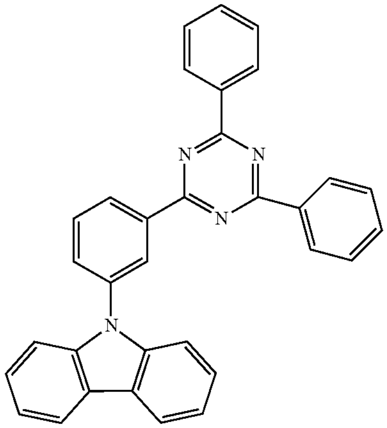
E-2-22
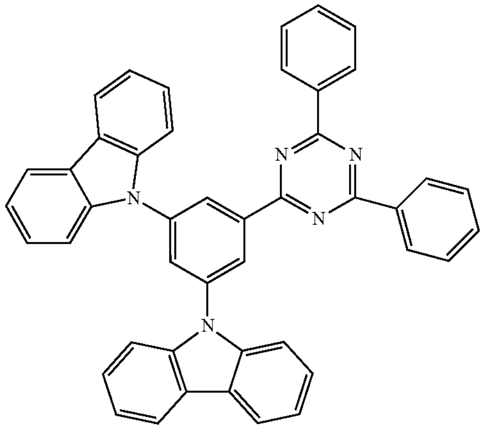
E-2-23
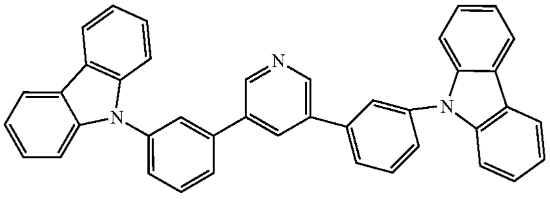

-continued

E-2-24

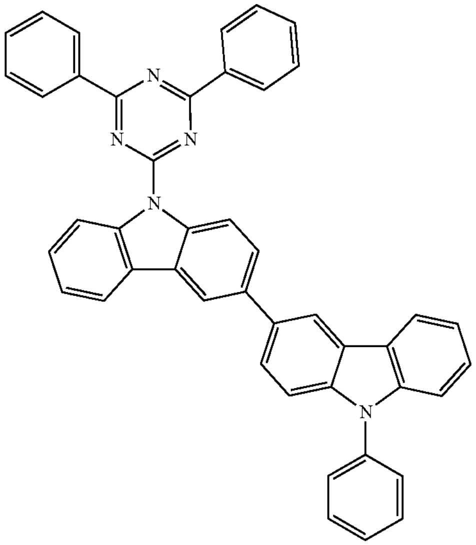

The emission layer EML may further include a material generally used in the art as a host material. For example, the emission layer EML may include as a host material, at least one of bis(4-(9H-carbazol-9-yl)phenyl)diphenylsilane (BCPDS), (4-(1-(4-(diphenylamino) phenyl) cyclohexyl) phenyl) diphenyl-phosphine oxide (POPCPA), bis[2-(diphenylphosphino)phenyl] ether oxide (DPEPO), 4,4'-bis(carbazol-9-yl)biphenyl (CBP), 1,3-bis(carbazol-9-yl)benzene (mCP), 2,8-bis(diphenylphosphoryl)dibenzo[b,d]furan (PPF), 4,4',4"-tris(carbazol-9-yl)-triphenylamine (TCTA), or 1,3,5-tris(1-phenyl-1H-benzo[d]imidazole-2-yl)benzene (TPBi). However, an embodiment of the present disclosure is not limited thereto. For example, tris(8-hydroxyquinolino) aluminum (Alq3), 9,10-di(naphthalene-2-yl)anthracene (ADN), 2-tert-butyl-9,10-di(naphth-2-yl)anthracene (TBADN), distyrylarylene (DSA), 4,4'-bis(9-carbazolyl)-2, 2'-dimethyl-biphenyl (CDBP), 2-methyl-9,10-bis(naphthalen-2-yl)anthracene (MADN), hexaphenyl cyclotriphosphazene (CP1), 1,4-bis(triphenylsilyl)benzene (UGH2), hexaphenylcyclotrisiloxane ($DPSiO_3$), octaphenylcyclotetra siloxane ($DPSiO_4$), etc. may also be used as the host material.

The emission layer EML may include a compound represented by Formula M-a or Formula M-b. The compound represented by Formula M-a or Formula M-b may be used as a phosphorescence dopant material.

Formula M-a

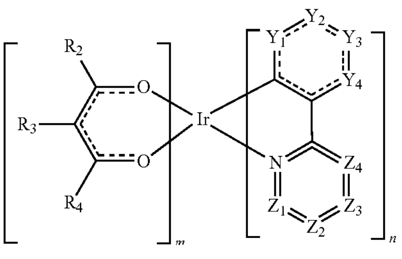

In Formula M-a, $Y_1$ to $Y_4$, and $Z_1$ to $Z_4$ may each independently be $CR_1$ or N, and $R_1$ to $R_4$ may each independently be a hydrogen atom, a deuterium atom, a substituted or unsubstituted amine group, a substituted or unsubstituted thio group, a substituted or unsubstituted oxy group, a substituted or unsubstituted alkyl group of 1 to 20 carbon atoms, a substituted or unsubstituted alkenyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring. In Formula M-a, "m" may be 0 or 1, and "n" may be 2 or 3. In Formula M-a, when "m" is 0, "n" is 3, and when "m" is 1, "n" is 2.

The compound represented by Formula M-a may be used as a phosphorescence dopant.

The compound represented by Formula M-a may be represented by any one among Compounds M-a1 to M-a25. However, Compounds M-a1 to M-a25 are merely examples, and the compound represented by Formula M-a is not limited to the compounds represented by Compounds M-a1 to M-a25.

M-a1

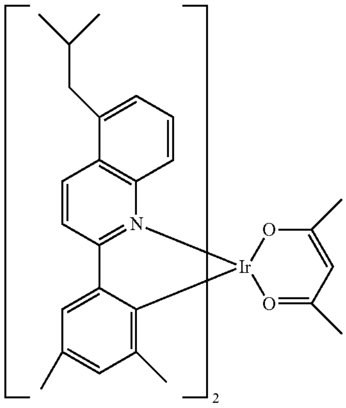

M-a2

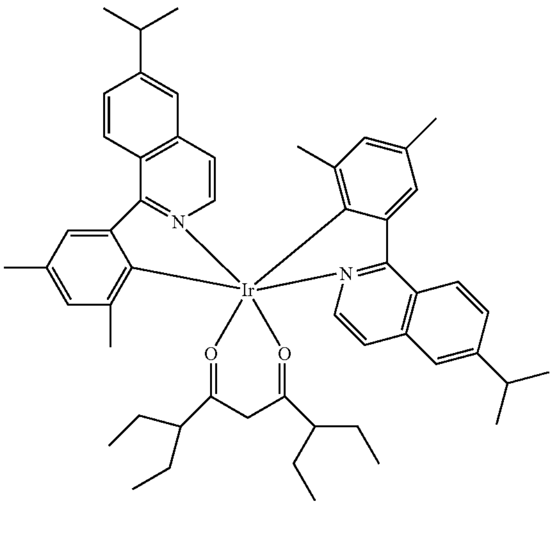

-continued
M-a3
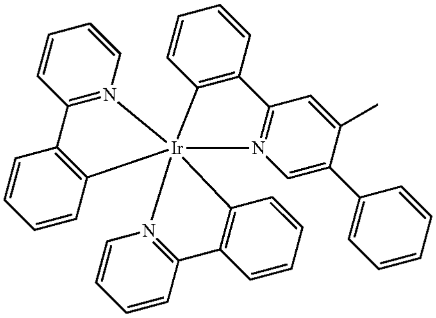
M-a4
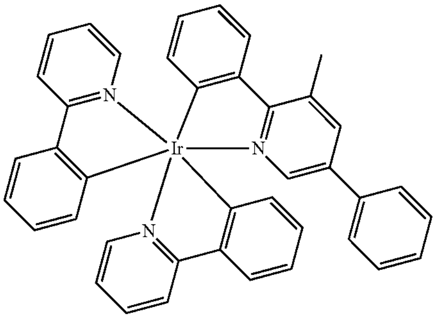
M-a5
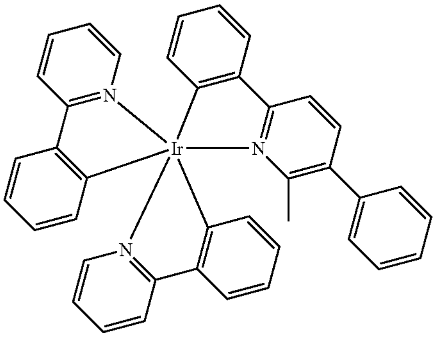
M-a6
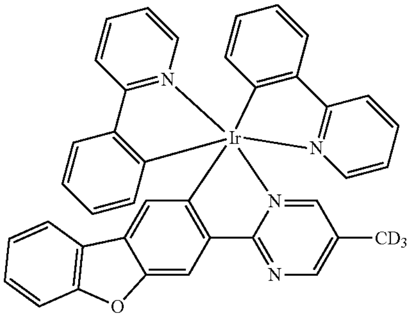
-continued
M-a7
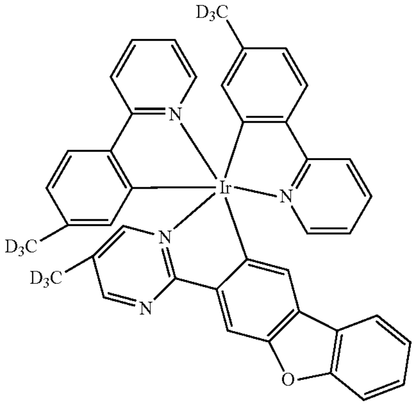
M-a8
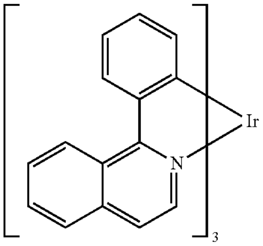
M-a9
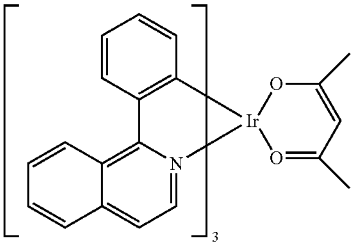
M-a10
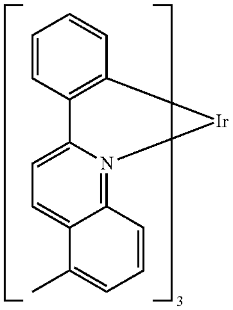
M-a11
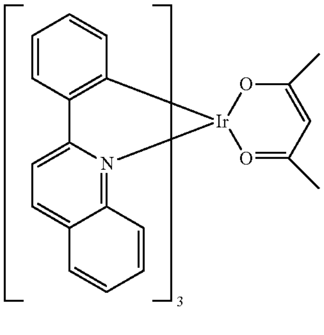

-continued
M-a12
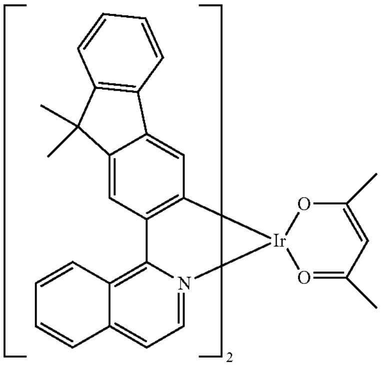
M-a13
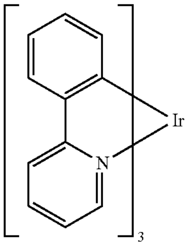
M-a14
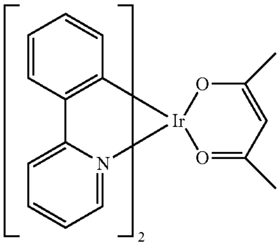
M-a15
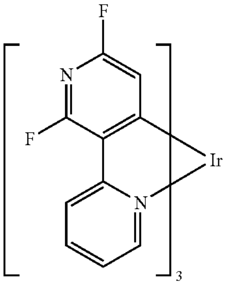
M-a16
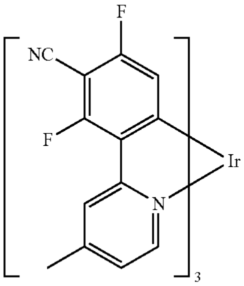
-continued
M-a17
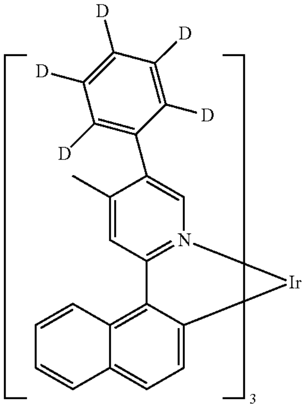
M-a18
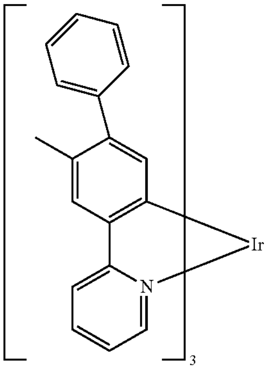
M-a19
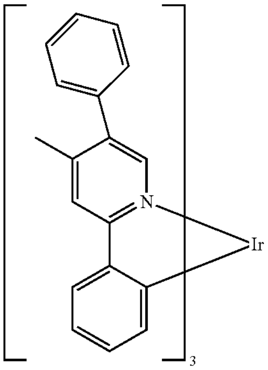
M-a20
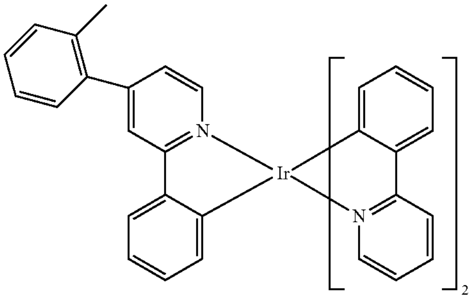

-continued

M-a21

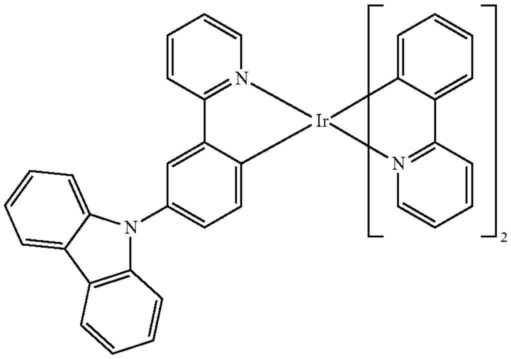

M-a22

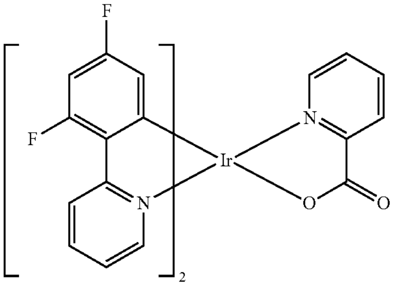

M-a23

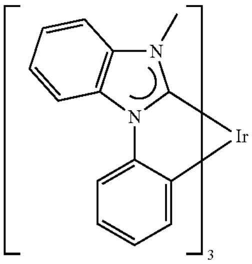

M-a24

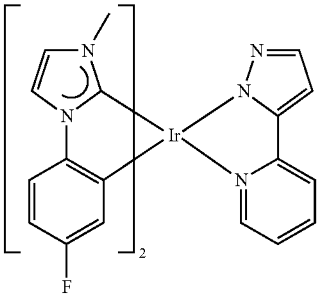

M-a25

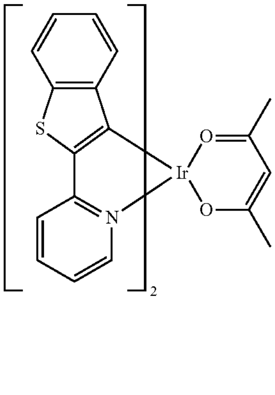

Formula M-b

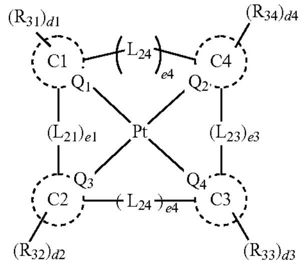

In Formula M-b, $Q_1$ to $Q_4$ may each independently be C or N, C1 to C4 may each independently be a substituted or unsubstituted hydrocarbon ring of 5 to 30 ring-forming carbon atoms, or a substituted or unsubstituted heterocycle of 2 to 30 ring-forming carbon atoms. $L_{21}$ to $L_{24}$ may each independently be a direct linkage,

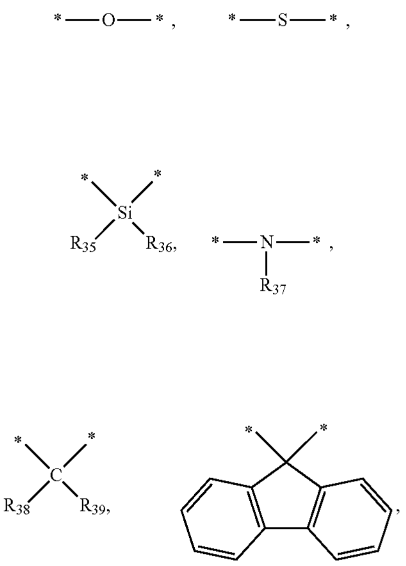

a substituted or unsubstituted divalent alkyl group of 1 to 20 carbon atoms, a substituted or unsubstituted arylene group of 6 to 30 ring-forming carbon atoms, or a substituted or unsubstituted heteroarylene group of 2 to 30 ring-forming carbon atoms, and e1 to e4 are each independently 0 or 1. $R_{31}$ to $R_{39}$ are each independently a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or combined with an adjacent group to form a ring, and d1 to d4 may each independently be an integer from 0 to 4.

The compound represented by Formula M-b may be used as a blue phosphorescence dopant or a green phosphorescence dopant.

The compound represented by Formula M-b may be represented by any one among the following compounds. However, the following compounds are merely examples, and the compound represented by Formula M-b is not limited to the compounds represented below.

M-b-1
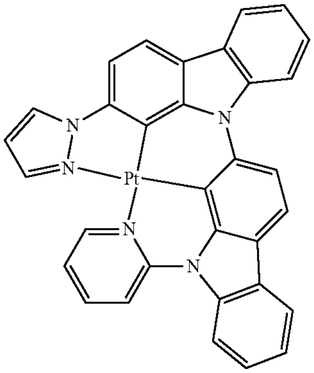
M-b-2
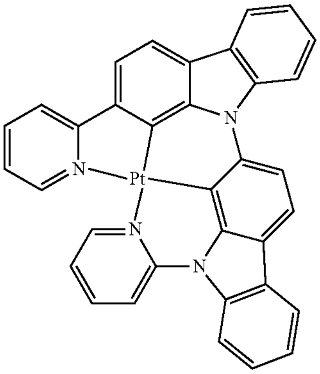
M-b-3
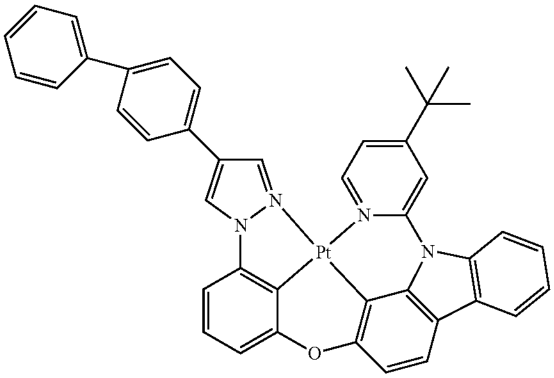
M-b-4
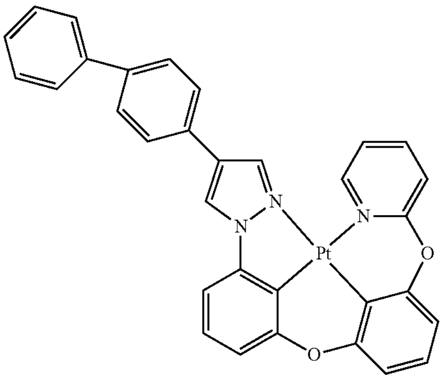
-continued
M-b-5
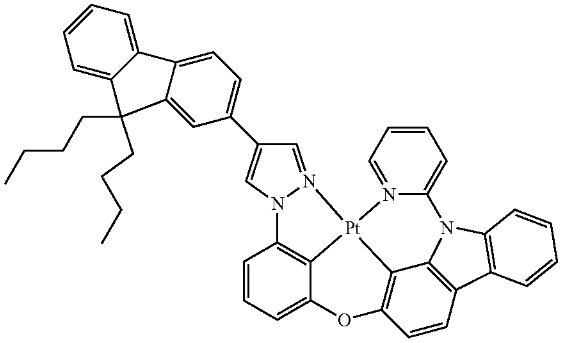
M-b-6
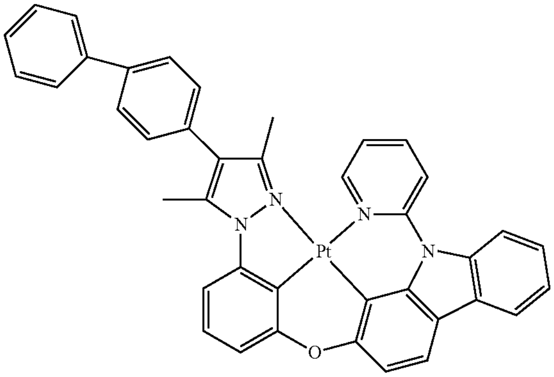
M-b-7
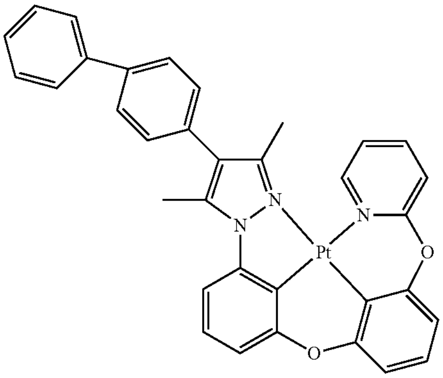
M-b-8
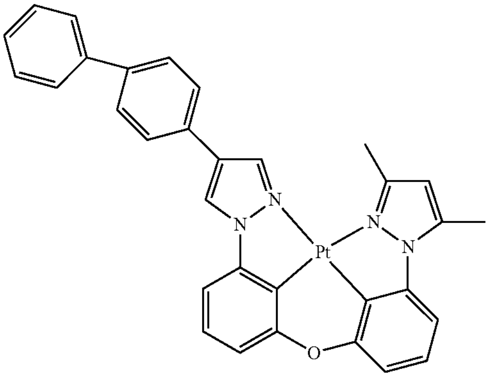

-continued

M-b-9

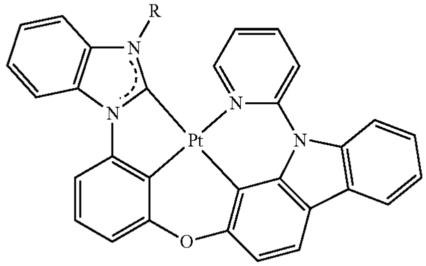

M-b-10

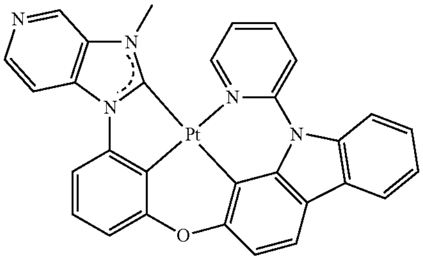

M-b-11

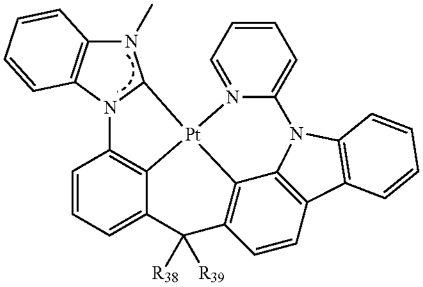

R, $R_{38}$, and $R_{39}$ may each independently be a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms.

The emission layer EML may include any one among Formula F-a to Formula F-c. The compounds represented by Formula F-a to Formula F-c may be used as fluorescence dopant materials.

Formula F-a

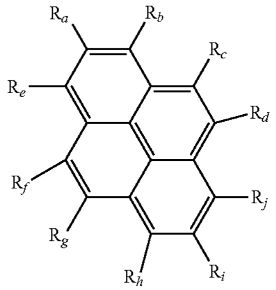

In Formula F-a, two selected from $R_a$ to $R_j$ may each independently be substituted with $*-NAr_1Ar_2$. The remainder not substituted with $*-NAr_1Ar_2$ among $R_a$ to $R_j$ may each independently be a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms.

In $*-NAr_1Ar_2$, $Ar_1$ and $Ar_2$ may each independently be a substituted or unsubstituted aryl group of 6 to 30 ring-forming carbon atoms, or a substituted or unsubstituted heteroaryl group of 2 to 30 ring-forming carbon atoms. For example, at least one among $Ar_1$ and $Ar_2$ may be a heteroaryl group including O or S as a ring-forming atom.

Formula F-b

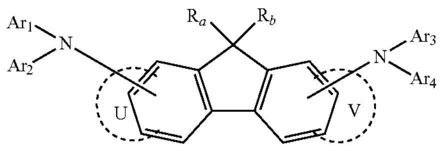

In Formula F-b, $R_a$ and $R_b$ may each independently be a hydrogen atom, a deuterium atom, a substituted or unsubstituted alkyl group of 1 to 20 carbon atoms, a substituted or unsubstituted alkenyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring. $Ar_1$ to $Ar_4$ may be each independently a substituted or unsubstituted aryl group of 6 to 30 ring-forming carbon atoms, or a substituted or unsubstituted heteroaryl group of 2 to 30 ring-forming carbon atoms.

In Formula F-b, U and V may each independently be a substituted or unsubstituted hydrocarbon ring of 5 to 30 ring-forming carbon atoms, or a substituted or unsubstituted heterocycle of 2 to 30 ring-forming carbon atoms. At least one among $Ar_1$ to $Ar_4$ may be a heteroaryl group including O or S as a ring-forming atom.

In Formula F-b, the number of rings represented by U and V may each independently be 0 or 1. For example, in Formula F-b, when the number of U or V is 1, one ring forms a fused ring at the designated part by U or V, and when the number of U or V is 0, a ring is not present at the designated part by U or V. For example, when the number of U is 0, and the number of V is 1, or when the number of U is 1, and the number of V is 0, a fused ring having the fluorene core of Formula F-b may be a ring compound with four rings. In some embodiments, when the number of both U and V is 0, the fused ring of Formula F-b may be a ring compound with three rings. In some embodiments, when the number of both U and V is 1, a fused ring having the fluorene core of Formula F-b may be a ring compound with five rings.

Formula F-c

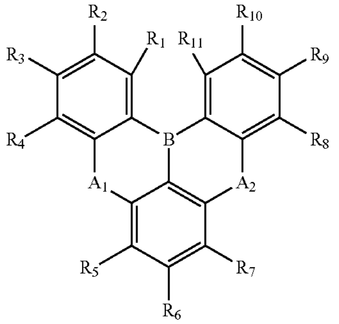

In Formula F-c, $A_1$ and $A_2$ may each independently be O, S, Se, or $NR_m$, and $R_m$ may be a hydrogen atom, a deuterium atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms. $R_1$ to $R_{11}$ may each independently be a hydrogen atom, a deuterium atom, a halogen atom, a cyano group, a substituted or unsubstituted amine group, a substituted or unsubstituted boryl group, a substituted or unsubstituted oxy group, a substituted or unsubstituted thio group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or combined with an adjacent group to form a ring.

In Formula F-c, $A_1$ and $A_2$ may each independently be combined with the substituents of an adjacent ring to form a fused ring. For example, if $A_1$ and $A_2$ may each independently be $NR_m$, $A_1$ may be combined with $R_4$ or $R_5$ to form a ring. In some embodiments, $A_2$ may be combined with $R_7$ or $R_8$ to form a ring.

In an embodiment, the emission layer EML may include as a generally used dopant material, styryl derivatives (for example, 1,4-bis[2-(3-N-ethylcarbazoryl)vinyl]benzene (BCzVB), 4-(di-p-tolylamino)-4'-[(di-p-tolylamino)styryl]stilbene (DPAVB), N-(4-((E)-2-(6-((E)-4-(diphenylamino)styryl)naphthalen-2-yl)vinyl)phenyl)-N-phenylbenzenamine (N-BDAVBi), and 4,4'-bis[2-(4-(N,N-diphenylamino)phenyl)vinyl]biphenyl (DPAVBi)), perylene and the derivatives thereof (for example, 2,5,8,11-tetra-t-butylperylene (TBP)), pyrene and the derivatives thereof (for example, 1,1-dipyrene, 1,4-dipyrenylbenzene, and 1,4-bis(N,N-diphenylamino)pyrene), etc.

The emission layer EML may include a generally used phosphorescence dopant material. For example, the phosphorescence dopant may use a metal complex including iridium (Ir), platinum (Pt), osmium (Os), gold (Au), titanium (Ti), zirconium (Zr), hafnium (Hf), europium (Eu), terbium (Tb) or thulium (Tm). For example, iridium(III) bis(4,6-difluorophenylpyridinato-N,C2')picolinate (Flrpic), bis(2,4-difluorophenylpyridinato)-tetrakis(1-pyrazolyl)borate iridium(III) (Fir6), or platinum octaethyl porphyrin (PtOEP) may be used as the phosphorescence dopant. However, an embodiment of the present disclosure is not limited thereto.

The emission layer EML may include a quantum dot material. The core of the quantum dot may be selected from among II-VI group compounds, III-VI group compounds, I-III-VI group compounds, III-V group compounds, III-II-V group compounds, IV-VI group compounds, IV group elements, IV group compounds, and one or more combinations thereof.

The II-VI group compound may be selected from the group including (e.g., consisting of) a binary compound selected from the group including (e.g., consisting of) CdSe, CdTe, CdS, ZnS, ZnSe, ZnTe, ZnO, HgS, HgSe, HgTe, MgSe, MgS, and mixtures thereof; a ternary compound selected from the group including (e.g., consisting of) CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, and mixtures thereof; and a quaternary compound selected from the group including (e.g., consisting of) HgZnTeS, CdZnSeS, CdZnSeTe, CdZnSTe, CdHgSeS, CdHgSeTe, CdHgSTe, HgZnSeS, HgZnSeTe, HgZnSTe, and one or more mixtures thereof.

The III-VI group compound may include a binary compound such as $In_2S_3$, and $In_2Se_3$, a ternary compound such as $InGaS_3$, and InGaSes, or one or more combinations thereof.

The I-III-VI group compound may be selected from a ternary compound selected from the group including (e.g., consisting of) AgInS, $AgInS_2$, CuInS, $CuInS_2$, $AgGaS_2$, $CuGaS_2$, $CuGaO_2$, $AgGaO_2$, $AgAlO_2$ and one or more mixtures thereof, or a quaternary compound such as $AgInGaS_2$, and $CuInGaS_2$.

The III-V group compound may be selected from the group including (e.g., consisting of) a binary compound selected from the group including (e.g., consisting of) GaN, GaP, GaAs, GaSb, AlN, AlP, AlAs, AlSb, InN, InP, InAs, InSb, and mixtures thereof, a ternary compound selected from the group including (e.g., consisting of) GaNP, GaNAs, GaNSb, GaPAs, GaPSb, AlNP, AlNAs, AlNSb, AlPAs, AlPSb, InGaP, InAlP, InNP, InNAs, InNSb, InPAs, InPSb, and one or more mixtures thereof, and a quaternary compound selected from the group including (e.g., consisting of) GaAlNP, GaAlNAs, GaAlNSb, GaAlPAs, GaAlPSb, GaInNP, GaInNAs, GalnNSb, GaInPAs, GalnPSb, InAlNP, InAlNAs, InAlNSb, InAlPAs, InAlPSb, and one or more mixtures thereof. In some embodiments, the III-V group compound may further include a II group metal. For example, InZnP, etc. may be selected as a III-II-V group compound.

The IV-VI group compound may be selected from the group including (e.g., consisting of) a binary compound selected from the group including (e.g., consisting of) SnS, SnSe, SnTe, PbS, PbSe, PbTe, and mixtures thereof, a ternary compound selected from the group including (e.g., consisting of) SnSeS, SnSeTe, SnSTe, PbSeS, PbSeTe, PbSTe, SnPbS, SnPbSe, SnPbTe, and one or more mixtures thereof, and a quaternary compound selected from the group including (e.g., consisting of) SnPbSSe, SnPbSeTe, SnPbSTe, and one or more mixtures thereof. The IV group element may be selected from the group including (e.g., consisting of) Si, Ge, and one or more mixtures thereof. The IV group compound may be a binary compound selected from the group including (e.g., consisting of) SiC, SiGe, and a mixture thereof.

In this embodiment, the binary compound, the ternary compound or the quaternary compound may be present at a substantially uniform concentration in a particle or may be present at a partially different concentration distribution state in the same particle. In some embodiments, a core/shell structure in which one quantum dot wraps another quantum dot may be possible. The interface of the core and the shell may have a concentration gradient in which the concentration of an element present in the shell is decreased toward the center.

In some embodiments, the quantum dot may have the above-described core-shell structure including a core including a nanocrystal and a shell wrapping the core. The shell of the quantum dot may play the role of a protection layer for preventing (or reducing) the chemical deformation of the core to maintain semiconductor properties and/or a charging layer for imparting the quantum dot with electrophoretic properties. The shell may have a single layer or a multilayer. Examples of the shell of the quantum dot may include a metal or non-metal oxide, a semiconductor compound, or one or more combinations thereof.

For example, the metal or non-metal oxide may include a binary compound such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$ and/or NiO, or a ternary compound such as $MgAl_2O_4$, $CoFe_2O_4$, $NiFe_2O_4$ and/or $CoMn_2O_4$, but an embodiment of the present disclosure is not limited thereto.

In some embodiments, the semiconductor compound may include CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, etc., but an embodiment of the present disclosure is not limited thereto.

The quantum dot may have a full width of half maximum (FWHM) of emission wavelength spectrum of about 45 nm or less, about 40 nm or less, or about 30 nm or less. Within the foregoing ranges, color purity or color reproducibility may be improved (increased). In some embodiments, light emitted via such a quantum dot is emitted in all directions, and light view angle properties may be improved.

In some embodiments, the shape of the quantum dot may be shapes generally used in the art, without specific limitation. For example, the shape of a substantially spherical, pyramidal, multi-arm, or cubic nanoparticle, nanotube, nanowire, nanofiber, nanoplate particle, etc. may be used.

The quantum dot may control the color of light emitted according to the particle size, and accordingly, the quantum dot may have one or more suitable emission colors such as blue, red and green.

In the light emitting devices ED of embodiments, as shown in FIG. 3 to FIG. 6, the electron transport region ETR is provided on the emission layer EML. The electron transport region ETR may include at least one of an electron blocking layer HBL, an electron transport layer ETL or an electron injection layer EIL. However, an embodiment of the present disclosure is not limited thereto.

The electron transport region ETR may have a single layer formed using a single material, a single layer formed using multiple different materials, or a multilayer structure having multiple layers formed using multiple different materials.

For example, the electron transport region ETR may have a single layer structure of an electron injection layer EIL or an electron transport layer ETL, or a single layer structure formed using an electron injection material and an electron transport material. Further, the electron transport region ETR may have a single layer structure formed using multiple different materials, or a structure stacked from the emission layer EML of electron transport layer ETL/electron injection layer EIL, or hole blocking layer HBL/electron transport layer ETL/electron injection layer EIL, without limitation. The thickness of the electron transport region ETR may be, for example, from about 1,000 Å to about 1,500 Å.

The electron transport region ETR may be formed using one or more suitable methods such as a vacuum deposition method, a spin coating method, a cast method, a Langmuir-Blodgett (LB) method, an inkjet printing method, a laser printing method, and a laser induced thermal imaging (LITI) method.

The electron transport region ETR may include a compound represented by Formula ET-1.

Formula ET-1

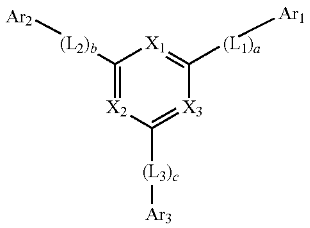

In Formula ET-1, at least one among $X_1$ to $X_3$ is N, and the remainder are $CR_a$. $R_a$ may be a hydrogen atom, a deuterium atom, a substituted or unsubstituted alkyl of 1 to 20 carbon atoms, a substituted or unsubstituted aryl group of 6 to 30 ring-forming carbon atoms, or a substituted or unsubstituted heteroaryl group of 2 to 30 ring-forming carbon atoms. $Ar_1$ to $Ar_3$ may be each independently a hydrogen atom, a deuterium atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms.

In Formula ET-1, "a" to "c" may each independently be an integer from 0 to 10. In Formula ET-1, $L_1$ to $L_3$ may each independently be a direct linkage, a substituted or unsubstituted arylene group of 6 to 30 ring-forming carbon atoms, or a substituted or unsubstituted heteroarylene group of 2 to 30 ring-forming carbon atoms. In some embodiments, when "a" to "c" are integers of 2 or more, $L_1$ to $L_3$ may each independently be a substituted or unsubstituted arylene group of 6 to 30 ring-forming carbon atoms, or a substituted or unsubstituted heteroarylene group of 2 to 30 ring-forming carbon atoms.

The electron transport region ETR may include an anthracene-based compound. However, an embodiment of the present disclosure is not limited thereto, and the electron transport region ETR may include, for example, tris(8-hydroxyquinolinato)aluminum ($Alq_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), berylliumbis(benzoquinolin-10-olate ($Bebq_2$), 9,10-di(naphthalene-2-yl)anthracene (ADN), 1,3-bis[3,5-di(pyridin-3-yl)phenyl]benzene (BmPyPhB), and/or one or more mixtures thereof, without limitation.

The electron transport region ETR may include at least one among Compounds ET1 to ET36.

ET1
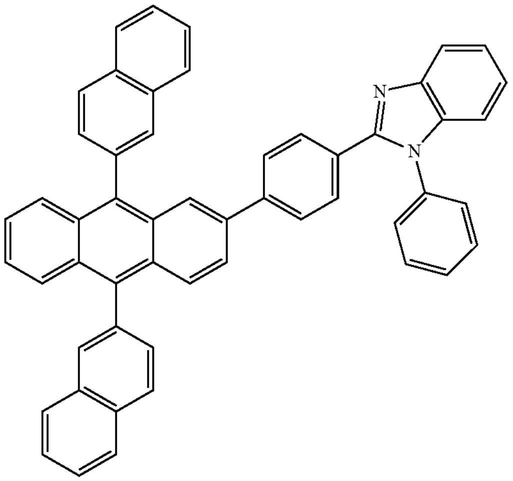
ET2
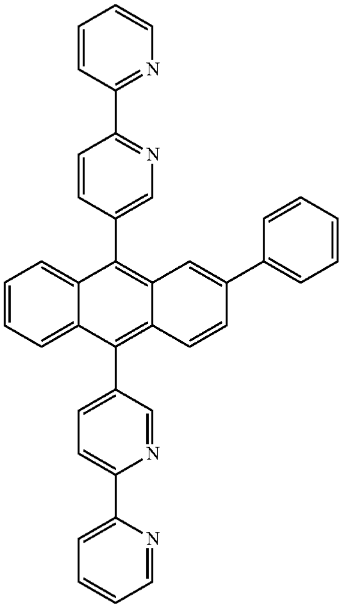
ET3
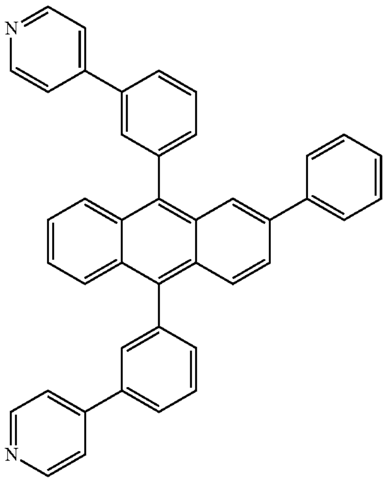
-continued
ET4
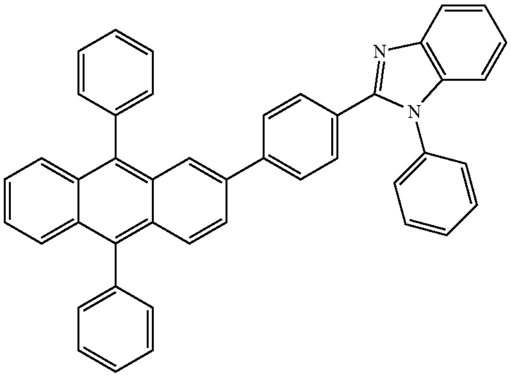
ET5
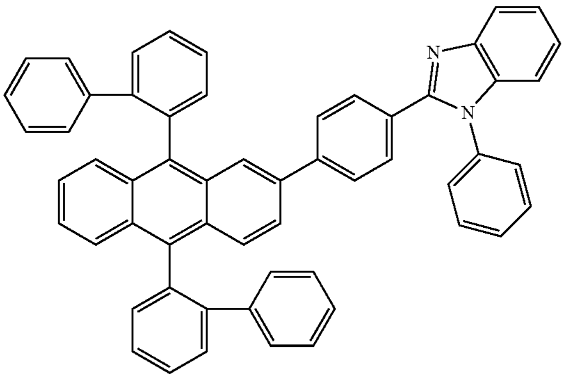
ET6
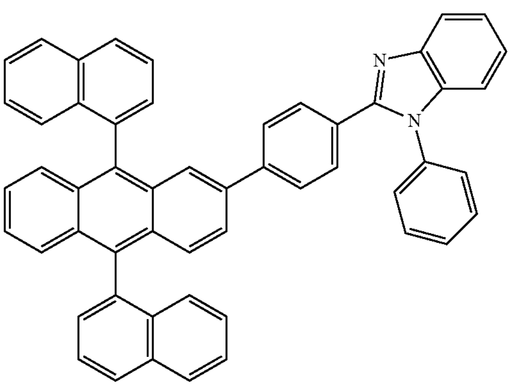

-continued
ET7
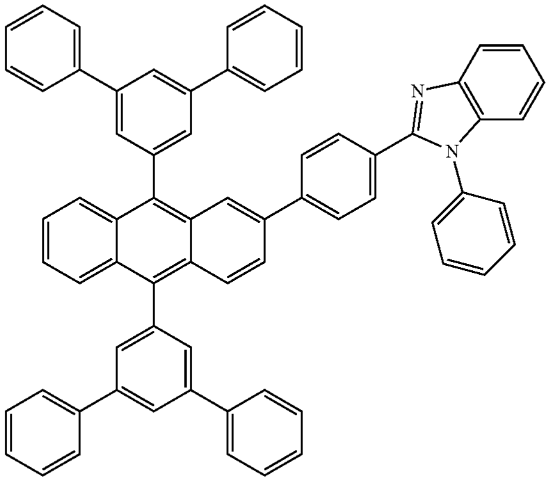
ET8
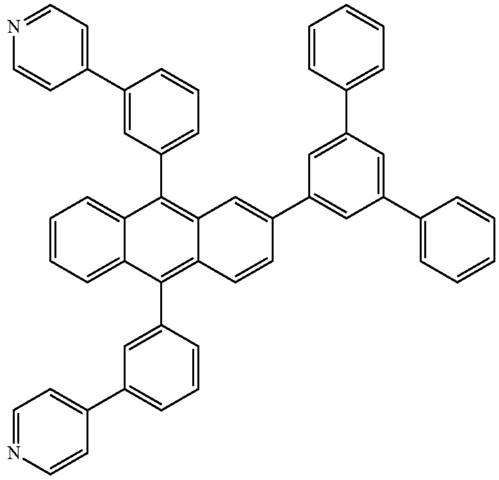
ET9
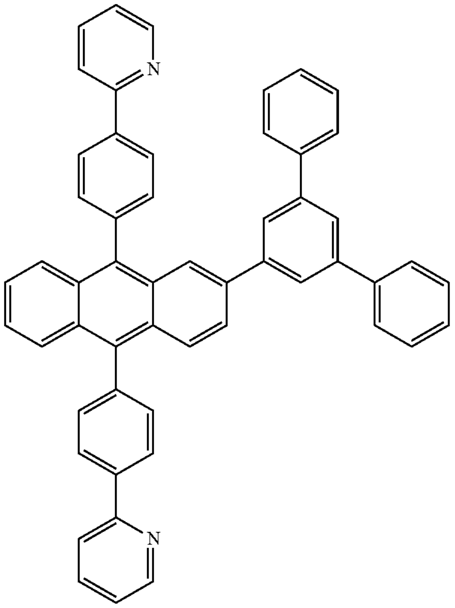
-continued
ET10
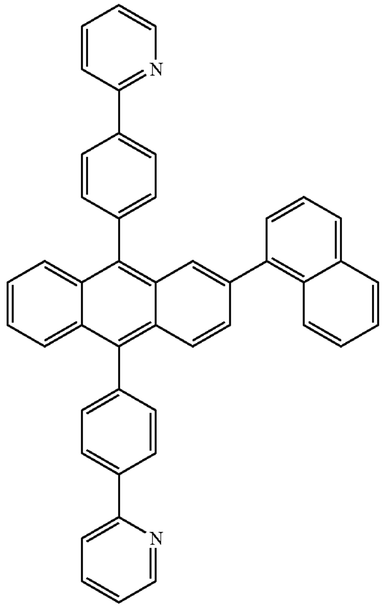
ET11
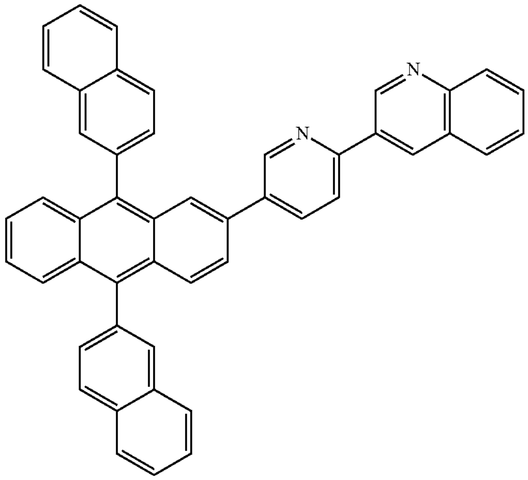
ET12
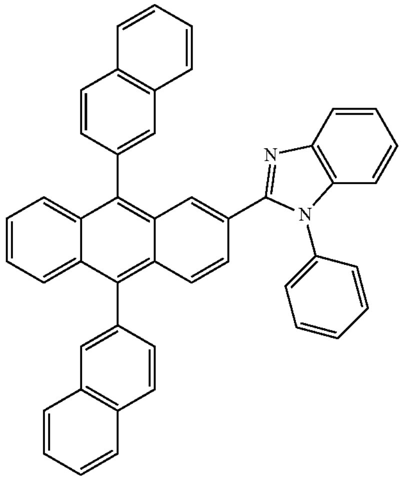

-continued
ET13
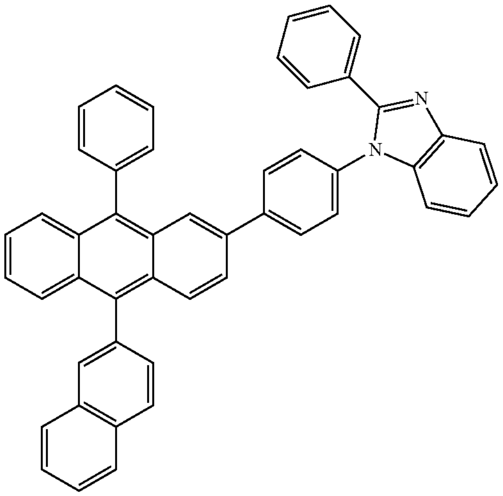
ET14
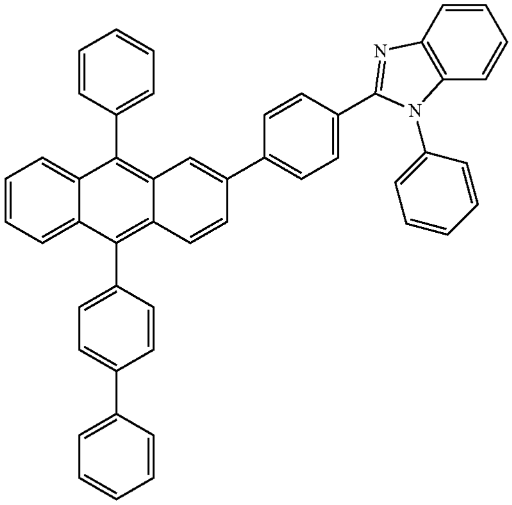
ET15
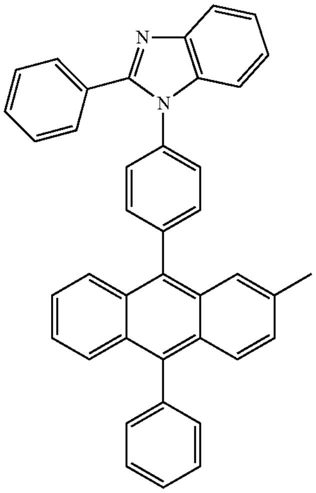
-continued
ET16
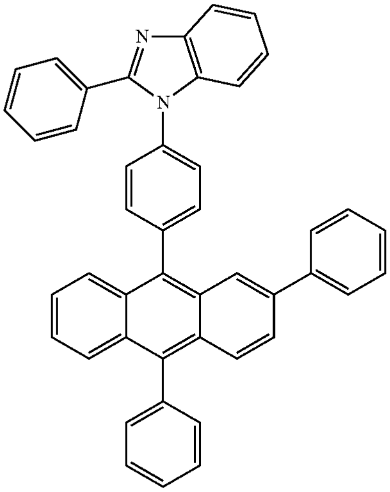
ET17
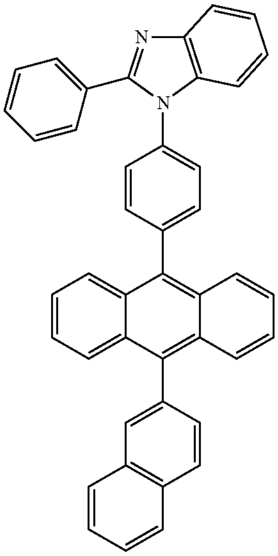
ET18
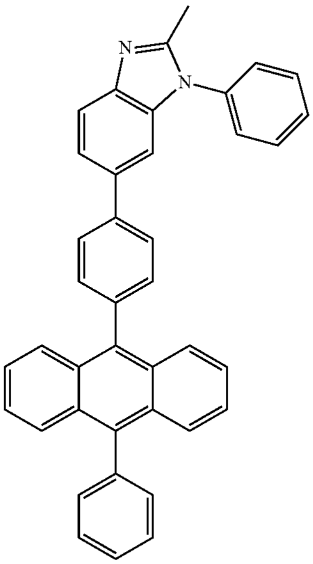

-continued
ET19
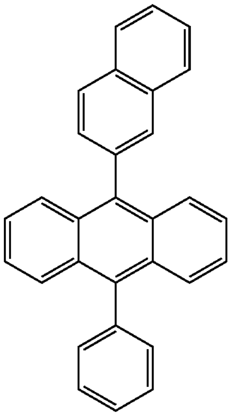
ET20
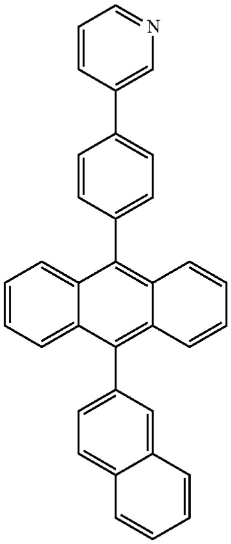
ET21
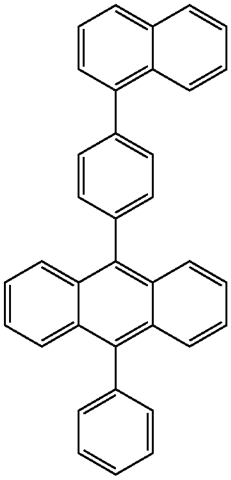
-continued
ET22
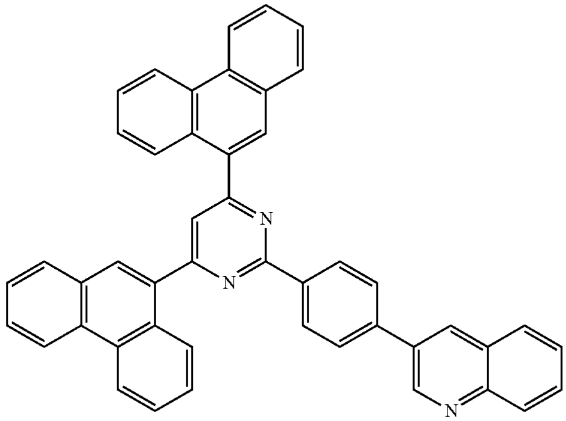
ET23
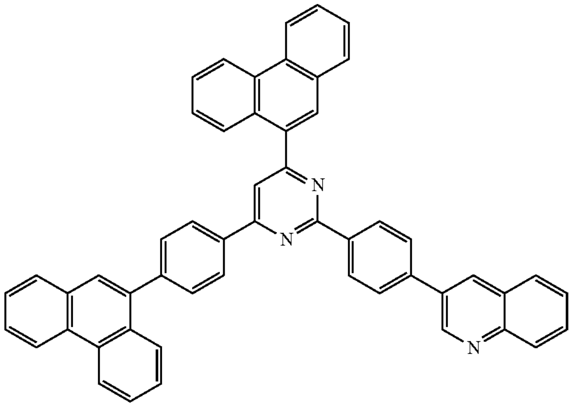
ET24
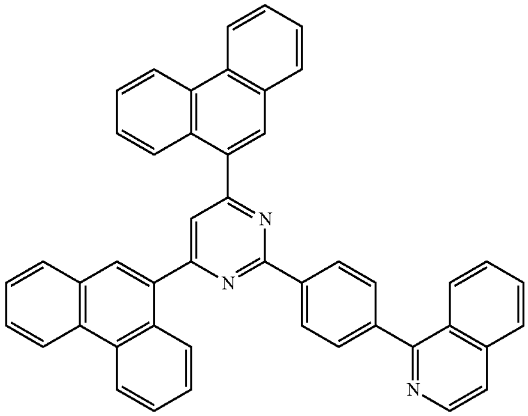

-continued
ET25
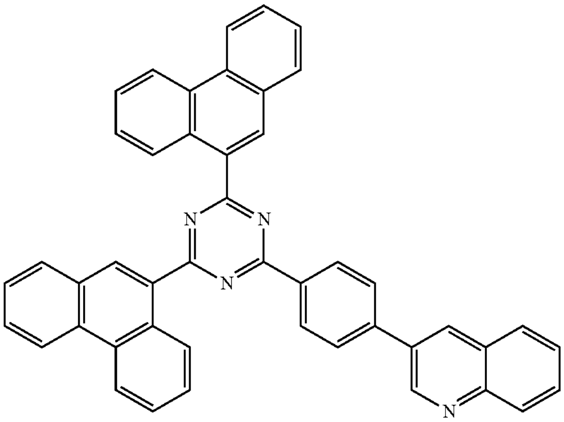
ET26
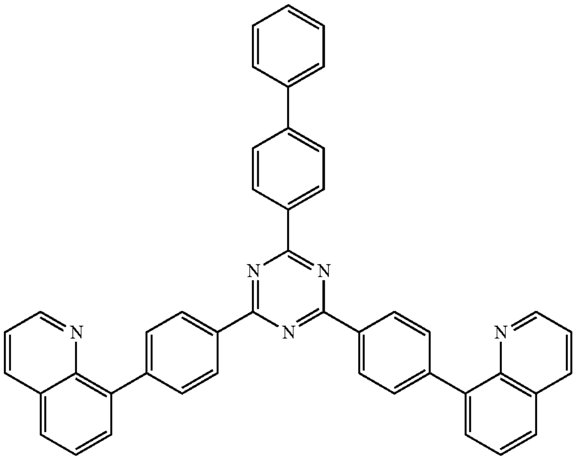
ET27
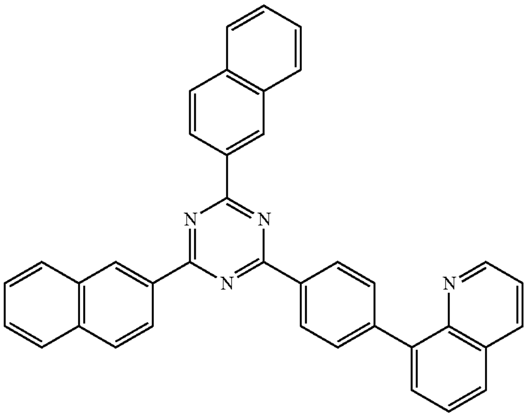
-continued
ET28
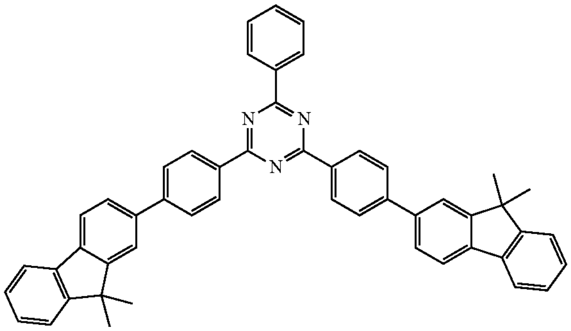
ET29
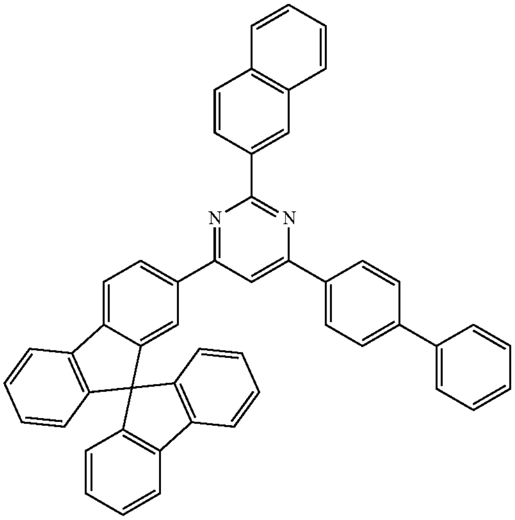
ET30
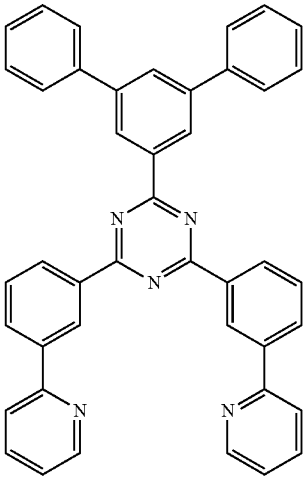

-continued

ET31

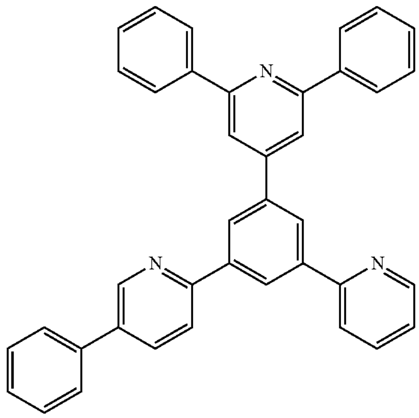

ET32

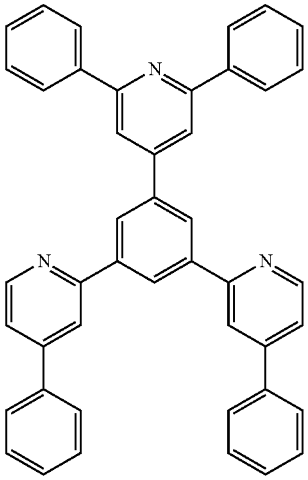

ET33

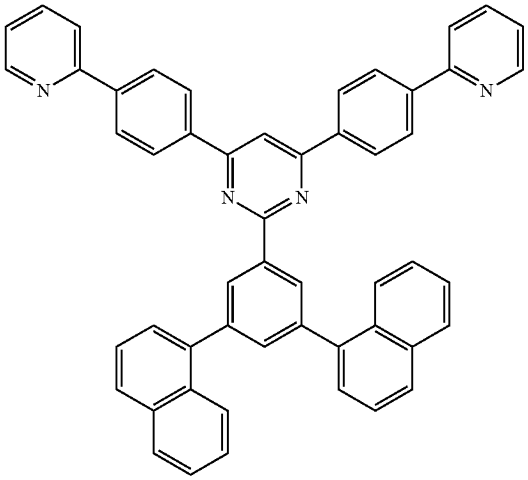

-continued

ET34

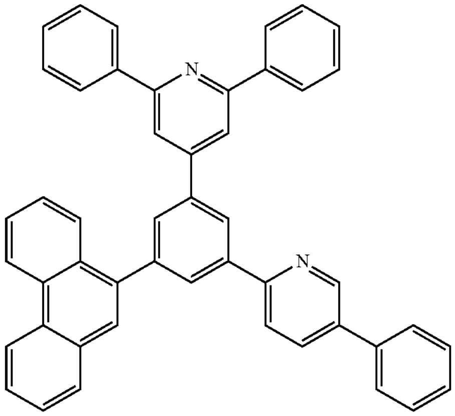

ET35

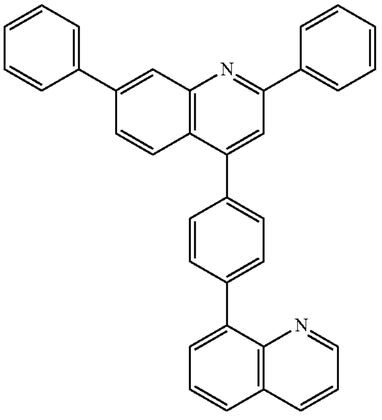

ET36

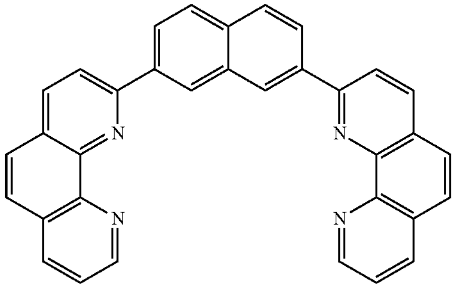

In some embodiments, the electron transport region ETR may include a metal halide such as LiF, NaCl, CsF, RbCl, RbI, CuI and/or KI, a metal in lanthanoides such as Yb, and/or a co-depositing material of the metal halide and/or the metal in lanthanoides. For example, the electron transport region ETR may include KI:Yb, RbI:Yb, LiF:Yb, etc., as the co-depositing material. In some embodiments, the electron transport region ETR may use a metal oxide such as $Li_2O$ and BaO, or 8-hydroxy-lithium quinolate (Liq). However, an embodiment of the present disclosure is not limited thereto. The electron transport region ETR also may be formed using a mixture material of an electron transport material and an insulating organo metal salt. The organo metal salt may be a material having an energy band gap of about 4 eV or more. For example, the organo metal salt may include, for example, metal acetates, metal benzoates, metal acetoacetates, metal acetylacetonates, and/or metal stearates.

The electron transport region ETR may include at least one of 2,9-dimethyl-4,7-diphenyl-1,10-phenanthroline (BCP), diphenyl(4-(triphenylsilyl)phenyl)phosphine oxide (TSPO1), or 4,7-diphenyl-1,10-phenanthroline (Bphen) in addition to the aforementioned materials. However, an embodiment of the present disclosure is not limited thereto.

The electron transport region ETR may include the compounds of the electron transport region in at least one selected from among an electron injection layer EIL, an electron transport layer ETL, and a hole blocking layer HBL.

When the electron transport region ETR includes the electron transport layer ETL, the thickness of the electron transport layer ETL may be from about 100 Å to about 1,000 Å, for example, from about 150 Å to about 500 Å. When the thickness of the electron transport layer ETL satisfies the above-described ranges, satisfactory (suitable) electron transport properties may be obtained without substantial increase of a driving voltage. When the electron transport region ETR includes the electron injection layer EIL, the thickness of the electron injection layer EIL may be from about 1 Å to about 100 Å, and from about 3 Å to about 90 Å. When the thickness of the electron injection layer EIL satisfies the above described ranges, satisfactory (suitable) electron injection properties may be obtained without inducing substantial increase of a driving voltage.

The second electrode EL2 may be provided on the electron transport region ETR. The second electrode EL2 may be a common electrode. The second electrode EL2 may be a cathode or an anode, but an embodiment of the present disclosure is not limited thereto. For example, when the first electrode EL1 is an anode, the second cathode EL2 may be a cathode, and when the first electrode EL1 is a cathode, the second electrode EL2 may be an anode.

The second electrode EL2 may be a transmissive electrode, a transflective electrode or a reflective electrode. When the second electrode EL2 is the transmissive electrode, the second electrode EL2 may include a transparent metal oxide, for example, ITO, IZO, ZnO, ITZO, etc.

When the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, Yb, W, one or more compounds including thereof, or one or more mixtures thereof (for example, AgMg, AgYb, or MgAg). Or, the second electrode EL2 may have a multilayered structure including a reflective layer or a transflective layer formed using the above-described materials and a transparent conductive layer formed using ITO, IZO, ZnO, ITZO, etc. For example, the second electrode EL2 may include the aforementioned metal materials, combinations of two or more metal materials selected from the aforementioned metal materials, or oxides of the aforementioned metal materials.

The second electrode EL2 may be connected with an auxiliary electrode. When the second electrode EL2 is connected with the auxiliary electrode, the resistance of the second electrode EL2 may decrease.

In some embodiments, on the second electrode EL2 in the light emitting device ED of an embodiment, a capping layer CPL may be further disposed. The capping layer CPL may include a multilayer or a single layer.

In an embodiment, the capping layer CPL may be an organic layer or an inorganic layer. For example, if the capping layer CPL includes an inorganic material, the inorganic material may include an alkali metal compound such as LiF, an alkaline earth metal compound such as $MgF_2$, SiON, SiNx, SiOy, etc.

For example, if the capping layer CPL includes an organic material, the organic material may include 2,2'-dimethyl-N,N'-di-[(1-naphthyl)-N,N'-diphenyl]-1,1'-biphenyl-4,4'-diamine (α-NPD), NPB, TPD, m-MTDATA, Alq3, CuPc, N4,N4,N4',N4'-tetra(biphenyl-4-yl) biphenyl-4,4'-diamine (TPD15), 4,4',4"-tris(carbazol-9-yl) triphenylamine (TCTA), etc., or includes an epoxy resin, or acrylate such as methacrylate. In addition, a capping layer CPL may include at least one among Compounds P1 to P5, but an embodiment of the present disclosure is not limited thereto.

P1

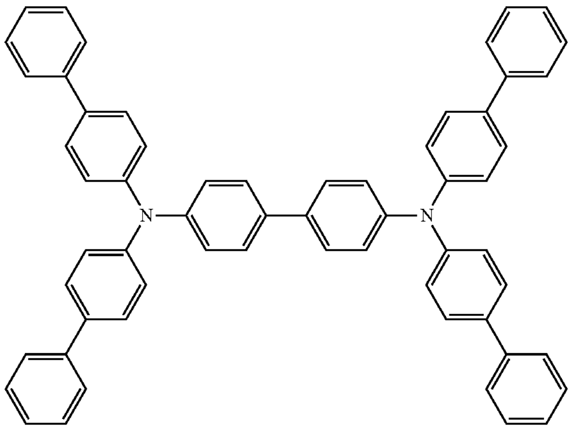

P2

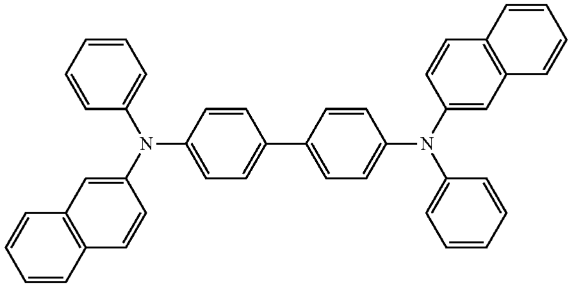

P3

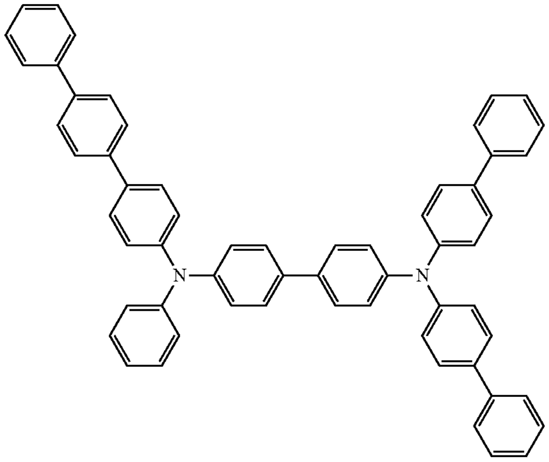

-continued

P4

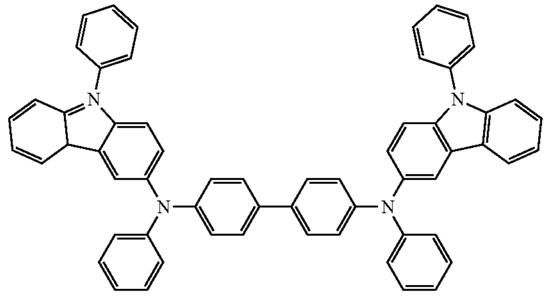

P5

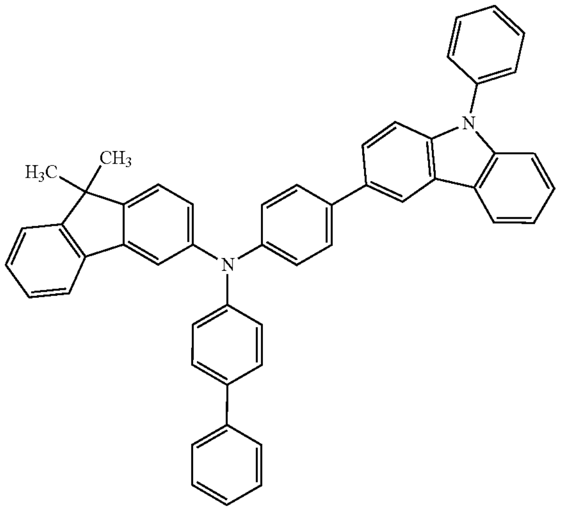

In some embodiments, the refractive index of the capping layer CPL may be about 1.6 or more. For example, the refractive index of the capping layer CPL with respect to light in a wavelength range of about 550 nm to about 660 nm may be about 1.6 or more.

Figure 7:
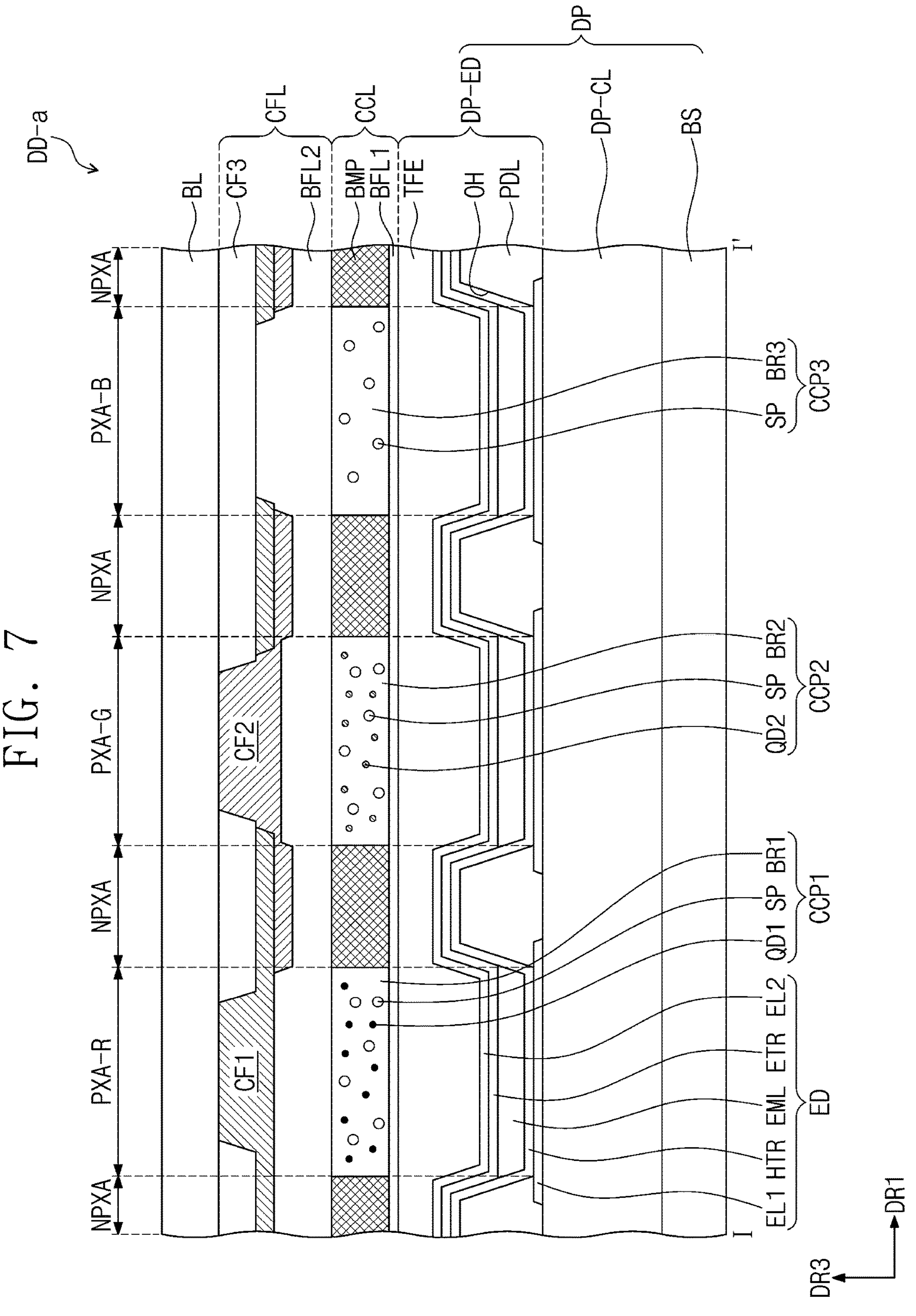
FIG. 7 is a cross-sectional view of a display apparatus according to an embodiment.
Figure 8:
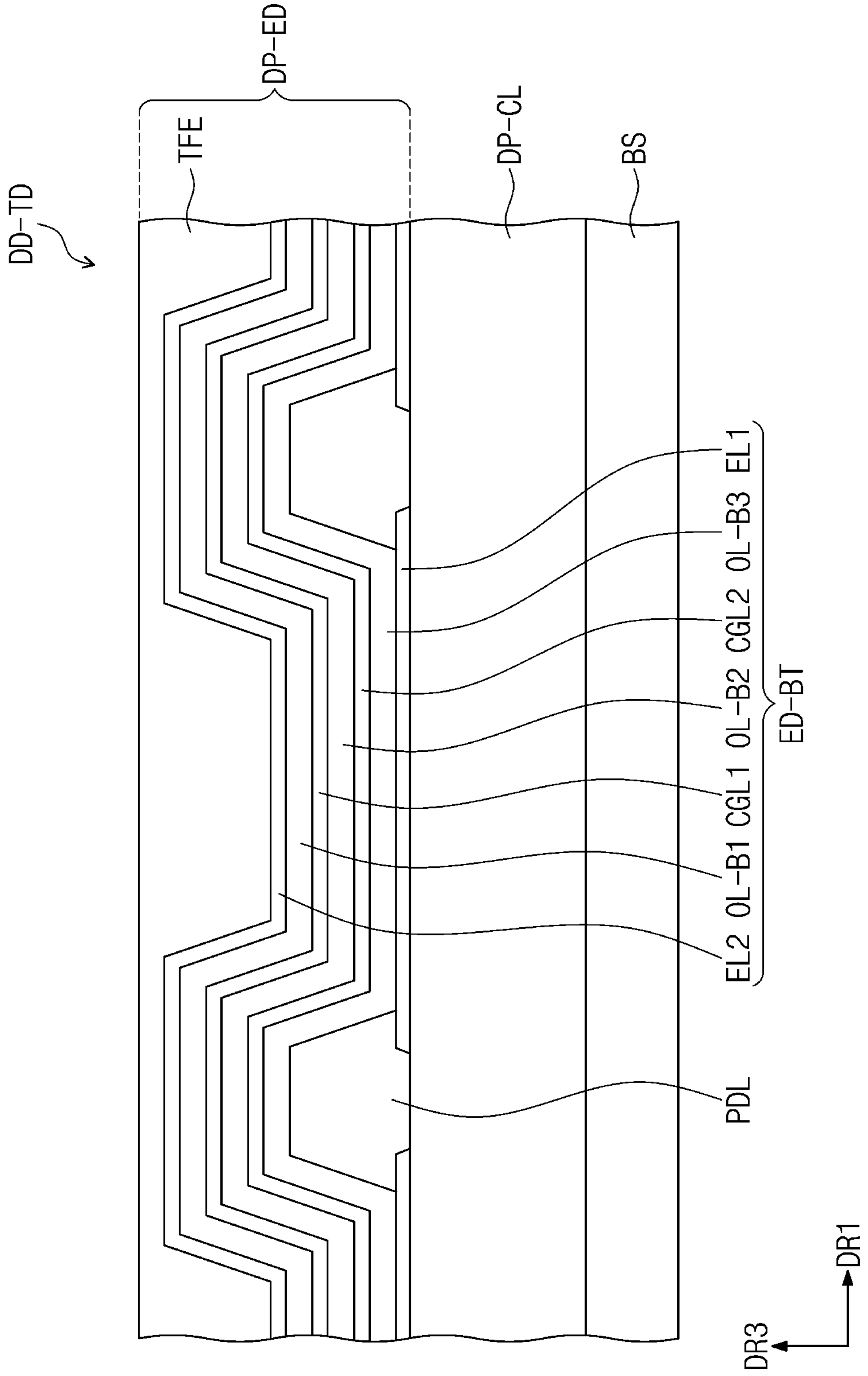
FIG. 8 is a cross-sectional view of a display apparatus according to an embodiment.

FIG. 7 and FIG. 8 are cross-sectional views on display apparatuses according to embodiments. In the explanation on the display apparatuses of embodiments, referring to FIG. 7 and FIG. 8, the overlapping parts with the explanation on FIG. 1 to FIG. 6 may not be explained again, and the different features will primarily be explained.

Referring to FIG. 7, the display apparatus DD according to an embodiment may include a display panel DP including a display device layer DP-ED, a light controlling layer CCL on the display panel DP and a color filter layer CFL.

In an embodiment shown in FIG. 7, the display panel DP includes a base layer BS, a circuit layer DP-CL provided on the base layer BS and a display device layer DP-ED, and the display device layer DP-ED may include a light emitting device ED.

The light emitting device ED may include a first electrode EL1, a hole transport region HTR on the first electrode EL1, an emission layer EML on the hole transport region HTR, an electron transport region ETR on the emission layer EML, and a second electrode EL2 on the electron transport region ETR. In some embodiments, substantially the same structures of the light emitting devices of FIG. 3 to FIG. 6 may be applied to the structure of the light emitting device ED shown in FIG. 7.

Referring to FIG. 7, the emission layer EML may be in an opening part OH defined in a pixel definition layer PDL. For example, the emission layer EML divided by the pixel definition layer PDL and correspondingly provided to each of luminous areas PXA-R, PXA-G and PXA-B may emit light in substantially the same wavelength region. In the display apparatus DD of an embodiment, the emission layer EML may emit blue light. In some embodiments, the emission layer EML may be provided as a common layer for all luminous areas PXA-R, PXA-G and PXA-B.

The light controlling layer CCL may be on the display panel DP. The light controlling layer CCL may include a light converter. The light converter may be a quantum dot or a phosphor. The light converter may transform the wavelength of light provided and then emit the light. For example, the light controlling layer CCL may be a layer including a quantum dot or a layer including a phosphor.

The light controlling layer CCL may include multiple light controlling parts CCP1, CCP2 and CCP3. The light controlling parts CCP1, CCP2 and CCP3 may be separated from one another.

Referring to FIG. 7, a partition pattern BMP may be between the separated light controlling parts CCP1, CCP2 and CCP3, but an embodiment of the present disclosure is not limited thereto. In FIG. 7, the partition pattern BMP is shown not to be overlapped with the light controlling parts CCP1, CCP2 and CCP3, but at least a portion of the edge of the light controlling parts CCP1, CCP2 and CCP3 may be overlapped with the partition pattern BMP.

The light controlling layer CCL may include a first light controlling part CCP1 including a first quantum dot QD1 converting first color light provided from the light emitting device ED into second color light, a second light controlling part CCP2 including a second quantum dot QD2 converting first color light into third color light, and a third light controlling part CCP3 transmitting first color light.

In an embodiment, the first light controlling part CCP1 may provide red light which is the second color light, and the second light controlling part CCP2 may provide green light which is the third color light. The third color controlling part CCP3 may transmit and provide blue light which is the first color light provided from the light emitting device ED. For example, the first quantum dot QD1 may be a red quantum dot, and the second quantum dot QD2 may be a green quantum dot. For the quantum dots QD1 and QD2, substantially the same contents (materials/criteria) as those described above may be applied.

In some embodiments, the light controlling layer CCL may further include a scatterer SP. The first light controlling part CCP1 may include the first quantum dot QD1 and the scatterer SP, the second light controlling part CCP2 may include the second quantum dot QD2 and the scatterer SP, and the third light controlling part CCP3 may not include (e.g., may exclude) a quantum dot but include the scatterer SP.

The scatterer SP may be an inorganic particle. For example, the scatterer SP may include at least one selected from among $TiO_2$, ZnO, $Al_2O_3$, $SiO_2$, and hollow silica. The scatterer SP may include at least one selected from among $TiO_2$, ZnO, $Al_2O_3$, $SiO_2$, and hollow silica, or may be a mixture or mixtures of two or more materials selected from among $TiO_2$, ZnO, $Al_2O_3$, $SiO_2$, and hollow silica.

Each of the first light controlling part CCP1, the second light controlling part CCP2, and the third light controlling part CCP3 may include base resins BR1, BR2 and BR3 dispersing the quantum dots QD1 and QD2 and the scatterer SP. In an embodiment, the first light controlling part CCP1 may include the first quantum dot QD1 and the scatterer SP dispersed in the first base resin BR1, the second light controlling part CCP2 may include the second quantum dot QD2 and the scatterer SP dispersed in the second base resin BR2, and the third light controlling part CCP3 may include the scatterer particle SP dispersed in the third base resin BR3. The base resins BR1, BR2 and BR3 are mediums in which the quantum dots QD1 and QD2 and the scatterer SP are dispersed, and may be composed of one or more suitable resin compositions which may be generally referred to as a binder. For example, the base resins BR1, BR2 and BR3 may be acrylic resins, urethane-based resins, silicone-based resins, epoxy-based resins, etc. The base resins BR1, BR2 and BR3 may be transparent resins. In an embodiment, the first base resin BR1, the second base resin BR2 and the third base resin BR3 may be the same or different from each other.

The light controlling layer CCL may include a barrier layer BFL1. The barrier layer BFL1 may play the role of blocking (reducing) the penetration of moisture and/or oxygen (hereinafter, will be referred to as "humidity/oxygen"). The barrier layer BFL1 may be on the light controlling parts CCP1, CCP2 and CCP3 to block (reduce) the exposure of the light controlling parts CCP1, CCP2 and CCP3 to humidity/oxygen. In some embodiments, the barrier layer BFL1 may cover the light controlling parts CCP1, CCP2 and CCP3. In some embodiments, the barrier layer BFL2 may be provided between the light controlling parts CCP1, CCP2 and CCP3 and a color filter layer CFL.

The barrier layers BFL1 and BFL2 may include at least one inorganic layer. For example, the barrier layers BFL1 and BFL2 may be formed by including an inorganic material. For example, the barrier layers BFL1 and BFL2 may be formed by including silicon nitride, aluminum nitride, zirconium nitride, titanium nitride, hafnium nitride, tantalum nitride, silicon oxide, aluminum oxide, titanium oxide, tin oxide, cerium oxide and/or silicon oxynitride and/or a metal thin film securing light transmittance. In some embodiments, the barrier layers BFL1 and BFL2 may further include an organic layer. The barrier layers BFL1 and BFL2 may be composed of a single layer of multiple layers.

In the display apparatus DD of an embodiment, the color filter layer CFL may be on the light controlling layer CCL. For example, the color filter layer CFL may be directly on the light controlling layer CCL. In this embodiment, the barrier layer BFL2 may not be provided.

The color filter layer CFL may include a light blocking part BM and filters CF1, CF2 and CF3. The color filter layer CFL may include a first filter CF1 transmitting a second color light, a second filter CF2 transmitting a third color light, and a third filter CF3 transmitting a first color light. For example, the first filter CF1 may be a red filter, the second filter CF2 may be a green filter, and the third filter CF3 may be a blue filter. Each of the filters CF1, CF2 and CF3 may include a polymer photosensitive resin and a pigment or dye. The first filter CF1 may include a red pigment or dye, the second filter CF2 may include a green pigment or dye, and the third filter CF3 may include a blue pigment or dye. Although, an embodiment of the present disclosure is not limited thereto, and the third filter CF3 may not include the pigment or dye. The third filter CF3 may include a polymer photosensitive resin and not include (e.g., may exclude) a pigment or dye. The third filter CF3 may be transparent. The third filter CF3 may be formed using a transparent photosensitive resin.

In some embodiments, the first filter CF1 and the second filter CF2 may be yellow filters. The first filter CF1 and the second filter CF2 may be provided in one body without distinction.

The light blocking part BM may be a black matrix. The light blocking part BM may be formed by including an organic light blocking material or an inorganic light blocking material including a black pigment or black dye. The light blocking part BM may prevent (reduce) a light leakage phenomenon and divide the boundaries among adjacent filters CF1, CF2 and CF3. In some embodiments, the light blocking part BM may be formed as a blue filter.

Each of the first to third filters CF1, CF2 and CF3 may be disposed corresponding to each of a red luminous area PXA-R, green luminous area PXA-G, and blue luminous area PXA-B.

On the color filter layer CFL, a base substrate BL may be disposed. The base substrate BL may be a member providing a base surface on which the color filter layer CFL, the light controlling layer CCL, etc. are disposed. The base substrate BL may be a glass substrate, a metal substrate, a plastic substrate, etc. However, an embodiment of the present disclosure is not limited thereto, and the base substrate BL may be an inorganic layer, an organic layer or a composite material layer. In some embodiments, the base substrate BL may not be provided.

FIG. 8 is a cross-sectional view showing a portion of the display apparatus according to an embodiment. FIG. 8 shows the cross-sectional view of a part corresponding to the display panel DP of FIG. 7. In a display apparatus DD-TD of an embodiment, the light emitting device ED-BT may include multiple light emitting structures OL-B1, OL-B2 and OL-B3. The light emitting device ED-BT may include oppositely disposed first electrode EL1 and second electrode EL2, and the multiple light emitting structures OL-B1, OL-B2 and OL-B3 stacked in order in a thickness direction and provided between the first electrode EL1 and the second electrode EL2. Each of the light emitting structures OL-B1, OL-B2 and OL-B3 may include an emission layer EML (FIG. 7), and a hole transport region HTR and an electron transport region ETR disposed with the emission layer EML (FIG. 7) therebetween.

For example, the light emitting device ED-BT included in the display apparatus DD-TD of an embodiment may be a light emitting device of a tandem structure including multiple emission layers.

In an embodiment shown in FIG. 8, light emitted from the light emitting structures OL-B1, OL-B2 and OL-B3 may be all blue light. However, an embodiment of the present disclosure is not limited thereto, and the wavelength regions of light emitted from the light emitting structures OL-B1, OL-B2 and OL-B3 may be different from each other. For example, the light emitting device ED-BT including the multiple light emitting structures OL-B1, OL-B2 and OL-B3 emitting light in different wavelength regions may emit white light.

Between neighboring light emitting structures OL-B1, OL-B2 and OL-B3, a charge generating layer CGL may be disposed. The charge generating layer CGL may include a p-type (kind) charge generating layer and/or an n-type (kind) charge generating layer.

Figure 9:
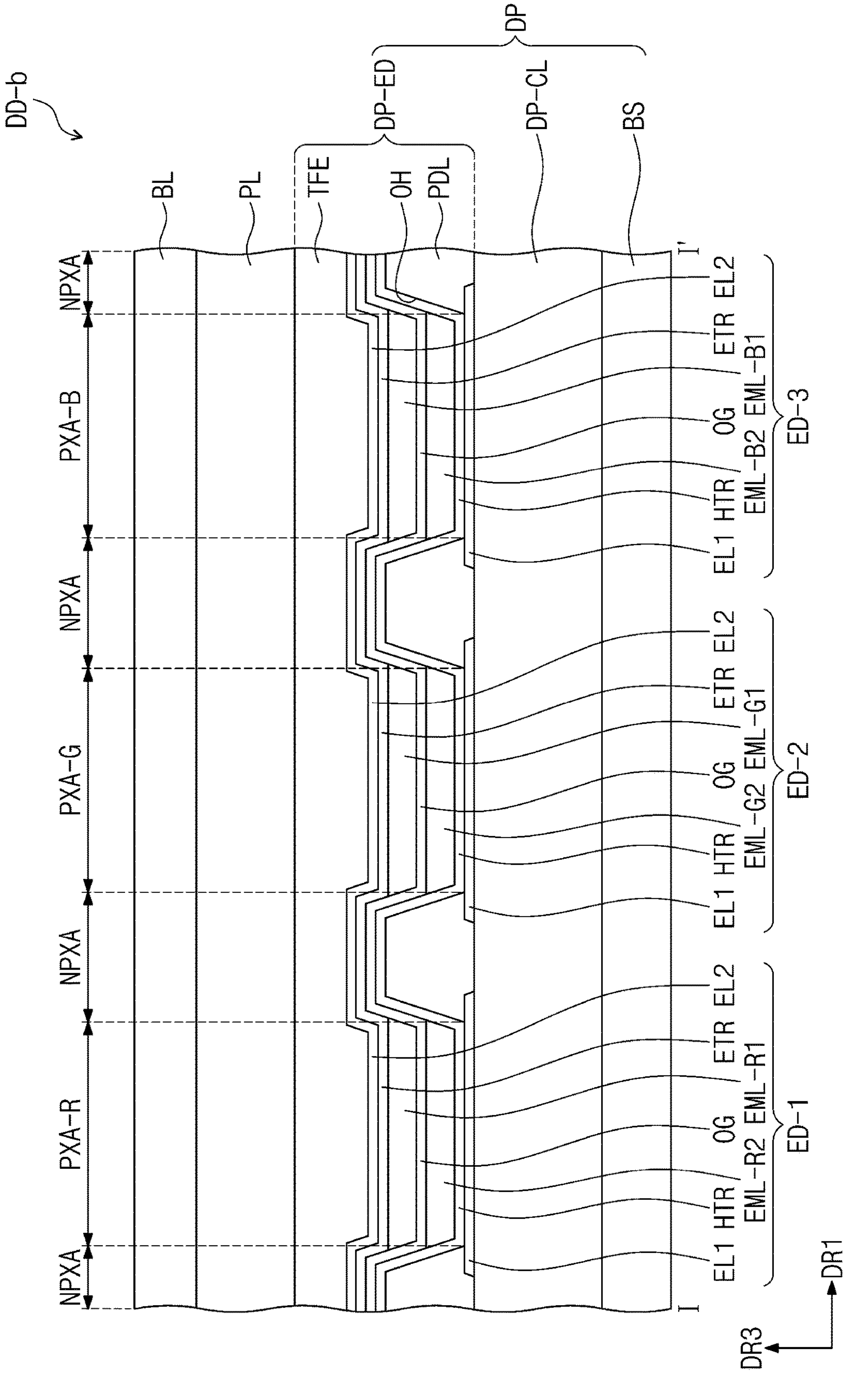
FIG. 9 is a cross-sectional view showing a display apparatus according to an embodiment.

Referring to FIG. 9, a display apparatus DD-b according to an embodiment may include light emitting devices ED-1, ED-2 and ED-3, formed by stacking two emission layers. Compared to the display apparatus DD of an embodiment, shown in FIG. 2, an embodiment shown in FIG. 9 is different in that first to third light emitting devices ED-1, ED-2 and ED-3 include two emission layers stacked in a thickness direction, each. In the first to third light emitting devices ED-1, ED-2 and ED-3, two emission layers may emit light in substantially the same wavelength region.

The first light emitting device ED-1 may include a first red emission layer EML-R1 and a second red emission layer EML-R2. The second light emitting device ED-2 may include a first green emission layer EML-G1 and a second green emission layer EML-G2. In some embodiments, the third light emitting device ED-3 may include a first blue emission layer EML-B1 and a second blue emission layer EML-B2. Between the first red emission layer EML-R1 and the second red emission layer EML-R2, between the first green emission layer EML-G1 and the second green emission layer EML-G2, and between the first blue emission layer EML-B1 and the second blue emission layer EML-B2, an emission auxiliary part OG may be disposed.

The emission auxiliary part OG may include a single layer or a multilayer. The emission auxiliary part OG may include a charge generating layer. For example, the emission auxiliary part OG may include an electron transport region, a charge generating layer, and a hole transport region stacked in order. The emission auxiliary part OG may be provided as a common layer in all of the first to third light emitting devices ED-1, ED-2 and ED-3. However, an embodiment of the present disclosure is not limited thereto, and the emission auxiliary part OG may be patterned and provided in an opening part OH defined in a pixel definition layer PDL.

The first red emission layer EML-R1, the first green emission layer EML-G1 and the first blue emission layer EML-B1 may be between the electron transport region ETR and the emission auxiliary part OG. The second red emission layer EML-R2, the second green emission layer EML-G2 and the second blue emission layer EML-B2 may be between the emission auxiliary part OG and the hole transport region HTR.

For example, the first light emitting device ED-1 may include a first electrode EL1, a hole transport region HTR, a second red emission layer EML-R2, an emission auxiliary part OG, a first red emission layer EML-R1, an electron transport region ETR, and a second electrode EL2, stacked in order from the first electrode EL1. The second light emitting device ED-2 may include a first electrode EL1, a hole transport region HTR, a second green emission layer EML-G2, an emission auxiliary part OG, a first green emission layer EML-G1, an electron transport region ETR, and a second electrode EL2, stacked in order from the first electrode EL1. The third light emitting device ED-3 may include a first electrode EL1, a hole transport region HTR, a second blue emission layer EML-B2, an emission auxiliary part OG, a first blue emission layer EML-B1, an electron transport region ETR, and a second electrode EL2, stacked in order from the first electrode EL1.

In some embodiments, an optical auxiliary layer PL may be on a display element layer DP-ED. The optical auxiliary layer PL may include a polarization layer. The optical auxiliary layer PL may be on a display panel DP and may control reflected light at the display panel DP by external light. In some embodiments, the optical auxiliary layer PL may not be provided from the display apparatus.

Figure 10:
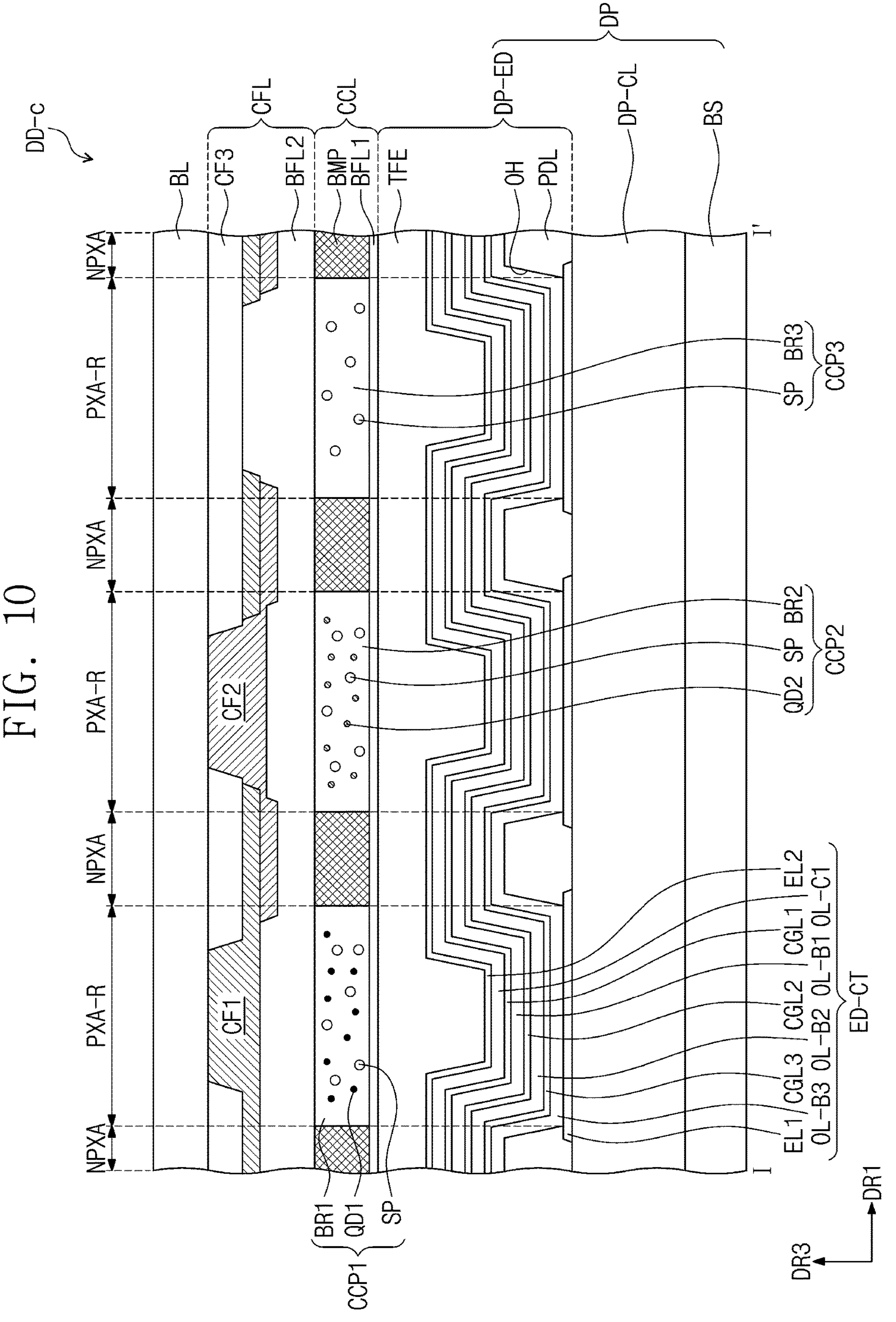
FIG. 10 is a cross-sectional view showing a display apparatus according to an embodiment.

Different from FIG. 8 and FIG. 9, a display apparatus DD-c in FIG. 10 is shown to include four light emitting structures OL-B1, OL-B2, OL-B3 and OL-C1. A light emitting device ED-CT may include oppositely disposed first electrode EL1 and second electrode EL2, and first to fourth light emitting structures OL-B1, OL-B2, OL-B3 and OL-C1 stacked in order in a thickness direction between the first electrode EL1 and the second electrode EL2. Between the first to fourth light emitting structures OL-B1, OL-B2, OL-B3 and OL-C1, charge generating layers CGL1, CGL2 and CGL3 may be disposed. Among the four light emitting structures, the first to third light emitting structures OL-B1, OL-B2 and OL-B3 may emit blue light, and the fourth light emitting structure OL-C1 may emit green light. However, an embodiment of the present disclosure is not limited thereto, and the first to fourth light emitting structures OL-B1, OL-B2, OL-B3 and OL-C1 may emit different wavelengths of light.

The charge generating layers CGL1, CGL2 and CGL3 disposed between neighboring light emitting structures OL-B1, OL-B2, OL-B3, and OL-C1 may include a p-type (kind) charge generating layer and/or an n-type (kind) charge generating layer.

The amine compound of an embodiment may be included in at least one among the light emitting structures OL-B1, OL-B2, OL-B3, and OL-C1, included in the display apparatus DD-c of an embodiment.

Hereinafter, the amine compound according to an embodiment and the light emitting device of an embodiment of the present disclosure are explained in more detail referring to embodiments and comparative examples. The embodiments are only illustrations to assist the understanding of the present disclosure, and the scope of the present disclosure is not limited thereto.

EXAMPLES

1. Synthesis of Amine Compounds

First, the synthetic method of an amine compound according to an embodiment will be explained by, for example, illustrating the synthetic methods of Compounds 7, 1024, 511, 514, 889, 1436, 1473, 1394, 1726, 1586, 260, and 1509. The synthetic methods of the amine compounds explained hereinafter are merely examples, and the synthetic method of the amine compound according to the present disclosure is not limited to the embodiments below. The schematic synthetic methods of the compounds are shown below. The summary of the synthetic methods of each compound is shown in Table 1.

TABLE 1

| Compound | Material A | Material B | Reaction Scheme | Yield | m/z |
|---|---|---|---|---|---|
| 7 | M4a | M5 | 2 | 82% | 651 |
| 1024 | M4d | M6a | 3 | 75% | 651 |
| 511 | M4c | M6a | 3 | 77% | 727 |
| 514 | M4a | M6b | 3 | 68% | 675 |
| 889 | M4a | M6c | 3 | 53% | 701 |
| 1436 | M4a | M6d | 3 | 66% | 665 |
| 1473 | M4a | M6e | 3 | 59% | 715 |
| 1394 | M4a | M6f | 3 | 72% | 771 |
| 1726 | M4a | M6g | 3 | 65% | 815 |
| 1586 | M4a | M6h | 3 | 74% | 740 |
| 260 | M4b | M6i | 3 | 78% | 727 |
| 1509 | M4a | M6j | 3 | 76% | 741 |

In the synthesis of the Example Compounds, Intermediate M6a to Intermediate M6j, used as Material B are shown below.

M6a

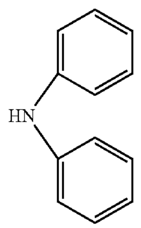

M6b

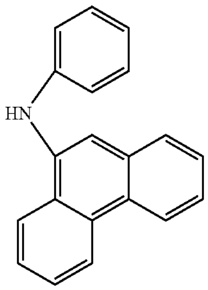

M6c

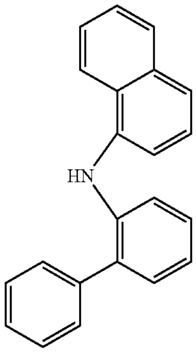

M6d

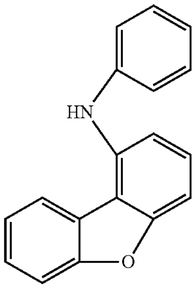

M6e

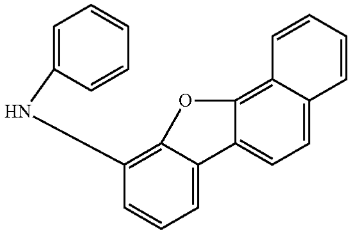

M6f

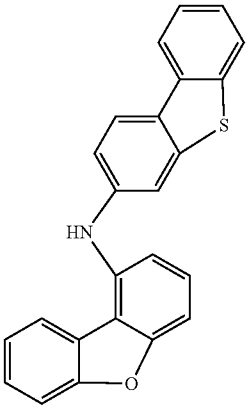

M6g

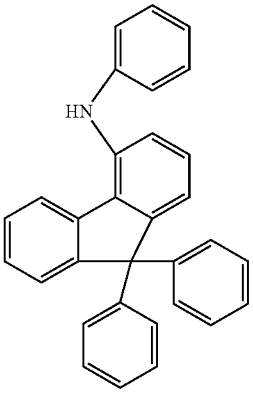

M6h

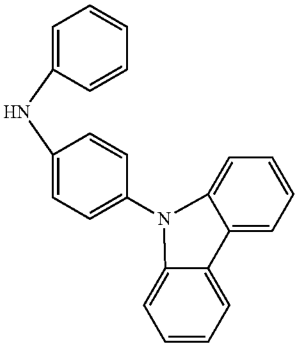

M6i

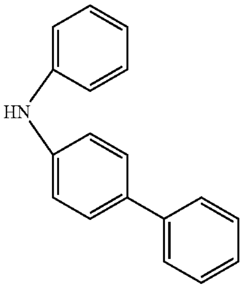

M6j

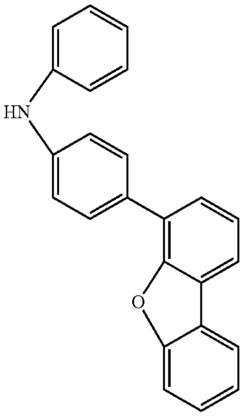

In the embodiment of Formula 1 in which $L_1$ or $L_2$ is not a single bond, as in Compound 7, a corresponding part was synthesized by producing a C—C bond using Suzuki Coupling reaction, as shown in Scheme 2, and in the embodiment of synthesizing a compound of Formula 1 in which $L_1$ or $L_2$ is a single bond, a corresponding part was synthesized by producing a C—N bond using Buchwald-amination reaction, as shown in Scheme 3. The materials necessary for the synthesis were purchased, or synthesized (see, for example Scheme 1).

Scheme 1

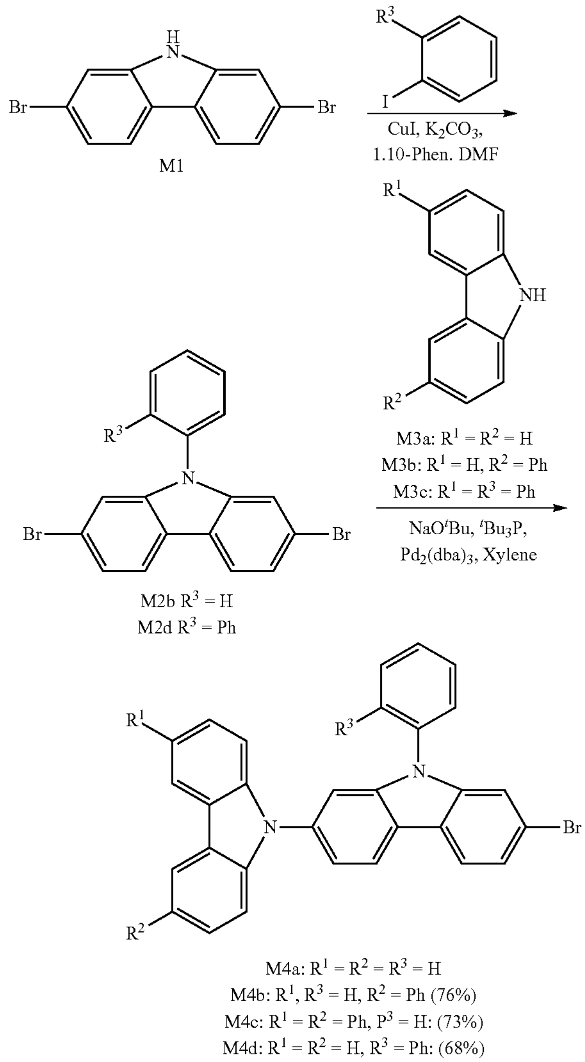

(1-1) Synthesis of Intermediate M2d (Scheme 1)

A DMF suspension (100 mL) of dibromocarbazole M1 (7.40 g, 22.8 mmol), 2-iodobiphenyl (7.66 g, 27.3 mmol), cuprous iodide (1.04 g, 5.47 mmol), 1,10-phenanthroline hydrate (1.08 g, 5.47 mmol), and potassium carbonate (11.3 g, 82.0 mmol) was degassed and heated to about 160° C. under an argon atmosphere for about 24 hours. After cooling, the reaction solution was filtered using Florisil and concentrated, and the crude product thus obtained was separated by column chromatography to obtain Intermediate M2d (4.13 g, 38%).

(1-2) Synthesis of Intermediate M4b (Scheme 1)

A xylene suspension (600 mL) of Intermediate M2b (11.7 g, 29.2 mmol), Intermediate M3b (7.10 g, 29.2 mmol), tris(dibenzilideneacetone)dipalladium(0) (802 mg, 0.876 mmol), tri(tert-butylphosphine) (1.6 M solution, 1.10 mL, 1.75 mmol), and sodium tert-butoxide (8.42 g, 87.6 mmol) was degassed and heated to about 130° C. under an argon atmosphere for about 8 hours. After cooling, the reaction solution was filtered using Florisil and concentrated, and the crude product thus obtained was separated by column chromatography to obtain Intermediate M4b (12.5 g, 76%).

(1-3) Synthesis of Intermediate M4c (Scheme 1)

Intermediate M4c (15.1 g, 72%) was obtained by substantially the same method as the synthesis of Intermediate M4b, except for using Intermediate M3c instead of Intermediate M3b, in the synthesis of Intermediate M4b.

(1-4) Synthesis of Intermediate M4d (Scheme 1)

Intermediate M4d (17.2 g, 68%) was obtained by substantially the same method as the synthesis of Intermediate M4b, except for using Intermediate M2d instead of Intermediate M2b and using Intermediate M3a instead of Intermediate M3b, in the synthesis of Intermediate M4b.

Scheme 2

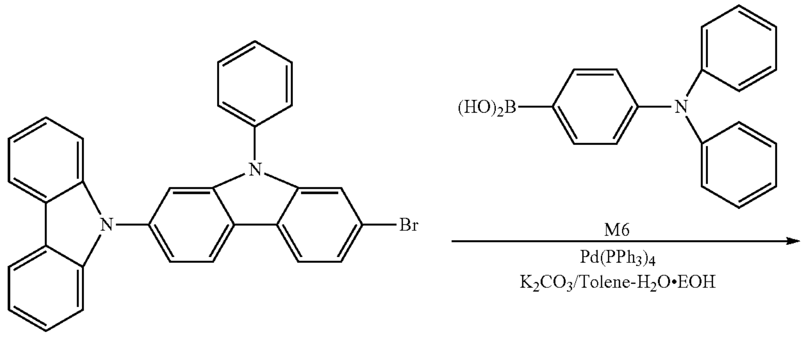

M4a

-continued

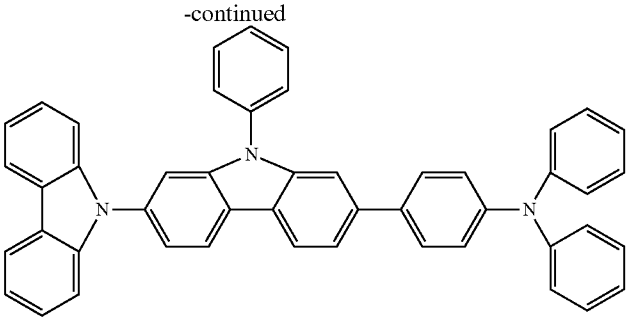

7

(1-5) Synthesis of Compound 7 (Scheme 2)

A mixture of Intermediate M4a (3.20 g, 6.57 mmol), Intermediate M5 (2.28 g, 7.88 mmol), tetrakis(triphenylphosphine)palladium(0) (228 mg, 0.197 mmol), potassium carbonate (4.54 g, 32.8 mmol), toluene (300 mL), and 66% ethanol (100 mL) was degassed and heated to about 90° C. under an argon atmosphere for about 10 hours. The reaction mixture was filtered using Celite and extracted with toluene, and an organic layer was dried over anhydrous magnesium sulfate and concentrated. The residue thus obtained was separated by column chromatography to obtain Compound 7 (3.50 g, yield 82%). By FAB-MS measurement of the product, m/z=651 was observed, and Compound 7 was confirmed.

Scheme 3

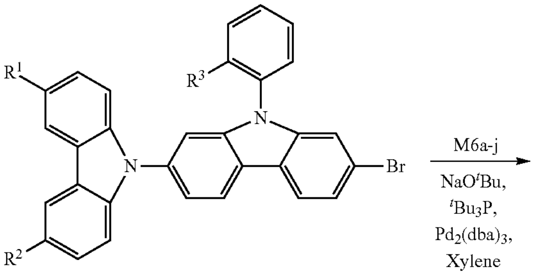

M4a-d

M4a: $R^1 = R^2 = R^3 = H$

M4b: $R^1$, $R^3 = H$, $R^2 = Ph$ (76%)

M4c: $R^1 = R^2 = Ph$, $P^3 = H$: (73%)

M4d: $R^1 = R^2 = H$, $R^3 = Ph$: (68%)

1024, 511, 514, 889, 1436, 1473
1394, 1726, 1586, 260, 1509

(1-6) Synthesis of Compound 1438 (Scheme 3)

A xylene suspension (300 mL) of Intermediate M4a (4.58 g, 9.40 mmol), Intermediate M6d (2.56 g, 9.87 mmol), tris(dibenzilideneacetone)dipalladium (0) (258 mg, 0.282 mmol), tri(tert-butylphosphine) (1.6 M solution, 0.352 mL, 0.560 mmol), and sodium tert-butoxide (2.71 g, 28.2 mmol) was degassed and heated to about 130° C. under an argon atmosphere for about 10 hours. After cooling, the reaction solution was filtered using Florisil and concentrated, and the residue thus obtained was separated by column chromatography to obtain Compound 1438 (4.13 g, yield 66%). By FAB-MS measurement of the product, m/z=665 was observed, and Example Compound 1438 was confirmed.

(1-7) Synthesis of Compounds 1024, 511, 514, 889, 1436, 1473, 1394, 1726, 1586, 260, and 1509 (Scheme 3)

Compounds 1024, 511, 514, 889, 1436, 1473, 1394, 1726, 1586, 260, and 1509 were obtained in the yields recorded in the yield column in Table 1 by substantially the same method as the synthesis of Example Compound 1436 except for using Material A corresponding to each compound of Table 1 instead of Intermediate M4a in the synthesis of Example Compound 1436 and using Material B instead of Intermediate M6d in the synthesis of Example Compound 1436, in the synthesis of Compound 1436. By FAB-MS measurement of each product, values recorded in the m/z column in Table 1 were observed, and the production of Compounds 1024, 511, 514, 889, 1436, 1473, 1394, 1726, 1586, 260, and 1509 were confirmed.

2. Manufacture and Evaluation of Light Emitting Devices Including Amine Compounds (1) Manufacture and Evaluation of Light Emitting Devices Including Amine Compounds as Materials of Hole Transport Layers Manufacture of Light Emitting Devices Light emitting devices of Examples 1 to 12 were manufactured using Compounds 7, 1024, 511, 514, 889, 1436, 1473, 1394, 1726, 1586, 260, and 1509, as materials of hole transport layers.

Example Compounds

7

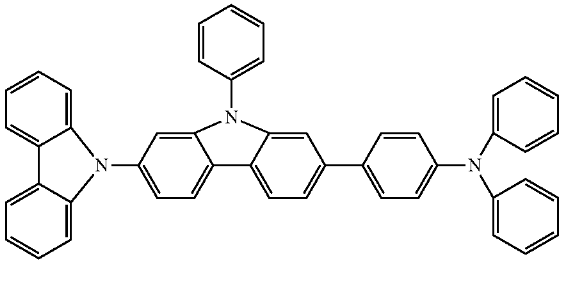

1024
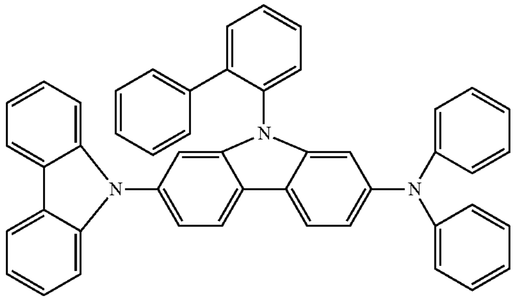
511
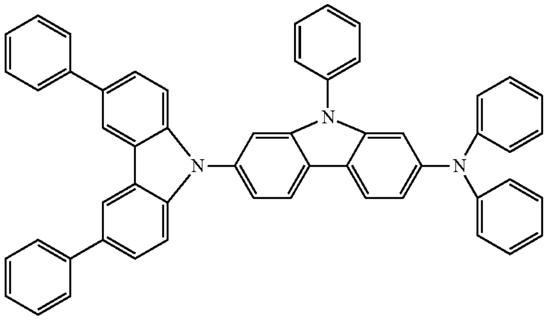
514
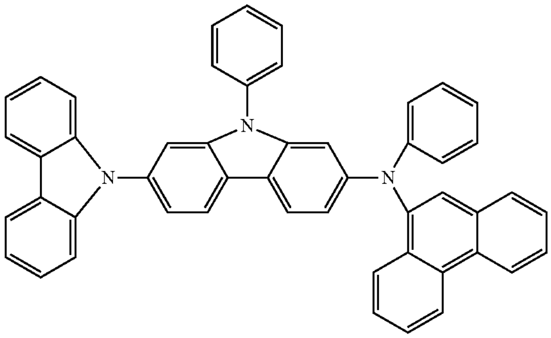
889
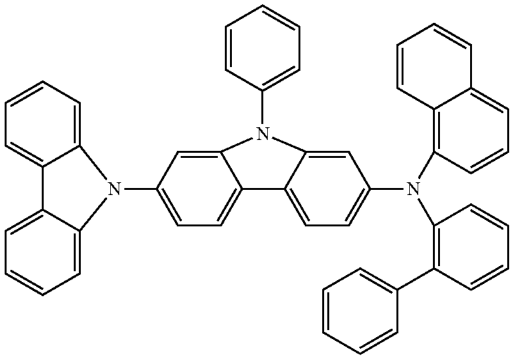
1436
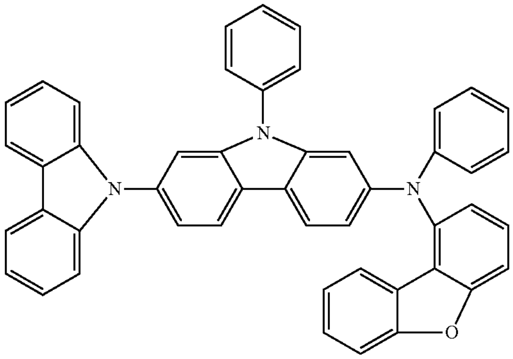
1473
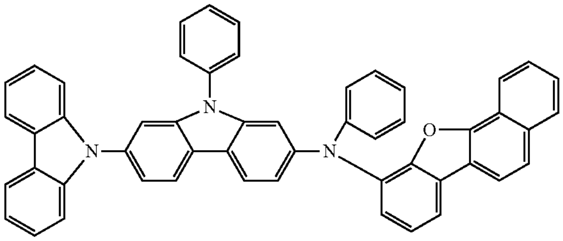
1394
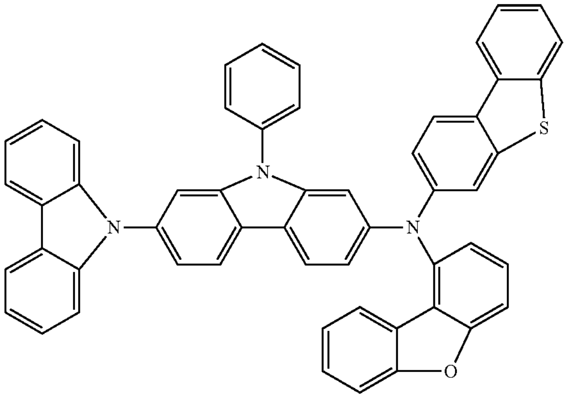
1726
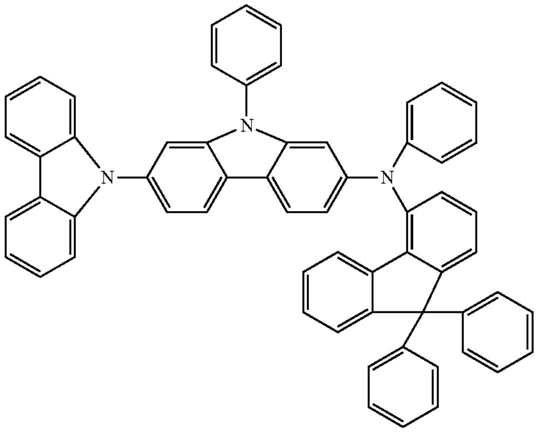

-continued
1586
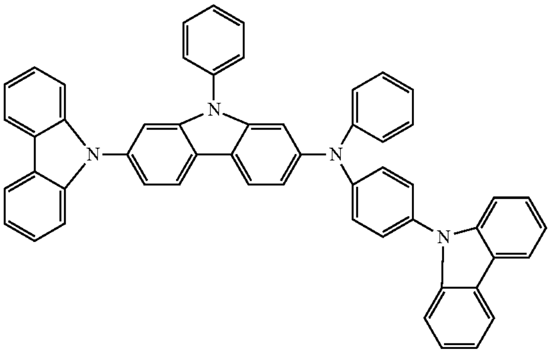
260
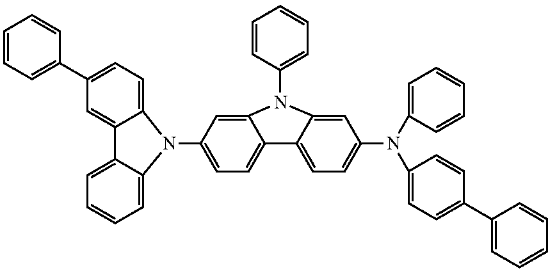
-continued
1509
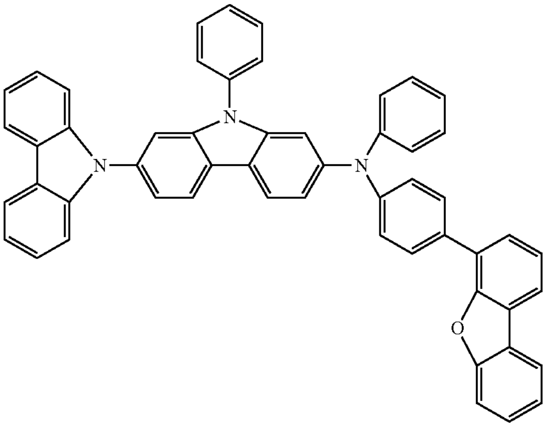
Comparative Compounds C1 to C7 were used for the manufacture of the devices of the Comparative Examples.
Comparative Compounds
C1
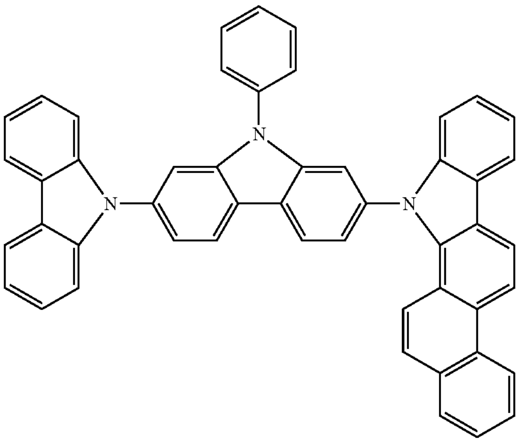
C2
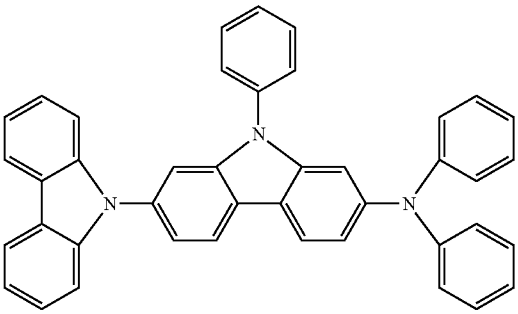
C3
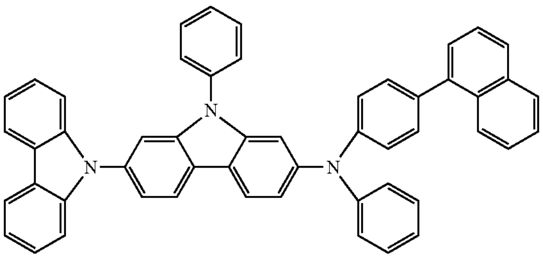
C4
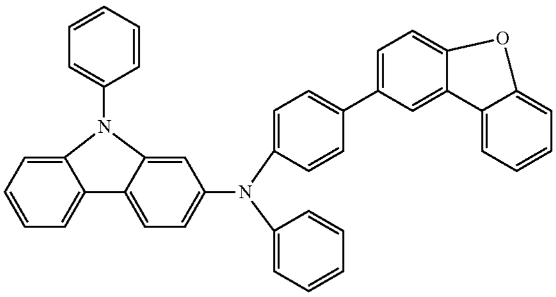

-continued

C5

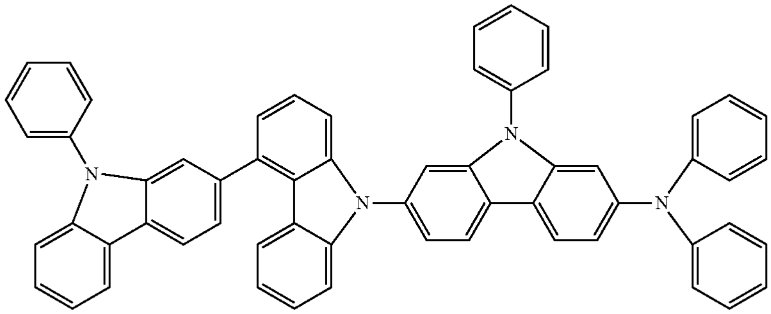

C6

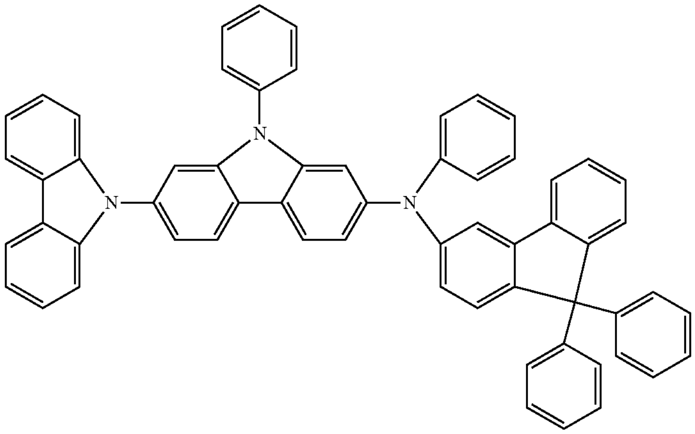

C7

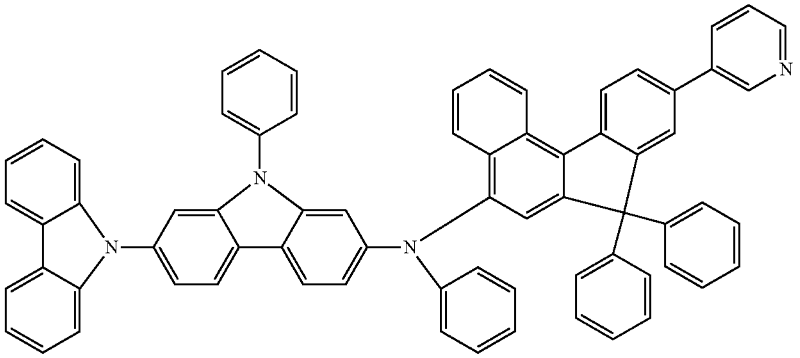

A light emitting device of an embodiment, including the amine compound of an embodiment in a hole transport layer was manufactured by a method described below. Example 1 to Example 12 corresponds to light emitting devices manufactured using the Example Compounds of Compounds 7, 1024, 511, 514, 889, 1436, 1473, 1394, 1726, 1586, 260, and 1509 as the materials of the hole transport layers. Comparative Example 1 to Comparative Example 7 correspond to light emitting devices manufactured using Comparative Compound C1 to Comparative Compound C7 as the materials of hole transport layers.

A first electrode with a thickness of about 150 nm was formed using ITO, a hole injection layer with a thickness of about 60 nm was formed using 4,4',4"-tris[N(2-naphthyl)-N-phenylamino]-triphenylamine (2-TNATA), a hole transport layer with a thickness of about 30 nm was formed using the Example Compound or Comparative Compound, an emission layer with a thickness of about 25 nm was formed using 9,10-di(naphthalene-2-yl)anthracene (ADN) doped with 3% of 2,5,8,11-tetra-t-butylperylene (TBP), an electron transport layer with a thickness of about 25 nm was formed using tris(8-hydroxyquinolinato)aluminum ($Alq_3$), an electron injection layer with a thickness of about 1 nm was formed using LiF, and a second electrode with a thickness of about 100 nm was formed using Al. All layers were formed by a deposition method under a vacuum atmosphere.

The compounds used for the manufacture of the light emitting devices of the Examples and Comparative Examples are shown below. Commercially available products were used for the manufacture of the devices after sublimation purification.

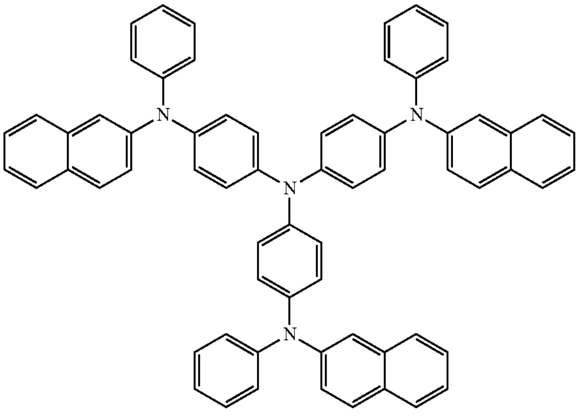

2-TNATA

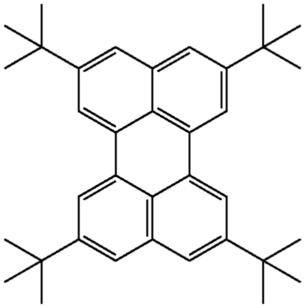

TBP

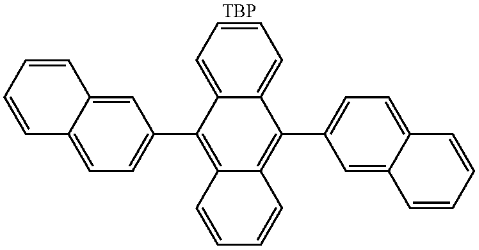

ADN

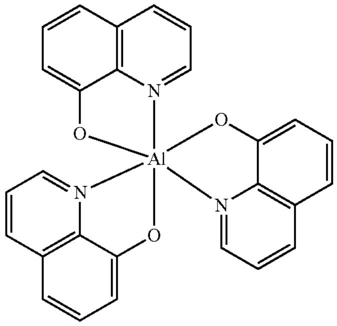

Alq3

Experimental Example

The device efficiency of the light emitting devices manufactured using the Example Compounds of Compounds 7, 1024, 511, 514, 889, 1436, 1473, 1394, 1726, 1586, 260, and 1509 and Comparative Compound C1 to Comparative Compound C7 was evaluated. Evaluation results are shown in Table 2. For the evaluation of the devices, the emission efficiency and device life of the light emitting devices were measured at a current density of about 10 mA/$cm^2$ and recorded.

The evaluation of the current density and emission efficiency of the devices was conducted using a Source Meter of a product of 2400 Series of Keithley Instruments Co., a product of Color luminance meter CS-200 of Konica Minolta Co., Ltd., and a product of PC Program LabVIEW8.2 for measurement of Japanese National Instruments Co., Ltd., in a dark room.

In addition, the emission efficiency and device life were shown as relative values regarding the emission efficiency and device life of Comparative Example 2 were 100%.

TABLE 2

| Device manufacturing example | Hole transport layer Compound | Emission efficiency (%) | Device life ($LT_{50}$, %) |
|---|---|---|---|
| Example 1 | Compound 7 | 116% | 129% |
| Example 2 | Compound 1024 | 120% | 128% |
| Example 3 | Compound 511 | 117% | 128% |
| Example 4 | Compound 514 | 122% | 137% |
| Example 5 | Compound 889 | 127% | 132% |
| Example 6 | Compound 1436 | 119% | 128% |
| Example 7 | Compound 1473 | 120% | 127% |
| Example 8 | Compound 1394 | 125% | 128% |
| Example 9 | Compound 1726 | 127% | 136% |
| Example 10 | Compound 1586 | 122% | 132% |
| Example 11 | Compound 260 | 116% | 126% |
| Example 12 | Compound 1509 | 117% | 129% |
| Comparative Example 1 | Comparative Compound C1 | 85% | 68% |
| Comparative Example 2 | Comparative Compound C2 | 100% | 100% |
| Comparative Example 3 | Comparative Compound C3 | 102% | 105% |
| Comparative Example 4 | Comparative Compound C4 | 77% | 55% |
| Comparative Example 5 | Comparative Compound C5 | 81% | 97% |
| Comparative Example 6 | Comparative Compound C6 | 105% | 92% |
| Comparative Example 7 | Comparative Compound C7 | 88% | 73% |

Referring to the results of Table 1, it could be confirmed that the Examples of the light emitting devices using the amine compounds according to embodiments of the present disclosure as the materials of hole transport layers showed improved emission efficiency and device life when compared to the Comparative Examples. The amine compound of an embodiment includes an amine group and may have a structure in which the nitrogen atom of the amine group is connected with a carbazole moiety including a first carbazole group and a second carbazole group. In the amine compound of an embodiment, any one among benzene rings composing the first carbazole group may be connected with nitrogen at position 9 of the second carbazole group, and the remaining one may be connected with the nitrogen atom of the amine group. Accordingly, the amine compound of an embodiment may include a conjugation system from the second carbazole group via the first carbazole group to the nitrogen atom of the amine group, and the amine group connected with a second carbazole group-substituted first carbazole group may form a central skeleton in a whole molecule. The amine compound of an embodiment may have a connected structure with two substituents in addition to the first carbazole group. For example, the amine compound may include a second carbazole group-substituted first carbazole group, a first substituent, and a second substituent as a substituent connected with an amine group.

The Example Compounds may introduce a specific substituent at a specific position or introduce at least one linker to a central skeleton. For example, in the amine compound of an embodiment, at least one linker among a linker connecting the first carbazole group and the second carbazole group and a linker connecting the first carbazole group and the nitrogen atom of the amine compound may be a substituted or unsubstituted arylene group, the second carbazole group may include at least one substituent, at least one among the first and second substituents substituted at the amine group, and a substituent connected with the nitrogen atom at position 9 of the first carbazole group may be an o-biphenyl group, or at least one among the first substituent and the second substituent may be substituted with a specific substituent. Accordingly, the central skeleton of the amine compound may be sterically protected and electronically stabilized. As a result, the Example Compounds may show improved stability of a whole molecule and increased hole transport capacity, and when applied to a light emitting device, the efficiency and life of the light emitting device may be improved. For example, the light emitting device of an embodiment includes the amine compound of an embodiment as a material for a hole transport layer of the light emitting device, thereby improving the efficiency and life of the light emitting device.

In Comparative Compound C1 included in Comparative Example 1, an amine group was not included, and 9-carbazole groups were substituted at both terminals of a carbazol-2,7-diyl group, and both emission efficiency and life were degraded. In comparison to this, in the Example Compounds, a 9-carbazole group was substituted at one terminal of a carbazole-2,7-diyl group, and the nitrogen atom of the amine group was connected with the other terminal, and it could be confirmed that the HOMO energy level approached to the hole transport material, and both emission efficiency and device life were excellent (suitable).

Comparative Compound C2 and Comparative Compound C3 included in Comparative Example 2 and Comparative Example 3 included a carbazole moiety including two carbazole groups and had structures in which one among two carbazole groups and the nitrogen atom of an amine group are connected, but did not include a linker sterically protecting the central skeleton of the amine compound, thereby degrading the emission efficiency and device life when compared to the Examples. Comparative Compound C2 and Comparative Compound C3 included a phenyl group or a naphthylphenyl group as a substituent connected with the amine group in addition to the carbazole group, but such a substituent was difficult to sterically protect the central skeleton, and accordingly, hole transport capacity was changed, and charge balance in an emission layer was degraded.

A plurality of the Example Compounds include a compound composed of only a phenyl group as the substituent connected with the amine group other than the carbazole group, as in Comparative Compound C2 and Comparative Compound C3. However, the Example Compounds such as (1) Example Compound 7 in which a phenylene group is introduced as a linker between the first carbazole group and the nitrogen of the amine group, (2) Example Compound 1025 in which an o-biphenyl group is substituted at nitrogen at position 9 of the first carbazole group to provide a sterically protected central skeleton, (3) Example Compound 890 in which an o-biphenyl group is substituted as a substituent connected with an amine group other than the carbazole group to provide a sterically protected central skeleton, and (4) Example Compounds 1278 and 261, in which an aryl group is substituted at the second carbazole group to improve the stability of the central skeleton, introduced specific substituents or linkers stabilizing a conjugation system at a substituent portion connected with the amine group, and could improve the stability of a whole molecule and increase hole transport capacity, and when applied to a light emitting device, the efficiency and life of the light emitting device may be improved.

Comparative Compound C4 included in Comparative Example 4 included a carbazole group connected with the amine group but excluded a 9-carbazole group connected with the carbazole group, and it could be confirmed that the emission efficiency and life characteristics were degraded when compared to the Examples. The difference of device performance between Comparative Example 4 and the Examples was greater than with other Comparative Examples, and although not wanting to be bound by theory, it is believed that both steric protecting effects of a conjugation system from 9-carbazole via carbazole-2,7-diyl to the nitrogen atom of the amine group, and the controlling function of a HOMO energy level, contributed to the improved device performance.

Comparative Compound C5 included in Comparative Example 5 included a carbazole moiety including two carbazole groups and had a structure in which any one among the two carbazole groups and the nitrogen atom of the amine group were connected, but a carbazole group which was an aromatic heterocycle was additionally substituted at the remaining carbazole group, and emission efficiency and device life were degraded when compared to the Examples. It is believed that an aromatic heterocycle was substituted at 9-carbazole as in Comparative Compound C5, and negative effects other than the conjugation stabilization of conjugation system were induced.

Comparative Compound C6 included in Comparative Example 6 included two carbazole groups, had a structure in which any one among two carbazole groups and the nitrogen atom of the amine group were connected, and included a fluorenyl group as a substituent connected with the amine group other than the carbazole group. However, it could be confirmed that emission efficiency and device-life characteristics were degraded when compared to the Examples.

When comparing Example 9 with Comparative Example 6, Comparative Compound C6 included a fluorenyl group as a substituent like in Example Compound 1629, but it could be confirmed that emission efficiency and device life were reduced. It is believed to be because, in Comparative Compound C6, carbon at position 3 or 6 of the fluorenyl group was connected, and the separation and decomposition of a phenyl group substituted at quaternary carbon at position 9 of the fluorenyl group was favorably promoted. When carbocation is produced by the separation of the phenyl group substituted at carbon at position 9 of the fluorenyl group, as in Comparative Compound C6, the carbocation is present at the p-position to the nitrogen atom of the amine group, and the structure is stabilized by the nitrogen atom of the amine group, it is believed that the separation and decomposition effects of the phenyl group are promoted. In contrast, as in Example Compound 1629, if carbon not at position 3 or 6 of the fluorenyl group is connected with the amine group, the separation and decomposition promoting effects may be reduced, and device life may be expected to improve greatly.

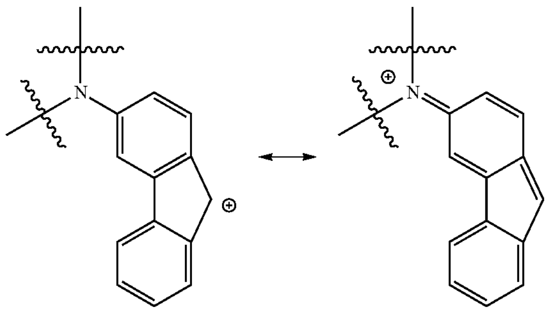

Comparative Compound C7 included in Comparative Example 7 included a carbazole moiety including two carbazole groups in which any one among the two carbazole groups was connected with the amine group, and included a fluorenyl group as a substituent connected with the amine group other than the carbazole group. However, it was confirmed that emission efficiency and device life were degraded when compared to the Examples. Comparative Compound C7 had an additionally fused structure of a benzene ring to one among benzene ring composing the fluorenyl group. As the substituent of the amine group, a fused structure is necessary to some extent for the stabilization of a conjugation system, but if the steric volume of the substituent is exaggerated, twist might arise at the bond with the nitrogen atom of the amine group, and the stability of a whole molecule might be reduced. Accordingly, emission efficiency and device life might be degraded. In addition, Comparative Compound C7 is thought to increase efficiency degradation, because an aromatic heterocycle was additionally substituted at the fluorenyl group. Such an aromatic heterocycle, for example, an aromatic heterocycle including a nitrogen-containing six-membered ring such as pyridine, pyrazine, and/or triazine greatly influenced a molecular orbital, and was deemed not to be a suitable substituent in the present disclosure.

The light emitting device of an embodiment may show improved device properties of high efficiency and long-life characteristics.

The amine compound of an embodiment may be included in the hole transport region of a light emitting device to contribute to the increase of the efficiency and life of the light emitting device.

The use of "may" when describing embodiments of the present disclosure refers to "one or more embodiments of the present disclosure."

As used herein, the term "substantially," "about," and similar terms are used as terms of approximation and not as terms of degree, and are intended to account for the inherent deviations in measured or calculated values that would be recognized by those of ordinary skill in the art. "About" or "approximately," as used herein, is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" may mean within one or more standard deviations, or within ±30%, 20%, 10%, 5% of the stated value.

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this disclosure is intended to include all higher numerical limitations subsumed therein. Accordingly, Applicant reserves the right to amend this disclosure, including the claims, to expressly recite any sub-range subsumed within the ranges expressly recited herein.

The light emitting device or any other relevant devices or components according to embodiments of the present disclosure described herein may be implemented utilizing any suitable hardware, firmware (e.g., an application-specific integrated circuit), software, or a combination of software, firmware, and hardware. For example, the various components of the device may be formed on one integrated circuit (IC) chip or on separate IC chips. Further, the various components of the device may be implemented on a flexible printed circuit film, a tape carrier package (TCP), a printed circuit board (PCB), or formed on one substrate. Further, the various components of the device may be a process or thread, running on one or more processors, in one or more computing devices, executing computer program instructions and interacting with other system components for performing the various functionalities described herein. The computer program instructions are stored in a memory which may be implemented in a computing device using a standard memory device, such as, for example, a random access memory (RAM). The computer program instructions may also be stored in other non-transitory computer readable media such as, for example, a CD-ROM, flash drive, or the like. Also, a person of skill in the art should recognize that the functionality of various computing devices may be combined or integrated into a single computing device, or the functionality of a particular computing device may be distributed across one or more other computing devices without departing from the scope of the embodiments of the present disclosure.

Although the embodiments of the present disclosure have been described, it is understood that the present disclosure should not be limited to these embodiments but one or more suitable changes and modifications can be made by one of ordinary skill in the art without departing from the spirit and scope of the present disclosure as defined by the following claims and equivalents thereof.

What is claimed is:

1. A light emitting device, comprising:

a first electrode;

a second electrode oppositely disposed to the first electrode; and multiple functional layers between the first electrode and the second electrode, wherein at least one functional layer among the multiple functional layers comprises an amine compound represented by Formula 1:

Formula 1

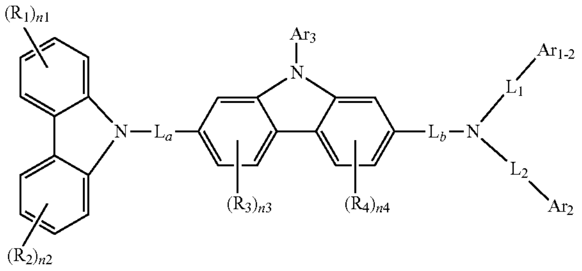

wherein in Formula 1, $Ar_1$ to $Ar_3$ are each independently a substituted or unsubstituted alkyl group of 1 to 20 carbon atoms, a substituted or unsubstituted silyl group, a substituted or unsubstituted aryl group of 6 to 30 ring-forming carbon atoms, or a substituted or unsubstituted heteroaryl group of 2 to 30 ring-forming carbon atoms, $L_a$, $L_b$, $L_1$, and $L_2$ are each independently a direct linkage, or a substituted or unsubstituted arylene group of 6 to 30 ring-forming carbon atoms, $R_1$ to $R_4$ are each independently a substituted or unsubstituted alkyl group of 1 to 20 carbon atoms, or a substituted or unsubstituted aryl group of 6 to 30 ring-forming carbon atoms, n1 and n2 are each independently an integer from 0 to 4, and n3 and n4 are each independently an integer from 0 to 3, wherein in Formula 1, a sum of n1 and n2 is 1 or more, at least one among $Ar_1$ to $Ar_3$ is a substituent represented by Formula a, at least one among $Ar_1$ and $Ar_2$ is a substituted or unsubstituted dibenzofuran group, a substituted or unsubstituted dibenzothiophene group, a substituted or unsubstituted phenanthrene group, a substituted or unsubstituted carbazole group, or a substituent represented by Formula b, or at least one among $L_a$ and $L_b$ is a substituted or unsubstituted arylene group of 6 to 30 ring-forming carbon atoms:

Formula a

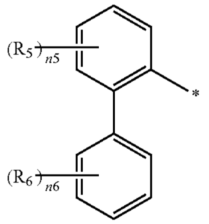

wherein in Formula a, $R_5$ and $R_6$ are each independently a hydrogen atom, a deuterium atom, a halogen atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, n5 is an integer from 0 to 4, and n6 is an integer from 0 to 5, Formula b

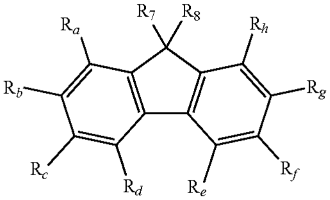

wherein in Formula b, $R_a$ to $R_h$, $R_7$, and $R_8$ are each independently a hydrogen atom, a deuterium atom, a halogen atom, a substituted or unsubstituted alkyl group of 1 to 20 carbon atoms, or a substituted or unsubstituted aryl group of 6 to 30 ring-forming carbon atoms, and any one among $R_a$, $R_b$, $R_d$, $R_e$, $R_g$, and $R_h$ is connected to $L_1$ or $L_2$, the amine compound comprising a structure of Formula 1, wherein optionally a hydrogen atom is substituted with a deuterium atom.

2. The light emitting device of claim 1, wherein the multiple functional layers comprise:

a hole transport region on the first electrode;

an emission layer on the hole transport region; and an electron transport region on the emission layer, and the hole transport region comprises the amine compound.

3. The light emitting device of claim 2, wherein the hole transport region comprises:

a hole injection layer on the first electrode; and a hole transport layer on the hole injection layer, wherein the hole transport layer comprises the amine compound.

4. The light emitting device of claim 1, wherein the amine compound represented by Formula 1 is a monoamine compound.

5. The light emitting device of claim 1, wherein the amine compound represented by Formula 1 is represented by any one among the following Formula 2-1 to Formula 2-3:

Formula 2-1

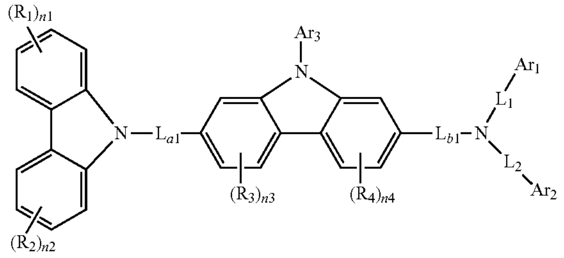

Formula 2-2

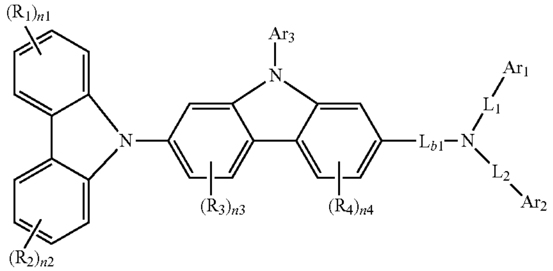

-continued

Formula 2-3

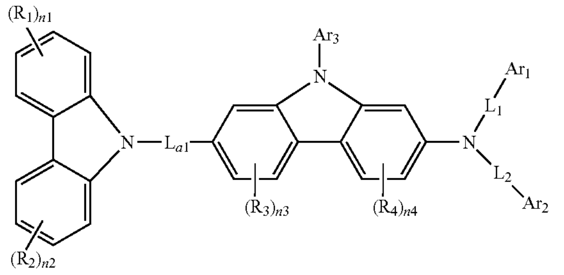

wherein in Formula 2-1 to Formula 2-3, $L_{a1}$ and $L_{b1}$ are each independently a substituted or unsubstituted arylene group of 6 to 30 ring-forming carbon atoms, and $Ar_1$ to $Ar_3$, $R_1$ to $R_4$, $L_1$, $L_2$, and n1 to n4 are the same as defined in Formula 1.

6. The light emitting device of claim 1, wherein the amine compound represented by Formula 1 is represented by Formula 3:

Formula 3

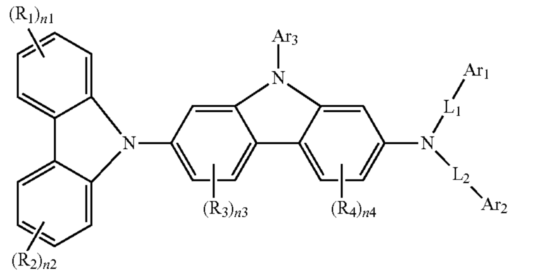

wherein in Formula 3, $Ar_1$ to $Ar_3$, $R_1$ to $R_4$, $L_1$, $L_2$, and n1 to n4 are the same as defined in Formula 1.

7. The light emitting device of claim 1, wherein the amine compound represented by Formula 1 is represented by any one among the following Formula 4-1 to Formula 4-3:

Formula 4-1

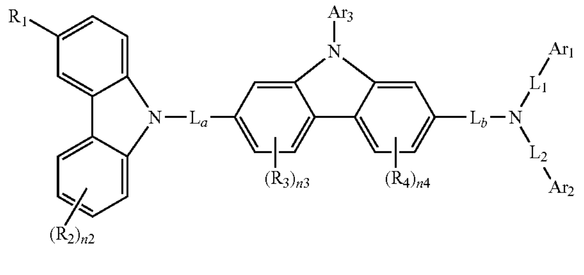

-continued

Formula 4-2

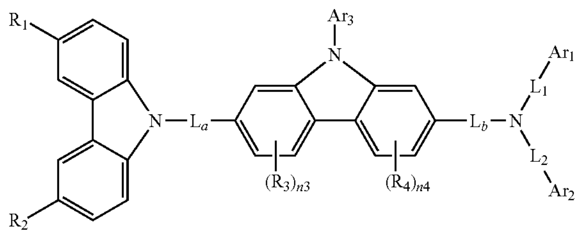

Formula 4-3

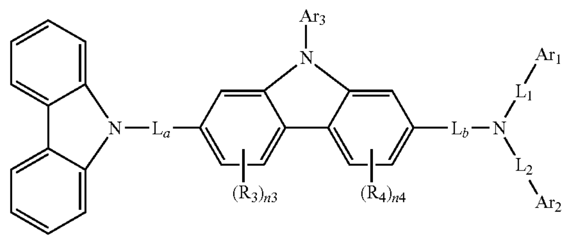

wherein in Formula 4-1 to Formula 4-3, $Ar_1$ to $Ar_3$, $R_1$ to $R_4$, $L_a$, $L_b$, $L_1$, $L_2$, and n2 to n4 are the same as defined in Formula 1.

8. The light emitting device of claim 1, wherein the amine compound represented by Formula 1 is represented by any one among Formula 5-1 to Formula 5-3:

Formula 5-1

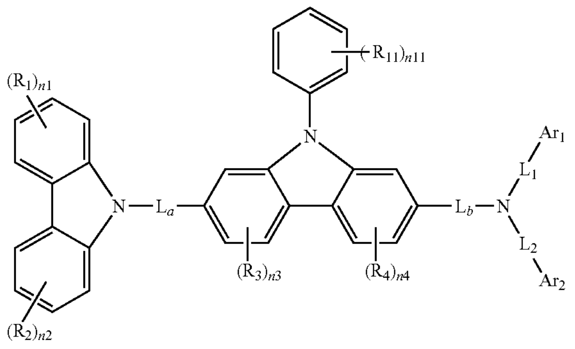

Formula 5-2

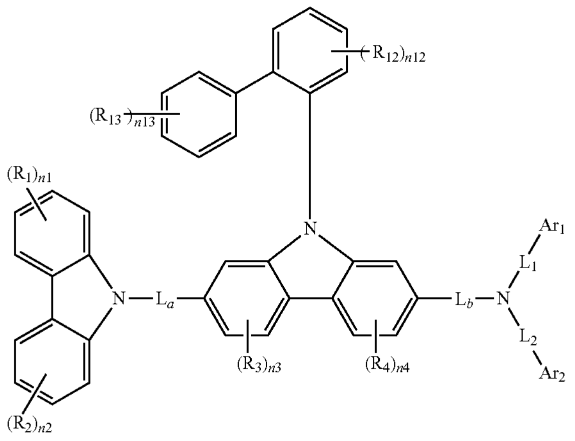

-continued

Formula 5-3

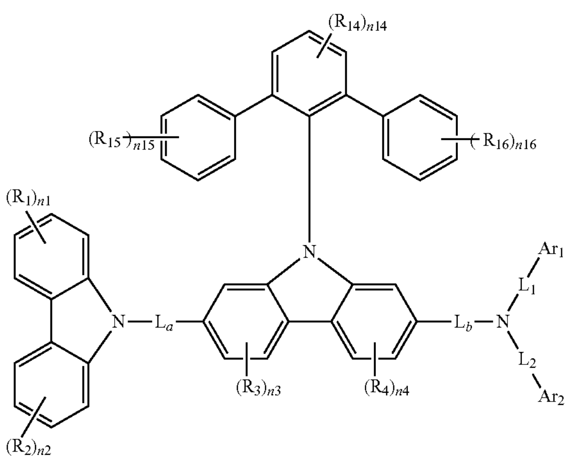

wherein in Formula 5-1 to Formula 5-3, $R_{11}$ to $R_{16}$ are each independently a hydrogen atom, a deuterium atom, a halogen atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, n11, n13, n15, and n16 are each independently an integer from 0 to 5, n12 is an integer from 0 to 4, n14 is an integer from 0 to 3, and $Ar_1$, $Ar_2$, $R_1$ to $R_4$, $L_a$, $L_b$, $L_1$, $L_2$, and n1 to n4 are the same as defined in Formula 1.

9. The light emitting device of claim 1, wherein the amine compound represented by Formula 1 is represented by any one among Formula 6-1 to Formula 6-3:

Formula 6-1

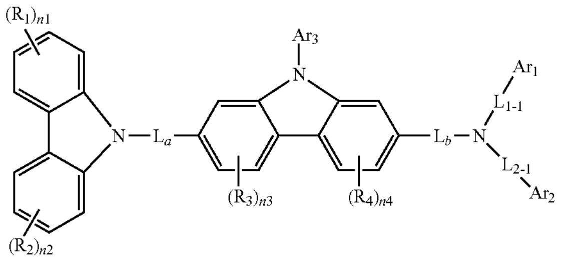

Formula 6-2

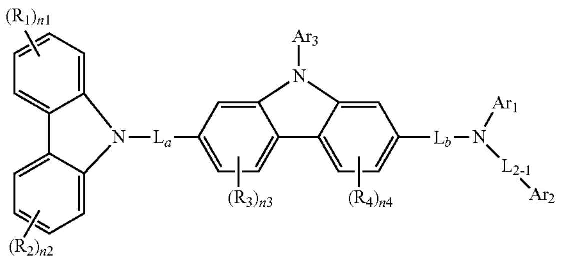

-continued

Formula 6-3

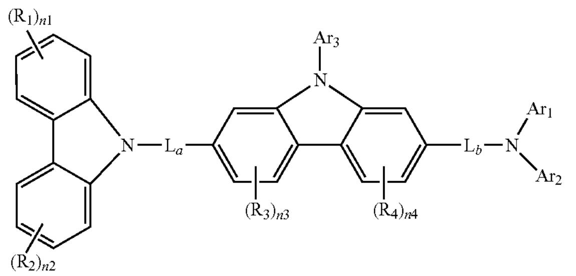

wherein in Formula 6-1 to Formula 6-3, $L_{1-1}$ and $L_{21}$ are each independently a substituted or unsubstituted arylene group of 6 to 30 ring-forming carbon atoms, and $Ar_1$ to $Ar_3$, $R_1$ to $R_4$, $L_a$, $L_b$, and n1 to n4 are the same as defined in Formula 1.

10. The light emitting device of claim 1, wherein the amine compound represented by Formula 1 is represented by any one among the following Formula 7-1 to Formula 7-3:

Formula 7-1

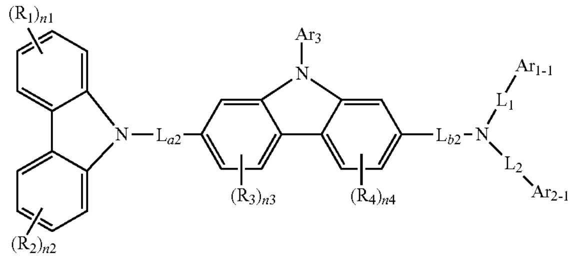

Formula 7-2

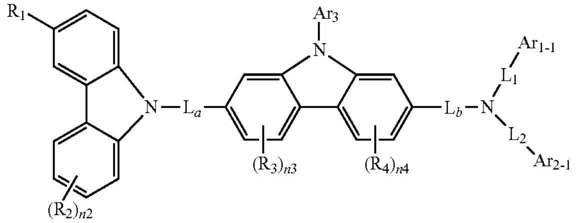

Formula 7-3

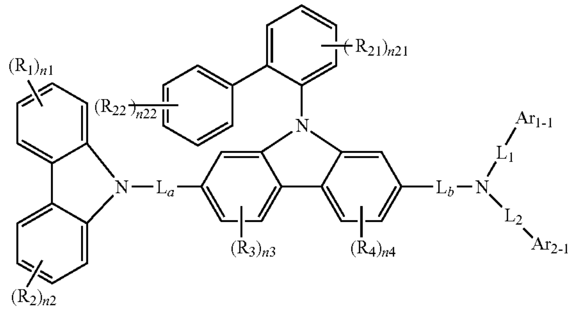

wherein in Formula 7-1, any one among $L_{a2}$ and $L_{b2}$ is a substituted or unsubstituted arylene group of 6 to 30 ring-forming carbon atoms, and the remainder is a direct linkage or a substituted or unsubstituted arylene group of 6 to 30 ring-forming carbon atoms, wherein in Formula 7-3, $R_{21}$, and $R_{22}$ are each independently a hydrogen atom, a deuterium atom, a halogen atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, n21 is an integer from 0 to 4, and n22 is an integer from 0 to 5, wherein in Formula 7-1 to Formula 7-3, any one among $Ar_{1-1}$ and $Ar_{2-1}$ is represented by any one among Formula A1 to Formula A4, and the remainder is a substituted or unsubstituted alkyl group of 1 to 20 carbon atoms, a substituted or unsubstituted silyl group, a substituted or unsubstituted aryl group of 6 to 30 ring-forming carbon atoms, or a substituted or unsubstituted heteroaryl group of 2 to 30 ring-forming carbon atoms, Formula A1

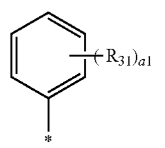

Formula A2

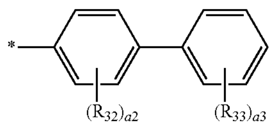

Formula A3

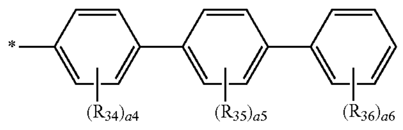

Formula A4

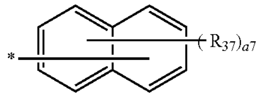

wherein in Formula A1 to Formula A4, $R_{31}$ to $R_{37}$ are each independently a hydrogen atom, a deuterium atom, a halogen atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, a1, a3, and a6 are each independently an integer from 0 to 5, a2, a4, and a5 are each independently an integer from 0 to 4, and a7 is an integer from 0 to 7, and wherein in Formula 7-1 to Formula 7-3, $Ar_3$, $R_1$ to $R_4$, $L_a$, $L_b$, $L_1$, $L_2$, and n1 to n4 are the same as defined in Formula 1.

11. The light emitting device of claim 1, wherein $L_a$ and $L_b$ are each independently represented by any one among Formula L-1 to Formula L-5:

Formula L-1

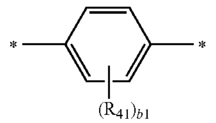

Formula L-2

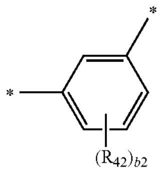

Formula L-3

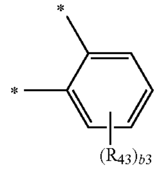

Formula L-4

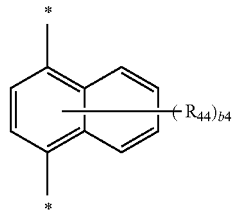

Formula L-5

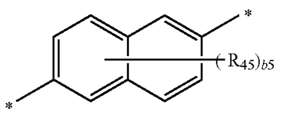

wherein in Formula L-1 to Formula L-5, $R_{41}$ to $R_{45}$ are each independently a hydrogen atom, a deuterium atom, a halogen atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, b1 to b3 are each independently an integer from 0 to 4, and b4, and b5 are each independently an integer from 0 to 6.

12. The light emitting device of claim 1, wherein the amine compound represented by Formula 1 is represented by Formula 8:

Formula 8

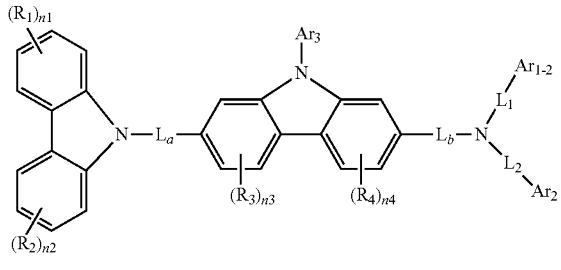

wherein in Formula 8, $Ar_{12}$ is represented by Formula a, or represented by any one among Formula B1 to Formula B3:

Formula B1

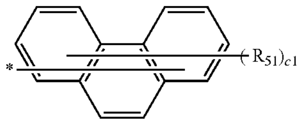

Formula B2

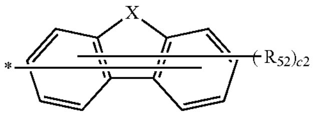

Formula B3

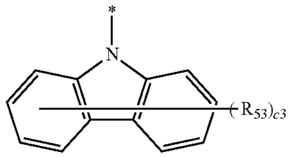

wherein in Formula B1 to Formula B3,

X is O, S, $NR_{54}$, or $CR_{55}R_{56}$, $R_{51}$ to $R_{53}$ are each independently a hydrogen atom, a deuterium atom, a halogen atom, a substituted or unsubstituted oxy group, a substituted or unsubstituted alkyl group of 1 to 20 carbon atoms, a substituted or unsubstituted alkenyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms, or combined with an adjacent group to form a ring, $R_{54}$ to $R_{56}$ are each independently a substituted or unsubstituted aryl group of 6 to 30 carbon atoms, c1 is an integer from 0 to 9, c2 is an integer from 0 to 7, and c3 is an integer from 0 to 8, and wherein in Formula 8, $Ar_2$, $Ar_3$, $R_1$ to $R_4$, $L_a$, $L_b$, $L_1$, $L_2$, and n1 to n4 are the same as defined in Formula 1.

13. The light emitting device of claim 1, wherein $Ar_1$ and $Ar_2$ each independently comprise at least one among compounds in Compound Group A to Compound Group E:

Compound Group A a1

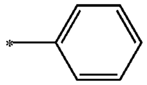

a2

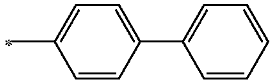

a3

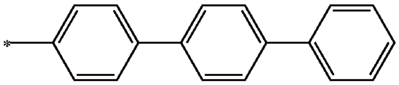

a4

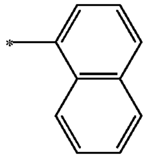

-continued a5

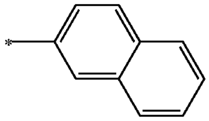

a6

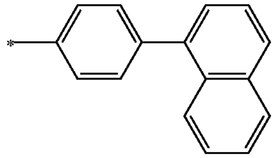

a7

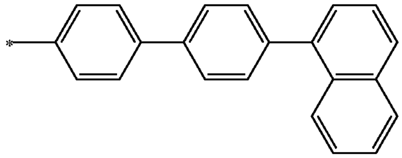

a8

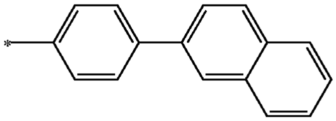

a9

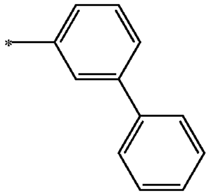

a10

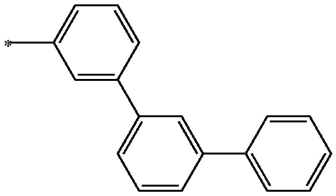

a11

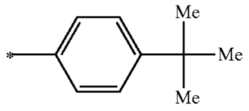

a12

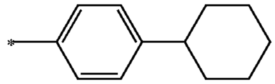

a14

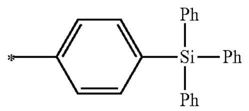

a15

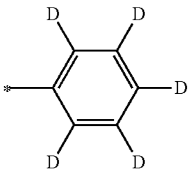

Compound Group B
b1
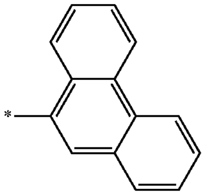
b2
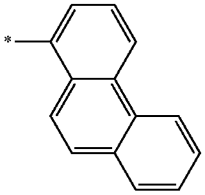
b3
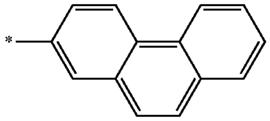
b4
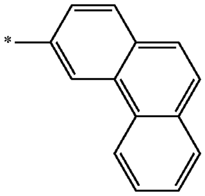
b5
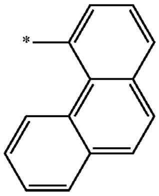
b6
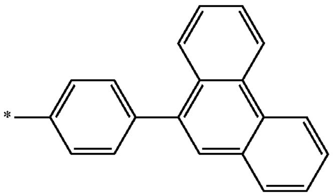
b7
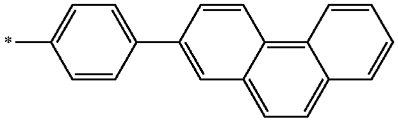
b8
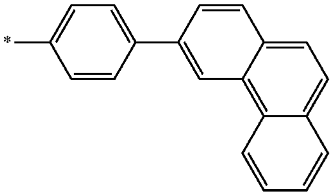
Compound Group C
c1
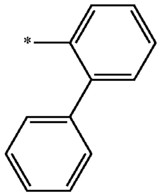
c2
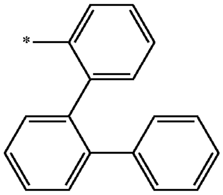
c3
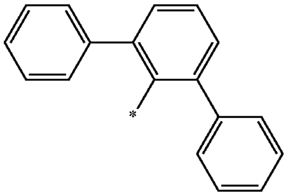
c4
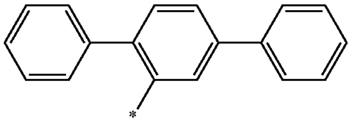
c5
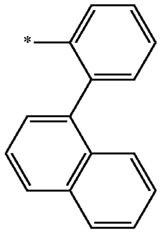
Compound Group D
d1
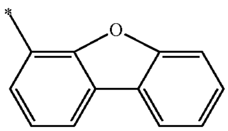
d2
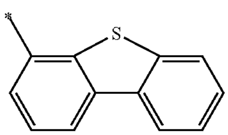
d3
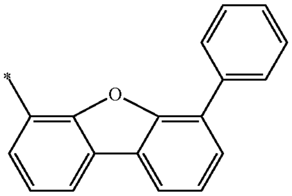

d4
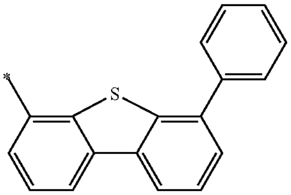
d5
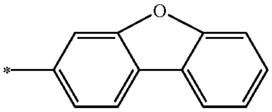
d6
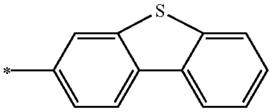
d7
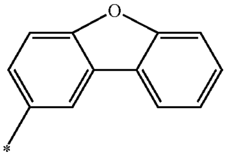
d8
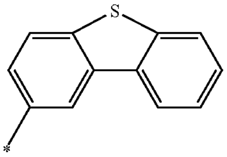
d9
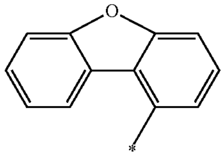
d10
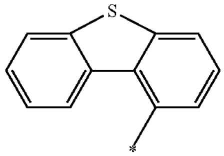
d11
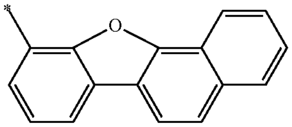
d12
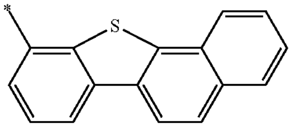
d13
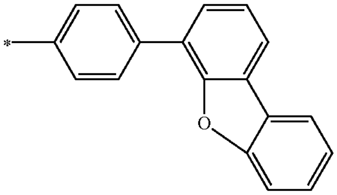
d14
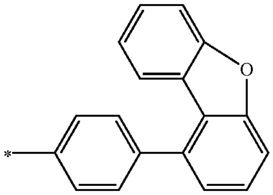
d15
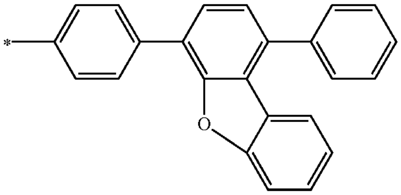
d16
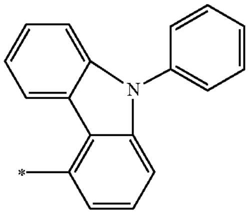
d17
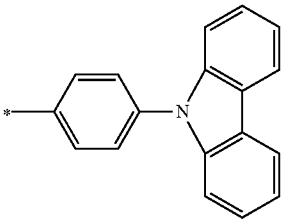
d18
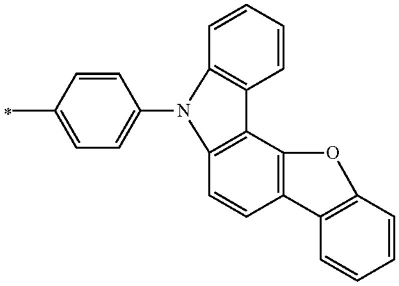

Compound Group E e1
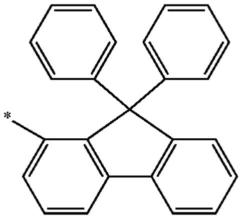

e2
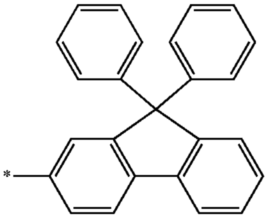

e3
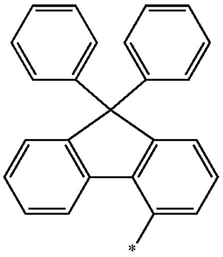

e4
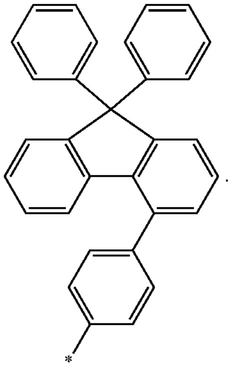

14. The light emitting device of claim 1, wherein the amine compound represented by Formula 1 is represented by Formula 9, and the amine compound is a compound satisfying any one among combinations represented in Compound Combination Table 1:

Formula 9
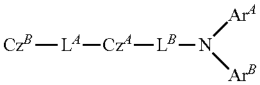

wherein in Formula 9, $Ar^A$ and $Ar^B$ are each independently selected from Compound Group A to Compound Group E, $Cz^A$ is selected from Compound Group G, $Cz^B$ is selected from Compound Group F, and $L^A$, and $L^B$ are selected from Compound Group H:

Compound Group A a1
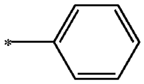

a2
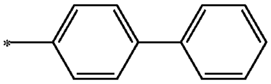

a3
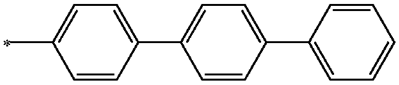

a4
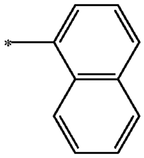

a5
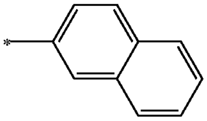

a6
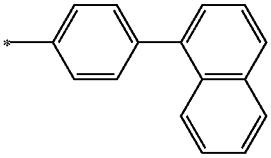

a7
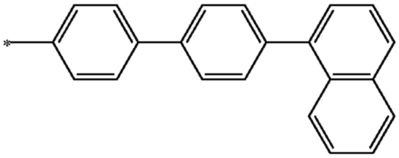

a8
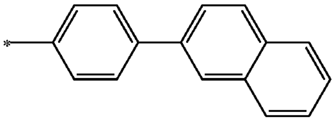

a9
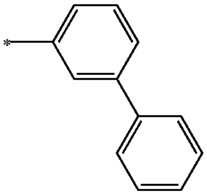

a10
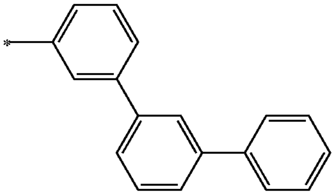

a11
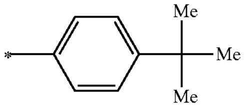

-continued
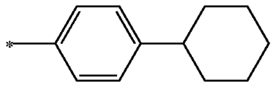
a12
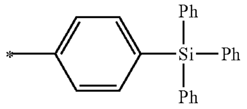
a14
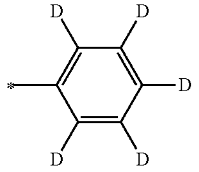
a15
Compound Group B
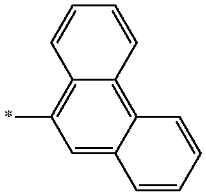
b1
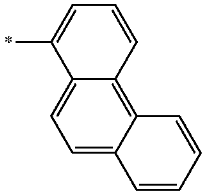
b2
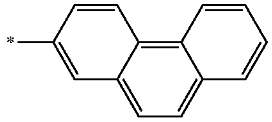
b3
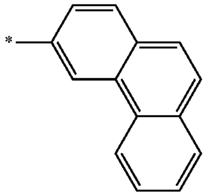
b4
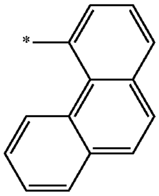
b5
-continued
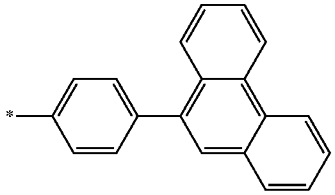
b6
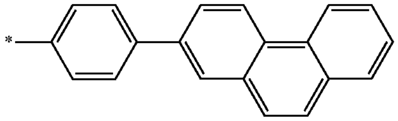
b7
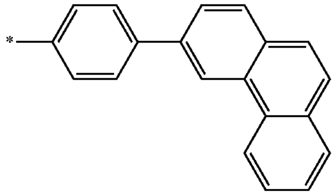
b8
Compound Group C
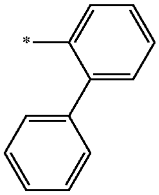
c1
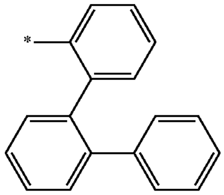
c2
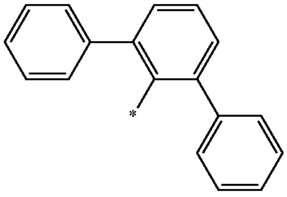
c3
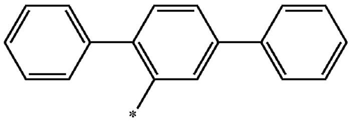
c4

-continued
c5
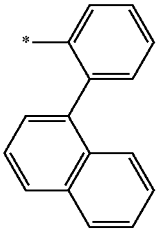
Compound Group D
d1
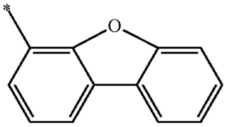
d2
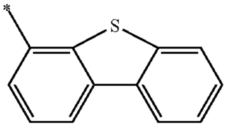
d3
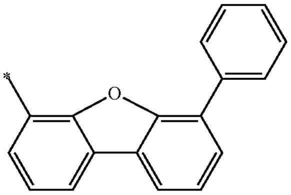
d4
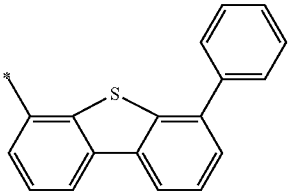
d5
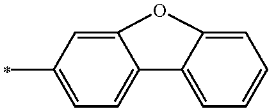
d6
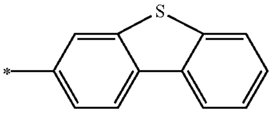
d7
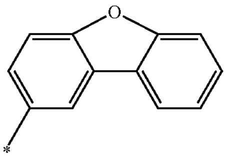
-continued
d8
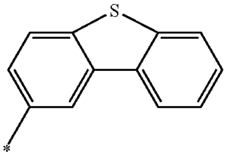
d9
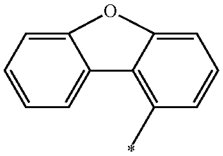
d10
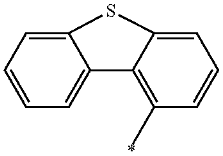
d11
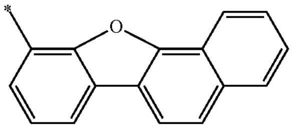
d12
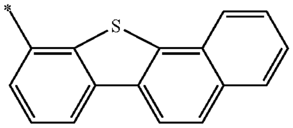
d13
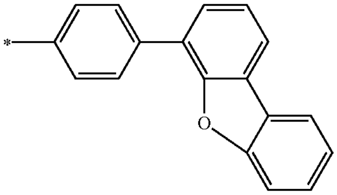
d14
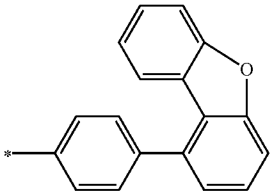
d15
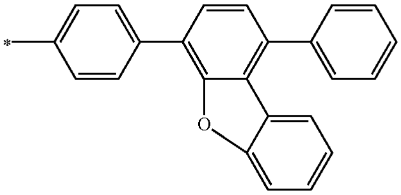

-continued
d16
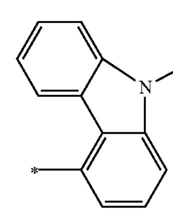
d17
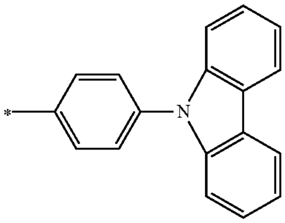
d18
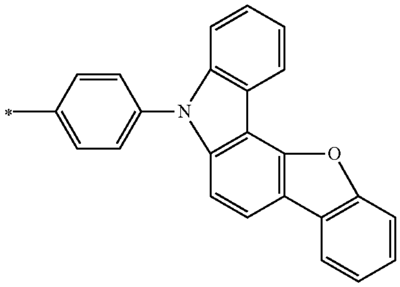
Compound Group E
e1
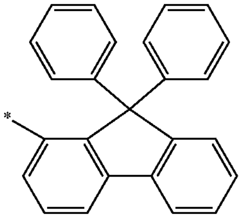
e2
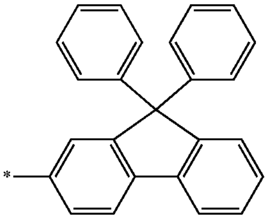
e3
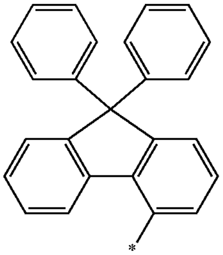
-continued
e4
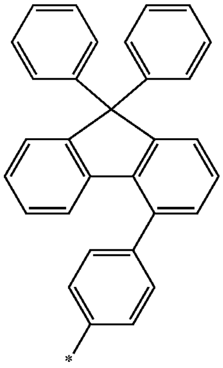
Compound Group F
f1
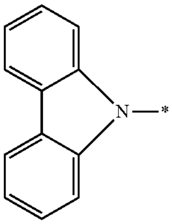
f2
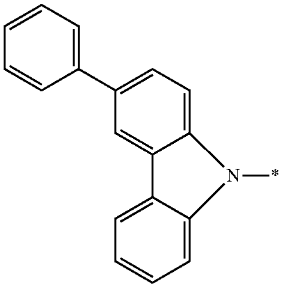
f3
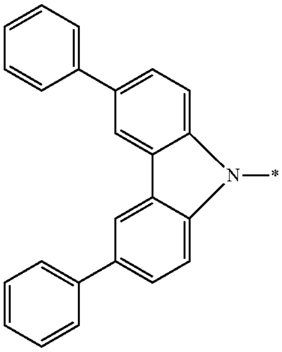

-continued f4

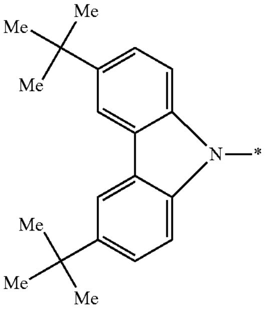

Compound Group G g1

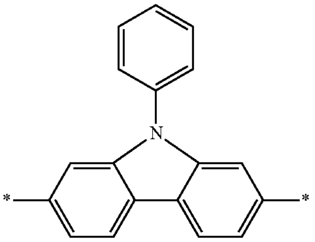

g2

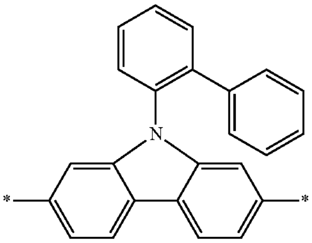

g3

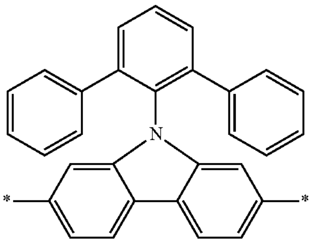

Compound Group H h1

*—* h2

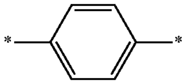

h3

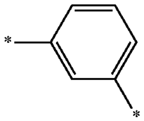

-continued h4

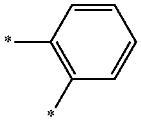

h5

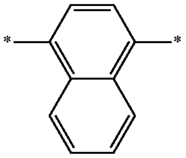

h6

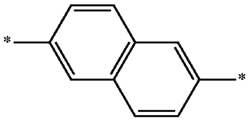

Compound Combination Table 1

| No. | $Cz^b$ | $L^A$ | $Cz^A$ | $L^B$ | $Ar^A$ | $Ar^B$ |
|---|---|---|---|---|---|---|
| 1 | f1 | h2 | g1 | h2 | a1 | a1 |
| 2 | f1 | h2 | g1 | h1 | a1 | a1 |
| 3 | f1 | h3 | g1 | h1 | a1 | a1 |
| 4 | f1 | h4 | g1 | h1 | a1 | a1 |
| 5 | f1 | h5 | g1 | h1 | a1 | a1 |
| 6 | f1 | h6 | g1 | h1 | a1 | a1 |
| 7 | f1 | h1 | g1 | h2 | a1 | a1 |
| 8 | f1 | h1 | g1 | h2 | a1 | a2 |
| 9 | f1 | h1 | g1 | h2 | a1 | a4 |
| 10 | f1 | h1 | g1 | h2 | a1 | a5 |
| 11 | f1 | h1 | g1 | h2 | a1 | a6 |
| 12 | f1 | h1 | g1 | h2 | a1 | a11 |
| 13 | f1 | h1 | g1 | h2 | a1 | a15 |
| 14 | f1 | h1 | g1 | h2 | a1 | b1 |
| 15 | f1 | h1 | g1 | h2 | a1 | b3 |
| 16 | f1 | h1 | g1 | h2 | a1 | b4 |
| 17 | f1 | h1 | g1 | h2 | a1 | b6 |
| 18 | f1 | h1 | g1 | h2 | a1 | c1 |
| 19 | f1 | h1 | g1 | h2 | a1 | d1 |
| 20 | f1 | h1 | g1 | h2 | a1 | d2 |
| 21 | f1 | h1 | g1 | h2 | a1 | d3 |
| 22 | f1 | h1 | g1 | h2 | a1 | d5 |
| 23 | f1 | h1 | g1 | h2 | a1 | d7 |
| 24 | f1 | h1 | g1 | h2 | a1 | d9 |
| 25 | f1 | h1 | g1 | h2 | a1 | d11 |
| 26 | f1 | h1 | g1 | h2 | a1 | d13 |
| 27 | f1 | h1 | g1 | h2 | a1 | d17 |
| 28 | f1 | h1 | g1 | h2 | a1 | e3 |
| 29 | f1 | h1 | g1 | h2 | a2 | a2 |
| 30 | f1 | h1 | g1 | h2 | a2 | a4 |
| 31 | f1 | h1 | g1 | h2 | a2 | a5 |
| 32 | f1 | h1 | g1 | h2 | a2 | a6 |
| 33 | f1 | h1 | g1 | h2 | a2 | a11 |
| 34 | f1 | h1 | g1 | h2 | a2 | a15 |
| 35 | f1 | h1 | g1 | h2 | a2 | b1 |
| 36 | f1 | h1 | g1 | h2 | a2 | b3 |
| 37 | f1 | h1 | g1 | h2 | a2 | b4 |
| 38 | f1 | h1 | g1 | h2 | a2 | b6 |
| 39 | f1 | h1 | g1 | h2 | a2 | c1 |
| 40 | f1 | h1 | g1 | h2 | a2 | d1 |
| 41 | f1 | h1 | g1 | h2 | a2 | d2 |
| 42 | f1 | h1 | g1 | h2 | a2 | d3 |
| 43 | f1 | h1 | g1 | h2 | a2 | d5 |
| 44 | f1 | h1 | g1 | h2 | a2 | d7 |
| 45 | f1 | h1 | g1 | h2 | a2 | d9 |
| 46 | f1 | h1 | g1 | h2 | a2 | d11 |
| 47 | f1 | h1 | g1 | h2 | a2 | d13 |
| 48 | f1 | h1 | g1 | h2 | a2 | d17 |
| 49 | f1 | h1 | g1 | h2 | a2 | e3 |
| 50 | f1 | h1 | g1 | h2 | a4 | a4 |
| 51 | f1 | h1 | g1 | h2 | a4 | a5 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 52 | f1 | h1 | g1 | h2 | a4 | a6 |
| 53 | f1 | h1 | g1 | h2 | a4 | a11 |
| 54 | f1 | h1 | g1 | h2 | a4 | a15 |
| 55 | f1 | h1 | g1 | h2 | a4 | b1 |
| 56 | f1 | h1 | g1 | h2 | a4 | b3 |
| 57 | f1 | h1 | g1 | h2 | a4 | b4 |
| 58 | f1 | h1 | g1 | h2 | a4 | b6 |
| 59 | f1 | h1 | g1 | h2 | a4 | c1 |
| 60 | f1 | h1 | g1 | h2 | a4 | d1 |
| 61 | f1 | h1 | g1 | h2 | a4 | d2 |
| 62 | f1 | h1 | g1 | h2 | a4 | d3 |
| 63 | f1 | h1 | g1 | h2 | a4 | d5 |
| 64 | f1 | h1 | g1 | h2 | a4 | d7 |
| 65 | f1 | h1 | g1 | h2 | a4 | d9 |
| 66 | f1 | h1 | g1 | h2 | a4 | d11 |
| 67 | f1 | h1 | g1 | h2 | a4 | d13 |
| 68 | f1 | h1 | g1 | h2 | a4 | d17 |
| 69 | f1 | h1 | g1 | h2 | a4 | e3 |
| 70 | f1 | h1 | g1 | h2 | a5 | a5 |
| 71 | f1 | h1 | g1 | h2 | a5 | a6 |
| 72 | f1 | h1 | g1 | h2 | a5 | a11 |
| 73 | f1 | h1 | g1 | h2 | a5 | a15 |
| 74 | f1 | h1 | g1 | h2 | a5 | b1 |
| 75 | f1 | h1 | g1 | h2 | a5 | b3 |
| 76 | f1 | h1 | g1 | h2 | a5 | b4 |
| 77 | f1 | h1 | g1 | h2 | a5 | b6 |
| 78 | f1 | h1 | g1 | h2 | a5 | c1 |
| 79 | f1 | h1 | g1 | h2 | a5 | d1 |
| 80 | f1 | h1 | g1 | h2 | a5 | d2 |
| 81 | f1 | h1 | g1 | h2 | a5 | d3 |
| 82 | f1 | h1 | g1 | h2 | a5 | d5 |
| 83 | f1 | h1 | g1 | h2 | a5 | d7 |
| 84 | f1 | h1 | g1 | h2 | a5 | d9 |
| 85 | f1 | h1 | g1 | h2 | a5 | d11 |
| 86 | f1 | h1 | g1 | h2 | a5 | d13 |
| 87 | f1 | h1 | g1 | h2 | a5 | d17 |
| 88 | f1 | h1 | g1 | h2 | a5 | e3 |
| 89 | f1 | h1 | g1 | h2 | a6 | a6 |
| 90 | f1 | h1 | g1 | h2 | a6 | a11 |
| 91 | f1 | h1 | g1 | h2 | a6 | a15 |
| 92 | f1 | h1 | g1 | h2 | a6 | b1 |
| 93 | f1 | h1 | g1 | h2 | a6 | b3 |
| 94 | f1 | h1 | g1 | h2 | a6 | b4 |
| 95 | f1 | h1 | g1 | h2 | a6 | b6 |
| 96 | f1 | h1 | g1 | h2 | a6 | c1 |
| 97 | f1 | h1 | g1 | h2 | a6 | d1 |
| 98 | f1 | h1 | g1 | h2 | a6 | d2 |
| 99 | f1 | h1 | g1 | h2 | a6 | d3 |
| 100 | f1 | h1 | g1 | h2 | a6 | d5 |
| 101 | f1 | h1 | g1 | h2 | a6 | d7 |
| 102 | f1 | h1 | g1 | h2 | a6 | d9 |
| 103 | f1 | h1 | g1 | h2 | a6 | d11 |
| 104 | f1 | h1 | g1 | h2 | a6 | d13 |
| 105 | f1 | h1 | g1 | h2 | a6 | d17 |
| 106 | f1 | h1 | g1 | h2 | a6 | e3 |
| 107 | f1 | h1 | g1 | h2 | a11 | a11 |
| 108 | f1 | h1 | g1 | h2 | a11 | a15 |
| 109 | f1 | h1 | g1 | h2 | a11 | b1 |
| 110 | f1 | h1 | g1 | h2 | a11 | b3 |
| 111 | f1 | h1 | g1 | h2 | a11 | b4 |
| 112 | f1 | h1 | g1 | h2 | a11 | b6 |
| 113 | f1 | h1 | g1 | h2 | a11 | c1 |
| 114 | f1 | h1 | g1 | h2 | a11 | d1 |
| 115 | f1 | h1 | g1 | h2 | a11 | d2 |
| 116 | f1 | h1 | g1 | h2 | a11 | d3 |
| 117 | f1 | h1 | g1 | h2 | a11 | d5 |
| 118 | f1 | h1 | g1 | h2 | a11 | d7 |
| 119 | f1 | h1 | g1 | h2 | a11 | d9 |
| 120 | f1 | h1 | g1 | h2 | a11 | d11 |
| 121 | f1 | h1 | g1 | h2 | a11 | d13 |
| 122 | f1 | h1 | g1 | h2 | a11 | d17 |
| 123 | f1 | h1 | g1 | h2 | a11 | e3 |
| 124 | f1 | h1 | g1 | h2 | a15 | a15 |
| 125 | f1 | h1 | g1 | h2 | a15 | b1 |
| 126 | f1 | h1 | g1 | h2 | a15 | b3 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 127 | f1 | h1 | g1 | h2 | a15 | b4 |
| 128 | f1 | h1 | g1 | h2 | a15 | b6 |
| 129 | f1 | h1 | g1 | h2 | a15 | c1 |
| 130 | f1 | h1 | g1 | h2 | a15 | d1 |
| 131 | f1 | h1 | g1 | h2 | a15 | d2 |
| 132 | f1 | h1 | g1 | h2 | a15 | d3 |
| 133 | f1 | h1 | g1 | h2 | a15 | d5 |
| 134 | f1 | h1 | g1 | h2 | a15 | d7 |
| 135 | f1 | h1 | g1 | h2 | a15 | d9 |
| 136 | f1 | h1 | g1 | h2 | a15 | d11 |
| 137 | f1 | h1 | g1 | h2 | a15 | d13 |
| 138 | f1 | h1 | g1 | h2 | a15 | d17 |
| 139 | f1 | h1 | g1 | h2 | a15 | e3 |
| 140 | f1 | h1 | g1 | h2 | b1 | b1 |
| 141 | f1 | h1 | g1 | h2 | b1 | b3 |
| 142 | f1 | h1 | g1 | h2 | b1 | b4 |
| 143 | f1 | h1 | g1 | h2 | b1 | b6 |
| 144 | f1 | h1 | g1 | h2 | b1 | c1 |
| 145 | f1 | h1 | g1 | h2 | b1 | d1 |
| 146 | f1 | h1 | g1 | h2 | b1 | d2 |
| 147 | f1 | h1 | g1 | h2 | b1 | d3 |
| 148 | f1 | h1 | g1 | h2 | b1 | d5 |
| 149 | f1 | h1 | g1 | h2 | b1 | d7 |
| 150 | f1 | h1 | g1 | h2 | b1 | d9 |
| 151 | f1 | h1 | g1 | h2 | b1 | d11 |
| 152 | f1 | h1 | g1 | h2 | b1 | d13 |
| 153 | f1 | h1 | g1 | h2 | b1 | d17 |
| 154 | f1 | h1 | g1 | h2 | b1 | e3 |
| 155 | f1 | h1 | g1 | h2 | b3 | b3 |
| 156 | f1 | h1 | g1 | h2 | b3 | b4 |
| 157 | f1 | h1 | g1 | h2 | b3 | b6 |
| 158 | f1 | h1 | g1 | h2 | b3 | c1 |
| 159 | f1 | h1 | g1 | h2 | b3 | d1 |
| 160 | f1 | h1 | g1 | h2 | b3 | d2 |
| 161 | f1 | h1 | g1 | h2 | b3 | d3 |
| 162 | f1 | h1 | g1 | h2 | b3 | d5 |
| 163 | f1 | h1 | g1 | h2 | b3 | d7 |
| 164 | f1 | h1 | g1 | h2 | b3 | d9 |
| 165 | f1 | h1 | g1 | h2 | b3 | d11 |
| 166 | f1 | h1 | g1 | h2 | b3 | d13 |
| 167 | f1 | h1 | g1 | h2 | b3 | d17 |
| 168 | f1 | h1 | g1 | h2 | b3 | e3 |
| 169 | f1 | h1 | g1 | h2 | b4 | b4 |
| 170 | f1 | h1 | g1 | h2 | b4 | b6 |
| 171 | f1 | h1 | g1 | h2 | b4 | c1 |
| 172 | f1 | h1 | g1 | h2 | b4 | d1 |
| 173 | f1 | h1 | g1 | h2 | b4 | d2 |
| 174 | f1 | h1 | g1 | h2 | b4 | d3 |
| 175 | f1 | h1 | g1 | h2 | b4 | d5 |
| 176 | f1 | h1 | g1 | h2 | b4 | d7 |
| 177 | f1 | h1 | g1 | h2 | b4 | d9 |
| 178 | f1 | h1 | g1 | h2 | b4 | d11 |
| 179 | f1 | h1 | g1 | h2 | b4 | d13 |
| 180 | f1 | h1 | g1 | h2 | b4 | d17 |
| 181 | f1 | h1 | g1 | h2 | b4 | e3 |
| 182 | f1 | h1 | g1 | h2 | b6 | b6 |
| 183 | f1 | h1 | g1 | h2 | b6 | c1 |
| 184 | f1 | h1 | g1 | h2 | b6 | d1 |
| 185 | f1 | h1 | g1 | h2 | b6 | d2 |
| 186 | f1 | h1 | g1 | h2 | b6 | d3 |
| 187 | f1 | h1 | g1 | h2 | b6 | d5 |
| 188 | f1 | h1 | g1 | h2 | b6 | d7 |
| 189 | f1 | h1 | g1 | h2 | b6 | d9 |
| 190 | f1 | h1 | g1 | h2 | b6 | d11 |
| 191 | f1 | h1 | g1 | h2 | b6 | d13 |
| 192 | f1 | h1 | g1 | h2 | b6 | d17 |
| 193 | f1 | h1 | g1 | h2 | b6 | e3 |
| 194 | f1 | h1 | g1 | h2 | c1 | c1 |
| 195 | f1 | h1 | g1 | h2 | c1 | d1 |
| 196 | f1 | h1 | g1 | h2 | c1 | d2 |
| 197 | f1 | h1 | g1 | h2 | c1 | d3 |
| 198 | f1 | h1 | g1 | h2 | c1 | d5 |
| 199 | f1 | h1 | g1 | h2 | c1 | d7 |
| 200 | f1 | h1 | g1 | h2 | c1 | d9 |
| 201 | f1 | h1 | g1 | h2 | c1 | d11 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 202 | f1 | h1 | g1 | h2 | c1 | d13 |
| 203 | f1 | h1 | g1 | h2 | c1 | d17 |
| 204 | f1 | h1 | g1 | h2 | c1 | e3 |
| 205 | f1 | h1 | g1 | h2 | d1 | d1 |
| 206 | f1 | h1 | g1 | h2 | d1 | d2 |
| 207 | f1 | h1 | g1 | h2 | d1 | d3 |
| 208 | f1 | h1 | g1 | h2 | d1 | d5 |
| 209 | f1 | h1 | g1 | h2 | d1 | d7 |
| 210 | f1 | h1 | g1 | h2 | d1 | d9 |
| 211 | f1 | h1 | g1 | h2 | d1 | d11 |
| 212 | f1 | h1 | g1 | h2 | d1 | d13 |
| 213 | f1 | h1 | g1 | h2 | d1 | d17 |
| 214 | f1 | h1 | g1 | h2 | d1 | e3 |
| 215 | f1 | h1 | g1 | h2 | d2 | d2 |
| 216 | f1 | h1 | g1 | h2 | d2 | d3 |
| 217 | f1 | h1 | g1 | h2 | d2 | d5 |
| 218 | f1 | h1 | g1 | h2 | d2 | d7 |
| 219 | f1 | h1 | g1 | h2 | d2 | d9 |
| 220 | f1 | h1 | g1 | h2 | d2 | d11 |
| 221 | f1 | h1 | g1 | h2 | d2 | d13 |
| 222 | f1 | h1 | g1 | h2 | d2 | d17 |
| 223 | f1 | h1 | g1 | h2 | d2 | e3 |
| 224 | f1 | h1 | g1 | h2 | d3 | d3 |
| 225 | f1 | h1 | g1 | h2 | d3 | d5 |
| 226 | f1 | h1 | g1 | h2 | d3 | d7 |
| 227 | f1 | h1 | g1 | h2 | d3 | d9 |
| 228 | f1 | h1 | g1 | h2 | d3 | d11 |
| 229 | f1 | h1 | g1 | h2 | d3 | d13 |
| 230 | f1 | h1 | g1 | h2 | d3 | d17 |
| 231 | f1 | h1 | g1 | h2 | d3 | e3 |
| 232 | f1 | h1 | g1 | h2 | d5 | d5 |
| 233 | f1 | h1 | g1 | h2 | d5 | d7 |
| 234 | f1 | h1 | g1 | h2 | d5 | d9 |
| 235 | f1 | h1 | g1 | h2 | d5 | d11 |
| 236 | f1 | h1 | g1 | h2 | d5 | d13 |
| 237 | f1 | h1 | g1 | h2 | d5 | d17 |
| 238 | f1 | h1 | g1 | h2 | d5 | e3 |
| 239 | f1 | h1 | g1 | h2 | d7 | d7 |
| 240 | f1 | h1 | g1 | h2 | d7 | d9 |
| 241 | f1 | h1 | g1 | h2 | d7 | d11 |
| 242 | f1 | h1 | g1 | h2 | d7 | d13 |
| 243 | f1 | h1 | g1 | h2 | d7 | d17 |
| 244 | f1 | h1 | g1 | h2 | d7 | e3 |
| 245 | f1 | h1 | g1 | h2 | d9 | d9 |
| 246 | f1 | h1 | g1 | h2 | d9 | d11 |
| 247 | f1 | h1 | g1 | h2 | d9 | d13 |
| 248 | f1 | h1 | g1 | h2 | d9 | d17 |
| 249 | f1 | h1 | g1 | h2 | d9 | e3 |
| 250 | f1 | h1 | g1 | h2 | d11 | d11 |
| 251 | f1 | h1 | g1 | h2 | d11 | d13 |
| 252 | f1 | h1 | g1 | h2 | d11 | d17 |
| 253 | f1 | h1 | g1 | h2 | d11 | e3 |
| 254 | f1 | h1 | g1 | h2 | d13 | d13 |
| 255 | f1 | h1 | g1 | h2 | d13 | d17 |
| 256 | f1 | h1 | g1 | h2 | d13 | e3 |
| 257 | f1 | h1 | g1 | h2 | d17 | d17 |
| 258 | f1 | h1 | g1 | h2 | e3 | e3 |
| 259 | f2 | h1 | g1 | h1 | a1 | a1 |
| 260 | f2 | h1 | g1 | h1 | a1 | a2 |
| 261 | f2 | h1 | g1 | h1 | a1 | a4 |
| 262 | f2 | h1 | g1 | h1 | a1 | a5 |
| 263 | f2 | h1 | g1 | h1 | a1 | a6 |
| 264 | f2 | h1 | g1 | h1 | a1 | a11 |
| 265 | f2 | h1 | g1 | h1 | a1 | a15 |
| 266 | f2 | h1 | g1 | h1 | a1 | b1 |
| 267 | f2 | h1 | g1 | h1 | a1 | b3 |
| 268 | f2 | h1 | g1 | h1 | a1 | b4 |
| 269 | f2 | h1 | g1 | h1 | a1 | b6 |
| 270 | f2 | h1 | g1 | h1 | a1 | c1 |
| 271 | f2 | h1 | g1 | h1 | a1 | d1 |
| 272 | f2 | h1 | g1 | h1 | a1 | d2 |
| 273 | f2 | h1 | g1 | h1 | a1 | d3 |
| 274 | f2 | h1 | g1 | h1 | a1 | d5 |
| 275 | f2 | h1 | g1 | h1 | a1 | d7 |
| 276 | f2 | h1 | g1 | h1 | a1 | d9 |
| 277 | f2 | h1 | g1 | h1 | a1 | d11 |
| 278 | f2 | h1 | g1 | h1 | a1 | d13 |
| 279 | f2 | h1 | g1 | h1 | a1 | d17 |
| 280 | f2 | h1 | g1 | h1 | a1 | e3 |
| 281 | f2 | h1 | g1 | h1 | a2 | a2 |
| 282 | f2 | h1 | g1 | h1 | a2 | a4 |
| 283 | f2 | h1 | g1 | h1 | a2 | a5 |
| 284 | f2 | h1 | g1 | h1 | a2 | a6 |
| 285 | f2 | h1 | g1 | h1 | a2 | a11 |
| 286 | f2 | h1 | g1 | h1 | a2 | a15 |
| 287 | f2 | h1 | g1 | h1 | a2 | b1 |
| 288 | f2 | h1 | g1 | h1 | a2 | b3 |
| 289 | f2 | h1 | g1 | h1 | a2 | b4 |
| 290 | f2 | h1 | g1 | h1 | a2 | b6 |
| 291 | f2 | h1 | g1 | h1 | a2 | c1 |
| 292 | f2 | h1 | g1 | h1 | a2 | d1 |
| 293 | f2 | h1 | g1 | h1 | a2 | d2 |
| 294 | f2 | h1 | g1 | h1 | a2 | d3 |
| 295 | f2 | h1 | g1 | h1 | a2 | d5 |
| 296 | f2 | h1 | g1 | h1 | a2 | d7 |
| 297 | f2 | h1 | g1 | h1 | a2 | d9 |
| 298 | f2 | h1 | g1 | h1 | a2 | d11 |
| 299 | f2 | h1 | g1 | h1 | a2 | d13 |
| 300 | f2 | h1 | g1 | h1 | a2 | d17 |
| 301 | f2 | h1 | g1 | h1 | a2 | e3 |
| 302 | f2 | h1 | g1 | h1 | a4 | a4 |
| 303 | f2 | h1 | g1 | h1 | a4 | a5 |
| 304 | f2 | h1 | g1 | h1 | a4 | a6 |
| 305 | f2 | h1 | g1 | h1 | a4 | a11 |
| 306 | f2 | h1 | g1 | h1 | a4 | a15 |
| 307 | f2 | h1 | g1 | h1 | a4 | b1 |
| 308 | f2 | h1 | g1 | h1 | a4 | b3 |
| 309 | f2 | h1 | g1 | h1 | a4 | b4 |
| 310 | f2 | h1 | g1 | h1 | a4 | b6 |
| 311 | f2 | h1 | g1 | h1 | a4 | c1 |
| 312 | f2 | h1 | g1 | h1 | a4 | d1 |
| 313 | f2 | h1 | g1 | h1 | a4 | d2 |
| 314 | f2 | h1 | g1 | h1 | a4 | d3 |
| 315 | f2 | h1 | g1 | h1 | a4 | d5 |
| 316 | f2 | h1 | g1 | h1 | a4 | d7 |
| 317 | f2 | h1 | g1 | h1 | a4 | d9 |
| 318 | f2 | h1 | g1 | h1 | a4 | d11 |
| 319 | f2 | h1 | g1 | h1 | a4 | d13 |
| 320 | f2 | h1 | g1 | h1 | a4 | d17 |
| 321 | f2 | h1 | g1 | h1 | a4 | e3 |
| 322 | f2 | h1 | g1 | h1 | a5 | a5 |
| 323 | f2 | h1 | g1 | h1 | a5 | a6 |
| 324 | f2 | h1 | g1 | h1 | a5 | a11 |
| 325 | f2 | h1 | g1 | h1 | a5 | a15 |
| 326 | f2 | h1 | g1 | h1 | a5 | b1 |
| 327 | f2 | h1 | g1 | h1 | a5 | b3 |
| 328 | f2 | h1 | g1 | h1 | a5 | b4 |
| 329 | f2 | h1 | g1 | h1 | a5 | b6 |
| 330 | f2 | h1 | g1 | h1 | a5 | c1 |
| 331 | f2 | h1 | g1 | h1 | a5 | d1 |
| 332 | f2 | h1 | g1 | h1 | a5 | d2 |
| 333 | f2 | h1 | g1 | h1 | a5 | d3 |
| 334 | f2 | h1 | g1 | h1 | a5 | d5 |
| 335 | f2 | h1 | g1 | h1 | a5 | d7 |
| 336 | f2 | h1 | g1 | h1 | a5 | d9 |
| 337 | f2 | h1 | g1 | h1 | a5 | d11 |
| 338 | f2 | h1 | g1 | h1 | a5 | d13 |
| 339 | f2 | h1 | g1 | h1 | a5 | d17 |
| 340 | f2 | h1 | g1 | h1 | a5 | e3 |
| 341 | f2 | h1 | g1 | h1 | a6 | a6 |
| 342 | f2 | h1 | g1 | h1 | a6 | a11 |
| 343 | f2 | h1 | g1 | h1 | a6 | a15 |
| 344 | f2 | h1 | g1 | h1 | a6 | b1 |
| 345 | f2 | h1 | g1 | h1 | a6 | b3 |
| 346 | f2 | h1 | g1 | h1 | a6 | b4 |
| 347 | f2 | h1 | g1 | h1 | a6 | b6 |
| 348 | f2 | h1 | g1 | h1 | a6 | c1 |
| 349 | f2 | h1 | g1 | h1 | a6 | d1 |
| 350 | f2 | h1 | g1 | h1 | a6 | d2 |
| 351 | f2 | h1 | g1 | h1 | a6 | d3 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 352 | f2 | h1 | g1 | h1 | a6 | d5 |
| 353 | f2 | h1 | g1 | h1 | a6 | d7 |
| 354 | f2 | h1 | g1 | h1 | a6 | d9 |
| 355 | f2 | h1 | g1 | h1 | a6 | d11 |
| 356 | f2 | h1 | g1 | h1 | a6 | d13 |
| 357 | f2 | h1 | g1 | h1 | a6 | d17 |
| 358 | f2 | h1 | g1 | h1 | a6 | e3 |
| 359 | f2 | h1 | g1 | h1 | a11 | a11 |
| 360 | f2 | h1 | g1 | h1 | a11 | a15 |
| 361 | f2 | h1 | g1 | h1 | a11 | b1 |
| 362 | f2 | h1 | g1 | h1 | a11 | b3 |
| 363 | f2 | h1 | g1 | h1 | a11 | b4 |
| 364 | f2 | h1 | g1 | h1 | a11 | b6 |
| 365 | f2 | h1 | g1 | h1 | a11 | c1 |
| 366 | f2 | h1 | g1 | h1 | a11 | d1 |
| 367 | f2 | h1 | g1 | h1 | a11 | d2 |
| 368 | f2 | h1 | g1 | h1 | a11 | d3 |
| 369 | f2 | h1 | g1 | h1 | a11 | d5 |
| 370 | f2 | h1 | g1 | h1 | a11 | d7 |
| 371 | f2 | h1 | g1 | h1 | a11 | d9 |
| 372 | f2 | h1 | g1 | h1 | a11 | d11 |
| 373 | f2 | h1 | g1 | h1 | a11 | d13 |
| 374 | f2 | h1 | g1 | h1 | a11 | d17 |
| 375 | f2 | h1 | g1 | h1 | a11 | e3 |
| 376 | f2 | h1 | g1 | h1 | a15 | a15 |
| 377 | f2 | h1 | g1 | h1 | a15 | b1 |
| 378 | f2 | h1 | g1 | h1 | a15 | b3 |
| 379 | f2 | h1 | g1 | h1 | a15 | b4 |
| 380 | f2 | h1 | g1 | h1 | a15 | b6 |
| 381 | f2 | h1 | g1 | h1 | a15 | c1 |
| 382 | f2 | h1 | g1 | h1 | a15 | d1 |
| 383 | f2 | h1 | g1 | h1 | a15 | d2 |
| 384 | f2 | h1 | g1 | h1 | a15 | d3 |
| 385 | f2 | h1 | g1 | h1 | a15 | d5 |
| 386 | f2 | h1 | g1 | h1 | a15 | d7 |
| 387 | f2 | h1 | g1 | h1 | a15 | d9 |
| 388 | f2 | h1 | g1 | h1 | a15 | d11 |
| 389 | f2 | h1 | g1 | h1 | a15 | d13 |
| 390 | f2 | h1 | g1 | h1 | a15 | d17 |
| 391 | f2 | h1 | g1 | h1 | a15 | e3 |
| 392 | f2 | h1 | g1 | h1 | b1 | b1 |
| 393 | f2 | h1 | g1 | h1 | b1 | b3 |
| 394 | f2 | h1 | g1 | h1 | b1 | b4 |
| 395 | f2 | h1 | g1 | h1 | b1 | b6 |
| 396 | f2 | h1 | g1 | h1 | b1 | c1 |
| 397 | f2 | h1 | g1 | h1 | b1 | d1 |
| 398 | f2 | h1 | g1 | h1 | b1 | d2 |
| 399 | f2 | h1 | g1 | h1 | b1 | d3 |
| 400 | f2 | h1 | g1 | h1 | b1 | d5 |
| 401 | f2 | h1 | g1 | h1 | b1 | d7 |
| 402 | f2 | h1 | g1 | h1 | b1 | d9 |
| 403 | f2 | h1 | g1 | h1 | b1 | d11 |
| 404 | f2 | h1 | g1 | h1 | b1 | d13 |
| 405 | f2 | h1 | g1 | h1 | b1 | d17 |
| 406 | f2 | h1 | g1 | h1 | b1 | e3 |
| 407 | f2 | h1 | g1 | h1 | b3 | b3 |
| 408 | f2 | h1 | g1 | h1 | b3 | b4 |
| 409 | f2 | h1 | g1 | h1 | b3 | b6 |
| 410 | f2 | h1 | g1 | h1 | b3 | c1 |
| 411 | f2 | h1 | g1 | h1 | b3 | d1 |
| 412 | f2 | h1 | g1 | h1 | b3 | d2 |
| 413 | f2 | h1 | g1 | h1 | b3 | d3 |
| 414 | f2 | h1 | g1 | h1 | b3 | d5 |
| 415 | f2 | h1 | g1 | h1 | b3 | d7 |
| 416 | f2 | h1 | g1 | h1 | b3 | d9 |
| 417 | f2 | h1 | g1 | h1 | b3 | d11 |
| 418 | f2 | h1 | g1 | h1 | b3 | d13 |
| 419 | f2 | h1 | g1 | h1 | b3 | d17 |
| 420 | f2 | h1 | g1 | h1 | b3 | e3 |
| 421 | f2 | h1 | g1 | h1 | b4 | b4 |
| 422 | f2 | h1 | g1 | h1 | b4 | b6 |
| 423 | f2 | h1 | g1 | h1 | b4 | c1 |
| 424 | f2 | h1 | g1 | h1 | b4 | d1 |
| 425 | f2 | h1 | g1 | h1 | b4 | d2 |
| 426 | f2 | h1 | g1 | h1 | b4 | d3 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 427 | f2 | h1 | g1 | h1 | b4 | d5 |
| 428 | f2 | h1 | g1 | h1 | b4 | d7 |
| 429 | f2 | h1 | g1 | h1 | b4 | d9 |
| 430 | f2 | h1 | g1 | h1 | b4 | d11 |
| 431 | f2 | h1 | g1 | h1 | b4 | d13 |
| 432 | f2 | h1 | g1 | h1 | b4 | d17 |
| 433 | f2 | h1 | g1 | h1 | b4 | e3 |
| 434 | f2 | h1 | g1 | h1 | b6 | b6 |
| 435 | f2 | h1 | g1 | h1 | b6 | c1 |
| 436 | f2 | h1 | g1 | h1 | b6 | d1 |
| 437 | f2 | h1 | g1 | h1 | b6 | d2 |
| 438 | f2 | h1 | g1 | h1 | b6 | d3 |
| 439 | f2 | h1 | g1 | h1 | b6 | d5 |
| 440 | f2 | h1 | g1 | h1 | b6 | d7 |
| 441 | f2 | h1 | g1 | h1 | b6 | d9 |
| 442 | f2 | h1 | g1 | h1 | b6 | d11 |
| 443 | f2 | h1 | g1 | h1 | b6 | d13 |
| 444 | f2 | h1 | g1 | h1 | b6 | d17 |
| 445 | f2 | h1 | g1 | h1 | b6 | e3 |
| 446 | f2 | h1 | g1 | h1 | c1 | c1 |
| 447 | f2 | h1 | g1 | h1 | c1 | d1 |
| 448 | f2 | h1 | g1 | h1 | c1 | d2 |
| 449 | f2 | h1 | g1 | h1 | c1 | d3 |
| 450 | f2 | h1 | g1 | h1 | c1 | d5 |
| 451 | f2 | h1 | g1 | h1 | c1 | d7 |
| 452 | f2 | h1 | g1 | h1 | c1 | d9 |
| 453 | f2 | h1 | g1 | h1 | c1 | d11 |
| 454 | f2 | h1 | g1 | h1 | c1 | d13 |
| 455 | f2 | h1 | g1 | h1 | c1 | d17 |
| 456 | f2 | h1 | g1 | h1 | c1 | e3 |
| 457 | f2 | h1 | g1 | h1 | d1 | d1 |
| 458 | f2 | h1 | g1 | h1 | d1 | d2 |
| 459 | f2 | h1 | g1 | h1 | d1 | d3 |
| 460 | f2 | h1 | g1 | h1 | d1 | d5 |
| 461 | f2 | h1 | g1 | h1 | d1 | d7 |
| 462 | f2 | h1 | g1 | h1 | d1 | d9 |
| 463 | f2 | h1 | g1 | h1 | d1 | d11 |
| 464 | f2 | h1 | g1 | h1 | d1 | d13 |
| 465 | f2 | h1 | g1 | h1 | d1 | d17 |
| 466 | f2 | h1 | g1 | h1 | d1 | e3 |
| 467 | f2 | h1 | g1 | h1 | d2 | d2 |
| 468 | f2 | h1 | g1 | h1 | d2 | d3 |
| 469 | f2 | h1 | g1 | h1 | d2 | d5 |
| 470 | f2 | h1 | g1 | h1 | d2 | d7 |
| 471 | f2 | h1 | g1 | h1 | d2 | d9 |
| 472 | f2 | h1 | g1 | h1 | d2 | d11 |
| 473 | f2 | h1 | g1 | h1 | d2 | d13 |
| 474 | f2 | h1 | g1 | h1 | d2 | d17 |
| 475 | f2 | h1 | g1 | h1 | d2 | e3 |
| 476 | f2 | h1 | g1 | h1 | d3 | d3 |
| 477 | f2 | h1 | g1 | h1 | d3 | d5 |
| 478 | f2 | h1 | g1 | h1 | d3 | d7 |
| 479 | f2 | h1 | g1 | h1 | d3 | d9 |
| 480 | f2 | h1 | g1 | h1 | d3 | d11 |
| 481 | f2 | h1 | g1 | h1 | d3 | d13 |
| 482 | f2 | h1 | g1 | h1 | d3 | d17 |
| 483 | f2 | h1 | g1 | h1 | d3 | e3 |
| 484 | f2 | h1 | g1 | h1 | d5 | d5 |
| 485 | f2 | h1 | g1 | h1 | d5 | d7 |
| 486 | f2 | h1 | g1 | h1 | d5 | d9 |
| 487 | f2 | h1 | g1 | h1 | d5 | d11 |
| 488 | f2 | h1 | g1 | h1 | d5 | d13 |
| 489 | f2 | h1 | g1 | h1 | d5 | d17 |
| 490 | f2 | h1 | g1 | h1 | d5 | e3 |
| 491 | f2 | h1 | g1 | h1 | d7 | d7 |
| 492 | f2 | h1 | g1 | h1 | d7 | d9 |
| 493 | f2 | h1 | g1 | h1 | d7 | d11 |
| 494 | f2 | h1 | g1 | h1 | d7 | d13 |
| 495 | f2 | h1 | g1 | h1 | d7 | d17 |
| 496 | f2 | h1 | g1 | h1 | d7 | e3 |
| 497 | f2 | h1 | g1 | h1 | d9 | d9 |
| 498 | f2 | h1 | g1 | h1 | d9 | d11 |
| 499 | f2 | h1 | g1 | h1 | d9 | d13 |
| 500 | f2 | h1 | g1 | h1 | d9 | d17 |
| 501 | f2 | h1 | g1 | h1 | d9 | e3 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 502 | f2 | h1 | g1 | h1 | d11 | d11 |
| 503 | f2 | h1 | g1 | h1 | d11 | d13 |
| 504 | f2 | h1 | g1 | h1 | d11 | d17 |
| 505 | f2 | h1 | g1 | h1 | d11 | e3 |
| 506 | f2 | h1 | g1 | h1 | d13 | d13 |
| 507 | f2 | h1 | g1 | h1 | d13 | d17 |
| 508 | f2 | h1 | g1 | h1 | d13 | e3 |
| 509 | f2 | h1 | g1 | h1 | d17 | d17 |
| 510 | f2 | h1 | g1 | h1 | e3 | e3 |
| 511 | f3 | h1 | g1 | h1 | a1 | a1 |
| 512 | f4 | h1 | g1 | h1 | a1 | a1 |
| 513 | f5 | h1 | g1 | h1 | a1 | a1 |
| 514 | f1 | h1 | g1 | h1 | b1 | a1 |
| 515 | f1 | h1 | g1 | h1 | b1 | a2 |
| 516 | f1 | h1 | g1 | h1 | b1 | a3 |
| 517 | f1 | h1 | g1 | h1 | b1 | a4 |
| 518 | f1 | h1 | g1 | h1 | b1 | a5 |
| 519 | f1 | h1 | g1 | h1 | b1 | a6 |
| 520 | f1 | h1 | g1 | h1 | b1 | a7 |
| 521 | f1 | h1 | g1 | h1 | b1 | a8 |
| 522 | f1 | h1 | g1 | h1 | b1 | a9 |
| 523 | f1 | h1 | g1 | h1 | b1 | a10 |
| 524 | f1 | h1 | g1 | h1 | b1 | a11 |
| 525 | f1 | h1 | g1 | h1 | b1 | a12 |
| 526 | f1 | h1 | g1 | h1 | b1 | a13 |
| 527 | f1 | h1 | g1 | h1 | b1 | a14 |
| 528 | f1 | h1 | g1 | h1 | b1 | a15 |
| 529 | f1 | h1 | g1 | h1 | b1 | b1 |
| 530 | f1 | h1 | g1 | h1 | b1 | b2 |
| 531 | f1 | h1 | g1 | h1 | b1 | b3 |
| 532 | f1 | h1 | g1 | h1 | b1 | b4 |
| 533 | f1 | h1 | g1 | h1 | b1 | b5 |
| 534 | f1 | h1 | g1 | h1 | b1 | b6 |
| 535 | f1 | h1 | g1 | h1 | b1 | b7 |
| 536 | f1 | h1 | g1 | h1 | b1 | b8 |
| 537 | f1 | h1 | g1 | h1 | b1 | c1 |
| 538 | f1 | h1 | g1 | h1 | b1 | c2 |
| 539 | f1 | h1 | g1 | h1 | b1 | c3 |
| 540 | f1 | h1 | g1 | h1 | b1 | c4 |
| 541 | f1 | h1 | g1 | h1 | b1 | c6 |
| 542 | f1 | h1 | g1 | h1 | b1 | d1 |
| 543 | f1 | h1 | g1 | h1 | b1 | d2 |
| 544 | f1 | h1 | g1 | h1 | b1 | d3 |
| 545 | f1 | h1 | g1 | h1 | b1 | d4 |
| 546 | f1 | h1 | g1 | h1 | b1 | d5 |
| 547 | f1 | h1 | g1 | h1 | b1 | d6 |
| 548 | f1 | h1 | g1 | h1 | b1 | d7 |
| 549 | f1 | h1 | g1 | h1 | b1 | d8 |
| 550 | f1 | h1 | g1 | h1 | b1 | d9 |
| 551 | f1 | h1 | g1 | h1 | b1 | d10 |
| 552 | f1 | h1 | g1 | h1 | b1 | d11 |
| 553 | f1 | h1 | g1 | h1 | b1 | d12 |
| 554 | f1 | h1 | g1 | h1 | b1 | d13 |
| 555 | f1 | h1 | g1 | h1 | b1 | d14 |
| 556 | f1 | h1 | g1 | h1 | b1 | d15 |
| 557 | f1 | h1 | g1 | h1 | b1 | d16 |
| 558 | f1 | h1 | g1 | h1 | b1 | d17 |
| 559 | f1 | h1 | g1 | h1 | b1 | d18 |
| 560 | f1 | h1 | g1 | h1 | b1 | e1 |
| 561 | f1 | h1 | g1 | h1 | b1 | e2 |
| 562 | f1 | h1 | g1 | h1 | b1 | e3 |
| 563 | f1 | h1 | g1 | h1 | b1 | e4 |
| 564 | f1 | h1 | g1 | h1 | b2 | a1 |
| 565 | f1 | h1 | g1 | h1 | b2 | a2 |
| 566 | f1 | h1 | g1 | h1 | b2 | a3 |
| 567 | f1 | h1 | g1 | h1 | b2 | a4 |
| 568 | f1 | h1 | g1 | h1 | b2 | a5 |
| 569 | f1 | h1 | g1 | h1 | b2 | a6 |
| 570 | f1 | h1 | g1 | h1 | b2 | a7 |
| 571 | f1 | h1 | g1 | h1 | b2 | a8 |
| 572 | f1 | h1 | g1 | h1 | b2 | a9 |
| 573 | f1 | h1 | g1 | h1 | b2 | a10 |
| 574 | f1 | h1 | g1 | h1 | b2 | a11 |
| 575 | f1 | h1 | g1 | h1 | b2 | a12 |
| 576 | f1 | h1 | g1 | h1 | b2 | a13 |
| 577 | f1 | h1 | g1 | h1 | b2 | a14 |
| 578 | f1 | h1 | g1 | h1 | b2 | a15 |
| 579 | f1 | h1 | g1 | h1 | b2 | b2 |
| 580 | f1 | h1 | g1 | h1 | b2 | b3 |
| 581 | f1 | h1 | g1 | h1 | b2 | b4 |
| 582 | f1 | h1 | g1 | h1 | b2 | b5 |
| 583 | f1 | h1 | g1 | h1 | b2 | b6 |
| 584 | f1 | h1 | g1 | h1 | b2 | b7 |
| 585 | f1 | h1 | g1 | h1 | b2 | b8 |
| 586 | f1 | h1 | g1 | h1 | b2 | c1 |
| 587 | f1 | h1 | g1 | h1 | b2 | c2 |
| 588 | f1 | h1 | g1 | h1 | b2 | c3 |
| 589 | f1 | h1 | g1 | h1 | b2 | c4 |
| 590 | f1 | h1 | g1 | h1 | b2 | c6 |
| 591 | f1 | h1 | g1 | h1 | b2 | d1 |
| 592 | f1 | h1 | g1 | h1 | b2 | d2 |
| 593 | f1 | h1 | g1 | h1 | b2 | d3 |
| 594 | f1 | h1 | g1 | h1 | b2 | d4 |
| 595 | f1 | h1 | g1 | h1 | b2 | d5 |
| 596 | f1 | h1 | g1 | h1 | b2 | d6 |
| 597 | f1 | h1 | g1 | h1 | b2 | d7 |
| 598 | f1 | h1 | g1 | h1 | b2 | d8 |
| 599 | f1 | h1 | g1 | h1 | b2 | d9 |
| 600 | f1 | h1 | g1 | h1 | b2 | d10 |
| 601 | f1 | h1 | g1 | h1 | b2 | d11 |
| 602 | f1 | h1 | g1 | h1 | b2 | d12 |
| 603 | f1 | h1 | g1 | h1 | b2 | d13 |
| 604 | f1 | h1 | g1 | h1 | b2 | d14 |
| 605 | f1 | h1 | g1 | h1 | b2 | d15 |
| 606 | f1 | h1 | g1 | h1 | b2 | d16 |
| 607 | f1 | h1 | g1 | h1 | b2 | d17 |
| 608 | f1 | h1 | g1 | h1 | b2 | d18 |
| 609 | f1 | h1 | g1 | h1 | b2 | e1 |
| 610 | f1 | h1 | g1 | h1 | b2 | e2 |
| 611 | f1 | h1 | g1 | h1 | b2 | e3 |
| 612 | f1 | h1 | g1 | h1 | b2 | e4 |
| 613 | f1 | h1 | g1 | h1 | b3 | a1 |
| 614 | f1 | h1 | g1 | h1 | b3 | a2 |
| 615 | f1 | h1 | g1 | h1 | b3 | a3 |
| 616 | f1 | h1 | g1 | h1 | b3 | a4 |
| 617 | f1 | h1 | g1 | h1 | b3 | a5 |
| 618 | f1 | h1 | g1 | h1 | b3 | a6 |
| 619 | f1 | h1 | g1 | h1 | b3 | a7 |
| 620 | f1 | h1 | g1 | h1 | b3 | a8 |
| 621 | f1 | h1 | g1 | h1 | b3 | a9 |
| 622 | f1 | h1 | g1 | h1 | b3 | a10 |
| 623 | f1 | h1 | g1 | h1 | b3 | a11 |
| 624 | f1 | h1 | g1 | h1 | b3 | a12 |
| 625 | f1 | h1 | g1 | h1 | b3 | a13 |
| 626 | f1 | h1 | g1 | h1 | b3 | a14 |
| 627 | f1 | h1 | g1 | h1 | b3 | a15 |
| 628 | f1 | h1 | g1 | h1 | b3 | b3 |
| 629 | f1 | h1 | g1 | h1 | b3 | b4 |
| 630 | f1 | h1 | g1 | h1 | b3 | b5 |
| 631 | f1 | h1 | g1 | h1 | b3 | b6 |
| 632 | f1 | h1 | g1 | h1 | b3 | b7 |
| 633 | f1 | h1 | g1 | h1 | b3 | b8 |
| 634 | f1 | h1 | g1 | h1 | b3 | c1 |
| 635 | f1 | h1 | g1 | h1 | b3 | c2 |
| 636 | f1 | h1 | g1 | h1 | b3 | c3 |
| 637 | f1 | h1 | g1 | h1 | b3 | c4 |
| 638 | f1 | h1 | g1 | h1 | b3 | c6 |
| 639 | f1 | h1 | g1 | h1 | b3 | d1 |
| 640 | f1 | h1 | g1 | h1 | b3 | d2 |
| 641 | f1 | h1 | g1 | h1 | b3 | d3 |
| 642 | f1 | h1 | g1 | h1 | b3 | d4 |
| 643 | f1 | h1 | g1 | h1 | b3 | d5 |
| 644 | f1 | h1 | g1 | h1 | b3 | d6 |
| 645 | f1 | h1 | g1 | h1 | b3 | d7 |
| 646 | f1 | h1 | g1 | h1 | b3 | d8 |
| 647 | f1 | h1 | g1 | h1 | b3 | d9 |
| 648 | f1 | h1 | g1 | h1 | b3 | d10 |
| 649 | f1 | h1 | g1 | h1 | b3 | d11 |
| 650 | f1 | h1 | g1 | h1 | b3 | d12 |
| 651 | f1 | h1 | g1 | h1 | b3 | d13 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 652 | f1 | h1 | g1 | h1 | b3 | d14 |
| 653 | f1 | h1 | g1 | h1 | b3 | d15 |
| 654 | f1 | h1 | g1 | h1 | b3 | d16 |
| 655 | f1 | h1 | g1 | h1 | b3 | d17 |
| 656 | f1 | h1 | g1 | h1 | b3 | d18 |
| 657 | f1 | h1 | g1 | h1 | b3 | e1 |
| 658 | f1 | h1 | g1 | h1 | b3 | e2 |
| 659 | f1 | h1 | g1 | h1 | b3 | e3 |
| 660 | f1 | h1 | g1 | h1 | b3 | e4 |
| 661 | f1 | h1 | g1 | h1 | b4 | a1 |
| 662 | f1 | h1 | g1 | h1 | b4 | a2 |
| 663 | f1 | h1 | g1 | h1 | b4 | a3 |
| 664 | f1 | h1 | g1 | h1 | b4 | a4 |
| 665 | f1 | h1 | g1 | h1 | b4 | a5 |
| 666 | f1 | h1 | g1 | h1 | b4 | a6 |
| 667 | f1 | h1 | g1 | h1 | b4 | a7 |
| 668 | f1 | h1 | g1 | h1 | b4 | a8 |
| 669 | f1 | h1 | g1 | h1 | b4 | a9 |
| 670 | f1 | h1 | g1 | h1 | b4 | a10 |
| 671 | f1 | h1 | g1 | h1 | b4 | a11 |
| 672 | f1 | h1 | g1 | h1 | b4 | a12 |
| 673 | f1 | h1 | g1 | h1 | b4 | a13 |
| 674 | f1 | h1 | g1 | h1 | b4 | a14 |
| 675 | f1 | h1 | g1 | h1 | b4 | a15 |
| 676 | f1 | h1 | g1 | h1 | b4 | b4 |
| 677 | f1 | h1 | g1 | h1 | b4 | b5 |
| 678 | f1 | h1 | g1 | h1 | b4 | b6 |
| 679 | f1 | h1 | g1 | h1 | b4 | b7 |
| 680 | f1 | h1 | g1 | h1 | b4 | b8 |
| 681 | f1 | h1 | g1 | h1 | b4 | c1 |
| 682 | f1 | h1 | g1 | h1 | b4 | c2 |
| 683 | f1 | h1 | g1 | h1 | b4 | c3 |
| 684 | f1 | h1 | g1 | h1 | b4 | c4 |
| 685 | f1 | h1 | g1 | h1 | b4 | c6 |
| 686 | f1 | h1 | g1 | h1 | b4 | d1 |
| 687 | f1 | h1 | g1 | h1 | b4 | d2 |
| 688 | f1 | h1 | g1 | h1 | b4 | d3 |
| 689 | f1 | h1 | g1 | h1 | b4 | d4 |
| 690 | f1 | h1 | g1 | h1 | b4 | d5 |
| 691 | f1 | h1 | g1 | h1 | b4 | d6 |
| 692 | f1 | h1 | g1 | h1 | b4 | d7 |
| 693 | f1 | h1 | g1 | h1 | b4 | d8 |
| 694 | f1 | h1 | g1 | h1 | b4 | d9 |
| 695 | f1 | h1 | g1 | h1 | b4 | d10 |
| 696 | f1 | h1 | g1 | h1 | b4 | d11 |
| 697 | f1 | h1 | g1 | h1 | b4 | d12 |
| 698 | f1 | h1 | g1 | h1 | b4 | d13 |
| 699 | f1 | h1 | g1 | h1 | b4 | d14 |
| 700 | f1 | h1 | g1 | h1 | b4 | d15 |
| 701 | f1 | h1 | g1 | h1 | b4 | d16 |
| 702 | f1 | h1 | g1 | h1 | b4 | d17 |
| 703 | f1 | h1 | g1 | h1 | b4 | d18 |
| 704 | f1 | h1 | g1 | h1 | b4 | e1 |
| 705 | f1 | h1 | g1 | h1 | b4 | e2 |
| 706 | f1 | h1 | g1 | h1 | b4 | e3 |
| 707 | f1 | h1 | g1 | h1 | b4 | e4 |
| 708 | f1 | h1 | g1 | h1 | b5 | a1 |
| 709 | f1 | h1 | g1 | h1 | b5 | a2 |
| 710 | f1 | h1 | g1 | h1 | b5 | a3 |
| 711 | f1 | h1 | g1 | h1 | b5 | a4 |
| 712 | f1 | h1 | g1 | h1 | b5 | a5 |
| 713 | f1 | h1 | g1 | h1 | b5 | a6 |
| 714 | f1 | h1 | g1 | h1 | b5 | a7 |
| 715 | f1 | h1 | g1 | h1 | b5 | a8 |
| 716 | f1 | h1 | g1 | h1 | b5 | a9 |
| 717 | f1 | h1 | g1 | h1 | b5 | a10 |
| 718 | f1 | h1 | g1 | h1 | b5 | a11 |
| 719 | f1 | h1 | g1 | h1 | b5 | a12 |
| 720 | f1 | h1 | g1 | h1 | b5 | a13 |
| 721 | f1 | h1 | g1 | h1 | b5 | a14 |
| 722 | f1 | h1 | g1 | h1 | b5 | a15 |
| 723 | f1 | h1 | g1 | h1 | b5 | b5 |
| 724 | f1 | h1 | g1 | h1 | b5 | b6 |
| 725 | f1 | h1 | g1 | h1 | b5 | b7 |
| 726 | f1 | h1 | g1 | h1 | b5 | b8 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 727 | f1 | h1 | g1 | h1 | b5 | c1 |
| 728 | f1 | h1 | g1 | h1 | b5 | c2 |
| 729 | f1 | h1 | g1 | h1 | b5 | c3 |
| 730 | f1 | h1 | g1 | h1 | b5 | c4 |
| 731 | f1 | h1 | g1 | h1 | b5 | c6 |
| 732 | f1 | h1 | g1 | h1 | b5 | d1 |
| 733 | f1 | h1 | g1 | h1 | b5 | d2 |
| 734 | f1 | h1 | g1 | h1 | b5 | d3 |
| 735 | f1 | h1 | g1 | h1 | b5 | d4 |
| 736 | f1 | h1 | g1 | h1 | b5 | d5 |
| 737 | f1 | h1 | g1 | h1 | b5 | d6 |
| 738 | f1 | h1 | g1 | h1 | b5 | d7 |
| 739 | f1 | h1 | g1 | h1 | b5 | d8 |
| 740 | f1 | h1 | g1 | h1 | b5 | d9 |
| 741 | f1 | h1 | g1 | h1 | b5 | d10 |
| 742 | f1 | h1 | g1 | h1 | b5 | d11 |
| 743 | f1 | h1 | g1 | h1 | b5 | d12 |
| 744 | f1 | h1 | g1 | h1 | b5 | d13 |
| 745 | f1 | h1 | g1 | h1 | b5 | d14 |
| 746 | f1 | h1 | g1 | h1 | b5 | d15 |
| 747 | f1 | h1 | g1 | h1 | b5 | d16 |
| 748 | f1 | h1 | g1 | h1 | b5 | d17 |
| 749 | f1 | h1 | g1 | h1 | b5 | d18 |
| 750 | f1 | h1 | g1 | h1 | b5 | e1 |
| 751 | f1 | h1 | g1 | h1 | b5 | e2 |
| 752 | f1 | h1 | g1 | h1 | b5 | e3 |
| 753 | f1 | h1 | g1 | h1 | b5 | e4 |
| 754 | f1 | h1 | g1 | h1 | b6 | a1 |
| 755 | f1 | h1 | g1 | h1 | b6 | a2 |
| 756 | f1 | h1 | g1 | h1 | b6 | a3 |
| 757 | f1 | h1 | g1 | h1 | b6 | a4 |
| 758 | f1 | h1 | g1 | h1 | b6 | a5 |
| 759 | f1 | h1 | g1 | h1 | b6 | a6 |
| 760 | f1 | h1 | g1 | h1 | b6 | a7 |
| 761 | f1 | h1 | g1 | h1 | b6 | a8 |
| 762 | f1 | h1 | g1 | h1 | b6 | a9 |
| 763 | f1 | h1 | g1 | h1 | b6 | a10 |
| 764 | f1 | h1 | g1 | h1 | b6 | a11 |
| 765 | f1 | h1 | g1 | h1 | b6 | a12 |
| 766 | f1 | h1 | g1 | h1 | b6 | a13 |
| 767 | f1 | h1 | g1 | h1 | b6 | a14 |
| 768 | f1 | h1 | g1 | h1 | b6 | a15 |
| 769 | f1 | h1 | g1 | h1 | b6 | b6 |
| 770 | f1 | h1 | g1 | h1 | b6 | b7 |
| 771 | f1 | h1 | g1 | h1 | b6 | b8 |
| 772 | f1 | h1 | g1 | h1 | b6 | c1 |
| 773 | f1 | h1 | g1 | h1 | b6 | c2 |
| 774 | f1 | h1 | g1 | h1 | b6 | c3 |
| 775 | f1 | h1 | g1 | h1 | b6 | c4 |
| 776 | f1 | h1 | g1 | h1 | b6 | c6 |
| 777 | f1 | h1 | g1 | h1 | b6 | d1 |
| 778 | f1 | h1 | g1 | h1 | b6 | d2 |
| 779 | f1 | h1 | g1 | h1 | b6 | d3 |
| 780 | f1 | h1 | g1 | h1 | b6 | d4 |
| 781 | f1 | h1 | g1 | h1 | b6 | d5 |
| 782 | f1 | h1 | g1 | h1 | b6 | d6 |
| 783 | f1 | h1 | g1 | h1 | b6 | d7 |
| 784 | f1 | h1 | g1 | h1 | b6 | d8 |
| 785 | f1 | h1 | g1 | h1 | b6 | d9 |
| 786 | f1 | h1 | g1 | h1 | b6 | d10 |
| 787 | f1 | h1 | g1 | h1 | b6 | d11 |
| 788 | f1 | h1 | g1 | h1 | b6 | d12 |
| 789 | f1 | h1 | g1 | h1 | b6 | d13 |
| 790 | f1 | h1 | g1 | h1 | b6 | d14 |
| 791 | f1 | h1 | g1 | h1 | b6 | d15 |
| 792 | f1 | h1 | g1 | h1 | b6 | d16 |
| 793 | f1 | h1 | g1 | h1 | b6 | d17 |
| 794 | f1 | h1 | g1 | h1 | b6 | d18 |
| 795 | f1 | h1 | g1 | h1 | b6 | e1 |
| 796 | f1 | h1 | g1 | h1 | b6 | e2 |
| 797 | f1 | h1 | g1 | h1 | b6 | e3 |
| 798 | f1 | h1 | g1 | h1 | b6 | e4 |
| 799 | f1 | h1 | g1 | h1 | b7 | a1 |
| 800 | f1 | h1 | g1 | h1 | b7 | a2 |
| 801 | f1 | h1 | g1 | h1 | b7 | a3 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 802 | f1 | h1 | g1 | h1 | b7 | a4 |
| 803 | f1 | h1 | g1 | h1 | b7 | a5 |
| 804 | f1 | h1 | g1 | h1 | b7 | a6 |
| 805 | f1 | h1 | g1 | h1 | b7 | a7 |
| 806 | f1 | h1 | g1 | h1 | b7 | a8 |
| 807 | f1 | h1 | g1 | h1 | b7 | a9 |
| 808 | f1 | h1 | g1 | h1 | b7 | a10 |
| 809 | f1 | h1 | g1 | h1 | b7 | a11 |
| 810 | f1 | h1 | g1 | h1 | b7 | a12 |
| 811 | f1 | h1 | g1 | h1 | b7 | a13 |
| 812 | f1 | h1 | g1 | h1 | b7 | a14 |
| 813 | f1 | h1 | g1 | h1 | b7 | a15 |
| 814 | f1 | h1 | g1 | h1 | b7 | b7 |
| 815 | f1 | h1 | g1 | h1 | b7 | b8 |
| 816 | f1 | h1 | g1 | h1 | b7 | c1 |
| 817 | f1 | h1 | g1 | h1 | b7 | c2 |
| 818 | f1 | h1 | g1 | h1 | b7 | c3 |
| 819 | f1 | h1 | g1 | h1 | b7 | c4 |
| 820 | f1 | h1 | g1 | h1 | b7 | c6 |
| 821 | f1 | h1 | g1 | h1 | b7 | d1 |
| 822 | f1 | h1 | g1 | h1 | b7 | d2 |
| 823 | f1 | h1 | g1 | h1 | b7 | d3 |
| 824 | f1 | h1 | g1 | h1 | b7 | d4 |
| 825 | f1 | h1 | g1 | h1 | b7 | d5 |
| 826 | f1 | h1 | g1 | h1 | b7 | d6 |
| 827 | f1 | h1 | g1 | h1 | b7 | d7 |
| 828 | f1 | h1 | g1 | h1 | b7 | d8 |
| 829 | f1 | h1 | g1 | h1 | b7 | d9 |
| 830 | f1 | h1 | g1 | h1 | b7 | d10 |
| 831 | f1 | h1 | g1 | h1 | b7 | d11 |
| 832 | f1 | h1 | g1 | h1 | b7 | d12 |
| 833 | f1 | h1 | g1 | h1 | b7 | d13 |
| 834 | f1 | h1 | g1 | h1 | b7 | d14 |
| 835 | f1 | h1 | g1 | h1 | b7 | d15 |
| 836 | f1 | h1 | g1 | h1 | b7 | d16 |
| 837 | f1 | h1 | g1 | h1 | b7 | d17 |
| 838 | f1 | h1 | g1 | h1 | b7 | d18 |
| 839 | f1 | h1 | g1 | h1 | b7 | e1 |
| 840 | f1 | h1 | g1 | h1 | b7 | e2 |
| 841 | f1 | h1 | g1 | h1 | b7 | e3 |
| 842 | f1 | h1 | g1 | h1 | b7 | e4 |
| 843 | f1 | h1 | g1 | h1 | b8 | a1 |
| 844 | f1 | h1 | g1 | h1 | b8 | a2 |
| 845 | f1 | h1 | g1 | h1 | b8 | a3 |
| 846 | f1 | h1 | g1 | h1 | b8 | a4 |
| 847 | f1 | h1 | g1 | h1 | b8 | a5 |
| 848 | f1 | h1 | g1 | h1 | b8 | a6 |
| 849 | f1 | h1 | g1 | h1 | b8 | a7 |
| 850 | f1 | h1 | g1 | h1 | b8 | a8 |
| 851 | f1 | h1 | g1 | h1 | b8 | a9 |
| 852 | f1 | h1 | g1 | h1 | b8 | a10 |
| 853 | f1 | h1 | g1 | h1 | b8 | a11 |
| 854 | f1 | h1 | g1 | h1 | b8 | a12 |
| 855 | f1 | h1 | g1 | h1 | b8 | a13 |
| 856 | f1 | h1 | g1 | h1 | b8 | a14 |
| 857 | f1 | h1 | g1 | h1 | b8 | a15 |
| 858 | f1 | h1 | g1 | h1 | b8 | b8 |
| 859 | f1 | h1 | g1 | h1 | b8 | c1 |
| 860 | f1 | h1 | g1 | h1 | b8 | c2 |
| 861 | f1 | h1 | g1 | h1 | b8 | c3 |
| 862 | f1 | h1 | g1 | h1 | b8 | c4 |
| 863 | f1 | h1 | g1 | h1 | b8 | c6 |
| 864 | f1 | h1 | g1 | h1 | b8 | d1 |
| 865 | f1 | h1 | g1 | h1 | b8 | d2 |
| 866 | f1 | h1 | g1 | h1 | b8 | d3 |
| 867 | f1 | h1 | g1 | h1 | b8 | d4 |
| 868 | f1 | h1 | g1 | h1 | b8 | d5 |
| 869 | f1 | h1 | g1 | h1 | b8 | d6 |
| 870 | f1 | h1 | g1 | h1 | b8 | d7 |
| 871 | f1 | h1 | g1 | h1 | b8 | d8 |
| 872 | f1 | h1 | g1 | h1 | b8 | d9 |
| 873 | f1 | h1 | g1 | h1 | b8 | d10 |
| 874 | f1 | h1 | g1 | h1 | b8 | d11 |
| 875 | f1 | h1 | g1 | h1 | b8 | d12 |
| 876 | f1 | h1 | g1 | h1 | b8 | d13 |
| 877 | f1 | h1 | g1 | h1 | b8 | d14 |
| 878 | f1 | h1 | g1 | h1 | b8 | d15 |
| 879 | f1 | h1 | g1 | h1 | b8 | d16 |
| 880 | f1 | h1 | g1 | h1 | b8 | d17 |
| 881 | f1 | h1 | g1 | h1 | b8 | d18 |
| 882 | f1 | h1 | g1 | h1 | b8 | e1 |
| 883 | f1 | h1 | g1 | h1 | b8 | e2 |
| 884 | f1 | h1 | g1 | h1 | b8 | e3 |
| 885 | f1 | h1 | g1 | h1 | b8 | e4 |
| 886 | f1 | h1 | g1 | h1 | c1 | a1 |
| 887 | f1 | h1 | g1 | h1 | c1 | a2 |
| 888 | f1 | h1 | g1 | h1 | c1 | a3 |
| 889 | f1 | h1 | g1 | h1 | c1 | a4 |
| 890 | f1 | h1 | g1 | h1 | c1 | a5 |
| 891 | f1 | h1 | g1 | h1 | c1 | a6 |
| 892 | f1 | h1 | g1 | h1 | c1 | a7 |
| 893 | f1 | h1 | g1 | h1 | c1 | a8 |
| 894 | f1 | h1 | g1 | h1 | c1 | a9 |
| 895 | f1 | h1 | g1 | h1 | c1 | a10 |
| 896 | f1 | h1 | g1 | h1 | c1 | a11 |
| 897 | f1 | h1 | g1 | h1 | c1 | a12 |
| 898 | f1 | h1 | g1 | h1 | c1 | a13 |
| 899 | f1 | h1 | g1 | h1 | c1 | a14 |
| 900 | f1 | h1 | g1 | h1 | c1 | a15 |
| 901 | f1 | h1 | g1 | h1 | c1 | b1 |
| 902 | f1 | h1 | g1 | h1 | c1 | b2 |
| 903 | f1 | h1 | g1 | h1 | c1 | b3 |
| 904 | f1 | h1 | g1 | h1 | c1 | b4 |
| 905 | f1 | h1 | g1 | h1 | c1 | b5 |
| 906 | f1 | h1 | g1 | h1 | c1 | b6 |
| 907 | f1 | h1 | g1 | h1 | c1 | b7 |
| 908 | f1 | h1 | g1 | h1 | c1 | b8 |
| 909 | f1 | h1 | g1 | h1 | c1 | c1 |
| 910 | f1 | h1 | g1 | h1 | c1 | d1 |
| 911 | f1 | h1 | g1 | h1 | c1 | d2 |
| 912 | f1 | h1 | g1 | h1 | c1 | d3 |
| 913 | f1 | h1 | g1 | h1 | c1 | d4 |
| 914 | f1 | h1 | g1 | h1 | c1 | d5 |
| 915 | f1 | h1 | g1 | h1 | c1 | d6 |
| 916 | f1 | h1 | g1 | h1 | c1 | d7 |
| 917 | f1 | h1 | g1 | h1 | c1 | d8 |
| 918 | f1 | h1 | g1 | h1 | c1 | d9 |
| 919 | f1 | h1 | g1 | h1 | c1 | d10 |
| 920 | f1 | h1 | g1 | h1 | c1 | d11 |
| 921 | f1 | h1 | g1 | h1 | c1 | d12 |
| 922 | f1 | h1 | g1 | h1 | c1 | d13 |
| 923 | f1 | h1 | g1 | h1 | c1 | d14 |
| 924 | f1 | h1 | g1 | h1 | c1 | d15 |
| 925 | f1 | h1 | g1 | h1 | c1 | d16 |
| 926 | f1 | h1 | g1 | h1 | c1 | d17 |
| 927 | f1 | h1 | g1 | h1 | c1 | d18 |
| 928 | f1 | h1 | g1 | h1 | c1 | e1 |
| 929 | f1 | h1 | g1 | h1 | c1 | e2 |
| 930 | f1 | h1 | g1 | h1 | c1 | e3 |
| 931 | f1 | h1 | g1 | h1 | c1 | e4 |
| 932 | f1 | h1 | g1 | h1 | c2 | a1 |
| 933 | f1 | h1 | g1 | h1 | c2 | a2 |
| 934 | f1 | h1 | g1 | h1 | c2 | a3 |
| 935 | f1 | h1 | g1 | h1 | c2 | a4 |
| 936 | f1 | h1 | g1 | h1 | c2 | a5 |
| 937 | f1 | h1 | g1 | h1 | c2 | a6 |
| 938 | f1 | h1 | g1 | h1 | c2 | a7 |
| 939 | f1 | h1 | g1 | h1 | c2 | a8 |
| 940 | f1 | h1 | g1 | h1 | c2 | a9 |
| 941 | f1 | h1 | g1 | h1 | c2 | a10 |
| 942 | f1 | h1 | g1 | h1 | c2 | a11 |
| 943 | f1 | h1 | g1 | h1 | c2 | a12 |
| 944 | f1 | h1 | g1 | h1 | c2 | a13 |
| 945 | f1 | h1 | g1 | h1 | c2 | a14 |
| 946 | f1 | h1 | g1 | h1 | c2 | a15 |
| 947 | f1 | h1 | g1 | h1 | c2 | b1 |
| 948 | f1 | h1 | g1 | h1 | c2 | b2 |
| 949 | f1 | h1 | g1 | h1 | c2 | b3 |
| 950 | f1 | h1 | g1 | h1 | c2 | b4 |
| 951 | f1 | h1 | g1 | h1 | c2 | b5 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 952 | f1 | h1 | g1 | h1 | c2 | b6 |
| 953 | f1 | h1 | g1 | h1 | c2 | b7 |
| 954 | f1 | h1 | g1 | h1 | c2 | b8 |
| 955 | f1 | h1 | g1 | h1 | c2 | c1 |
| 956 | f1 | h1 | g1 | h1 | c2 | d1 |
| 957 | f1 | h1 | g1 | h1 | c2 | d2 |
| 958 | f1 | h1 | g1 | h1 | c2 | d3 |
| 959 | f1 | h1 | g1 | h1 | c2 | d4 |
| 960 | f1 | h1 | g1 | h1 | c2 | d5 |
| 961 | f1 | h1 | g1 | h1 | c2 | d6 |
| 962 | f1 | h1 | g1 | h1 | c2 | d7 |
| 963 | f1 | h1 | g1 | h1 | c2 | d8 |
| 964 | f1 | h1 | g1 | h1 | c2 | d9 |
| 965 | f1 | h1 | g1 | h1 | c2 | d10 |
| 966 | f1 | h1 | g1 | h1 | c2 | d11 |
| 967 | f1 | h1 | g1 | h1 | c2 | d12 |
| 968 | f1 | h1 | g1 | h1 | c2 | d13 |
| 969 | f1 | h1 | g1 | h1 | c2 | d14 |
| 970 | f1 | h1 | g1 | h1 | c2 | d15 |
| 971 | f1 | h1 | g1 | h1 | c2 | d16 |
| 972 | f1 | h1 | g1 | h1 | c2 | d17 |
| 973 | f1 | h1 | g1 | h1 | c2 | d18 |
| 974 | f1 | h1 | g1 | h1 | c2 | e1 |
| 975 | f1 | h1 | g1 | h1 | c2 | e2 |
| 976 | f1 | h1 | g1 | h1 | c2 | e3 |
| 977 | f1 | h1 | g1 | h1 | c2 | e4 |
| 978 | f1 | h1 | g1 | h1 | c5 | a1 |
| 979 | f1 | h1 | g1 | h1 | c5 | a2 |
| 980 | f1 | h1 | g1 | h1 | c5 | a3 |
| 981 | f1 | h1 | g1 | h1 | c5 | a4 |
| 982 | f1 | h1 | g1 | h1 | c5 | a5 |
| 983 | f1 | h1 | g1 | h1 | c5 | a6 |
| 984 | f1 | h1 | g1 | h1 | c5 | a7 |
| 985 | f1 | h1 | g1 | h1 | c5 | a8 |
| 986 | f1 | h1 | g1 | h1 | c5 | a9 |
| 987 | f1 | h1 | g1 | h1 | c5 | a10 |
| 988 | f1 | h1 | g1 | h1 | c5 | a11 |
| 989 | f1 | h1 | g1 | h1 | c5 | a12 |
| 990 | f1 | h1 | g1 | h1 | c5 | a13 |
| 991 | f1 | h1 | g1 | h1 | c5 | a14 |
| 992 | f1 | h1 | g1 | h1 | c5 | a15 |
| 993 | f1 | h1 | g1 | h1 | c5 | b1 |
| 994 | f1 | h1 | g1 | h1 | c5 | b2 |
| 995 | f1 | h1 | g1 | h1 | c5 | b3 |
| 996 | f1 | h1 | g1 | h1 | c5 | b4 |
| 997 | f1 | h1 | g1 | h1 | c5 | b5 |
| 998 | f1 | h1 | g1 | h1 | c5 | b6 |
| 999 | f1 | h1 | g1 | h1 | c5 | b7 |
| 1000 | f1 | h1 | g1 | h1 | c5 | b8 |
| 1001 | f1 | h1 | g1 | h1 | c5 | c1 |
| 1002 | f1 | h1 | g1 | h1 | c5 | d1 |
| 1003 | f1 | h1 | g1 | h1 | c5 | d2 |
| 1004 | f1 | h1 | g1 | h1 | c5 | d3 |
| 1005 | f1 | h1 | g1 | h1 | c5 | d4 |
| 1006 | f1 | h1 | g1 | h1 | c5 | d5 |
| 1007 | f1 | h1 | g1 | h1 | c5 | d6 |
| 1008 | f1 | h1 | g1 | h1 | c5 | d7 |
| 1009 | f1 | h1 | g1 | h1 | c5 | d8 |
| 1010 | f1 | h1 | g1 | h1 | c5 | d9 |
| 1011 | f1 | h1 | g1 | h1 | c5 | d10 |
| 1012 | f1 | h1 | g1 | h1 | c5 | d11 |
| 1013 | f1 | h1 | g1 | h1 | c5 | d12 |
| 1014 | f1 | h1 | g1 | h1 | c5 | d13 |
| 1015 | f1 | h1 | g1 | h1 | c5 | d14 |
| 1016 | f1 | h1 | g1 | h1 | c5 | d15 |
| 1017 | f1 | h1 | g1 | h1 | c5 | d16 |
| 1018 | f1 | h1 | g1 | h1 | c5 | d17 |
| 1019 | f1 | h1 | g1 | h1 | c5 | d18 |
| 1020 | f1 | h1 | g1 | h1 | c5 | e1 |
| 1021 | f1 | h1 | g1 | h1 | c5 | e2 |
| 1022 | f1 | h1 | g1 | h1 | c5 | e3 |
| 1023 | f1 | h1 | g1 | h1 | c5 | e4 |
| 1024 | f1 | h1 | g2 | h1 | a1 | a1 |
| 1025 | f1 | h1 | g2 | h1 | a1 | a2 |
| 1026 | f1 | h1 | g2 | h1 | a1 | a4 |
| 1027 | f1 | h1 | g2 | h1 | a1 | a5 |
| 1028 | f1 | h1 | g2 | h1 | a1 | a6 |
| 1029 | f1 | h1 | g2 | h1 | a1 | a11 |
| 1030 | f1 | h1 | g2 | h1 | a1 | a15 |
| 1031 | f1 | h1 | g2 | h1 | a1 | b1 |
| 1032 | f1 | h1 | g2 | h1 | a1 | b3 |
| 1033 | f1 | h1 | g2 | h1 | a1 | b4 |
| 1034 | f1 | h1 | g2 | h1 | a1 | b6 |
| 1035 | f1 | h1 | g2 | h1 | a1 | c1 |
| 1036 | f1 | h1 | g2 | h1 | a1 | d1 |
| 1037 | f1 | h1 | g2 | h1 | a1 | d2 |
| 1038 | f1 | h1 | g2 | h1 | a1 | d3 |
| 1039 | f1 | h1 | g2 | h1 | a1 | d5 |
| 1040 | f1 | h1 | g2 | h1 | a1 | d7 |
| 1041 | f1 | h1 | g2 | h1 | a1 | d9 |
| 1042 | f1 | h1 | g2 | h1 | a1 | d11 |
| 1043 | f1 | h1 | g2 | h1 | a1 | d13 |
| 1044 | f1 | h1 | g2 | h1 | a1 | d17 |
| 1045 | f1 | h1 | g2 | h1 | a1 | e3 |
| 1046 | f1 | h1 | g2 | h1 | a2 | a2 |
| 1047 | f1 | h1 | g2 | h1 | a2 | a4 |
| 1048 | f1 | h1 | g2 | h1 | a2 | a5 |
| 1049 | f1 | h1 | g2 | h1 | a2 | a6 |
| 1050 | f1 | h1 | g2 | h1 | a2 | a11 |
| 1051 | f1 | h1 | g2 | h1 | a2 | a15 |
| 1052 | f1 | h1 | g2 | h1 | a2 | b1 |
| 1053 | f1 | h1 | g2 | h1 | a2 | b3 |
| 1054 | f1 | h1 | g2 | h1 | a2 | b4 |
| 1055 | f1 | h1 | g2 | h1 | a2 | b6 |
| 1056 | f1 | h1 | g2 | h1 | a2 | c1 |
| 1057 | f1 | h1 | g2 | h1 | a2 | d1 |
| 1058 | f1 | h1 | g2 | h1 | a2 | d2 |
| 1059 | f1 | h1 | g2 | h1 | a2 | d3 |
| 1060 | f1 | h1 | g2 | h1 | a2 | d5 |
| 1061 | f1 | h1 | g2 | h1 | a2 | d7 |
| 1062 | f1 | h1 | g2 | h1 | a2 | d9 |
| 1063 | f1 | h1 | g2 | h1 | a2 | d11 |
| 1064 | f1 | h1 | g2 | h1 | a2 | d13 |
| 1065 | f1 | h1 | g2 | h1 | a2 | d17 |
| 1066 | f1 | h1 | g2 | h1 | a2 | e3 |
| 1067 | f1 | h1 | g2 | h1 | a4 | a4 |
| 1068 | f1 | h1 | g2 | h1 | a4 | a5 |
| 1069 | f1 | h1 | g2 | h1 | a4 | a6 |
| 1070 | f1 | h1 | g2 | h1 | a4 | a11 |
| 1071 | f1 | h1 | g2 | h1 | a4 | a15 |
| 1072 | f1 | h1 | g2 | h1 | a4 | b1 |
| 1073 | f1 | h1 | g2 | h1 | a4 | b3 |
| 1074 | f1 | h1 | g2 | h1 | a4 | b4 |
| 1075 | f1 | h1 | g2 | h1 | a4 | b6 |
| 1076 | f1 | h1 | g2 | h1 | a4 | c1 |
| 1077 | f1 | h1 | g2 | h1 | a4 | d1 |
| 1078 | f1 | h1 | g2 | h1 | a4 | d2 |
| 1079 | f1 | h1 | g2 | h1 | a4 | d3 |
| 1080 | f1 | h1 | g2 | h1 | a4 | d5 |
| 1081 | f1 | h1 | g2 | h1 | a4 | d7 |
| 1082 | f1 | h1 | g2 | h1 | a4 | d9 |
| 1083 | f1 | h1 | g2 | h1 | a4 | d11 |
| 1084 | f1 | h1 | g2 | h1 | a4 | d13 |
| 1085 | f1 | h1 | g2 | h1 | a4 | d17 |
| 1086 | f1 | h1 | g2 | h1 | a4 | e3 |
| 1087 | f1 | h1 | g2 | h1 | a5 | a5 |
| 1088 | f1 | h1 | g2 | h1 | a5 | a6 |
| 1089 | f1 | h1 | g2 | h1 | a5 | a11 |
| 1090 | f1 | h1 | g2 | h1 | a5 | a15 |
| 1091 | f1 | h1 | g2 | h1 | a5 | b1 |
| 1092 | f1 | h1 | g2 | h1 | a5 | b3 |
| 1093 | f1 | h1 | g2 | h1 | a5 | b4 |
| 1094 | f1 | h1 | g2 | h1 | a5 | b6 |
| 1095 | f1 | h1 | g2 | h1 | a5 | c1 |
| 1096 | f1 | h1 | g2 | h1 | a5 | d1 |
| 1097 | f1 | h1 | g2 | h1 | a5 | d2 |
| 1098 | f1 | h1 | g2 | h1 | a5 | d3 |
| 1099 | f1 | h1 | g2 | h1 | a5 | d5 |
| 1100 | f1 | h1 | g2 | h1 | a5 | d7 |
| 1101 | f1 | h1 | g2 | h1 | a5 | d9 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 1102 | f1 | h1 | g2 | h1 | a5 | d11 |
| 1103 | f1 | h1 | g2 | h1 | a5 | d13 |
| 1104 | f1 | h1 | g2 | h1 | a5 | d17 |
| 1105 | f1 | h1 | g2 | h1 | a5 | e3 |
| 1106 | f1 | h1 | g2 | h1 | a6 | a6 |
| 1107 | f1 | h1 | g2 | h1 | a6 | a11 |
| 1108 | f1 | h1 | g2 | h1 | a6 | a15 |
| 1109 | f1 | h1 | g2 | h1 | a6 | b1 |
| 1110 | f1 | h1 | g2 | h1 | a6 | b3 |
| 1111 | f1 | h1 | g2 | h1 | a6 | b4 |
| 1112 | f1 | h1 | g2 | h1 | a6 | b6 |
| 1113 | f1 | h1 | g2 | h1 | a6 | c1 |
| 1114 | f1 | h1 | g2 | h1 | a6 | d1 |
| 1115 | f1 | h1 | g2 | h1 | a6 | d2 |
| 1116 | f1 | h1 | g2 | h1 | a6 | d3 |
| 1117 | f1 | h1 | g2 | h1 | a6 | d5 |
| 1118 | f1 | h1 | g2 | h1 | a6 | d7 |
| 1119 | f1 | h1 | g2 | h1 | a6 | d9 |
| 1120 | f1 | h1 | g2 | h1 | a6 | d11 |
| 1121 | f1 | h1 | g2 | h1 | a6 | d13 |
| 1122 | f1 | h1 | g2 | h1 | a6 | d17 |
| 1123 | f1 | h1 | g2 | h1 | a6 | e3 |
| 1124 | f1 | h1 | g2 | h1 | a11 | a11 |
| 1125 | f1 | h1 | g2 | h1 | a11 | a15 |
| 1126 | f1 | h1 | g2 | h1 | a11 | b1 |
| 1127 | f1 | h1 | g2 | h1 | a11 | b3 |
| 1128 | f1 | h1 | g2 | h1 | a11 | b4 |
| 1129 | f1 | h1 | g2 | h1 | a11 | b6 |
| 1130 | f1 | h1 | g2 | h1 | a11 | c1 |
| 1131 | f1 | h1 | g2 | h1 | a11 | d1 |
| 1132 | f1 | h1 | g2 | h1 | a11 | d2 |
| 1133 | f1 | h1 | g2 | h1 | a11 | d3 |
| 1134 | f1 | h1 | g2 | h1 | a11 | d5 |
| 1135 | f1 | h1 | g2 | h1 | a11 | d7 |
| 1136 | f1 | h1 | g2 | h1 | a11 | d9 |
| 1137 | f1 | h1 | g2 | h1 | a11 | d11 |
| 1138 | f1 | h1 | g2 | h1 | a11 | d13 |
| 1139 | f1 | h1 | g2 | h1 | a11 | d17 |
| 1140 | f1 | h1 | g2 | h1 | a11 | e3 |
| 1141 | f1 | h1 | g2 | h1 | a15 | a15 |
| 1142 | f1 | h1 | g2 | h1 | a15 | b1 |
| 1143 | f1 | h1 | g2 | h1 | a15 | b3 |
| 1144 | f1 | h1 | g2 | h1 | a15 | b4 |
| 1145 | f1 | h1 | g2 | h1 | a15 | b6 |
| 1146 | f1 | h1 | g2 | h1 | a15 | c1 |
| 1147 | f1 | h1 | g2 | h1 | a15 | d1 |
| 1148 | f1 | h1 | g2 | h1 | a15 | d2 |
| 1149 | f1 | h1 | g2 | h1 | a15 | d3 |
| 1150 | f1 | h1 | g2 | h1 | a15 | d5 |
| 1151 | f1 | h1 | g2 | h1 | a15 | d7 |
| 1152 | f1 | h1 | g2 | h1 | a15 | d9 |
| 1153 | f1 | h1 | g2 | h1 | a15 | d11 |
| 1154 | f1 | h1 | g2 | h1 | a15 | d13 |
| 1155 | f1 | h1 | g2 | h1 | a15 | d17 |
| 1156 | f1 | h1 | g2 | h1 | a15 | e3 |
| 1157 | f1 | h1 | g2 | h1 | b1 | b1 |
| 1158 | f1 | h1 | g2 | h1 | b1 | b3 |
| 1159 | f1 | h1 | g2 | h1 | b1 | b4 |
| 1160 | f1 | h1 | g2 | h1 | b1 | b6 |
| 1161 | f1 | h1 | g2 | h1 | b1 | c1 |
| 1162 | f1 | h1 | g2 | h1 | b1 | d1 |
| 1163 | f1 | h1 | g2 | h1 | b1 | d2 |
| 1164 | f1 | h1 | g2 | h1 | b1 | d3 |
| 1165 | f1 | h1 | g2 | h1 | b1 | d5 |
| 1166 | f1 | h1 | g2 | h1 | b1 | d7 |
| 1167 | f1 | h1 | g2 | h1 | b1 | d9 |
| 1168 | f1 | h1 | g2 | h1 | b1 | d11 |
| 1169 | f1 | h1 | g2 | h1 | b1 | d13 |
| 1170 | f1 | h1 | g2 | h1 | b1 | d17 |
| 1171 | f1 | h1 | g2 | h1 | b1 | e3 |
| 1172 | f1 | h1 | g2 | h1 | b3 | b3 |
| 1173 | f1 | h1 | g2 | h1 | b3 | b4 |
| 1174 | f1 | h1 | g2 | h1 | b3 | b6 |
| 1175 | f1 | h1 | g2 | h1 | b3 | c1 |
| 1176 | f1 | h1 | g2 | h1 | b3 | d1 |
| 1177 | f1 | h1 | g2 | h1 | b3 | d2 |
| 1178 | f1 | h1 | g2 | h1 | b3 | d3 |
| 1179 | f1 | h1 | g2 | h1 | b3 | d5 |
| 1180 | f1 | h1 | g2 | h1 | b3 | d7 |
| 1181 | f1 | h1 | g2 | h1 | b3 | d9 |
| 1182 | f1 | h1 | g2 | h1 | b3 | d11 |
| 1183 | f1 | h1 | g2 | h1 | b3 | d13 |
| 1184 | f1 | h1 | g2 | h1 | b3 | d17 |
| 1185 | f1 | h1 | g2 | h1 | b3 | e3 |
| 1186 | f1 | h1 | g2 | h1 | b4 | b4 |
| 1187 | f1 | h1 | g2 | h1 | b4 | b6 |
| 1188 | f1 | h1 | g2 | h1 | b4 | c1 |
| 1189 | f1 | h1 | g2 | h1 | b4 | d1 |
| 1190 | f1 | h1 | g2 | h1 | b4 | d2 |
| 1191 | f1 | h1 | g2 | h1 | b4 | d3 |
| 1192 | f1 | h1 | g2 | h1 | b4 | d5 |
| 1193 | f1 | h1 | g2 | h1 | b4 | d7 |
| 1194 | f1 | h1 | g2 | h1 | b4 | d9 |
| 1195 | f1 | h1 | g2 | h1 | b4 | d11 |
| 1196 | f1 | h1 | g2 | h1 | b4 | d13 |
| 1197 | f1 | h1 | g2 | h1 | b4 | d17 |
| 1198 | f1 | h1 | g2 | h1 | b4 | e3 |
| 1199 | f1 | h1 | g2 | h1 | b6 | b6 |
| 1200 | f1 | h1 | g2 | h1 | b6 | c1 |
| 1201 | f1 | h1 | g2 | h1 | b6 | d1 |
| 1202 | f1 | h1 | g2 | h1 | b6 | d2 |
| 1203 | f1 | h1 | g2 | h1 | b6 | d3 |
| 1204 | f1 | h1 | g2 | h1 | b6 | d5 |
| 1205 | f1 | h1 | g2 | h1 | b6 | d7 |
| 1206 | f1 | h1 | g2 | h1 | b6 | d9 |
| 1207 | f1 | h1 | g2 | h1 | b6 | d11 |
| 1208 | f1 | h1 | g2 | h1 | b6 | d13 |
| 1209 | f1 | h1 | g2 | h1 | b6 | d17 |
| 1210 | f1 | h1 | g2 | h1 | b6 | e3 |
| 1211 | f1 | h1 | g2 | h1 | c1 | c1 |
| 1212 | f1 | h1 | g2 | h1 | c1 | d1 |
| 1213 | f1 | h1 | g2 | h1 | c1 | d2 |
| 1214 | f1 | h1 | g2 | h1 | c1 | d3 |
| 1215 | f1 | h1 | g2 | h1 | c1 | d5 |
| 1216 | f1 | h1 | g2 | h1 | c1 | d7 |
| 1217 | f1 | h1 | g2 | h1 | c1 | d9 |
| 1218 | f1 | h1 | g2 | h1 | c1 | d11 |
| 1219 | f1 | h1 | g2 | h1 | c1 | d13 |
| 1220 | f1 | h1 | g2 | h1 | c1 | d17 |
| 1221 | f1 | h1 | g2 | h1 | c1 | e3 |
| 1222 | f1 | h1 | g2 | h1 | d1 | d1 |
| 1223 | f1 | h1 | g2 | h1 | d1 | d2 |
| 1224 | f1 | h1 | g2 | h1 | d1 | d3 |
| 1225 | f1 | h1 | g2 | h1 | d1 | d5 |
| 1226 | f1 | h1 | g2 | h1 | d1 | d7 |
| 1227 | f1 | h1 | g2 | h1 | d1 | d9 |
| 1228 | f1 | h1 | g2 | h1 | d1 | d11 |
| 1229 | f1 | h1 | g2 | h1 | d1 | d13 |
| 1230 | f1 | h1 | g2 | h1 | d1 | d17 |
| 1231 | f1 | h1 | g2 | h1 | d1 | e3 |
| 1232 | f1 | h1 | g2 | h1 | d2 | d2 |
| 1233 | f1 | h1 | g2 | h1 | d2 | d3 |
| 1234 | f1 | h1 | g2 | h1 | d2 | d5 |
| 1235 | f1 | h1 | g2 | h1 | d2 | d7 |
| 1236 | f1 | h1 | g2 | h1 | d2 | d9 |
| 1237 | f1 | h1 | g2 | h1 | d2 | d11 |
| 1238 | f1 | h1 | g2 | h1 | d2 | d13 |
| 1239 | f1 | h1 | g2 | h1 | d2 | d17 |
| 1240 | f1 | h1 | g2 | h1 | d2 | e3 |
| 1241 | f1 | h1 | g2 | h1 | d3 | d3 |
| 1242 | f1 | h1 | g2 | h1 | d3 | d5 |
| 1243 | f1 | h1 | g2 | h1 | d3 | d7 |
| 1244 | f1 | h1 | g2 | h1 | d3 | d9 |
| 1245 | f1 | h1 | g2 | h1 | d3 | d11 |
| 1246 | f1 | h1 | g2 | h1 | d3 | d13 |
| 1247 | f1 | h1 | g2 | h1 | d3 | d17 |
| 1248 | f1 | h1 | g2 | h1 | d3 | e3 |
| 1249 | f1 | h1 | g2 | h1 | d5 | d5 |
| 1250 | f1 | h1 | g2 | h1 | d5 | d7 |
| 1251 | f1 | h1 | g2 | h1 | d5 | d9 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 1252 | f1 | h1 | g2 | h1 | d5 | d11 |
| 1253 | f1 | h1 | g2 | h1 | d5 | d13 |
| 1254 | f1 | h1 | g2 | h1 | d5 | d17 |
| 1255 | f1 | h1 | g2 | h1 | d5 | e3 |
| 1256 | f1 | h1 | g2 | h1 | d7 | d7 |
| 1257 | f1 | h1 | g2 | h1 | d7 | d9 |
| 1258 | f1 | h1 | g2 | h1 | d7 | d11 |
| 1259 | f1 | h1 | g2 | h1 | d7 | d13 |
| 1260 | f1 | h1 | g2 | h1 | d7 | d17 |
| 1261 | f1 | h1 | g2 | h1 | d7 | e3 |
| 1262 | f1 | h1 | g2 | h1 | d9 | d9 |
| 1263 | f1 | h1 | g2 | h1 | d9 | d11 |
| 1264 | f1 | h1 | g2 | h1 | d9 | d13 |
| 1265 | f1 | h1 | g2 | h1 | d9 | d17 |
| 1266 | f1 | h1 | g2 | h1 | d9 | e3 |
| 1267 | f1 | h1 | g2 | h1 | d11 | d11 |
| 1268 | f1 | h1 | g2 | h1 | d11 | d13 |
| 1269 | f1 | h1 | g2 | h1 | d11 | d17 |
| 1270 | f1 | h1 | g2 | h1 | d11 | e3 |
| 1271 | f1 | h1 | g2 | h1 | d13 | d13 |
| 1272 | f1 | h1 | g2 | h1 | d13 | d17 |
| 1273 | f1 | h1 | g2 | h1 | d13 | e3 |
| 1274 | f1 | h1 | g2 | h1 | d17 | d17 |
| 1275 | f1 | h1 | g2 | h1 | e3 | e3 |
| 1276 | f1 | h1 | g3 | h1 | a1 | a1 |
| 1277 | f1 | h1 | g4 | h1 | a1 | a1 |
| 1278 | f1 | h1 | g1 | h1 | d1 | a1 |
| 1279 | f1 | h1 | g1 | h1 | d1 | a2 |
| 1280 | f1 | h1 | g1 | h1 | d1 | a4 |
| 1281 | f1 | h1 | g1 | h1 | d1 | a5 |
| 1282 | f1 | h1 | g1 | h1 | d1 | a6 |
| 1283 | f1 | h1 | g1 | h1 | d1 | a11 |
| 1284 | f1 | h1 | g1 | h1 | d1 | a15 |
| 1285 | f1 | h1 | g1 | h1 | d1 | b1 |
| 1286 | f1 | h1 | g1 | h1 | d1 | b3 |
| 1287 | f1 | h1 | g1 | h1 | d1 | b4 |
| 1288 | f1 | h1 | g1 | h1 | d1 | b6 |
| 1289 | f1 | h1 | g1 | h1 | d1 | c1 |
| 1290 | f1 | h1 | g1 | h1 | d1 | d1 |
| 1291 | f1 | h1 | g1 | h1 | d1 | d2 |
| 1292 | f1 | h1 | g1 | h1 | d1 | d3 |
| 1293 | f1 | h1 | g1 | h1 | d1 | d5 |
| 1294 | f1 | h1 | g1 | h1 | d1 | d7 |
| 1295 | f1 | h1 | g1 | h1 | d1 | d9 |
| 1296 | f1 | h1 | g1 | h1 | d1 | d11 |
| 1297 | f1 | h1 | g1 | h1 | d1 | d13 |
| 1298 | f1 | h1 | g1 | h1 | d1 | e3 |
| 1299 | f1 | h1 | g1 | h1 | d2 | a1 |
| 1300 | f1 | h1 | g1 | h1 | d2 | a2 |
| 1301 | f1 | h1 | g1 | h1 | d2 | a4 |
| 1302 | f1 | h1 | g1 | h1 | d2 | a5 |
| 1303 | f1 | h1 | g1 | h1 | d2 | a6 |
| 1304 | f1 | h1 | g1 | h1 | d2 | a11 |
| 1305 | f1 | h1 | g1 | h1 | d2 | a15 |
| 1306 | f1 | h1 | g1 | h1 | d2 | b1 |
| 1307 | f1 | h1 | g1 | h1 | d2 | b3 |
| 1308 | f1 | h1 | g1 | h1 | d2 | b4 |
| 1309 | f1 | h1 | g1 | h1 | d2 | b6 |
| 1310 | f1 | h1 | g1 | h1 | d2 | c1 |
| 1311 | f1 | h1 | g1 | h1 | d2 | d2 |
| 1312 | f1 | h1 | g1 | h1 | d2 | d3 |
| 1313 | f1 | h1 | g1 | h1 | d2 | d5 |
| 1314 | f1 | h1 | g1 | h1 | d2 | d7 |
| 1315 | f1 | h1 | g1 | h1 | d2 | d9 |
| 1316 | f1 | h1 | g1 | h1 | d2 | d11 |
| 1317 | f1 | h1 | g1 | h1 | d2 | d13 |
| 1318 | f1 | h1 | g1 | h1 | d2 | e3 |
| 1319 | f1 | h1 | g1 | h1 | d3 | a1 |
| 1320 | f1 | h1 | g1 | h1 | d3 | a2 |
| 1321 | f1 | h1 | g1 | h1 | d3 | a4 |
| 1322 | f1 | h1 | g1 | h1 | d3 | a5 |
| 1323 | f1 | h1 | g1 | h1 | d3 | a6 |
| 1324 | f1 | h1 | g1 | h1 | d3 | a11 |
| 1325 | f1 | h1 | g1 | h1 | d3 | a15 |
| 1326 | f1 | h1 | g1 | h1 | d3 | b1 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 1327 | f1 | h1 | g1 | h1 | d3 | b3 |
| 1328 | f1 | h1 | g1 | h1 | d3 | b4 |
| 1329 | f1 | h1 | g1 | h1 | d3 | b6 |
| 1330 | f1 | h1 | g1 | h1 | d3 | c1 |
| 1331 | f1 | h1 | g1 | h1 | d3 | d3 |
| 1332 | f1 | h1 | g1 | h1 | d3 | d5 |
| 1333 | f1 | h1 | g1 | h1 | d3 | d7 |
| 1334 | f1 | h1 | g1 | h1 | d3 | d9 |
| 1335 | f1 | h1 | g1 | h1 | d3 | d11 |
| 1336 | f1 | h1 | g1 | h1 | d3 | d13 |
| 1337 | f1 | h1 | g1 | h1 | d3 | e3 |
| 1338 | f1 | h1 | g1 | h1 | d4 | a1 |
| 1339 | f1 | h1 | g1 | h1 | d4 | a2 |
| 1340 | f1 | h1 | g1 | h1 | d4 | a4 |
| 1341 | f1 | h1 | g1 | h1 | d4 | a5 |
| 1342 | f1 | h1 | g1 | h1 | d4 | a6 |
| 1343 | f1 | h1 | g1 | h1 | d4 | a11 |
| 1344 | f1 | h1 | g1 | h1 | d4 | a15 |
| 1345 | f1 | h1 | g1 | h1 | d4 | b1 |
| 1346 | f1 | h1 | g1 | h1 | d4 | b3 |
| 1347 | f1 | h1 | g1 | h1 | d4 | b4 |
| 1348 | f1 | h1 | g1 | h1 | d4 | b6 |
| 1349 | f1 | h1 | g1 | h1 | d4 | c1 |
| 1350 | f1 | h1 | g1 | h1 | d4 | d1 |
| 1351 | f1 | h1 | g1 | h1 | d4 | d2 |
| 1352 | f1 | h1 | g1 | h1 | d4 | d3 |
| 1353 | f1 | h1 | g1 | h1 | d4 | d5 |
| 1354 | f1 | h1 | g1 | h1 | d4 | d7 |
| 1355 | f1 | h1 | g1 | h1 | d4 | d9 |
| 1356 | f1 | h1 | g1 | h1 | d4 | d11 |
| 1357 | f1 | h1 | g1 | h1 | d4 | d13 |
| 1358 | f1 | h1 | g1 | h1 | d4 | e3 |
| 1359 | f1 | h1 | g1 | h1 | d5 | a1 |
| 1360 | f1 | h1 | g1 | h1 | d5 | a2 |
| 1361 | f1 | h1 | g1 | h1 | d5 | a4 |
| 1362 | f1 | h1 | g1 | h1 | d5 | a5 |
| 1363 | f1 | h1 | g1 | h1 | d5 | a6 |
| 1364 | f1 | h1 | g1 | h1 | d5 | a11 |
| 1365 | f1 | h1 | g1 | h1 | d5 | a15 |
| 1366 | f1 | h1 | g1 | h1 | d5 | b1 |
| 1367 | f1 | h1 | g1 | h1 | d5 | b3 |
| 1368 | f1 | h1 | g1 | h1 | d5 | b4 |
| 1369 | f1 | h1 | g1 | h1 | d5 | b6 |
| 1370 | f1 | h1 | g1 | h1 | d5 | c1 |
| 1371 | f1 | h1 | g1 | h1 | d5 | d5 |
| 1372 | f1 | h1 | g1 | h1 | d5 | d7 |
| 1373 | f1 | h1 | g1 | h1 | d5 | d9 |
| 1374 | f1 | h1 | g1 | h1 | d5 | d11 |
| 1375 | f1 | h1 | g1 | h1 | d5 | d13 |
| 1376 | f1 | h1 | g1 | h1 | d5 | e3 |
| 1377 | f1 | h1 | g1 | h1 | d6 | a1 |
| 1378 | f1 | h1 | g1 | h1 | d6 | a2 |
| 1379 | f1 | h1 | g1 | h1 | d6 | a4 |
| 1380 | f1 | h1 | g1 | h1 | d6 | a5 |
| 1381 | f1 | h1 | g1 | h1 | d6 | a6 |
| 1382 | f1 | h1 | g1 | h1 | d6 | a11 |
| 1383 | f1 | h1 | g1 | h1 | d6 | a15 |
| 1384 | f1 | h1 | g1 | h1 | d6 | b1 |
| 1385 | f1 | h1 | g1 | h1 | d6 | b3 |
| 1386 | f1 | h1 | g1 | h1 | d6 | b4 |
| 1387 | f1 | h1 | g1 | h1 | d6 | b6 |
| 1388 | f1 | h1 | g1 | h1 | d6 | c1 |
| 1389 | f1 | h1 | g1 | h1 | d6 | d1 |
| 1390 | f1 | h1 | g1 | h1 | d6 | d2 |
| 1391 | f1 | h1 | g1 | h1 | d6 | d3 |
| 1392 | f1 | h1 | g1 | h1 | d6 | d5 |
| 1393 | f1 | h1 | g1 | h1 | d6 | d7 |
| 1394 | f1 | h1 | g1 | h1 | d6 | d9 |
| 1395 | f1 | h1 | g1 | h1 | d6 | d11 |
| 1396 | f1 | h1 | g1 | h1 | d6 | d13 |
| 1397 | f1 | h1 | g1 | h1 | d6 | e3 |
| 1398 | f1 | h1 | g1 | h1 | d7 | a1 |
| 1399 | f1 | h1 | g1 | h1 | d7 | a2 |
| 1400 | f1 | h1 | g1 | h1 | d7 | a4 |
| 1401 | f1 | h1 | g1 | h1 | d7 | a5 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 1402 | f1 | h1 | g1 | h1 | d7 | a6 |
| 1403 | f1 | h1 | g1 | h1 | d7 | a11 |
| 1404 | f1 | h1 | g1 | h1 | d7 | a15 |
| 1405 | f1 | h1 | g1 | h1 | d7 | b1 |
| 1406 | f1 | h1 | g1 | h1 | d7 | b3 |
| 1407 | f1 | h1 | g1 | h1 | d7 | b4 |
| 1408 | f1 | h1 | g1 | h1 | d7 | b6 |
| 1409 | f1 | h1 | g1 | h1 | d7 | c1 |
| 1410 | f1 | h1 | g1 | h1 | d7 | d7 |
| 1411 | f1 | h1 | g1 | h1 | d7 | d9 |
| 1412 | f1 | h1 | g1 | h1 | d7 | d11 |
| 1413 | f1 | h1 | g1 | h1 | d7 | d13 |
| 1414 | f1 | h1 | g1 | h1 | d7 | e3 |
| 1415 | f1 | h1 | g1 | h1 | d8 | a1 |
| 1416 | f1 | h1 | g1 | h1 | d8 | a2 |
| 1417 | f1 | h1 | g1 | h1 | d8 | a4 |
| 1418 | f1 | h1 | g1 | h1 | d8 | a5 |
| 1419 | f1 | h1 | g1 | h1 | d8 | a6 |
| 1420 | f1 | h1 | g1 | h1 | d8 | a11 |
| 1421 | f1 | h1 | g1 | h1 | d8 | a15 |
| 1422 | f1 | h1 | g1 | h1 | d8 | b1 |
| 1423 | f1 | h1 | g1 | h1 | d8 | b3 |
| 1424 | f1 | h1 | g1 | h1 | d8 | b4 |
| 1425 | f1 | h1 | g1 | h1 | d8 | b6 |
| 1426 | f1 | h1 | g1 | h1 | d8 | c1 |
| 1427 | f1 | h1 | g1 | h1 | d8 | d1 |
| 1428 | f1 | h1 | g1 | h1 | d8 | d2 |
| 1429 | f1 | h1 | g1 | h1 | d8 | d3 |
| 1430 | f1 | h1 | g1 | h1 | d8 | d5 |
| 1431 | f1 | h1 | g1 | h1 | d8 | d7 |
| 1432 | f1 | h1 | g1 | h1 | d8 | d9 |
| 1433 | f1 | h1 | g1 | h1 | d8 | d11 |
| 1434 | f1 | h1 | g1 | h1 | d8 | d13 |
| 1435 | f1 | h1 | g1 | h1 | d8 | e3 |
| 1436 | f1 | h1 | g1 | h1 | d9 | a1 |
| 1437 | f1 | h1 | g1 | h1 | d9 | a2 |
| 1438 | f1 | h1 | g1 | h1 | d9 | a4 |
| 1439 | f1 | h1 | g1 | h1 | d9 | a5 |
| 1440 | f1 | h1 | g1 | h1 | d9 | a6 |
| 1441 | f1 | h1 | g1 | h1 | d9 | a11 |
| 1442 | f1 | h1 | g1 | h1 | d9 | a15 |
| 1443 | f1 | h1 | g1 | h1 | d9 | b1 |
| 1444 | f1 | h1 | g1 | h1 | d9 | b3 |
| 1445 | f1 | h1 | g1 | h1 | d9 | b4 |
| 1446 | f1 | h1 | g1 | h1 | d9 | b6 |
| 1447 | f1 | h1 | g1 | h1 | d9 | c1 |
| 1448 | f1 | h1 | g1 | h1 | d9 | d9 |
| 1449 | f1 | h1 | g1 | h1 | d9 | d11 |
| 1450 | f1 | h1 | g1 | h1 | d9 | d13 |
| 1451 | f1 | h1 | g1 | h1 | d9 | e3 |
| 1452 | f1 | h1 | g1 | h1 | d10 | a1 |
| 1453 | f1 | h1 | g1 | h1 | d10 | a2 |
| 1454 | f1 | h1 | g1 | h1 | d10 | a4 |
| 1455 | f1 | h1 | g1 | h1 | d10 | a5 |
| 1456 | f1 | h1 | g1 | h1 | d10 | a6 |
| 1457 | f1 | h1 | g1 | h1 | d10 | a11 |
| 1458 | f1 | h1 | g1 | h1 | d10 | a15 |
| 1459 | f1 | h1 | g1 | h1 | d10 | b1 |
| 1460 | f1 | h1 | g1 | h1 | d10 | b3 |
| 1461 | f1 | h1 | g1 | h1 | d10 | b4 |
| 1462 | f1 | h1 | g1 | h1 | d10 | b6 |
| 1463 | f1 | h1 | g1 | h1 | d10 | c1 |
| 1464 | f1 | h1 | g1 | h1 | d10 | d1 |
| 1465 | f1 | h1 | g1 | h1 | d10 | d2 |
| 1466 | f1 | h1 | g1 | h1 | d10 | d3 |
| 1467 | f1 | h1 | g1 | h1 | d10 | d5 |
| 1468 | f1 | h1 | g1 | h1 | d10 | d7 |
| 1469 | f1 | h1 | g1 | h1 | d10 | d9 |
| 1470 | f1 | h1 | g1 | h1 | d10 | d11 |
| 1471 | f1 | h1 | g1 | h1 | d10 | d13 |
| 1472 | f1 | h1 | g1 | h1 | d10 | e3 |
| 1473 | f1 | h1 | g1 | h1 | d11 | a1 |
| 1474 | f1 | h1 | g1 | h1 | d11 | a2 |
| 1475 | f1 | h1 | g1 | h1 | d11 | a4 |
| 1476 | f1 | h1 | g1 | h1 | d11 | a5 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 1477 | f1 | h1 | g1 | h1 | d11 | a6 |
| 1478 | f1 | h1 | g1 | h1 | d11 | a11 |
| 1479 | f1 | h1 | g1 | h1 | d11 | a15 |
| 1480 | f1 | h1 | g1 | h1 | d11 | b1 |
| 1481 | f1 | h1 | g1 | h1 | d11 | b3 |
| 1482 | f1 | h1 | g1 | h1 | d11 | b4 |
| 1483 | f1 | h1 | g1 | h1 | d11 | b6 |
| 1484 | f1 | h1 | g1 | h1 | d11 | c1 |
| 1485 | f1 | h1 | g1 | h1 | d11 | d11 |
| 1486 | f1 | h1 | g1 | h1 | d11 | d13 |
| 1487 | f1 | h1 | g1 | h1 | d11 | e3 |
| 1488 | f1 | h1 | g1 | h1 | d12 | a1 |
| 1489 | f1 | h1 | g1 | h1 | d12 | a2 |
| 1490 | f1 | h1 | g1 | h1 | d12 | a4 |
| 1491 | f1 | h1 | g1 | h1 | d12 | a5 |
| 1492 | f1 | h1 | g1 | h1 | d12 | a6 |
| 1493 | f1 | h1 | g1 | h1 | d12 | a11 |
| 1494 | f1 | h1 | g1 | h1 | d12 | a15 |
| 1495 | f1 | h1 | g1 | h1 | d12 | b1 |
| 1496 | f1 | h1 | g1 | h1 | d12 | b3 |
| 1497 | f1 | h1 | g1 | h1 | d12 | b4 |
| 1498 | f1 | h1 | g1 | h1 | d12 | b6 |
| 1499 | f1 | h1 | g1 | h1 | d12 | c1 |
| 1500 | f1 | h1 | g1 | h1 | d12 | d1 |
| 1501 | f1 | h1 | g1 | h1 | d12 | d2 |
| 1502 | f1 | h1 | g1 | h1 | d12 | d3 |
| 1503 | f1 | h1 | g1 | h1 | d12 | d5 |
| 1504 | f1 | h1 | g1 | h1 | d12 | d7 |
| 1505 | f1 | h1 | g1 | h1 | d12 | d9 |
| 1506 | f1 | h1 | g1 | h1 | d12 | d11 |
| 1507 | f1 | h1 | g1 | h1 | d12 | d13 |
| 1508 | f1 | h1 | g1 | h1 | d12 | e3 |
| 1509 | f1 | h1 | g1 | h1 | d13 | a1 |
| 1510 | f1 | h1 | g1 | h1 | d13 | a2 |
| 1511 | f1 | h1 | g1 | h1 | d13 | a4 |
| 1512 | f1 | h1 | g1 | h1 | d13 | a5 |
| 1513 | f1 | h1 | g1 | h1 | d13 | a6 |
| 1514 | f1 | h1 | g1 | h1 | d13 | a11 |
| 1515 | f1 | h1 | g1 | h1 | d13 | a15 |
| 1516 | f1 | h1 | g1 | h1 | d13 | b1 |
| 1517 | f1 | h1 | g1 | h1 | d13 | b3 |
| 1518 | f1 | h1 | g1 | h1 | d13 | b4 |
| 1519 | f1 | h1 | g1 | h1 | d13 | b6 |
| 1520 | f1 | h1 | g1 | h1 | d13 | c1 |
| 1521 | f1 | h1 | g1 | h1 | d13 | d13 |
| 1522 | f1 | h1 | g1 | h1 | d13 | e3 |
| 1523 | f1 | h1 | g1 | h1 | d14 | a1 |
| 1524 | f1 | h1 | g1 | h1 | d14 | a2 |
| 1525 | f1 | h1 | g1 | h1 | d14 | a4 |
| 1526 | f1 | h1 | g1 | h1 | d14 | a5 |
| 1527 | f1 | h1 | g1 | h1 | d14 | a6 |
| 1528 | f1 | h1 | g1 | h1 | d14 | a11 |
| 1529 | f1 | h1 | g1 | h1 | d14 | a15 |
| 1530 | f1 | h1 | g1 | h1 | d14 | b1 |
| 1531 | f1 | h1 | g1 | h1 | d14 | b3 |
| 1532 | f1 | h1 | g1 | h1 | d14 | b4 |
| 1533 | f1 | h1 | g1 | h1 | d14 | b6 |
| 1534 | f1 | h1 | g1 | h1 | d14 | c1 |
| 1535 | f1 | h1 | g1 | h1 | d14 | d1 |
| 1536 | f1 | h1 | g1 | h1 | d14 | d2 |
| 1537 | f1 | h1 | g1 | h1 | d14 | d3 |
| 1538 | f1 | h1 | g1 | h1 | d14 | d5 |
| 1539 | f1 | h1 | g1 | h1 | d14 | d7 |
| 1540 | f1 | h1 | g1 | h1 | d14 | d9 |
| 1541 | f1 | h1 | g1 | h1 | d14 | d11 |
| 1542 | f1 | h1 | g1 | h1 | d14 | d13 |
| 1543 | f1 | h1 | g1 | h1 | d14 | e3 |
| 1544 | f1 | h1 | g1 | h1 | d15 | a1 |
| 1545 | f1 | h1 | g1 | h1 | d15 | a2 |
| 1546 | f1 | h1 | g1 | h1 | d15 | a4 |
| 1547 | f1 | h1 | g1 | h1 | d15 | a5 |
| 1548 | f1 | h1 | g1 | h1 | d15 | a6 |
| 1549 | f1 | h1 | g1 | h1 | d15 | a11 |
| 1550 | f1 | h1 | g1 | h1 | d15 | a15 |
| 1551 | f1 | h1 | g1 | h1 | d15 | b1 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 1552 | f1 | h1 | g1 | h1 | d15 | b3 |
| 1553 | f1 | h1 | g1 | h1 | d15 | b4 |
| 1554 | f1 | h1 | g1 | h1 | d15 | b6 |
| 1555 | f1 | h1 | g1 | h1 | d15 | c1 |
| 1556 | f1 | h1 | g1 | h1 | d15 | d1 |
| 1557 | f1 | h1 | g1 | h1 | d15 | d2 |
| 1558 | f1 | h1 | g1 | h1 | d15 | d3 |
| 1559 | f1 | h1 | g1 | h1 | d15 | d5 |
| 1560 | f1 | h1 | g1 | h1 | d15 | d7 |
| 1561 | f1 | h1 | g1 | h1 | d15 | d9 |
| 1562 | f1 | h1 | g1 | h1 | d15 | d11 |
| 1563 | f1 | h1 | g1 | h1 | d15 | d13 |
| 1564 | f1 | h1 | g1 | h1 | d15 | e3 |
| 1565 | f1 | h1 | g1 | h1 | d16 | a1 |
| 1566 | f1 | h1 | g1 | h1 | d16 | a2 |
| 1567 | f1 | h1 | g1 | h1 | d16 | a4 |
| 1568 | f1 | h1 | g1 | h1 | d16 | a5 |
| 1569 | f1 | h1 | g1 | h1 | d16 | a6 |
| 1570 | f1 | h1 | g1 | h1 | d16 | a11 |
| 1571 | f1 | h1 | g1 | h1 | d16 | a15 |
| 1572 | f1 | h1 | g1 | h1 | d16 | d1 |
| 1573 | f1 | h1 | g1 | h1 | d16 | b3 |
| 1574 | f1 | h1 | g1 | h1 | d16 | b4 |
| 1575 | f1 | h1 | g1 | h1 | d16 | b6 |
| 1576 | f1 | h1 | g1 | h1 | d16 | c1 |
| 1577 | f1 | h1 | g1 | h1 | d16 | d1 |
| 1578 | f1 | h1 | g1 | h1 | d16 | d2 |
| 1579 | f1 | h1 | g1 | h1 | d16 | d3 |
| 1580 | f1 | h1 | g1 | h1 | d16 | d5 |
| 1581 | f1 | h1 | g1 | h1 | d16 | d7 |
| 1582 | f1 | h1 | g1 | h1 | d16 | d9 |
| 1583 | f1 | h1 | g1 | h1 | d16 | d11 |
| 1584 | f1 | h1 | g1 | h1 | d16 | d13 |
| 1585 | f1 | h1 | g1 | h1 | d16 | e3 |
| 1586 | f1 | h1 | g1 | h1 | d17 | a1 |
| 1587 | f1 | h1 | g1 | h1 | d17 | a2 |
| 1588 | f1 | h1 | g1 | h1 | d17 | a4 |
| 1589 | f1 | h1 | g1 | h1 | d17 | a5 |
| 1590 | f1 | h1 | g1 | h1 | d17 | a6 |
| 1591 | f1 | h1 | g1 | h1 | d17 | a11 |
| 1592 | f1 | h1 | g1 | h1 | d17 | a15 |
| 1593 | f1 | h1 | g1 | h1 | d17 | b1 |
| 1594 | f1 | h1 | g1 | h1 | d17 | b3 |
| 1595 | f1 | h1 | g1 | h1 | d17 | b4 |
| 1596 | f1 | h1 | g1 | h1 | d17 | b6 |
| 1597 | f1 | h1 | g1 | h1 | d17 | c1 |
| 1598 | f1 | h1 | g1 | h1 | d17 | d1 |
| 1599 | f1 | h1 | g1 | h1 | d17 | d2 |
| 1600 | f1 | h1 | g1 | h1 | d17 | d3 |
| 1601 | f1 | h1 | g1 | h1 | d17 | d5 |
| 1602 | f1 | h1 | g1 | h1 | d17 | d7 |
| 1603 | f1 | h1 | g1 | h1 | d17 | d9 |
| 1604 | f1 | h1 | g1 | h1 | d17 | d11 |
| 1605 | f1 | h1 | g1 | h1 | d17 | d13 |
| 1606 | f1 | h1 | g1 | h1 | d17 | e3 |
| 1607 | f1 | h1 | g1 | h1 | d18 | a1 |
| 1608 | f1 | h1 | g1 | h1 | d18 | a2 |
| 1609 | f1 | h1 | g1 | h1 | d18 | a4 |
| 1610 | f1 | h1 | g1 | h1 | d18 | a5 |
| 1611 | f1 | h1 | g1 | h1 | d18 | a6 |
| 1612 | f1 | h1 | g1 | h1 | d18 | a11 |
| 1613 | f1 | h1 | g1 | h1 | d18 | a15 |
| 1614 | f1 | h1 | g1 | h1 | d18 | b1 |
| 1615 | f1 | h1 | g1 | h1 | d18 | b3 |
| 1616 | f1 | h1 | g1 | h1 | d18 | b4 |
| 1617 | f1 | h1 | g1 | h1 | d18 | b6 |
| 1618 | f1 | h1 | g1 | h1 | d18 | c1 |
| 1619 | f1 | h1 | g1 | h1 | d18 | d1 |
| 1620 | f1 | h1 | g1 | h1 | d18 | d2 |
| 1621 | f1 | h1 | g1 | h1 | d18 | d3 |
| 1622 | f1 | h1 | g1 | h1 | d18 | d5 |
| 1623 | f1 | h1 | g1 | h1 | d18 | d7 |
| 1624 | f1 | h1 | g1 | h1 | d18 | d9 |
| 1625 | f1 | h1 | g1 | h1 | d18 | d11 |
| 1626 | f1 | h1 | g1 | h1 | d18 | d13 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 1627 | f1 | h1 | g1 | h1 | e1 | a1 |
| 1628 | f1 | h1 | g1 | h1 | e1 | a2 |
| 1629 | f1 | h1 | g1 | h1 | e1 | a3 |
| 1630 | f1 | h1 | g1 | h1 | e1 | a4 |
| 1631 | f1 | h1 | g1 | h1 | e1 | a5 |
| 1632 | f1 | h1 | g1 | h1 | e1 | a6 |
| 1633 | f1 | h1 | g1 | h1 | e1 | a7 |
| 1634 | f1 | h1 | g1 | h1 | e1 | a8 |
| 1635 | f1 | h1 | g1 | h1 | e1 | a9 |
| 1636 | f1 | h1 | g1 | h1 | e1 | a10 |
| 1637 | f1 | h1 | g1 | h1 | e1 | a11 |
| 1638 | f1 | h1 | g1 | h1 | e1 | a12 |
| 1639 | f1 | h1 | g1 | h1 | e1 | a13 |
| 1640 | f1 | h1 | g1 | h1 | e1 | a14 |
| 1641 | f1 | h1 | g1 | h1 | e1 | a15 |
| 1642 | f1 | h1 | g1 | h1 | e1 | b1 |
| 1643 | f1 | h1 | g1 | h1 | e1 | b2 |
| 1644 | f1 | h1 | g1 | h1 | e1 | b3 |
| 1645 | f1 | h1 | g1 | h1 | e1 | b4 |
| 1646 | f1 | h1 | g1 | h1 | e1 | b5 |
| 1647 | f1 | h1 | g1 | h1 | e1 | b6 |
| 1648 | f1 | h1 | g1 | h1 | e1 | b7 |
| 1649 | f1 | h1 | g1 | h1 | e1 | b8 |
| 1650 | f1 | h1 | g1 | h1 | e1 | c1 |
| 1651 | f1 | h1 | g1 | h1 | e1 | c2 |
| 1652 | f1 | h1 | g1 | h1 | e1 | c3 |
| 1653 | f1 | h1 | g1 | h1 | e1 | c4 |
| 1654 | f1 | h1 | g1 | h1 | e1 | c5 |
| 1655 | f1 | h1 | g1 | h1 | e1 | d1 |
| 1656 | f1 | h1 | g1 | h1 | e1 | d2 |
| 1657 | f1 | h1 | g1 | h1 | e1 | d3 |
| 1658 | f1 | h1 | g1 | h1 | e1 | d4 |
| 1659 | f1 | h1 | g1 | h1 | e1 | d5 |
| 1660 | f1 | h1 | g1 | h1 | e1 | d6 |
| 1661 | f1 | h1 | g1 | h1 | e1 | d7 |
| 1662 | f1 | h1 | g1 | h1 | e1 | d8 |
| 1663 | f1 | h1 | g1 | h1 | e1 | d9 |
| 1664 | f1 | h1 | g1 | h1 | e1 | d10 |
| 1665 | f1 | h1 | g1 | h1 | e1 | d11 |
| 1666 | f1 | h1 | g1 | h1 | e1 | d12 |
| 1667 | f1 | h1 | g1 | h1 | e1 | d13 |
| 1668 | f1 | h1 | g1 | h1 | e1 | d14 |
| 1669 | f1 | h1 | g1 | h1 | e1 | d15 |
| 1670 | f1 | h1 | g1 | h1 | e1 | d16 |
| 1671 | f1 | h1 | g1 | h1 | e1 | d17 |
| 1672 | f1 | h1 | g1 | h1 | e1 | d18 |
| 1673 | f1 | h1 | g1 | h1 | e1 | e1 |
| 1674 | f1 | h1 | g1 | h1 | e1 | e2 |
| 1675 | f1 | h1 | g1 | h1 | e1 | e3 |
| 1676 | f1 | h1 | g1 | h1 | e1 | e4 |
| 1677 | f1 | h1 | g1 | h1 | e2 | a1 |
| 1678 | f1 | h1 | g1 | h1 | e2 | a2 |
| 1679 | f1 | h1 | g1 | h1 | e2 | a3 |
| 1680 | f1 | h1 | g1 | h1 | e2 | a4 |
| 1681 | f1 | h1 | g1 | h1 | e2 | a5 |
| 1682 | f1 | h1 | g1 | h1 | e2 | a6 |
| 1683 | f1 | h1 | g1 | h1 | e2 | a7 |
| 1684 | f1 | h1 | g1 | h1 | e2 | a8 |
| 1685 | f1 | h1 | g1 | h1 | e2 | a9 |
| 1686 | f1 | h1 | g1 | h1 | e2 | a10 |
| 1687 | f1 | h1 | g1 | h1 | e2 | a11 |
| 1688 | f1 | h1 | g1 | h1 | e2 | a12 |
| 1689 | f1 | h1 | g1 | h1 | e2 | a13 |
| 1690 | f1 | h1 | g1 | h1 | e2 | a14 |
| 1691 | f1 | h1 | g1 | h1 | e2 | a15 |
| 1692 | f1 | h1 | g1 | h1 | e2 | b1 |
| 1693 | f1 | h1 | g1 | h1 | e2 | b2 |
| 1694 | f1 | h1 | g1 | h1 | e2 | b3 |
| 1695 | f1 | h1 | g1 | h1 | e2 | b4 |
| 1696 | f1 | h1 | g1 | h1 | e2 | b5 |
| 1697 | f1 | h1 | g1 | h1 | e2 | b6 |
| 1698 | f1 | h1 | g1 | h1 | e2 | b7 |
| 1699 | f1 | h1 | g1 | h1 | e2 | b8 |
| 1700 | f1 | h1 | g1 | h1 | e2 | c1 |
| 1701 | f1 | h1 | g1 | h1 | e2 | c2 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 1702 | f1 | h1 | g1 | h1 | e2 | c3 |
| 1703 | f1 | h1 | g1 | h1 | e2 | c4 |
| 1704 | f1 | h1 | g1 | h1 | e2 | c5 |
| 1705 | f1 | h1 | g1 | h1 | e2 | d1 |
| 1706 | f1 | h1 | g1 | h1 | e2 | d2 |
| 1707 | f1 | h1 | g1 | h1 | e2 | d3 |
| 1708 | f1 | h1 | g1 | h1 | e2 | d4 |
| 1709 | f1 | h1 | g1 | h1 | e2 | d5 |
| 1710 | f1 | h1 | g1 | h1 | e2 | d6 |
| 1711 | f1 | h1 | g1 | h1 | e2 | d7 |
| 1712 | f1 | h1 | g1 | h1 | e2 | d8 |
| 1713 | f1 | h1 | g1 | h1 | e2 | d9 |
| 1714 | f1 | h1 | g1 | h1 | e2 | d10 |
| 1715 | f1 | h1 | g1 | h1 | e2 | d11 |
| 1716 | f1 | h1 | g1 | h1 | e2 | d12 |
| 1717 | f1 | h1 | g1 | h1 | e2 | d13 |
| 1718 | f1 | h1 | g1 | h1 | e2 | d14 |
| 1719 | f1 | h1 | g1 | h1 | e2 | d15 |
| 1720 | f1 | h1 | g1 | h1 | e2 | d16 |
| 1721 | f1 | h1 | g1 | h1 | e2 | d17 |
| 1722 | f1 | h1 | g1 | h1 | e2 | d18 |
| 1723 | f1 | h1 | g1 | h1 | e2 | e2 |
| 1724 | f1 | h1 | g1 | h1 | e2 | e3 |
| 1725 | f1 | h1 | g1 | h1 | e2 | e4 |
| 1726 | f1 | h1 | g1 | h1 | e3 | a1 |
| 1727 | f1 | h1 | g1 | h1 | e3 | a2 |
| 1728 | f1 | h1 | g1 | h1 | e3 | a3 |
| 1729 | f1 | h1 | g1 | h1 | e3 | a4 |
| 1730 | f1 | h1 | g1 | h1 | e3 | a5 |
| 1731 | f1 | h1 | g1 | h1 | e3 | a6 |
| 1732 | f1 | h1 | g1 | h1 | e3 | a7 |
| 1733 | f1 | h1 | g1 | h1 | e3 | a8 |
| 1734 | f1 | h1 | g1 | h1 | e3 | a9 |
| 1735 | f1 | h1 | g1 | h1 | e3 | a10 |
| 1736 | f1 | h1 | g1 | h1 | e3 | a11 |
| 1737 | f1 | h1 | g1 | h1 | e3 | a12 |
| 1738 | f1 | h1 | g1 | h1 | e3 | a13 |
| 1739 | f1 | h1 | g1 | h1 | e3 | a14 |
| 1740 | f1 | h1 | g1 | h1 | e3 | a15 |
| 1741 | f1 | h1 | g1 | h1 | e3 | b1 |
| 1742 | f1 | h1 | g1 | h1 | e3 | b2 |
| 1743 | f1 | h1 | g1 | h1 | e3 | b3 |
| 1744 | f1 | h1 | g1 | h1 | e3 | b4 |
| 1745 | f1 | h1 | g1 | h1 | e3 | b5 |
| 1746 | f1 | h1 | g1 | h1 | e3 | b6 |
| 1747 | f1 | h1 | g1 | h1 | e3 | b7 |
| 1748 | f1 | h1 | g1 | h1 | e3 | b8 |
| 1749 | f1 | h1 | g1 | h1 | e3 | c1 |
| 1750 | f1 | h1 | g1 | h1 | e3 | c2 |
| 1751 | f1 | h1 | g1 | h1 | e3 | c3 |
| 1752 | f1 | h1 | g1 | h1 | e3 | c3 |
| 1753 | f1 | h1 | g1 | h1 | e3 | c5 |
| 1754 | f1 | h1 | g1 | h1 | e3 | d1 |
| 1755 | f1 | h1 | g1 | h1 | e3 | d2 |
| 1756 | f1 | h1 | g1 | h1 | e3 | d3 |
| 1757 | f1 | h1 | g1 | h1 | e3 | d4 |
| 1758 | f1 | h1 | g1 | h1 | e3 | d5 |
| 1759 | f1 | h1 | g1 | h1 | e3 | d6 |
| 1760 | f1 | h1 | g1 | h1 | e3 | d7 |
| 1761 | f1 | h1 | g1 | h1 | e3 | d8 |
| 1762 | f1 | h1 | g1 | h1 | e3 | d9 |
| 1763 | f1 | h1 | g1 | h1 | e3 | d10 |
| 1764 | f1 | h1 | g1 | h1 | e3 | d11 |
| 1765 | f1 | h1 | g1 | h1 | e3 | d12 |
| 1766 | f1 | h1 | g1 | h1 | e3 | d13 |
| 1767 | f1 | h1 | g1 | h1 | e3 | d14 |
| 1768 | f1 | h1 | g1 | h1 | e3 | d15 |
| 1769 | f1 | h1 | g1 | h1 | e3 | d16 |
| 1770 | f1 | h1 | g1 | h1 | e3 | d17 |
| 1771 | f1 | h1 | g1 | h1 | e3 | d18 |
| 1772 | f1 | h1 | g1 | h1 | e3 | e3 |
| 1773 | f1 | h1 | g1 | h1 | e3 | e4 |
| 1774 | f1 | h1 | g1 | h1 | e4 | a1 |
| 1775 | f1 | h1 | g1 | h1 | e4 | a2 |
| 1776 | f1 | h1 | g1 | h1 | e4 | a3 |
| 1777 | f1 | h1 | g1 | h1 | e4 | a4 |
| 1778 | f1 | h1 | g1 | h1 | e4 | a5 |
| 1779 | f1 | h1 | g1 | h1 | e4 | a6 |
| 1780 | f1 | h1 | g1 | h1 | e4 | a7 |
| 1781 | f1 | h1 | g1 | h1 | e4 | a8 |
| 1782 | f1 | h1 | g1 | h1 | e4 | a9 |
| 1783 | f1 | h1 | g1 | h1 | e4 | a10 |
| 1784 | f1 | h1 | g1 | h1 | e4 | a11 |
| 1785 | f1 | h1 | g1 | h1 | e4 | a12 |
| 1786 | f1 | h1 | g1 | h1 | e4 | a13 |
| 1787 | f1 | h1 | g1 | h1 | e4 | a14 |
| 1788 | f1 | h1 | g1 | h1 | e4 | a15 |
| 1789 | f1 | h1 | g1 | h1 | e4 | b1 |
| 1790 | f1 | h1 | g1 | h1 | e4 | b2 |
| 1791 | f1 | h1 | g1 | h1 | e4 | b3 |
| 1792 | f1 | h1 | g1 | h1 | e4 | b4 |
| 1793 | f1 | h1 | g1 | h1 | e4 | b5 |
| 1794 | f1 | h1 | g1 | h1 | e4 | b6 |
| 1795 | f1 | h1 | g1 | h1 | e4 | b7 |
| 1796 | f1 | h1 | g1 | h1 | e4 | b8 |
| 1797 | f1 | h1 | g1 | h1 | e4 | c1 |
| 1798 | f1 | h1 | g1 | h1 | e4 | c2 |
| 1799 | f1 | h1 | g1 | h1 | e4 | c3 |
| 1800 | f1 | h1 | g1 | h1 | e4 | c4 |
| 1801 | f1 | h1 | g1 | h1 | e4 | c5 |
| 1802 | f1 | h1 | g1 | h1 | e4 | d1 |
| 1803 | f1 | h1 | g1 | h1 | e4 | d2 |
| 1804 | f1 | h1 | g1 | h1 | e4 | d3 |
| 1805 | f1 | h1 | g1 | h1 | e4 | d4 |
| 1806 | f1 | h1 | g1 | h1 | e4 | d5 |
| 1807 | f1 | h1 | g1 | h1 | e4 | d6 |
| 1808 | f1 | h1 | g1 | h1 | e4 | d7 |
| 1809 | f1 | h1 | g1 | h1 | e4 | d8 |
| 1810 | f1 | h1 | g1 | h1 | e4 | d9 |
| 1811 | f1 | h1 | g1 | h1 | e4 | d10 |
| 1812 | f1 | h1 | g1 | h1 | e4 | d11 |
| 1813 | f1 | h1 | g1 | h1 | e4 | d12 |
| 1814 | f1 | h1 | g1 | h1 | e4 | d13 |
| 1815 | f1 | h1 | g1 | h1 | e4 | d14 |
| 1816 | f1 | h1 | g1 | h1 | e4 | d15 |
| 1817 | f1 | h1 | g1 | h1 | e4 | d16 |
| 1818 | f1 | h1 | g1 | h1 | e4 | d17 |
| 1819 | f1 | h1 | g1 | h1 | e4 | d18 |
| 1820 | f1 | h1 | g1 | h1 | e4 | e4. |

15. An amine compound represented by Formula 1:

Formula 1

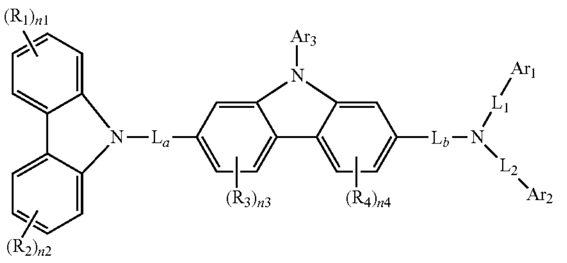

wherein in Formula 1, $Ar_1$ to $Ar_3$ are each independently a substituted or unsubstituted alkyl group of 1 to 20 carbon atoms, a substituted or unsubstituted silyl group, a substituted or unsubstituted aryl group of 6 to 30 ring-forming carbon atoms, or a substituted or unsubstituted heteroaryl group of 2 to 30 ring-forming carbon atoms, $L_a$, $L_b$, $L_1$, and $L_2$ are each independently a direct linkage, or a substituted or unsubstituted arylene group of 6 to 30 ring-forming carbon atoms, $R_1$ to $R_4$ are each independently a substituted or unsubstituted alkyl group of 1 to 20 carbon atoms, or a substituted or unsubstituted aryl group of 6 to 30 ring-forming carbon atoms, n1 and n2 are each independently an integer from 0 to 4, and n3 and n4 are each independently an integer from 0 to 3, wherein in Formula 1, a sum of n1 and n2 is 1 or more, at least one among $Ar_1$ to $Ar_3$ is a substituent represented by Formula a, at least one among $Ar_1$ and $Ar_2$ is a substituted or unsubstituted dibenzofuran group, a substituted or unsubstituted dibenzothiophene group, a substituted or unsubstituted phenanthrene group, a substituted or unsubstituted carbazole group, or a substituent represented by the following Formula b, or at least one among $L_a$ and $L_b$ is a substituted or unsubstituted arylene group of 6 to 30 ring-forming carbon atoms:

Formula a

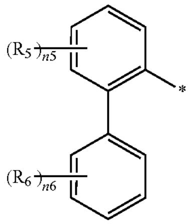

wherein in Formula a, $R_5$ and $R_6$ are each independently a hydrogen atom, a deuterium atom, a halogen atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, n5 is an integer from 0 to 4, and n6 is an integer from 0 to 5, Formula b

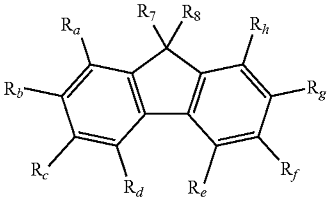

wherein in Formula b, $R_a$ to $R_h$, $R_7$, and $R_8$ are each independently a hydrogen atom, a deuterium atom, a halogen atom, a substituted or unsubstituted alkyl group of 1 to 20 carbon atoms, or a substituted or unsubstituted aryl group of 6 to 30 ring-forming carbon atoms, and any one among $R_a$, $R_b$, $R_d$, $R_e$, $R_g$, and $R_h$ is connected to $L_1$ or $L_2$, the amine compound comprising a structure of Formula 1, wherein optionally a hydrogen atom is substituted with a deuterium atom.

16. The amine compound of claim 15, wherein the amine compound represented by Formula 1 is represented by any one among Formula 2-1 to Formula 2-3:

Formula 2-1

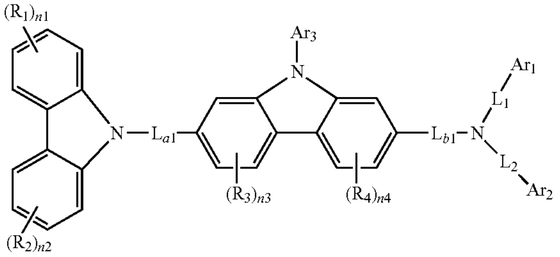

Formula 2-2

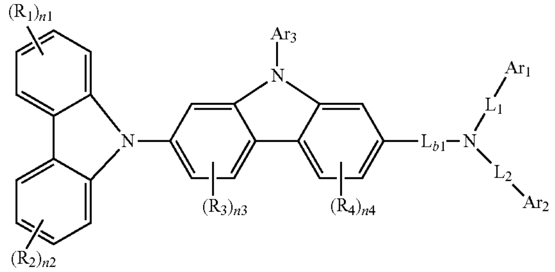

Formula 2-3

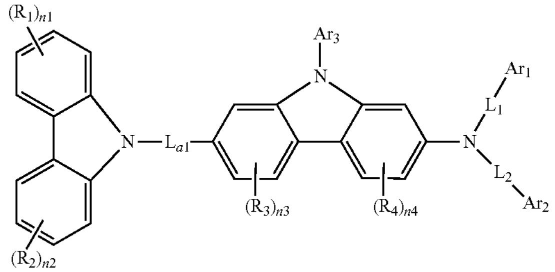

wherein in Formula 2-1 to Formula 2-3, $L_{a1}$ and $L_{b1}$ are each independently a substituted or unsubstituted arylene group of 6 to 30 ring-forming carbon atoms, and $Ar_1$ to $Ar_3$, $R_1$ to $R_4$, $L_1$, $L_2$, and n1 to n4 are the same as defined in Formula 1.

17. The amine compound of claim 15, wherein the amine compound represented by Formula 1 is represented by Formula 3:

Formula 3

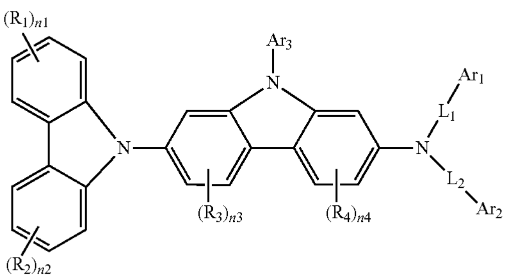

wherein in Formula 3, $Ar_1$ to $Ar_3$, $R_1$ to $R_4$, $L_1$, $L_2$, and n1 to n4 are the same as defined in Formula 1.

18. The amine compound of claim 15, wherein the amine compound represented by Formula 1 is represented by any one among Formula 4-1 to Formula 4-3:

Formula 4-1

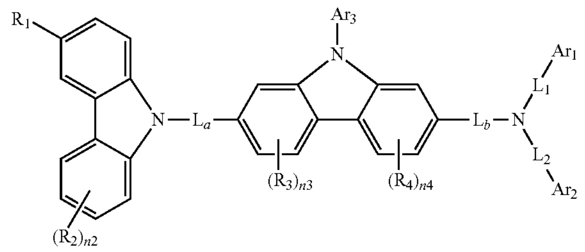

Formula 4-2

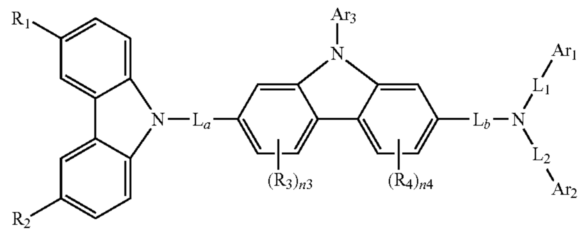

Formula 4-3

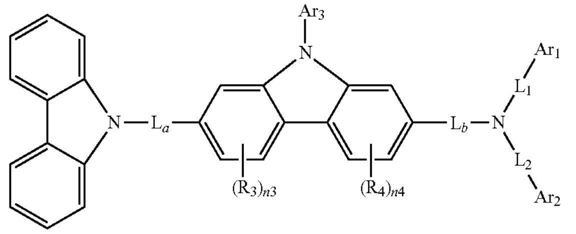

wherein in Formula 4-1 to Formula 4-3, $Ar_1$ to $Ar_3$, $R_1$ to $R_4$, $L_a$, $L_b$, $L_1$, $L_2$, and n2 to n4 are the same as defined in Formula 1.

19. The amine compound of claim 15, wherein the amine compound represented by Formula 1 is represented by any one among Formula 5-1 to Formula 5-3:

Formula 5-1

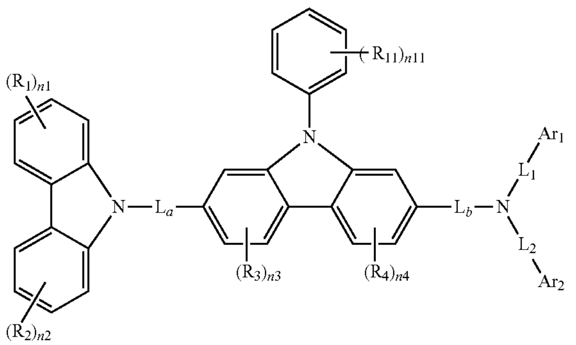

-continued

Formula 5-2

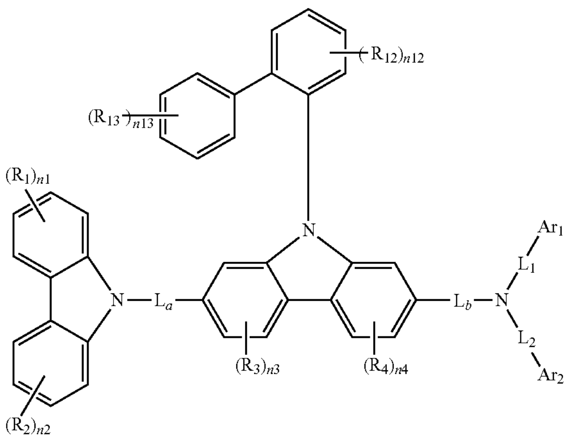

Formula 5-3

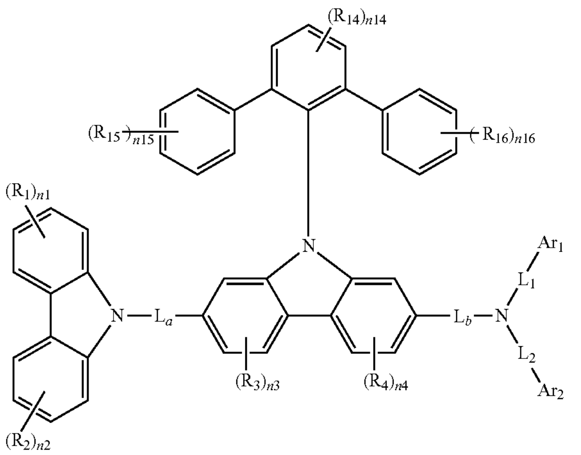

wherein in Formula 5-1 to Formula 5-3, $R_{11}$ to $R_{16}$ are each independently a hydrogen atom, a deuterium atom, a halogen atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, n11, n13, n15, and n16 are each independently an integer from 0 to 5, n12 is an integer from 0 to 4, n14 is an integer from 0 to 3, and $Ar_1$, $Ar_2$, $R_1$ to $R_4$, $L_a$, $L_b$, $L_1$, $L_2$, and n1 to n4 are the same as defined in Formula 1.

20. The amine compound of claim 15, wherein the amine compound is represented by Formula 9, and the amine compound is a compound satisfying any one among combinations represented Compound Combination Table 1:

Formula 9

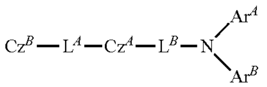

wherein in Formula 9, $Ar^A$ and $Ar^B$ are each independently selected from Compound Group A to Compound Group E, $Cz^A$ is selected from Compound Group G, $Cz^B$ is selected from Compound Group F, and $L^A$, and $L^B$ are selected from Compound Group H:
Compound Group A
a1
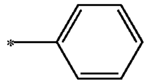
a2
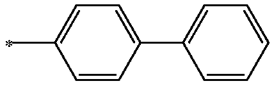
a3
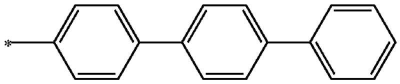
a4
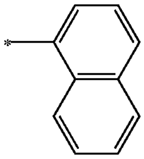
a5
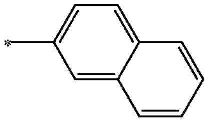
a6
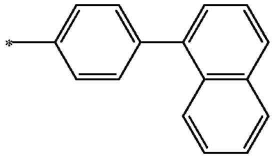
a7
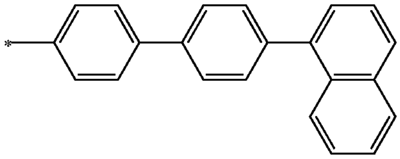
a8
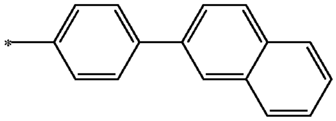
a9
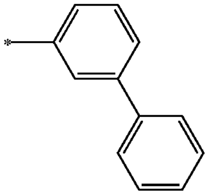
a10
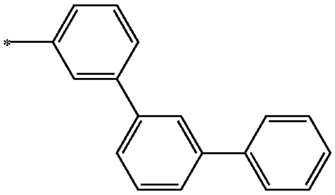
-continued
a11
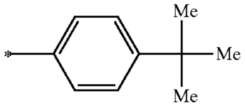
a12
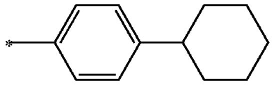
a14
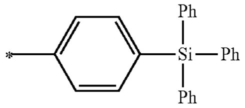
a15
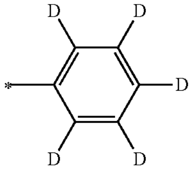
Compound Group B
b1
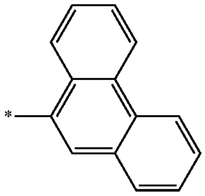
b2
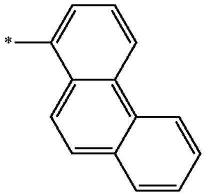
b3
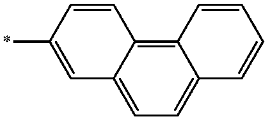
b4
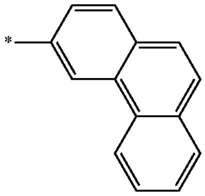
b5
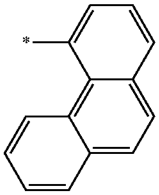

-continued
b6
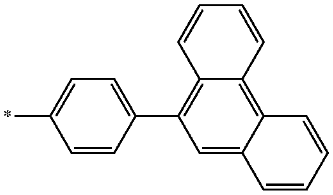
b7
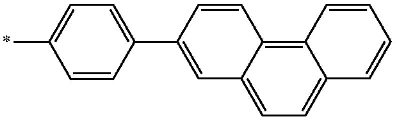
b8
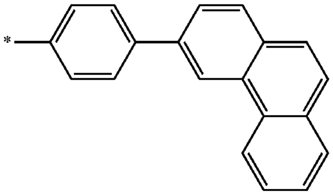
Compound Group C
c1
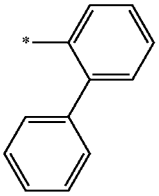
c2
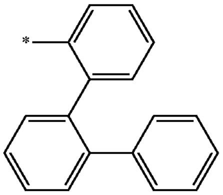
c3
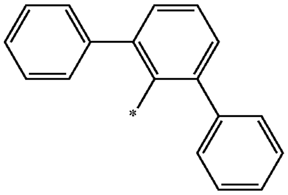
c4
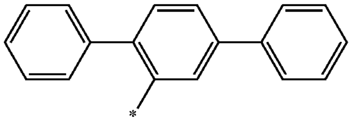
-continued
c5
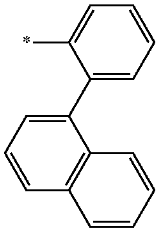
Compound Group D
d1
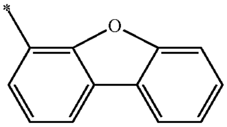
d2
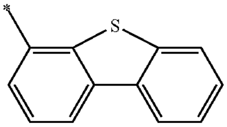
d3
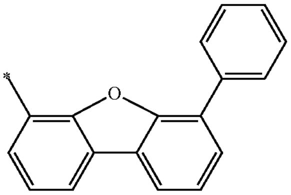
d4
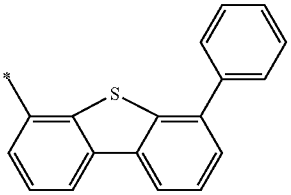
d5
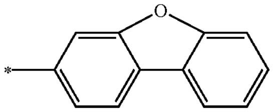
d6
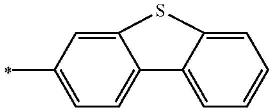
d7
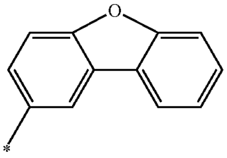

-continued
d8
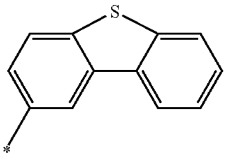
d9
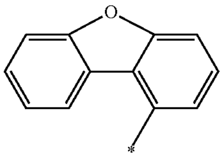
d10
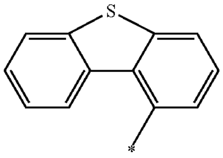
d11
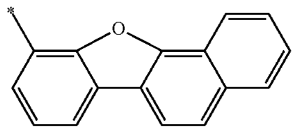
d12
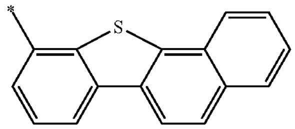
d13
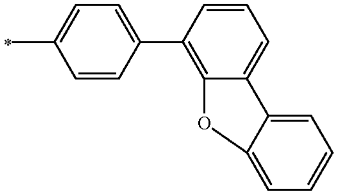
d14
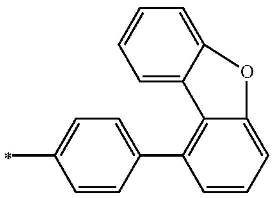
d15
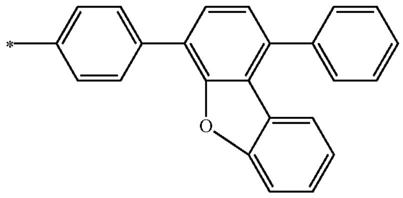
-continued
d16
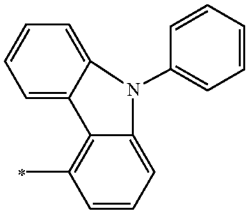
d17
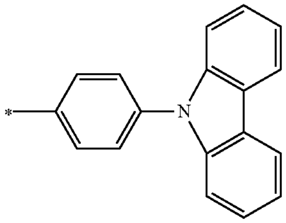
d18
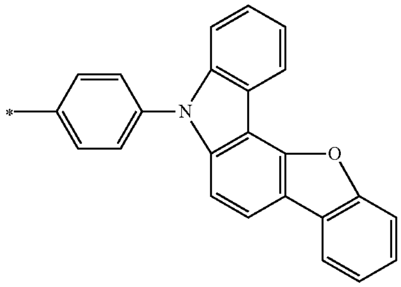
Compound Group E
e1
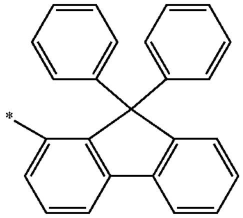
e2
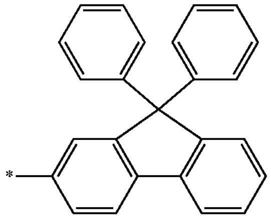
e3
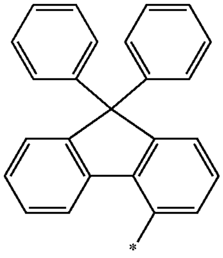

-continued
e4
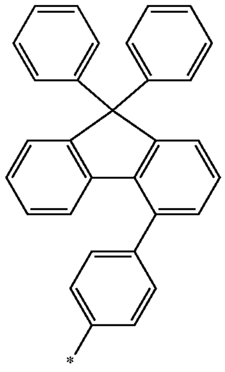
Compound Group F
f1
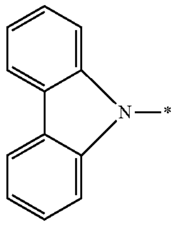
f2
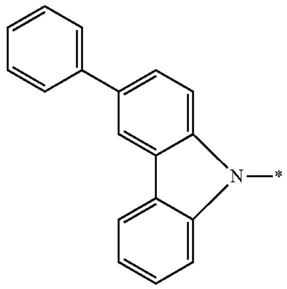
f3
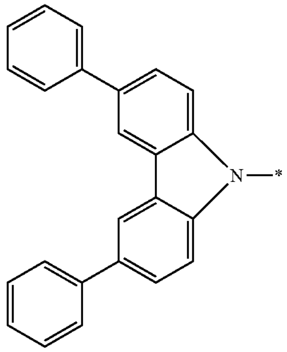
-continued
f4
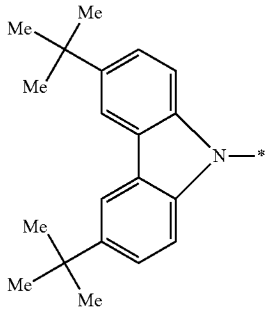
Compound Group G
g1
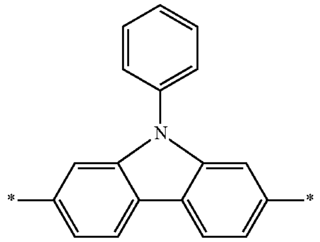
g2
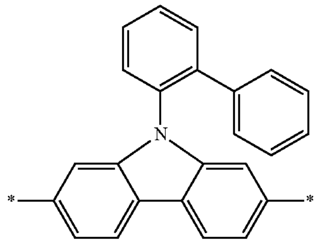
g3
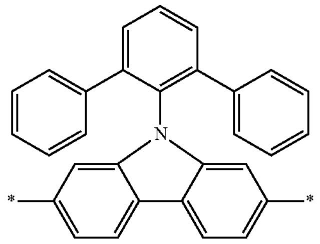
Compound Group H
h1
h2
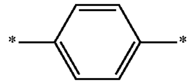
h3
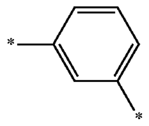

-continued h4

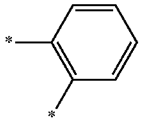

h5

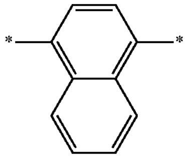

h6

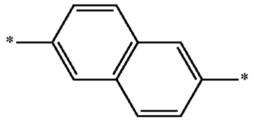

Compound Combination Table 1

| No. | $Cz^b$ | $L^A$ | $Cz^A$ | $L^B$ | $Ar^A$ | $Ar^B$ |
|---|---|---|---|---|---|---|
| 1 | f1 | h2 | g1 | h2 | a1 | a1 |
| 2 | f1 | h2 | g1 | h1 | a1 | a1 |
| 3 | f1 | h3 | g1 | h1 | a1 | a1 |
| 4 | f1 | h4 | g1 | h1 | a1 | a1 |
| 5 | f1 | h5 | g1 | h1 | a1 | a1 |
| 6 | f1 | h6 | g1 | h1 | a1 | a1 |
| 7 | f1 | h1 | g1 | h2 | a1 | a1 |
| 8 | f1 | h1 | g1 | h2 | a1 | a2 |
| 9 | f1 | h1 | g1 | h2 | a1 | a4 |
| 10 | f1 | h1 | g1 | h2 | a1 | a5 |
| 11 | f1 | h1 | g1 | h2 | a1 | a6 |
| 12 | f1 | h1 | g1 | h2 | a1 | a11 |
| 13 | f1 | h1 | g1 | h2 | a1 | a15 |
| 14 | f1 | h1 | g1 | h2 | a1 | b1 |
| 15 | f1 | h1 | g1 | h2 | a1 | b3 |
| 16 | f1 | h1 | g1 | h2 | a1 | b4 |
| 17 | f1 | h1 | g1 | h2 | a1 | b6 |
| 18 | f1 | h1 | g1 | h2 | a1 | c1 |
| 19 | f1 | h1 | g1 | h2 | a1 | d1 |
| 20 | f1 | h1 | g1 | h2 | a1 | d2 |
| 21 | f1 | h1 | g1 | h2 | a1 | d3 |
| 22 | f1 | h1 | g1 | h2 | a1 | d5 |
| 23 | f1 | h1 | g1 | h2 | a1 | d7 |
| 24 | f1 | h1 | g1 | h2 | a1 | d9 |
| 25 | f1 | h1 | g1 | h2 | a1 | d11 |
| 26 | f1 | h1 | g1 | h2 | a1 | d13 |
| 27 | f1 | h1 | g1 | h2 | a1 | d17 |
| 28 | f1 | h1 | g1 | h2 | a1 | e3 |
| 29 | f1 | h1 | g1 | h2 | a2 | a2 |
| 30 | f1 | h1 | g1 | h2 | a2 | a4 |
| 31 | f1 | h1 | g1 | h2 | a2 | a5 |
| 32 | f1 | h1 | g1 | h2 | a2 | a6 |
| 33 | f1 | h1 | g1 | h2 | a2 | a11 |
| 34 | f1 | h1 | g1 | h2 | a2 | a15 |
| 35 | f1 | h1 | g1 | h2 | a2 | b1 |
| 36 | f1 | h1 | g1 | h2 | a2 | b3 |
| 37 | f1 | h1 | g1 | h2 | a2 | b4 |
| 38 | f1 | h1 | g1 | h2 | a2 | b6 |
| 39 | f1 | h1 | g1 | h2 | a2 | c1 |
| 40 | f1 | h1 | g1 | h2 | a2 | d1 |
| 41 | f1 | h1 | g1 | h2 | a2 | d2 |
| 42 | f1 | h1 | g1 | h2 | a2 | d3 |
| 43 | f1 | h1 | g1 | h2 | a2 | d5 |
| 44 | f1 | h1 | g1 | h2 | a2 | d7 |
| 45 | f1 | h1 | g1 | h2 | a2 | d9 |
| 46 | f1 | h1 | g1 | h2 | a2 | d11 |
| 47 | f1 | h1 | g1 | h2 | a2 | d13 |
| 48 | f1 | h1 | g1 | h2 | a2 | d17 |
| 49 | f1 | h1 | g1 | h2 | a2 | e3 |
| 50 | f1 | h1 | g1 | h2 | a4 | a4 |
| 51 | f1 | h1 | g1 | h2 | a4 | a5 |
| 52 | f1 | h1 | g1 | h2 | a4 | a6 |
| 53 | f1 | h1 | g1 | h2 | a4 | a11 |
| 54 | f1 | h1 | g1 | h2 | a4 | a15 |
| 55 | f1 | h1 | g1 | h2 | a4 | b1 |
| 56 | f1 | h1 | g1 | h2 | a4 | b3 |
| 57 | f1 | h1 | g1 | h2 | a4 | b4 |
| 58 | f1 | h1 | g1 | h2 | a4 | b6 |
| 59 | f1 | h1 | g1 | h2 | a4 | c1 |
| 60 | f1 | h1 | g1 | h2 | a4 | d1 |
| 61 | f1 | h1 | g1 | h2 | a4 | d2 |
| 62 | f1 | h1 | g1 | h2 | a4 | d3 |
| 63 | f1 | h1 | g1 | h2 | a4 | d5 |
| 64 | f1 | h1 | g1 | h2 | a4 | d7 |
| 65 | f1 | h1 | g1 | h2 | a4 | d9 |
| 66 | f1 | h1 | g1 | h2 | a4 | d11 |
| 67 | f1 | h1 | g1 | h2 | a4 | d13 |
| 68 | f1 | h1 | g1 | h2 | a4 | d17 |
| 69 | f1 | h1 | g1 | h2 | a4 | e3 |
| 70 | f1 | h1 | g1 | h2 | a5 | a5 |
| 71 | f1 | h1 | g1 | h2 | a5 | a6 |
| 72 | f1 | h1 | g1 | h2 | a5 | a11 |
| 73 | f1 | h1 | g1 | h2 | a5 | a15 |
| 74 | f1 | h1 | g1 | h2 | a5 | b1 |
| 75 | f1 | h1 | g1 | h2 | a5 | b3 |
| 76 | f1 | h1 | g1 | h2 | a5 | b4 |
| 77 | f1 | h1 | g1 | h2 | a5 | b6 |
| 78 | f1 | h1 | g1 | h2 | a5 | c1 |
| 79 | f1 | h1 | g1 | h2 | a5 | d1 |
| 80 | f1 | h1 | g1 | h2 | a5 | d2 |
| 81 | f1 | h1 | g1 | h2 | a5 | d3 |
| 82 | f1 | h1 | g1 | h2 | a5 | d5 |
| 83 | f1 | h1 | g1 | h2 | a5 | d7 |
| 84 | f1 | h1 | g1 | h2 | a5 | d9 |
| 85 | f1 | h1 | g1 | h2 | a5 | d11 |
| 86 | f1 | h1 | g1 | h2 | a5 | d13 |
| 87 | f1 | h1 | g1 | h2 | a5 | d17 |
| 88 | f1 | h1 | g1 | h2 | a5 | e3 |
| 89 | f1 | h1 | g1 | h2 | a6 | a6 |
| 90 | f1 | h1 | g1 | h2 | a6 | a11 |
| 91 | f1 | h1 | g1 | h2 | a6 | a15 |
| 92 | f1 | h1 | g1 | h2 | a6 | b1 |
| 93 | f1 | h1 | g1 | h2 | a6 | b3 |
| 94 | f1 | h1 | g1 | h2 | a6 | b4 |
| 95 | f1 | h1 | g1 | h2 | a6 | b6 |
| 96 | f1 | h1 | g1 | h2 | a6 | c1 |
| 97 | f1 | h1 | g1 | h2 | a6 | d1 |
| 98 | f1 | h1 | g1 | h2 | a6 | d2 |
| 99 | f1 | h1 | g1 | h2 | a6 | d3 |
| 100 | f1 | h1 | g1 | h2 | a6 | d5 |
| 101 | f1 | h1 | g1 | h2 | a6 | d7 |
| 102 | f1 | h1 | g1 | h2 | a6 | d9 |
| 103 | f1 | h1 | g1 | h2 | a6 | d11 |
| 104 | f1 | h1 | g1 | h2 | a6 | d13 |
| 105 | f1 | h1 | g1 | h2 | a6 | d17 |
| 106 | f1 | h1 | g1 | h2 | a6 | e3 |
| 107 | f1 | h1 | g1 | h2 | a11 | a11 |
| 108 | f1 | h1 | g1 | h2 | a11 | a15 |
| 109 | f1 | h1 | g1 | h2 | a11 | b1 |
| 110 | f1 | h1 | g1 | h2 | a11 | b3 |
| 111 | f1 | h1 | g1 | h2 | a11 | b4 |
| 112 | f1 | h1 | g1 | h2 | a11 | b6 |
| 113 | f1 | h1 | g1 | h2 | a11 | c1 |
| 114 | f1 | h1 | g1 | h2 | a11 | d1 |
| 115 | f1 | h1 | g1 | h2 | a11 | d2 |
| 116 | f1 | h1 | g1 | h2 | a11 | d3 |
| 117 | f1 | h1 | g1 | h2 | a11 | d5 |
| 118 | f1 | h1 | g1 | h2 | a11 | d7 |
| 119 | f1 | h1 | g1 | h2 | a11 | d9 |
| 120 | f1 | h1 | g1 | h2 | a11 | d11 |
| 121 | f1 | h1 | g1 | h2 | a11 | d13 |
| 122 | f1 | h1 | g1 | h2 | a11 | d17 |
| 123 | f1 | h1 | g1 | h2 | a11 | e3 |
| 124 | f1 | h1 | g1 | h2 | a15 | a15 |
| 125 | f1 | h1 | g1 | h2 | a15 | b1 |
| 126 | f1 | h1 | g1 | h2 | a15 | b3 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 127 | f1 | h1 | g1 | h2 | a15 | b4 |
| 128 | f1 | h1 | g1 | h2 | a15 | b6 |
| 129 | f1 | h1 | g1 | h2 | a15 | c1 |
| 130 | f1 | h1 | g1 | h2 | a15 | d1 |
| 131 | f1 | h1 | g1 | h2 | a15 | d2 |
| 132 | f1 | h1 | g1 | h2 | a15 | d3 |
| 133 | f1 | h1 | g1 | h2 | a15 | d5 |
| 134 | f1 | h1 | g1 | h2 | a15 | d7 |
| 135 | f1 | h1 | g1 | h2 | a15 | d9 |
| 136 | f1 | h1 | g1 | h2 | a15 | d11 |
| 137 | f1 | h1 | g1 | h2 | a15 | d13 |
| 138 | f1 | h1 | g1 | h2 | a15 | d17 |
| 139 | f1 | h1 | g1 | h2 | a15 | e3 |
| 140 | f1 | h1 | g1 | h2 | b1 | b1 |
| 141 | f1 | h1 | g1 | h2 | b1 | b3 |
| 142 | f1 | h1 | g1 | h2 | b1 | b4 |
| 143 | f1 | h1 | g1 | h2 | b1 | b6 |
| 144 | f1 | h1 | g1 | h2 | b1 | c1 |
| 145 | f1 | h1 | g1 | h2 | b1 | d1 |
| 146 | f1 | h1 | g1 | h2 | b1 | d2 |
| 147 | f1 | h1 | g1 | h2 | b1 | d3 |
| 148 | f1 | h1 | g1 | h2 | b1 | d5 |
| 149 | f1 | h1 | g1 | h2 | b1 | d7 |
| 150 | f1 | h1 | g1 | h2 | b1 | d9 |
| 151 | f1 | h1 | g1 | h2 | b1 | d11 |
| 152 | f1 | h1 | g1 | h2 | b1 | d13 |
| 153 | f1 | h1 | g1 | h2 | b1 | d17 |
| 154 | f1 | h1 | g1 | h2 | b1 | e3 |
| 155 | f1 | h1 | g1 | h2 | b3 | b3 |
| 156 | f1 | h1 | g1 | h2 | b3 | b4 |
| 157 | f1 | h1 | g1 | h2 | b3 | b6 |
| 158 | f1 | h1 | g1 | h2 | b3 | c1 |
| 159 | f1 | h1 | g1 | h2 | b3 | d1 |
| 160 | f1 | h1 | g1 | h2 | b3 | d2 |
| 161 | f1 | h1 | g1 | h2 | b3 | d3 |
| 162 | f1 | h1 | g1 | h2 | b3 | d5 |
| 163 | f1 | h1 | g1 | h2 | b3 | d7 |
| 164 | f1 | h1 | g1 | h2 | b3 | d9 |
| 165 | f1 | h1 | g1 | h2 | b3 | d11 |
| 166 | f1 | h1 | g1 | h2 | b3 | d13 |
| 167 | f1 | h1 | g1 | h2 | b3 | d17 |
| 168 | f1 | h1 | g1 | h2 | b3 | e3 |
| 169 | f1 | h1 | g1 | h2 | b4 | b4 |
| 170 | f1 | h1 | g1 | h2 | b4 | b6 |
| 171 | f1 | h1 | g1 | h2 | b4 | c1 |
| 172 | f1 | h1 | g1 | h2 | b4 | d1 |
| 173 | f1 | h1 | g1 | h2 | b4 | d2 |
| 174 | f1 | h1 | g1 | h2 | b4 | d3 |
| 175 | f1 | h1 | g1 | h2 | b4 | d5 |
| 176 | f1 | h1 | g1 | h2 | b4 | d7 |
| 177 | f1 | h1 | g1 | h2 | b4 | d9 |
| 178 | f1 | h1 | g1 | h2 | b4 | d11 |
| 179 | f1 | h1 | g1 | h2 | b4 | d13 |
| 180 | f1 | h1 | g1 | h2 | b4 | d17 |
| 181 | f1 | h1 | g1 | h2 | b4 | e3 |
| 182 | f1 | h1 | g1 | h2 | b6 | b6 |
| 183 | f1 | h1 | g1 | h2 | b6 | c1 |
| 184 | f1 | h1 | g1 | h2 | b6 | d1 |
| 185 | f1 | h1 | g1 | h2 | b6 | d2 |
| 186 | f1 | h1 | g1 | h2 | b6 | d3 |
| 187 | f1 | h1 | g1 | h2 | b6 | d5 |
| 188 | f1 | h1 | g1 | h2 | b6 | d7 |
| 189 | f1 | h1 | g1 | h2 | b6 | d9 |
| 190 | f1 | h1 | g1 | h2 | b6 | d11 |
| 191 | f1 | h1 | g1 | h2 | b6 | d13 |
| 192 | f1 | h1 | g1 | h2 | b6 | d17 |
| 193 | f1 | h1 | g1 | h2 | b6 | e3 |
| 194 | f1 | h1 | g1 | h2 | c1 | c1 |
| 195 | f1 | h1 | g1 | h2 | c1 | d1 |
| 196 | f1 | h1 | g1 | h2 | c1 | d2 |
| 197 | f1 | h1 | g1 | h2 | c1 | d3 |
| 198 | f1 | h1 | g1 | h2 | c1 | d5 |
| 199 | f1 | h1 | g1 | h2 | c1 | d7 |
| 200 | f1 | h1 | g1 | h2 | c1 | d9 |
| 201 | f1 | h1 | g1 | h2 | c1 | d11 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 202 | f1 | h1 | g1 | h2 | c1 | d13 |
| 203 | f1 | h1 | g1 | h2 | c1 | d17 |
| 204 | f1 | h1 | g1 | h2 | c1 | e3 |
| 205 | f1 | h1 | g1 | h2 | d1 | d1 |
| 206 | f1 | h1 | g1 | h2 | d1 | d2 |
| 207 | f1 | h1 | g1 | h2 | d1 | d3 |
| 208 | f1 | h1 | g1 | h2 | d1 | d5 |
| 209 | f1 | h1 | g1 | h2 | d1 | d7 |
| 210 | f1 | h1 | g1 | h2 | d1 | d9 |
| 211 | f1 | h1 | g1 | h2 | d1 | d11 |
| 212 | f1 | h1 | g1 | h2 | d1 | d13 |
| 213 | f1 | h1 | g1 | h2 | d1 | d17 |
| 214 | f1 | h1 | g1 | h2 | d1 | e3 |
| 215 | f1 | h1 | g1 | h2 | d2 | d2 |
| 216 | f1 | h1 | g1 | h2 | d2 | d3 |
| 217 | f1 | h1 | g1 | h2 | d2 | d5 |
| 218 | f1 | h1 | g1 | h2 | d2 | d7 |
| 219 | f1 | h1 | g1 | h2 | d2 | d9 |
| 220 | f1 | h1 | g1 | h2 | d2 | d11 |
| 221 | f1 | h1 | g1 | h2 | d2 | d13 |
| 222 | f1 | h1 | g1 | h2 | d2 | d17 |
| 223 | f1 | h1 | g1 | h2 | d2 | e3 |
| 224 | f1 | h1 | g1 | h2 | d3 | d3 |
| 225 | f1 | h1 | g1 | h2 | d3 | d5 |
| 226 | f1 | h1 | g1 | h2 | d3 | d7 |
| 227 | f1 | h1 | g1 | h2 | d3 | d9 |
| 228 | f1 | h1 | g1 | h2 | d3 | d11 |
| 229 | f1 | h1 | g1 | h2 | d3 | d13 |
| 230 | f1 | h1 | g1 | h2 | d3 | d17 |
| 231 | f1 | h1 | g1 | h2 | d3 | e3 |
| 232 | f1 | h1 | g1 | h2 | d5 | d5 |
| 233 | f1 | h1 | g1 | h2 | d5 | d7 |
| 234 | f1 | h1 | g1 | h2 | d5 | d9 |
| 235 | f1 | h1 | g1 | h2 | d5 | d11 |
| 236 | f1 | h1 | g1 | h2 | d5 | d13 |
| 237 | f1 | h1 | g1 | h2 | d5 | d17 |
| 238 | f1 | h1 | g1 | h2 | d5 | e3 |
| 239 | f1 | h1 | g1 | h2 | d7 | d7 |
| 240 | f1 | h1 | g1 | h2 | d7 | d9 |
| 241 | f1 | h1 | g1 | h2 | d7 | d11 |
| 242 | f1 | h1 | g1 | h2 | d7 | d13 |
| 243 | f1 | h1 | g1 | h2 | d7 | d17 |
| 244 | f1 | h1 | g1 | h2 | d7 | e3 |
| 245 | f1 | h1 | g1 | h2 | d9 | d9 |
| 246 | f1 | h1 | g1 | h2 | d9 | d11 |
| 247 | f1 | h1 | g1 | h2 | d9 | d13 |
| 248 | f1 | h1 | g1 | h2 | d9 | d17 |
| 249 | f1 | h1 | g1 | h2 | d9 | e3 |
| 250 | f1 | h1 | g1 | h2 | d11 | d11 |
| 251 | f1 | h1 | g1 | h2 | d11 | d13 |
| 252 | f1 | h1 | g1 | h2 | d11 | d17 |
| 253 | f1 | h1 | g1 | h2 | d11 | e3 |
| 254 | f1 | h1 | g1 | h2 | d13 | d13 |
| 255 | f1 | h1 | g1 | h2 | d13 | d17 |
| 256 | f1 | h1 | g1 | h2 | d13 | e3 |
| 257 | f1 | h1 | g1 | h2 | d17 | d17 |
| 258 | f1 | h1 | g1 | h2 | e3 | e3 |
| 259 | f2 | h1 | g1 | h1 | a1 | a1 |
| 260 | f2 | h1 | g1 | h1 | a1 | a2 |
| 261 | f2 | h1 | g1 | h1 | a1 | a4 |
| 262 | f2 | h1 | g1 | h1 | a1 | a5 |
| 263 | f2 | h1 | g1 | h1 | a1 | a6 |
| 264 | f2 | h1 | g1 | h1 | a1 | a11 |
| 265 | f2 | h1 | g1 | h1 | a1 | a15 |
| 266 | f2 | h1 | g1 | h1 | a1 | b1 |
| 267 | f2 | h1 | g1 | h1 | a1 | b3 |
| 268 | f2 | h1 | g1 | h1 | a1 | b4 |
| 269 | f2 | h1 | g1 | h1 | a1 | b6 |
| 270 | f2 | h1 | g1 | h1 | a1 | c1 |
| 271 | f2 | h1 | g1 | h1 | a1 | d1 |
| 272 | f2 | h1 | g1 | h1 | a1 | d2 |
| 273 | f2 | h1 | g1 | h1 | a1 | d3 |
| 274 | f2 | h1 | g1 | h1 | a1 | d5 |
| 275 | f2 | h1 | g1 | h1 | a1 | d7 |
| 276 | f2 | h1 | g1 | h1 | a1 | d9 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 277 | f2 | h1 | g1 | h1 | a1 | d11 |
| 278 | f2 | h1 | g1 | h1 | a1 | d13 |
| 279 | f2 | h1 | g1 | h1 | a1 | d17 |
| 280 | f2 | h1 | g1 | h1 | a1 | e3 |
| 281 | f2 | h1 | g1 | h1 | a2 | a2 |
| 282 | f2 | h1 | g1 | h1 | a2 | a4 |
| 283 | f2 | h1 | g1 | h1 | a2 | a5 |
| 284 | f2 | h1 | g1 | h1 | a2 | a6 |
| 285 | f2 | h1 | g1 | h1 | a2 | a11 |
| 286 | f2 | h1 | g1 | h1 | a2 | a15 |
| 287 | f2 | h1 | g1 | h1 | a2 | b1 |
| 288 | f2 | h1 | g1 | h1 | a2 | b3 |
| 289 | f2 | h1 | g1 | h1 | a2 | b4 |
| 290 | f2 | h1 | g1 | h1 | a2 | b6 |
| 291 | f2 | h1 | g1 | h1 | a2 | c1 |
| 292 | f2 | h1 | g1 | h1 | a2 | d1 |
| 293 | f2 | h1 | g1 | h1 | a2 | d2 |
| 294 | f2 | h1 | g1 | h1 | a2 | d3 |
| 295 | f2 | h1 | g1 | h1 | a2 | d5 |
| 296 | f2 | h1 | g1 | h1 | a2 | d7 |
| 297 | f2 | h1 | g1 | h1 | a2 | d9 |
| 298 | f2 | h1 | g1 | h1 | a2 | d11 |
| 299 | f2 | h1 | g1 | h1 | a2 | d13 |
| 300 | f2 | h1 | g1 | h1 | a2 | d17 |
| 301 | f2 | h1 | g1 | h1 | a2 | e3 |
| 302 | f2 | h1 | g1 | h1 | a4 | a4 |
| 303 | f2 | h1 | g1 | h1 | a4 | a5 |
| 304 | f2 | h1 | g1 | h1 | a4 | a6 |
| 305 | f2 | h1 | g1 | h1 | a4 | a11 |
| 306 | f2 | h1 | g1 | h1 | a4 | a15 |
| 307 | f2 | h1 | g1 | h1 | a4 | b1 |
| 308 | f2 | h1 | g1 | h1 | a4 | b3 |
| 309 | f2 | h1 | g1 | h1 | a4 | b4 |
| 310 | f2 | h1 | g1 | h1 | a4 | b6 |
| 311 | f2 | h1 | g1 | h1 | a4 | c1 |
| 312 | f2 | h1 | g1 | h1 | a4 | d1 |
| 313 | f2 | h1 | g1 | h1 | a4 | d2 |
| 314 | f2 | h1 | g1 | h1 | a4 | d3 |
| 315 | f2 | h1 | g1 | h1 | a4 | d5 |
| 316 | f2 | h1 | g1 | h1 | a4 | d7 |
| 317 | f2 | h1 | g1 | h1 | a4 | d9 |
| 318 | f2 | h1 | g1 | h1 | a4 | d11 |
| 319 | f2 | h1 | g1 | h1 | a4 | d13 |
| 320 | f2 | h1 | g1 | h1 | a4 | d17 |
| 321 | f2 | h1 | g1 | h1 | a4 | e3 |
| 322 | f2 | h1 | g1 | h1 | a5 | a5 |
| 323 | f2 | h1 | g1 | h1 | a5 | a6 |
| 324 | f2 | h1 | g1 | h1 | a5 | a11 |
| 325 | f2 | h1 | g1 | h1 | a5 | a15 |
| 326 | f2 | h1 | g1 | h1 | a5 | b1 |
| 327 | f2 | h1 | g1 | h1 | a5 | b3 |
| 328 | f2 | h1 | g1 | h1 | a5 | b4 |
| 329 | f2 | h1 | g1 | h1 | a5 | b6 |
| 330 | f2 | h1 | g1 | h1 | a5 | c1 |
| 331 | f2 | h1 | g1 | h1 | a5 | d1 |
| 332 | f2 | h1 | g1 | h1 | a5 | d2 |
| 333 | f2 | h1 | g1 | h1 | a5 | d3 |
| 334 | f2 | h1 | g1 | h1 | a5 | d5 |
| 335 | f2 | h1 | g1 | h1 | a5 | d7 |
| 336 | f2 | h1 | g1 | h1 | a5 | d9 |
| 337 | f2 | h1 | g1 | h1 | a5 | d11 |
| 338 | f2 | h1 | g1 | h1 | a5 | d13 |
| 339 | f2 | h1 | g1 | h1 | a5 | d17 |
| 340 | f2 | h1 | g1 | h1 | a5 | e3 |
| 341 | f2 | h1 | g1 | h1 | a6 | a6 |
| 342 | f2 | h1 | g1 | h1 | a6 | a11 |
| 343 | f2 | h1 | g1 | h1 | a6 | a15 |
| 344 | f2 | h1 | g1 | h1 | a6 | b1 |
| 345 | f2 | h1 | g1 | h1 | a6 | b3 |
| 346 | f2 | h1 | g1 | h1 | a6 | b4 |
| 347 | f2 | h1 | g1 | h1 | a6 | b6 |
| 348 | f2 | h1 | g1 | h1 | a6 | c1 |
| 349 | f2 | h1 | g1 | h1 | a6 | d1 |
| 350 | f2 | h1 | g1 | h1 | a6 | d2 |
| 351 | f2 | h1 | g1 | h1 | a6 | d3 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 352 | f2 | h1 | g1 | h1 | a6 | d5 |
| 353 | f2 | h1 | g1 | h1 | a6 | d7 |
| 354 | f2 | h1 | g1 | h1 | a6 | d9 |
| 355 | f2 | h1 | g1 | h1 | a6 | d11 |
| 356 | f2 | h1 | g1 | h1 | a6 | d13 |
| 357 | f2 | h1 | g1 | h1 | a6 | d17 |
| 358 | f2 | h1 | g1 | h1 | a6 | e3 |
| 359 | f2 | h1 | g1 | h1 | a11 | a11 |
| 360 | f2 | h1 | g1 | h1 | a11 | a15 |
| 361 | f2 | h1 | g1 | h1 | a11 | b1 |
| 362 | f2 | h1 | g1 | h1 | a11 | b3 |
| 363 | f2 | h1 | g1 | h1 | a11 | b4 |
| 364 | f2 | h1 | g1 | h1 | a11 | b6 |
| 365 | f2 | h1 | g1 | h1 | a11 | c1 |
| 366 | f2 | h1 | g1 | h1 | a11 | d1 |
| 367 | f2 | h1 | g1 | h1 | a11 | d2 |
| 368 | f2 | h1 | g1 | h1 | a11 | d3 |
| 369 | f2 | h1 | g1 | h1 | a11 | d5 |
| 370 | f2 | h1 | g1 | h1 | a11 | d7 |
| 371 | f2 | h1 | g1 | h1 | a11 | d9 |
| 372 | f2 | h1 | g1 | h1 | a11 | d11 |
| 373 | f2 | h1 | g1 | h1 | a11 | d13 |
| 374 | f2 | h1 | g1 | h1 | a11 | d17 |
| 375 | f2 | h1 | g1 | h1 | a11 | e3 |
| 376 | f2 | h1 | g1 | h1 | a15 | a15 |
| 377 | f2 | h1 | g1 | h1 | a15 | b1 |
| 378 | f2 | h1 | g1 | h1 | a15 | b3 |
| 379 | f2 | h1 | g1 | h1 | a15 | b4 |
| 380 | f2 | h1 | g1 | h1 | a15 | b6 |
| 381 | f2 | h1 | g1 | h1 | a15 | c1 |
| 382 | f2 | h1 | g1 | h1 | a15 | d1 |
| 383 | f2 | h1 | g1 | h1 | a15 | d2 |
| 384 | f2 | h1 | g1 | h1 | a15 | d3 |
| 385 | f2 | h1 | g1 | h1 | a15 | d5 |
| 386 | f2 | h1 | g1 | h1 | a15 | d7 |
| 387 | f2 | h1 | g1 | h1 | a15 | d9 |
| 388 | f2 | h1 | g1 | h1 | a15 | d11 |
| 389 | f2 | h1 | g1 | h1 | a15 | d13 |
| 390 | f2 | h1 | g1 | h1 | a15 | d17 |
| 391 | f2 | h1 | g1 | h1 | a15 | e3 |
| 392 | f2 | h1 | g1 | h1 | b1 | b1 |
| 393 | f2 | h1 | g1 | h1 | b1 | b3 |
| 394 | f2 | h1 | g1 | h1 | b1 | b4 |
| 395 | f2 | h1 | g1 | h1 | b1 | b6 |
| 396 | f2 | h1 | g1 | h1 | b1 | c1 |
| 397 | f2 | h1 | g1 | h1 | b1 | d1 |
| 398 | f2 | h1 | g1 | h1 | b1 | d2 |
| 399 | f2 | h1 | g1 | h1 | b1 | d3 |
| 400 | f2 | h1 | g1 | h1 | b1 | d5 |
| 401 | f2 | h1 | g1 | h1 | b1 | d7 |
| 402 | f2 | h1 | g1 | h1 | b1 | d9 |
| 403 | f2 | h1 | g1 | h1 | b1 | d11 |
| 404 | f2 | h1 | g1 | h1 | b1 | d13 |
| 405 | f2 | h1 | g1 | h1 | b1 | d17 |
| 406 | f2 | h1 | g1 | h1 | b1 | e3 |
| 407 | f2 | h1 | g1 | h1 | b3 | b3 |
| 408 | f2 | h1 | g1 | h1 | b3 | b4 |
| 409 | f2 | h1 | g1 | h1 | b3 | b6 |
| 410 | f2 | h1 | g1 | h1 | b3 | c1 |
| 411 | f2 | h1 | g1 | h1 | b3 | d1 |
| 412 | f2 | h1 | g1 | h1 | b3 | d2 |
| 413 | f2 | h1 | g1 | h1 | b3 | d3 |
| 414 | f2 | h1 | g1 | h1 | b3 | d5 |
| 415 | f2 | h1 | g1 | h1 | b3 | d7 |
| 416 | f2 | h1 | g1 | h1 | b3 | d9 |
| 417 | f2 | h1 | g1 | h1 | b3 | d11 |
| 418 | f2 | h1 | g1 | h1 | b3 | d13 |
| 419 | f2 | h1 | g1 | h1 | b3 | d17 |
| 420 | f2 | h1 | g1 | h1 | b3 | e3 |
| 421 | f2 | h1 | g1 | h1 | b4 | b4 |
| 422 | f2 | h1 | g1 | h1 | b4 | b6 |
| 423 | f2 | h1 | g1 | h1 | b4 | c1 |
| 424 | f2 | h1 | g1 | h1 | b4 | d1 |
| 425 | f2 | h1 | g1 | h1 | b4 | d2 |
| 426 | f2 | h1 | g1 | h1 | b4 | d3 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 427 | f2 | h1 | g1 | h1 | b4 | d5 |
| 428 | f2 | h1 | g1 | h1 | b4 | d7 |
| 429 | f2 | h1 | g1 | h1 | b4 | d9 |
| 430 | f2 | h1 | g1 | h1 | b4 | d11 |
| 431 | f2 | h1 | g1 | h1 | b4 | d13 |
| 432 | f2 | h1 | g1 | h1 | b4 | d17 |
| 433 | f2 | h1 | g1 | h1 | b4 | e3 |
| 434 | f2 | h1 | g1 | h1 | b6 | b6 |
| 435 | f2 | h1 | g1 | h1 | b6 | c1 |
| 436 | f2 | h1 | g1 | h1 | b6 | d1 |
| 437 | f2 | h1 | g1 | h1 | b6 | d2 |
| 438 | f2 | h1 | g1 | h1 | b6 | d3 |
| 439 | f2 | h1 | g1 | h1 | b6 | d5 |
| 440 | f2 | h1 | g1 | h1 | b6 | d7 |
| 441 | f2 | h1 | g1 | h1 | b6 | d9 |
| 442 | f2 | h1 | g1 | h1 | b6 | d11 |
| 443 | f2 | h1 | g1 | h1 | b6 | d13 |
| 444 | f2 | h1 | g1 | h1 | b6 | d17 |
| 445 | f2 | h1 | g1 | h1 | b6 | e3 |
| 446 | f2 | h1 | g1 | h1 | c1 | c1 |
| 447 | f2 | h1 | g1 | h1 | c1 | d1 |
| 448 | f2 | h1 | g1 | h1 | c1 | d2 |
| 449 | f2 | h1 | g1 | h1 | c1 | d3 |
| 450 | f2 | h1 | g1 | h1 | c1 | d5 |
| 451 | f2 | h1 | g1 | h1 | c1 | d7 |
| 452 | f2 | h1 | g1 | h1 | c1 | d9 |
| 453 | f2 | h1 | g1 | h1 | c1 | d11 |
| 454 | f2 | h1 | g1 | h1 | c1 | d13 |
| 455 | f2 | h1 | g1 | h1 | c1 | d17 |
| 456 | f2 | h1 | g1 | h1 | c1 | e3 |
| 457 | f2 | h1 | g1 | h1 | d1 | d1 |
| 458 | f2 | h1 | g1 | h1 | d1 | d2 |
| 459 | f2 | h1 | g1 | h1 | d1 | d3 |
| 460 | f2 | h1 | g1 | h1 | d1 | d5 |
| 461 | f2 | h1 | g1 | h1 | d1 | d7 |
| 462 | f2 | h1 | g1 | h1 | d1 | d9 |
| 463 | f2 | h1 | g1 | h1 | d1 | d11 |
| 464 | f2 | h1 | g1 | h1 | d1 | d13 |
| 465 | f2 | h1 | g1 | h1 | d1 | d17 |
| 466 | f2 | h1 | g1 | h1 | d1 | e3 |
| 467 | f2 | h1 | g1 | h1 | d2 | d2 |
| 468 | f2 | h1 | g1 | h1 | d2 | d3 |
| 469 | f2 | h1 | g1 | h1 | d2 | d5 |
| 470 | f2 | h1 | g1 | h1 | d2 | d7 |
| 471 | f2 | h1 | g1 | h1 | d2 | d9 |
| 472 | f2 | h1 | g1 | h1 | d2 | d11 |
| 473 | f2 | h1 | g1 | h1 | d2 | d13 |
| 474 | f2 | h1 | g1 | h1 | d2 | d17 |
| 475 | f2 | h1 | g1 | h1 | d2 | e3 |
| 476 | f2 | h1 | g1 | h1 | d3 | d3 |
| 477 | f2 | h1 | g1 | h1 | d3 | d5 |
| 478 | f2 | h1 | g1 | h1 | d3 | d7 |
| 479 | f2 | h1 | g1 | h1 | d3 | d9 |
| 480 | f2 | h1 | g1 | h1 | d3 | d11 |
| 481 | f2 | h1 | g1 | h1 | d3 | d13 |
| 482 | f2 | h1 | g1 | h1 | d3 | d17 |
| 483 | f2 | h1 | g1 | h1 | d3 | e3 |
| 484 | f2 | h1 | g1 | h1 | d5 | d5 |
| 485 | f2 | h1 | g1 | h1 | d5 | d7 |
| 486 | f2 | h1 | g1 | h1 | d5 | d9 |
| 487 | f2 | h1 | g1 | h1 | d5 | d11 |
| 488 | f2 | h1 | g1 | h1 | d5 | d13 |
| 489 | f2 | h1 | g1 | h1 | d5 | d17 |
| 490 | f2 | h1 | g1 | h1 | d5 | e3 |
| 491 | f2 | h1 | g1 | h1 | d7 | d7 |
| 492 | f2 | h1 | g1 | h1 | d7 | d9 |
| 493 | f2 | h1 | g1 | h1 | d7 | d11 |
| 494 | f2 | h1 | g1 | h1 | d7 | d13 |
| 495 | f2 | h1 | g1 | h1 | d7 | d17 |
| 496 | f2 | h1 | g1 | h1 | d7 | e3 |
| 497 | f2 | h1 | g1 | h1 | d9 | d9 |
| 498 | f2 | h1 | g1 | h1 | d9 | d11 |
| 499 | f2 | h1 | g1 | h1 | d9 | d13 |
| 500 | f2 | h1 | g1 | h1 | d9 | d17 |
| 501 | f2 | h1 | g1 | h1 | d9 | e3 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 502 | f2 | h1 | g1 | h1 | d11 | d11 |
| 503 | f2 | h1 | g1 | h1 | d11 | d13 |
| 504 | f2 | h1 | g1 | h1 | d11 | d17 |
| 505 | f2 | h1 | g1 | h1 | d11 | e3 |
| 506 | f2 | h1 | g1 | h1 | d13 | d13 |
| 507 | f2 | h1 | g1 | h1 | d13 | d17 |
| 508 | f2 | h1 | g1 | h1 | d13 | e3 |
| 509 | f2 | h1 | g1 | h1 | d17 | d17 |
| 510 | f2 | h1 | g1 | h1 | e3 | e3 |
| 511 | f3 | h1 | g1 | h1 | a1 | a1 |
| 512 | f4 | h1 | g1 | h1 | a1 | a1 |
| 513 | f5 | h1 | g1 | h1 | a1 | a1 |
| 514 | f1 | h1 | g1 | h1 | b1 | a1 |
| 515 | f1 | h1 | g1 | h1 | b1 | a2 |
| 516 | f1 | h1 | g1 | h1 | b1 | a3 |
| 517 | f1 | h1 | g1 | h1 | b1 | a4 |
| 518 | f1 | h1 | g1 | h1 | b1 | a5 |
| 519 | f1 | h1 | g1 | h1 | b1 | a6 |
| 520 | f1 | h1 | g1 | h1 | b1 | a7 |
| 521 | f1 | h1 | g1 | h1 | b1 | a8 |
| 522 | f1 | h1 | g1 | h1 | b1 | a9 |
| 523 | f1 | h1 | g1 | h1 | b1 | a10 |
| 524 | f1 | h1 | g1 | h1 | b1 | a11 |
| 525 | f1 | h1 | g1 | h1 | b1 | a12 |
| 526 | f1 | h1 | g1 | h1 | b1 | a13 |
| 527 | f1 | h1 | g1 | h1 | b1 | a14 |
| 528 | f1 | h1 | g1 | h1 | b1 | a15 |
| 529 | f1 | h1 | g1 | h1 | b1 | b1 |
| 530 | f1 | h1 | g1 | h1 | b1 | b2 |
| 531 | f1 | h1 | g1 | h1 | b1 | b3 |
| 532 | f1 | h1 | g1 | h1 | b1 | b4 |
| 533 | f1 | h1 | g1 | h1 | b1 | b5 |
| 534 | f1 | h1 | g1 | h1 | b1 | b6 |
| 535 | f1 | h1 | g1 | h1 | b1 | b7 |
| 536 | f1 | h1 | g1 | h1 | b1 | b8 |
| 537 | f1 | h1 | g1 | h1 | b1 | c1 |
| 538 | f1 | h1 | g1 | h1 | b1 | c2 |
| 539 | f1 | h1 | g1 | h1 | b1 | c3 |
| 540 | f1 | h1 | g1 | h1 | b1 | c4 |
| 541 | f1 | h1 | g1 | h1 | b1 | c6 |
| 542 | f1 | h1 | g1 | h1 | b1 | d1 |
| 543 | f1 | h1 | g1 | h1 | b1 | d2 |
| 544 | f1 | h1 | g1 | h1 | b1 | d3 |
| 545 | f1 | h1 | g1 | h1 | b1 | d4 |
| 546 | f1 | h1 | g1 | h1 | b1 | d5 |
| 547 | f1 | h1 | g1 | h1 | b1 | d6 |
| 548 | f1 | h1 | g1 | h1 | b1 | d7 |
| 549 | f1 | h1 | g1 | h1 | b1 | d8 |
| 550 | f1 | h1 | g1 | h1 | b1 | d9 |
| 551 | f1 | h1 | g1 | h1 | b1 | d10 |
| 552 | f1 | h1 | g1 | h1 | b1 | d11 |
| 553 | f1 | h1 | g1 | h1 | b1 | d12 |
| 554 | f1 | h1 | g1 | h1 | b1 | d13 |
| 555 | f1 | h1 | g1 | h1 | b1 | d14 |
| 556 | f1 | h1 | g1 | h1 | b1 | d15 |
| 557 | f1 | h1 | g1 | h1 | b1 | d16 |
| 558 | f1 | h1 | g1 | h1 | b1 | d17 |
| 559 | f1 | h1 | g1 | h1 | b1 | d18 |
| 560 | f1 | h1 | g1 | h1 | b1 | e1 |
| 561 | f1 | h1 | g1 | h1 | b1 | e2 |
| 562 | f1 | h1 | g1 | h1 | b1 | e3 |
| 563 | f1 | h1 | g1 | h1 | b1 | e4 |
| 564 | f1 | h1 | g1 | h1 | b2 | a1 |
| 565 | f1 | h1 | g1 | h1 | b2 | a2 |
| 566 | f1 | h1 | g1 | h1 | b2 | a3 |
| 567 | f1 | h1 | g1 | h1 | b2 | a4 |
| 568 | f1 | h1 | g1 | h1 | b2 | a5 |
| 569 | f1 | h1 | g1 | h1 | b2 | a6 |
| 570 | f1 | h1 | g1 | h1 | b2 | a7 |
| 571 | f1 | h1 | g1 | h1 | b2 | a8 |
| 572 | f1 | h1 | g1 | h1 | b2 | a9 |
| 573 | f1 | h1 | g1 | h1 | b2 | a10 |
| 574 | f1 | h1 | g1 | h1 | b2 | a11 |
| 575 | f1 | h1 | g1 | h1 | b2 | a12 |
| 576 | f1 | h1 | g1 | h1 | b2 | a13 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 577 | f1 | h1 | g1 | h1 | b2 | a14 |
| 578 | f1 | h1 | g1 | h1 | b2 | a15 |
| 579 | f1 | h1 | g1 | h1 | b2 | b2 |
| 580 | f1 | h1 | g1 | h1 | b2 | b3 |
| 581 | f1 | h1 | g1 | h1 | b2 | b4 |
| 582 | f1 | h1 | g1 | h1 | b2 | b5 |
| 583 | f1 | h1 | g1 | h1 | b2 | b6 |
| 584 | f1 | h1 | g1 | h1 | b2 | b7 |
| 585 | f1 | h1 | g1 | h1 | b2 | b8 |
| 586 | f1 | h1 | g1 | h1 | b2 | c1 |
| 587 | f1 | h1 | g1 | h1 | b2 | c2 |
| 588 | f1 | h1 | g1 | h1 | b2 | c3 |
| 589 | f1 | h1 | g1 | h1 | b2 | c4 |
| 590 | f1 | h1 | g1 | h1 | b2 | c6 |
| 591 | f1 | h1 | g1 | h1 | b2 | d1 |
| 592 | f1 | h1 | g1 | h1 | b2 | d2 |
| 593 | f1 | h1 | g1 | h1 | b2 | d3 |
| 594 | f1 | h1 | g1 | h1 | b2 | d4 |
| 595 | f1 | h1 | g1 | h1 | b2 | d5 |
| 596 | f1 | h1 | g1 | h1 | b2 | d6 |
| 597 | f1 | h1 | g1 | h1 | b2 | d7 |
| 598 | f1 | h1 | g1 | h1 | b2 | d8 |
| 599 | f1 | h1 | g1 | h1 | b2 | d9 |
| 600 | f1 | h1 | g1 | h1 | b2 | d10 |
| 601 | f1 | h1 | g1 | h1 | b2 | d11 |
| 602 | f1 | h1 | g1 | h1 | b2 | d12 |
| 603 | f1 | h1 | g1 | h1 | b2 | d13 |
| 604 | f1 | h1 | g1 | h1 | b2 | d14 |
| 605 | f1 | h1 | g1 | h1 | b2 | d15 |
| 606 | f1 | h1 | g1 | h1 | b2 | d16 |
| 607 | f1 | h1 | g1 | h1 | b2 | d17 |
| 608 | f1 | h1 | g1 | h1 | b2 | d18 |
| 609 | f1 | h1 | g1 | h1 | b2 | e1 |
| 610 | f1 | h1 | g1 | h1 | b2 | e2 |
| 611 | f1 | h1 | g1 | h1 | b2 | e3 |
| 612 | f1 | h1 | g1 | h1 | b2 | e4 |
| 613 | f1 | h1 | g1 | h1 | b3 | a1 |
| 614 | f1 | h1 | g1 | h1 | b3 | a2 |
| 615 | f1 | h1 | g1 | h1 | b3 | a3 |
| 616 | f1 | h1 | g1 | h1 | b3 | a4 |
| 617 | f1 | h1 | g1 | h1 | b3 | a5 |
| 618 | f1 | h1 | g1 | h1 | b3 | a6 |
| 619 | f1 | h1 | g1 | h1 | b3 | a7 |
| 620 | f1 | h1 | g1 | h1 | b3 | a8 |
| 621 | f1 | h1 | g1 | h1 | b3 | a9 |
| 622 | f1 | h1 | g1 | h1 | b3 | a10 |
| 623 | f1 | h1 | g1 | h1 | b3 | a11 |
| 624 | f1 | h1 | g1 | h1 | b3 | a12 |
| 625 | f1 | h1 | g1 | h1 | b3 | a13 |
| 626 | f1 | h1 | g1 | h1 | b3 | a14 |
| 627 | f1 | h1 | g1 | h1 | b3 | a15 |
| 628 | f1 | h1 | g1 | h1 | b3 | b3 |
| 629 | f1 | h1 | g1 | h1 | b3 | b4 |
| 630 | f1 | h1 | g1 | h1 | b3 | b5 |
| 631 | f1 | h1 | g1 | h1 | b3 | b6 |
| 632 | f1 | h1 | g1 | h1 | b3 | b7 |
| 633 | f1 | h1 | g1 | h1 | b3 | b8 |
| 634 | f1 | h1 | g1 | h1 | b3 | c1 |
| 635 | f1 | h1 | g1 | h1 | b3 | c2 |
| 636 | f1 | h1 | g1 | h1 | b3 | c3 |
| 637 | f1 | h1 | g1 | h1 | b3 | c4 |
| 638 | f1 | h1 | g1 | h1 | b3 | c6 |
| 639 | f1 | h1 | g1 | h1 | b3 | d1 |
| 640 | f1 | h1 | g1 | h1 | b3 | d2 |
| 641 | f1 | h1 | g1 | h1 | b3 | d3 |
| 642 | f1 | h1 | g1 | h1 | b3 | d4 |
| 643 | f1 | h1 | g1 | h1 | b3 | d5 |
| 644 | f1 | h1 | g1 | h1 | b3 | d6 |
| 645 | f1 | h1 | g1 | h1 | b3 | d7 |
| 646 | f1 | h1 | g1 | h1 | b3 | d8 |
| 647 | f1 | h1 | g1 | h1 | b3 | d9 |
| 648 | f1 | h1 | g1 | h1 | b3 | d10 |
| 649 | f1 | h1 | g1 | h1 | b3 | d11 |
| 650 | f1 | h1 | g1 | h1 | b3 | d12 |
| 651 | f1 | h1 | g1 | h1 | b3 | d13 |
| 652 | f1 | h1 | g1 | h1 | b3 | d14 |
| 653 | f1 | h1 | g1 | h1 | b3 | d15 |
| 654 | f1 | h1 | g1 | h1 | b3 | d16 |
| 655 | f1 | h1 | g1 | h1 | b3 | d17 |
| 656 | f1 | h1 | g1 | h1 | b3 | d18 |
| 657 | f1 | h1 | g1 | h1 | b3 | e1 |
| 658 | f1 | h1 | g1 | h1 | b3 | e2 |
| 659 | f1 | h1 | g1 | h1 | b3 | e3 |
| 660 | f1 | h1 | g1 | h1 | b3 | e4 |
| 661 | f1 | h1 | g1 | h1 | b4 | a1 |
| 662 | f1 | h1 | g1 | h1 | b4 | a2 |
| 663 | f1 | h1 | g1 | h1 | b4 | a3 |
| 664 | f1 | h1 | g1 | h1 | b4 | a4 |
| 665 | f1 | h1 | g1 | h1 | b4 | a5 |
| 666 | f1 | h1 | g1 | h1 | b4 | a6 |
| 667 | f1 | h1 | g1 | h1 | b4 | a7 |
| 668 | f1 | h1 | g1 | h1 | b4 | a8 |
| 669 | f1 | h1 | g1 | h1 | b4 | a9 |
| 670 | f1 | h1 | g1 | h1 | b4 | a10 |
| 671 | f1 | h1 | g1 | h1 | b4 | a11 |
| 672 | f1 | h1 | g1 | h1 | b4 | a12 |
| 673 | f1 | h1 | g1 | h1 | b4 | a13 |
| 674 | f1 | h1 | g1 | h1 | b4 | a14 |
| 675 | f1 | h1 | g1 | h1 | b4 | a15 |
| 676 | f1 | h1 | g1 | h1 | b4 | b4 |
| 677 | f1 | h1 | g1 | h1 | b4 | b5 |
| 678 | f1 | h1 | g1 | h1 | b4 | b6 |
| 679 | f1 | h1 | g1 | h1 | b4 | b7 |
| 680 | f1 | h1 | g1 | h1 | b4 | b8 |
| 681 | f1 | h1 | g1 | h1 | b4 | c1 |
| 682 | f1 | h1 | g1 | h1 | b4 | c2 |
| 683 | f1 | h1 | g1 | h1 | b4 | c3 |
| 684 | f1 | h1 | g1 | h1 | b4 | c4 |
| 685 | f1 | h1 | g1 | h1 | b4 | c6 |
| 686 | f1 | h1 | g1 | h1 | b4 | d1 |
| 687 | f1 | h1 | g1 | h1 | b4 | d2 |
| 688 | f1 | h1 | g1 | h1 | b4 | d3 |
| 689 | f1 | h1 | g1 | h1 | b4 | d4 |
| 690 | f1 | h1 | g1 | h1 | b4 | d5 |
| 691 | f1 | h1 | g1 | h1 | b4 | d6 |
| 692 | f1 | h1 | g1 | h1 | b4 | d7 |
| 693 | f1 | h1 | g1 | h1 | b4 | d8 |
| 694 | f1 | h1 | g1 | h1 | b4 | d9 |
| 695 | f1 | h1 | g1 | h1 | b4 | d10 |
| 696 | f1 | h1 | g1 | h1 | b4 | d11 |
| 697 | f1 | h1 | g1 | h1 | b4 | d12 |
| 698 | f1 | h1 | g1 | h1 | b4 | d13 |
| 699 | f1 | h1 | g1 | h1 | b4 | d14 |
| 700 | f1 | h1 | g1 | h1 | b4 | d15 |
| 701 | f1 | h1 | g1 | h1 | b4 | d16 |
| 702 | f1 | h1 | g1 | h1 | b4 | d17 |
| 703 | f1 | h1 | g1 | h1 | b4 | d18 |
| 704 | f1 | h1 | g1 | h1 | b4 | e1 |
| 705 | f1 | h1 | g1 | h1 | b4 | e2 |
| 706 | f1 | h1 | g1 | h1 | b4 | e3 |
| 707 | f1 | h1 | g1 | h1 | b4 | e4 |
| 708 | f1 | h1 | g1 | h1 | b5 | a1 |
| 709 | f1 | h1 | g1 | h1 | b5 | a2 |
| 710 | f1 | h1 | g1 | h1 | b5 | a3 |
| 711 | f1 | h1 | g1 | h1 | b5 | a4 |
| 712 | f1 | h1 | g1 | h1 | b5 | a5 |
| 713 | f1 | h1 | g1 | h1 | b5 | a6 |
| 714 | f1 | h1 | g1 | h1 | b5 | a7 |
| 715 | f1 | h1 | g1 | h1 | b5 | a8 |
| 716 | f1 | h1 | g1 | h1 | b5 | a9 |
| 717 | f1 | h1 | g1 | h1 | b5 | a10 |
| 718 | f1 | h1 | g1 | h1 | b5 | a11 |
| 719 | f1 | h1 | g1 | h1 | b5 | a12 |
| 720 | f1 | h1 | g1 | h1 | b5 | a13 |
| 721 | f1 | h1 | g1 | h1 | b5 | a14 |
| 722 | f1 | h1 | g1 | h1 | b5 | a15 |
| 723 | f1 | h1 | g1 | h1 | b5 | b5 |
| 724 | f1 | h1 | g1 | h1 | b5 | b6 |
| 725 | f1 | h1 | g1 | h1 | b5 | b7 |
| 726 | f1 | h1 | g1 | h1 | b5 | b8 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 727 | f1 | h1 | g1 | h1 | b5 | c1 |
| 728 | f1 | h1 | g1 | h1 | b5 | c2 |
| 729 | f1 | h1 | g1 | h1 | b5 | c3 |
| 730 | f1 | h1 | g1 | h1 | b5 | c4 |
| 731 | f1 | h1 | g1 | h1 | b5 | c6 |
| 732 | f1 | h1 | g1 | h1 | b5 | d1 |
| 733 | f1 | h1 | g1 | h1 | b5 | d2 |
| 734 | f1 | h1 | g1 | h1 | b5 | d3 |
| 735 | f1 | h1 | g1 | h1 | b5 | d4 |
| 736 | f1 | h1 | g1 | h1 | b5 | d5 |
| 737 | f1 | h1 | g1 | h1 | b5 | d6 |
| 738 | f1 | h1 | g1 | h1 | b5 | d7 |
| 739 | f1 | h1 | g1 | h1 | b5 | d8 |
| 740 | f1 | h1 | g1 | h1 | b5 | d9 |
| 741 | f1 | h1 | g1 | h1 | b5 | d10 |
| 742 | f1 | h1 | g1 | h1 | b5 | d11 |
| 743 | f1 | h1 | g1 | h1 | b5 | d12 |
| 744 | f1 | h1 | g1 | h1 | b5 | d13 |
| 745 | f1 | h1 | g1 | h1 | b5 | d14 |
| 746 | f1 | h1 | g1 | h1 | b5 | d15 |
| 747 | f1 | h1 | g1 | h1 | b5 | d16 |
| 748 | f1 | h1 | g1 | h1 | b5 | d17 |
| 749 | f1 | h1 | g1 | h1 | b5 | d18 |
| 750 | f1 | h1 | g1 | h1 | b5 | e1 |
| 751 | f1 | h1 | g1 | h1 | b5 | e2 |
| 752 | f1 | h1 | g1 | h1 | b5 | e3 |
| 753 | f1 | h1 | g1 | h1 | b5 | e4 |
| 754 | f1 | h1 | g1 | h1 | b6 | a1 |
| 755 | f1 | h1 | g1 | h1 | b6 | a2 |
| 756 | f1 | h1 | g1 | h1 | b6 | a3 |
| 757 | f1 | h1 | g1 | h1 | b6 | a4 |
| 758 | f1 | h1 | g1 | h1 | b6 | a5 |
| 759 | f1 | h1 | g1 | h1 | b6 | a6 |
| 760 | f1 | h1 | g1 | h1 | b6 | a7 |
| 761 | f1 | h1 | g1 | h1 | b6 | a8 |
| 762 | f1 | h1 | g1 | h1 | b6 | a9 |
| 763 | f1 | h1 | g1 | h1 | b6 | a10 |
| 764 | f1 | h1 | g1 | h1 | b6 | a11 |
| 765 | f1 | h1 | g1 | h1 | b6 | a12 |
| 766 | f1 | h1 | g1 | h1 | b6 | a13 |
| 767 | f1 | h1 | g1 | h1 | b6 | a14 |
| 768 | f1 | h1 | g1 | h1 | b6 | a15 |
| 769 | f1 | h1 | g1 | h1 | b6 | b6 |
| 770 | f1 | h1 | g1 | h1 | b6 | b7 |
| 771 | f1 | h1 | g1 | h1 | b6 | b8 |
| 772 | f1 | h1 | g1 | h1 | b6 | c1 |
| 773 | f1 | h1 | g1 | h1 | b6 | c2 |
| 774 | f1 | h1 | g1 | h1 | b6 | c3 |
| 775 | f1 | h1 | g1 | h1 | b6 | c4 |
| 776 | f1 | h1 | g1 | h1 | b6 | c6 |
| 777 | f1 | h1 | g1 | h1 | b6 | d1 |
| 778 | f1 | h1 | g1 | h1 | b6 | d2 |
| 779 | f1 | h1 | g1 | h1 | b6 | d3 |
| 780 | f1 | h1 | g1 | h1 | b6 | d4 |
| 781 | f1 | h1 | g1 | h1 | b6 | d5 |
| 782 | f1 | h1 | g1 | h1 | b6 | d6 |
| 783 | f1 | h1 | g1 | h1 | b6 | d7 |
| 784 | f1 | h1 | g1 | h1 | b6 | d8 |
| 785 | f1 | h1 | g1 | h1 | b6 | d9 |
| 786 | f1 | h1 | g1 | h1 | b6 | d10 |
| 787 | f1 | h1 | g1 | h1 | b6 | d11 |
| 788 | f1 | h1 | g1 | h1 | b6 | d12 |
| 789 | f1 | h1 | g1 | h1 | b6 | d13 |
| 790 | f1 | h1 | g1 | h1 | b6 | d14 |
| 791 | f1 | h1 | g1 | h1 | b6 | d15 |
| 792 | f1 | h1 | g1 | h1 | b6 | d16 |
| 793 | f1 | h1 | g1 | h1 | b6 | d17 |
| 794 | f1 | h1 | g1 | h1 | b6 | d18 |
| 795 | f1 | h1 | g1 | h1 | b6 | e1 |
| 796 | f1 | h1 | g1 | h1 | b6 | e2 |
| 797 | f1 | h1 | g1 | h1 | b6 | e3 |
| 798 | f1 | h1 | g1 | h1 | b6 | e4 |
| 799 | f1 | h1 | g1 | h1 | b7 | a1 |
| 800 | f1 | h1 | g1 | h1 | b7 | a2 |
| 801 | f1 | h1 | g1 | h1 | b7 | a3 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 802 | f1 | h1 | g1 | h1 | b7 | a4 |
| 803 | f1 | h1 | g1 | h1 | b7 | a5 |
| 804 | f1 | h1 | g1 | h1 | b7 | a6 |
| 805 | f1 | h1 | g1 | h1 | b7 | a7 |
| 806 | f1 | h1 | g1 | h1 | b7 | a8 |
| 807 | f1 | h1 | g1 | h1 | b7 | a9 |
| 808 | f1 | h1 | g1 | h1 | b7 | a10 |
| 809 | f1 | h1 | g1 | h1 | b7 | a11 |
| 810 | f1 | h1 | g1 | h1 | b7 | a12 |
| 811 | f1 | h1 | g1 | h1 | b7 | a13 |
| 812 | f1 | h1 | g1 | h1 | b7 | a14 |
| 813 | f1 | h1 | g1 | h1 | b7 | a15 |
| 814 | f1 | h1 | g1 | h1 | b7 | b7 |
| 815 | f1 | h1 | g1 | h1 | b7 | b8 |
| 816 | f1 | h1 | g1 | h1 | b7 | c1 |
| 817 | f1 | h1 | g1 | h1 | b7 | c2 |
| 818 | f1 | h1 | g1 | h1 | b7 | c3 |
| 819 | f1 | h1 | g1 | h1 | b7 | c4 |
| 820 | f1 | h1 | g1 | h1 | b7 | c6 |
| 821 | f1 | h1 | g1 | h1 | b7 | d1 |
| 822 | f1 | h1 | g1 | h1 | b7 | d2 |
| 823 | f1 | h1 | g1 | h1 | b7 | d3 |
| 824 | f1 | h1 | g1 | h1 | b7 | d4 |
| 825 | f1 | h1 | g1 | h1 | b7 | d5 |
| 826 | f1 | h1 | g1 | h1 | b7 | d6 |
| 827 | f1 | h1 | g1 | h1 | b7 | d7 |
| 828 | f1 | h1 | g1 | h1 | b7 | d8 |
| 829 | f1 | h1 | g1 | h1 | b7 | d9 |
| 830 | f1 | h1 | g1 | h1 | b7 | d10 |
| 831 | f1 | h1 | g1 | h1 | b7 | d11 |
| 832 | f1 | h1 | g1 | h1 | b7 | d12 |
| 833 | f1 | h1 | g1 | h1 | b7 | d13 |
| 834 | f1 | h1 | g1 | h1 | b7 | d14 |
| 835 | f1 | h1 | g1 | h1 | b7 | d15 |
| 836 | f1 | h1 | g1 | h1 | b7 | d16 |
| 837 | f1 | h1 | g1 | h1 | b7 | d17 |
| 838 | f1 | h1 | g1 | h1 | b7 | d18 |
| 839 | f1 | h1 | g1 | h1 | b7 | e1 |
| 840 | f1 | h1 | g1 | h1 | b7 | e2 |
| 841 | f1 | h1 | g1 | h1 | b7 | e3 |
| 842 | f1 | h1 | g1 | h1 | b7 | e4 |
| 843 | f1 | h1 | g1 | h1 | b8 | a1 |
| 844 | f1 | h1 | g1 | h1 | b8 | a2 |
| 845 | f1 | h1 | g1 | h1 | b8 | a3 |
| 846 | f1 | h1 | g1 | h1 | b8 | a4 |
| 847 | f1 | h1 | g1 | h1 | b8 | a5 |
| 848 | f1 | h1 | g1 | h1 | b8 | a6 |
| 849 | f1 | h1 | g1 | h1 | b8 | a7 |
| 850 | f1 | h1 | g1 | h1 | b8 | a8 |
| 851 | f1 | h1 | g1 | h1 | b8 | a9 |
| 852 | f1 | h1 | g1 | h1 | b8 | a10 |
| 853 | f1 | h1 | g1 | h1 | b8 | a11 |
| 854 | f1 | h1 | g1 | h1 | b8 | a12 |
| 855 | f1 | h1 | g1 | h1 | b8 | a13 |
| 856 | f1 | h1 | g1 | h1 | b8 | a14 |
| 857 | f1 | h1 | g1 | h1 | b8 | a15 |
| 858 | f1 | h1 | g1 | h1 | b8 | b8 |
| 859 | f1 | h1 | g1 | h1 | b8 | c1 |
| 860 | f1 | h1 | g1 | h1 | b8 | c2 |
| 861 | f1 | h1 | g1 | h1 | b8 | c3 |
| 862 | f1 | h1 | g1 | h1 | b8 | c4 |
| 863 | f1 | h1 | g1 | h1 | b8 | c6 |
| 864 | f1 | h1 | g1 | h1 | b8 | d1 |
| 865 | f1 | h1 | g1 | h1 | b8 | d2 |
| 866 | f1 | h1 | g1 | h1 | b8 | d3 |
| 867 | f1 | h1 | g1 | h1 | b8 | d4 |
| 868 | f1 | h1 | g1 | h1 | b8 | d5 |
| 869 | f1 | h1 | g1 | h1 | b8 | d6 |
| 870 | f1 | h1 | g1 | h1 | b8 | d7 |
| 871 | f1 | h1 | g1 | h1 | b8 | d8 |
| 872 | f1 | h1 | g1 | h1 | b8 | d9 |
| 873 | f1 | h1 | g1 | h1 | b8 | d10 |
| 874 | f1 | h1 | g1 | h1 | b8 | d11 |
| 875 | f1 | h1 | g1 | h1 | b8 | d12 |
| 876 | f1 | h1 | g1 | h1 | b8 | d13 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 877 | f1 | h1 | g1 | h1 | b8 | d14 |
| 878 | f1 | h1 | g1 | h1 | b8 | d15 |
| 879 | f1 | h1 | g1 | h1 | b8 | d16 |
| 880 | f1 | h1 | g1 | h1 | b8 | d17 |
| 881 | f1 | h1 | g1 | h1 | b8 | d18 |
| 882 | f1 | h1 | g1 | h1 | b8 | e1 |
| 883 | f1 | h1 | g1 | h1 | b8 | e2 |
| 884 | f1 | h1 | g1 | h1 | b8 | e3 |
| 885 | f1 | h1 | g1 | h1 | b8 | e4 |
| 886 | f1 | h1 | g1 | h1 | c1 | a1 |
| 887 | f1 | h1 | g1 | h1 | c1 | a2 |
| 888 | f1 | h1 | g1 | h1 | c1 | a3 |
| 889 | f1 | h1 | g1 | h1 | c1 | a4 |
| 890 | f1 | h1 | g1 | h1 | c1 | a5 |
| 891 | f1 | h1 | g1 | h1 | c1 | a6 |
| 892 | f1 | h1 | g1 | h1 | c1 | a7 |
| 893 | f1 | h1 | g1 | h1 | c1 | a8 |
| 894 | f1 | h1 | g1 | h1 | c1 | a9 |
| 895 | f1 | h1 | g1 | h1 | c1 | a10 |
| 896 | f1 | h1 | g1 | h1 | c1 | a11 |
| 897 | f1 | h1 | g1 | h1 | c1 | a12 |
| 898 | f1 | h1 | g1 | h1 | c1 | a13 |
| 899 | f1 | h1 | g1 | h1 | c1 | a14 |
| 900 | f1 | h1 | g1 | h1 | c1 | a15 |
| 901 | f1 | h1 | g1 | h1 | c1 | b1 |
| 902 | f1 | h1 | g1 | h1 | c1 | b2 |
| 903 | f1 | h1 | g1 | h1 | c1 | b3 |
| 904 | f1 | h1 | g1 | h1 | c1 | b4 |
| 905 | f1 | h1 | g1 | h1 | c1 | b5 |
| 906 | f1 | h1 | g1 | h1 | c1 | b6 |
| 907 | f1 | h1 | g1 | h1 | c1 | b7 |
| 908 | f1 | h1 | g1 | h1 | c1 | b8 |
| 909 | f1 | h1 | g1 | h1 | c1 | c1 |
| 910 | f1 | h1 | g1 | h1 | c1 | d1 |
| 911 | f1 | h1 | g1 | h1 | c1 | d2 |
| 912 | f1 | h1 | g1 | h1 | c1 | d3 |
| 913 | f1 | h1 | g1 | h1 | c1 | d4 |
| 914 | f1 | h1 | g1 | h1 | c1 | d5 |
| 915 | f1 | h1 | g1 | h1 | c1 | d6 |
| 916 | f1 | h1 | g1 | h1 | c1 | d7 |
| 917 | f1 | h1 | g1 | h1 | c1 | d8 |
| 918 | f1 | h1 | g1 | h1 | c1 | d9 |
| 919 | f1 | h1 | g1 | h1 | c1 | d10 |
| 920 | f1 | h1 | g1 | h1 | c1 | d11 |
| 921 | f1 | h1 | g1 | h1 | c1 | d12 |
| 922 | f1 | h1 | g1 | h1 | c1 | d13 |
| 923 | f1 | h1 | g1 | h1 | c1 | d14 |
| 924 | f1 | h1 | g1 | h1 | c1 | d15 |
| 925 | f1 | h1 | g1 | h1 | c1 | d16 |
| 926 | f1 | h1 | g1 | h1 | c1 | d17 |
| 927 | f1 | h1 | g1 | h1 | c1 | d18 |
| 928 | f1 | h1 | g1 | h1 | c1 | e1 |
| 929 | f1 | h1 | g1 | h1 | c1 | e2 |
| 930 | f1 | h1 | g1 | h1 | c1 | e3 |
| 931 | f1 | h1 | g1 | h1 | c1 | e4 |
| 932 | f1 | h1 | g1 | h1 | c2 | a1 |
| 933 | f1 | h1 | g1 | h1 | c2 | a2 |
| 934 | f1 | h1 | g1 | h1 | c2 | a3 |
| 935 | f1 | h1 | g1 | h1 | c2 | a4 |
| 936 | f1 | h1 | g1 | h1 | c2 | a5 |
| 937 | f1 | h1 | g1 | h1 | c2 | a6 |
| 938 | f1 | h1 | g1 | h1 | c2 | a7 |
| 939 | f1 | h1 | g1 | h1 | c2 | a8 |
| 940 | f1 | h1 | g1 | h1 | c2 | a9 |
| 941 | f1 | h1 | g1 | h1 | c2 | a10 |
| 942 | f1 | h1 | g1 | h1 | c2 | a11 |
| 943 | f1 | h1 | g1 | h1 | c2 | a12 |
| 944 | f1 | h1 | g1 | h1 | c2 | a13 |
| 945 | f1 | h1 | g1 | h1 | c2 | a14 |
| 946 | f1 | h1 | g1 | h1 | c2 | a15 |
| 947 | f1 | h1 | g1 | h1 | c2 | b1 |
| 948 | f1 | h1 | g1 | h1 | c2 | b2 |
| 949 | f1 | h1 | g1 | h1 | c2 | b3 |
| 950 | f1 | h1 | g1 | h1 | c2 | b4 |
| 951 | f1 | h1 | g1 | h1 | c2 | b5 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 952 | f1 | h1 | g1 | h1 | c2 | b6 |
| 953 | f1 | h1 | g1 | h1 | c2 | b7 |
| 954 | f1 | h1 | g1 | h1 | c2 | b8 |
| 955 | f1 | h1 | g1 | h1 | c2 | c1 |
| 956 | f1 | h1 | g1 | h1 | c2 | d1 |
| 957 | f1 | h1 | g1 | h1 | c2 | d2 |
| 958 | f1 | h1 | g1 | h1 | c2 | d3 |
| 959 | f1 | h1 | g1 | h1 | c2 | d4 |
| 960 | f1 | h1 | g1 | h1 | c2 | d5 |
| 961 | f1 | h1 | g1 | h1 | c2 | d6 |
| 962 | f1 | h1 | g1 | h1 | c2 | d7 |
| 963 | f1 | h1 | g1 | h1 | c2 | d8 |
| 964 | f1 | h1 | g1 | h1 | c2 | d9 |
| 965 | f1 | h1 | g1 | h1 | c2 | d10 |
| 966 | f1 | h1 | g1 | h1 | c2 | d11 |
| 967 | f1 | h1 | g1 | h1 | c2 | d12 |
| 968 | f1 | h1 | g1 | h1 | c2 | d13 |
| 969 | f1 | h1 | g1 | h1 | c2 | d14 |
| 970 | f1 | h1 | g1 | h1 | c2 | d15 |
| 971 | f1 | h1 | g1 | h1 | c2 | d16 |
| 972 | f1 | h1 | g1 | h1 | c2 | d17 |
| 973 | f1 | h1 | g1 | h1 | c2 | d18 |
| 974 | f1 | h1 | g1 | h1 | c2 | e1 |
| 975 | f1 | h1 | g1 | h1 | c2 | e2 |
| 976 | f1 | h1 | g1 | h1 | c2 | e3 |
| 977 | f1 | h1 | g1 | h1 | c2 | e4 |
| 978 | f1 | h1 | g1 | h1 | c5 | a1 |
| 979 | f1 | h1 | g1 | h1 | c5 | a2 |
| 980 | f1 | h1 | g1 | h1 | c5 | a3 |
| 981 | f1 | h1 | g1 | h1 | c5 | a4 |
| 982 | f1 | h1 | g1 | h1 | c5 | a5 |
| 983 | f1 | h1 | g1 | h1 | c5 | a6 |
| 984 | f1 | h1 | g1 | h1 | c5 | a7 |
| 985 | f1 | h1 | g1 | h1 | c5 | a8 |
| 986 | f1 | h1 | g1 | h1 | c5 | a9 |
| 987 | f1 | h1 | g1 | h1 | c5 | a10 |
| 988 | f1 | h1 | g1 | h1 | c5 | a11 |
| 989 | f1 | h1 | g1 | h1 | c5 | a12 |
| 990 | f1 | h1 | g1 | h1 | c5 | a13 |
| 991 | f1 | h1 | g1 | h1 | c5 | a14 |
| 992 | f1 | h1 | g1 | h1 | c5 | a15 |
| 993 | f1 | h1 | g1 | h1 | c5 | b1 |
| 994 | f1 | h1 | g1 | h1 | c5 | b2 |
| 995 | f1 | h1 | g1 | h1 | c5 | b3 |
| 996 | f1 | h1 | g1 | h1 | c5 | b4 |
| 997 | f1 | h1 | g1 | h1 | c5 | b5 |
| 998 | f1 | h1 | g1 | h1 | c5 | b6 |
| 999 | f1 | h1 | g1 | h1 | c5 | b7 |
| 1000 | f1 | h1 | g1 | h1 | c5 | b8 |
| 1001 | f1 | h1 | g1 | h1 | c5 | c1 |
| 1002 | f1 | h1 | g1 | h1 | c5 | d1 |
| 1003 | f1 | h1 | g1 | h1 | c5 | d2 |
| 1004 | f1 | h1 | g1 | h1 | c5 | d3 |
| 1005 | f1 | h1 | g1 | h1 | c5 | d4 |
| 1006 | f1 | h1 | g1 | h1 | c5 | d5 |
| 1007 | f1 | h1 | g1 | h1 | c5 | d6 |
| 1008 | f1 | h1 | g1 | h1 | c5 | d7 |
| 1009 | f1 | h1 | g1 | h1 | c5 | d8 |
| 1010 | f1 | h1 | g1 | h1 | c5 | d9 |
| 1011 | f1 | h1 | g1 | h1 | c5 | d10 |
| 1012 | f1 | h1 | g1 | h1 | c5 | d11 |
| 1013 | f1 | h1 | g1 | h1 | c5 | d12 |
| 1014 | f1 | h1 | g1 | h1 | c5 | d13 |
| 1015 | f1 | h1 | g1 | h1 | c5 | d14 |
| 1016 | f1 | h1 | g1 | h1 | c5 | d15 |
| 1017 | f1 | h1 | g1 | h1 | c5 | d16 |
| 1018 | f1 | h1 | g1 | h1 | c5 | d17 |
| 1019 | f1 | h1 | g1 | h1 | c5 | d18 |
| 1020 | f1 | h1 | g1 | h1 | c5 | e1 |
| 1021 | f1 | h1 | g1 | h1 | c5 | e2 |
| 1022 | f1 | h1 | g1 | h1 | c5 | e3 |
| 1023 | f1 | h1 | g1 | h1 | c5 | e4 |
| 1024 | f1 | h1 | g2 | h1 | a1 | a1 |
| 1025 | f1 | h1 | g2 | h1 | a1 | a2 |
| 1026 | f1 | h1 | g2 | h1 | a1 | a4 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 1027 | f1 | h1 | g2 | h1 | a1 | a5 |
| 1028 | f1 | h1 | g2 | h1 | a1 | a6 |
| 1029 | f1 | h1 | g2 | h1 | a1 | a11 |
| 1030 | f1 | h1 | g2 | h1 | a1 | a15 |
| 1031 | f1 | h1 | g2 | h1 | a1 | b1 |
| 1032 | f1 | h1 | g2 | h1 | a1 | b3 |
| 1033 | f1 | h1 | g2 | h1 | a1 | b4 |
| 1034 | f1 | h1 | g2 | h1 | a1 | b6 |
| 1035 | f1 | h1 | g2 | h1 | a1 | c1 |
| 1036 | f1 | h1 | g2 | h1 | a1 | d1 |
| 1037 | f1 | h1 | g2 | h1 | a1 | d2 |
| 1038 | f1 | h1 | g2 | h1 | a1 | d3 |
| 1039 | f1 | h1 | g2 | h1 | a1 | d5 |
| 1040 | f1 | h1 | g2 | h1 | a1 | d7 |
| 1041 | f1 | h1 | g2 | h1 | a1 | d9 |
| 1042 | f1 | h1 | g2 | h1 | a1 | d11 |
| 1043 | f1 | h1 | g2 | h1 | a1 | d13 |
| 1044 | f1 | h1 | g2 | h1 | a1 | d17 |
| 1045 | f1 | h1 | g2 | h1 | a1 | e3 |
| 1046 | f1 | h1 | g2 | h1 | a2 | a2 |
| 1047 | f1 | h1 | g2 | h1 | a2 | a4 |
| 1048 | f1 | h1 | g2 | h1 | a2 | a5 |
| 1049 | f1 | h1 | g2 | h1 | a2 | a6 |
| 1050 | f1 | h1 | g2 | h1 | a2 | a11 |
| 1051 | f1 | h1 | g2 | h1 | a2 | a15 |
| 1052 | f1 | h1 | g2 | h1 | a2 | b1 |
| 1053 | f1 | h1 | g2 | h1 | a2 | b3 |
| 1054 | f1 | h1 | g2 | h1 | a2 | b4 |
| 1055 | f1 | h1 | g2 | h1 | a2 | b6 |
| 1056 | f1 | h1 | g2 | h1 | a2 | c1 |
| 1057 | f1 | h1 | g2 | h1 | a2 | d1 |
| 1058 | f1 | h1 | g2 | h1 | a2 | d2 |
| 1059 | f1 | h1 | g2 | h1 | a2 | d3 |
| 1060 | f1 | h1 | g2 | h1 | a2 | d5 |
| 1061 | f1 | h1 | g2 | h1 | a2 | d7 |
| 1062 | f1 | h1 | g2 | h1 | a2 | d9 |
| 1063 | f1 | h1 | g2 | h1 | a2 | d11 |
| 1064 | f1 | h1 | g2 | h1 | a2 | d13 |
| 1065 | f1 | h1 | g2 | h1 | a2 | d17 |
| 1066 | f1 | h1 | g2 | h1 | a2 | e3 |
| 1067 | f1 | h1 | g2 | h1 | a4 | a4 |
| 1068 | f1 | h1 | g2 | h1 | a4 | a5 |
| 1069 | f1 | h1 | g2 | h1 | a4 | a6 |
| 1070 | f1 | h1 | g2 | h1 | a4 | a11 |
| 1071 | f1 | h1 | g2 | h1 | a4 | a15 |
| 1072 | f1 | h1 | g2 | h1 | a4 | b1 |
| 1073 | f1 | h1 | g2 | h1 | a4 | b3 |
| 1074 | f1 | h1 | g2 | h1 | a4 | b4 |
| 1075 | f1 | h1 | g2 | h1 | a4 | b6 |
| 1076 | f1 | h1 | g2 | h1 | a4 | c1 |
| 1077 | f1 | h1 | g2 | h1 | a4 | d1 |
| 1078 | f1 | h1 | g2 | h1 | a4 | d2 |
| 1079 | f1 | h1 | g2 | h1 | a4 | d3 |
| 1080 | f1 | h1 | g2 | h1 | a4 | d5 |
| 1081 | f1 | h1 | g2 | h1 | a4 | d7 |
| 1082 | f1 | h1 | g2 | h1 | a4 | d9 |
| 1083 | f1 | h1 | g2 | h1 | a4 | d11 |
| 1084 | f1 | h1 | g2 | h1 | a4 | d13 |
| 1085 | f1 | h1 | g2 | h1 | a4 | d17 |
| 1086 | f1 | h1 | g2 | h1 | a4 | e3 |
| 1087 | f1 | h1 | g2 | h1 | a5 | a5 |
| 1088 | f1 | h1 | g2 | h1 | a5 | a6 |
| 1089 | f1 | h1 | g2 | h1 | a5 | a11 |
| 1090 | f1 | h1 | g2 | h1 | a5 | a15 |
| 1091 | f1 | h1 | g2 | h1 | a5 | b1 |
| 1092 | f1 | h1 | g2 | h1 | a5 | b3 |
| 1093 | f1 | h1 | g2 | h1 | a5 | b4 |
| 1094 | f1 | h1 | g2 | h1 | a5 | b6 |
| 1095 | f1 | h1 | g2 | h1 | a5 | c1 |
| 1096 | f1 | h1 | g2 | h1 | a5 | d1 |
| 1097 | f1 | h1 | g2 | h1 | a5 | d2 |
| 1098 | f1 | h1 | g2 | h1 | a5 | d3 |
| 1099 | f1 | h1 | g2 | h1 | a5 | d5 |
| 1100 | f1 | h1 | g2 | h1 | a5 | d7 |
| 1101 | f1 | h1 | g2 | h1 | a5 | d9 |
| 1102 | f1 | h1 | g2 | h1 | a5 | d11 |
| 1103 | f1 | h1 | g2 | h1 | a5 | d13 |
| 1104 | f1 | h1 | g2 | h1 | a5 | d17 |
| 1105 | f1 | h1 | g2 | h1 | a5 | e3 |
| 1106 | f1 | h1 | g2 | h1 | a6 | a6 |
| 1107 | f1 | h1 | g2 | h1 | a6 | a11 |
| 1108 | f1 | h1 | g2 | h1 | a6 | a15 |
| 1109 | f1 | h1 | g2 | h1 | a6 | b1 |
| 1110 | f1 | h1 | g2 | h1 | a6 | b3 |
| 1111 | f1 | h1 | g2 | h1 | a6 | b4 |
| 1112 | f1 | h1 | g2 | h1 | a6 | b6 |
| 1113 | f1 | h1 | g2 | h1 | a6 | c1 |
| 1114 | f1 | h1 | g2 | h1 | a6 | d1 |
| 1115 | f1 | h1 | g2 | h1 | a6 | d2 |
| 1116 | f1 | h1 | g2 | h1 | a6 | d3 |
| 1117 | f1 | h1 | g2 | h1 | a6 | d5 |
| 1118 | f1 | h1 | g2 | h1 | a6 | d7 |
| 1119 | f1 | h1 | g2 | h1 | a6 | d9 |
| 1120 | f1 | h1 | g2 | h1 | a6 | d11 |
| 1121 | f1 | h1 | g2 | h1 | a6 | d13 |
| 1122 | f1 | h1 | g2 | h1 | a6 | d17 |
| 1123 | f1 | h1 | g2 | h1 | a6 | e3 |
| 1124 | f1 | h1 | g2 | h1 | a11 | a11 |
| 1125 | f1 | h1 | g2 | h1 | a11 | a15 |
| 1126 | f1 | h1 | g2 | h1 | a11 | b1 |
| 1127 | f1 | h1 | g2 | h1 | a11 | b3 |
| 1128 | f1 | h1 | g2 | h1 | a11 | b4 |
| 1129 | f1 | h1 | g2 | h1 | a11 | b6 |
| 1130 | f1 | h1 | g2 | h1 | a11 | c1 |
| 1131 | f1 | h1 | g2 | h1 | a11 | d1 |
| 1132 | f1 | h1 | g2 | h1 | a11 | d2 |
| 1133 | f1 | h1 | g2 | h1 | a11 | d3 |
| 1134 | f1 | h1 | g2 | h1 | a11 | d5 |
| 1135 | f1 | h1 | g2 | h1 | a11 | d7 |
| 1136 | f1 | h1 | g2 | h1 | a11 | d9 |
| 1137 | f1 | h1 | g2 | h1 | a11 | d11 |
| 1138 | f1 | h1 | g2 | h1 | a11 | d13 |
| 1139 | f1 | h1 | g2 | h1 | a11 | d17 |
| 1140 | f1 | h1 | g2 | h1 | a11 | e3 |
| 1141 | f1 | h1 | g2 | h1 | a15 | a15 |
| 1142 | f1 | h1 | g2 | h1 | a15 | b1 |
| 1143 | f1 | h1 | g2 | h1 | a15 | b3 |
| 1144 | f1 | h1 | g2 | h1 | a15 | b4 |
| 1145 | f1 | h1 | g2 | h1 | a15 | b6 |
| 1146 | f1 | h1 | g2 | h1 | a15 | c1 |
| 1147 | f1 | h1 | g2 | h1 | a15 | d1 |
| 1148 | f1 | h1 | g2 | h1 | a15 | d2 |
| 1149 | f1 | h1 | g2 | h1 | a15 | d3 |
| 1150 | f1 | h1 | g2 | h1 | a15 | d5 |
| 1151 | f1 | h1 | g2 | h1 | a15 | d7 |
| 1152 | f1 | h1 | g2 | h1 | a15 | d9 |
| 1153 | f1 | h1 | g2 | h1 | a15 | d11 |
| 1154 | f1 | h1 | g2 | h1 | a15 | d13 |
| 1155 | f1 | h1 | g2 | h1 | a15 | d17 |
| 1156 | f1 | h1 | g2 | h1 | a15 | e3 |
| 1157 | f1 | h1 | g2 | h1 | b1 | b1 |
| 1158 | f1 | h1 | g2 | h1 | b1 | b3 |
| 1159 | f1 | h1 | g2 | h1 | b1 | b4 |
| 1160 | f1 | h1 | g2 | h1 | b1 | b6 |
| 1161 | f1 | h1 | g2 | h1 | b1 | c1 |
| 1162 | f1 | h1 | g2 | h1 | b1 | d1 |
| 1163 | f1 | h1 | g2 | h1 | b1 | d2 |
| 1164 | f1 | h1 | g2 | h1 | b1 | d3 |
| 1165 | f1 | h1 | g2 | h1 | b1 | d5 |
| 1166 | f1 | h1 | g2 | h1 | b1 | d7 |
| 1167 | f1 | h1 | g2 | h1 | b1 | d9 |
| 1168 | f1 | h1 | g2 | h1 | b1 | d11 |
| 1169 | f1 | h1 | g2 | h1 | b1 | d13 |
| 1170 | f1 | h1 | g2 | h1 | b1 | d17 |
| 1171 | f1 | h1 | g2 | h1 | b1 | e3 |
| 1172 | f1 | h1 | g2 | h1 | b3 | b3 |
| 1173 | f1 | h1 | g2 | h1 | b3 | b4 |
| 1174 | f1 | h1 | g2 | h1 | b3 | b6 |
| 1175 | f1 | h1 | g2 | h1 | b3 | c1 |
| 1176 | f1 | h1 | g2 | h1 | b3 | d1 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 1177 | f1 | h1 | g2 | h1 | b3 | d2 |
| 1178 | f1 | h1 | g2 | h1 | b3 | d3 |
| 1179 | f1 | h1 | g2 | h1 | b3 | d5 |
| 1180 | f1 | h1 | g2 | h1 | b3 | d7 |
| 1181 | f1 | h1 | g2 | h1 | b3 | d9 |
| 1182 | f1 | h1 | g2 | h1 | b3 | d11 |
| 1183 | f1 | h1 | g2 | h1 | b3 | d13 |
| 1184 | f1 | h1 | g2 | h1 | b3 | d17 |
| 1185 | f1 | h1 | g2 | h1 | b3 | e3 |
| 1186 | f1 | h1 | g2 | h1 | b4 | b4 |
| 1187 | f1 | h1 | g2 | h1 | b4 | b6 |
| 1188 | f1 | h1 | g2 | h1 | b4 | c1 |
| 1189 | f1 | h1 | g2 | h1 | b4 | d1 |
| 1190 | f1 | h1 | g2 | h1 | b4 | d2 |
| 1191 | f1 | h1 | g2 | h1 | b4 | d3 |
| 1192 | f1 | h1 | g2 | h1 | b4 | d5 |
| 1193 | f1 | h1 | g2 | h1 | b4 | d7 |
| 1194 | f1 | h1 | g2 | h1 | b4 | d9 |
| 1195 | f1 | h1 | g2 | h1 | b4 | d11 |
| 1196 | f1 | h1 | g2 | h1 | b4 | d13 |
| 1197 | f1 | h1 | g2 | h1 | b4 | d17 |
| 1198 | f1 | h1 | g2 | h1 | b4 | e3 |
| 1199 | f1 | h1 | g2 | h1 | b6 | b6 |
| 1200 | f1 | h1 | g2 | h1 | b6 | c1 |
| 1201 | f1 | h1 | g2 | h1 | b6 | d1 |
| 1202 | f1 | h1 | g2 | h1 | b6 | d2 |
| 1203 | f1 | h1 | g2 | h1 | b6 | d3 |
| 1204 | f1 | h1 | g2 | h1 | b6 | d5 |
| 1205 | f1 | h1 | g2 | h1 | b6 | d7 |
| 1206 | f1 | h1 | g2 | h1 | b6 | d9 |
| 1207 | f1 | h1 | g2 | h1 | b6 | d11 |
| 1208 | f1 | h1 | g2 | h1 | b6 | d13 |
| 1209 | f1 | h1 | g2 | h1 | b6 | d17 |
| 1210 | f1 | h1 | g2 | h1 | b6 | e3 |
| 1211 | f1 | h1 | g2 | h1 | c1 | c1 |
| 1212 | f1 | h1 | g2 | h1 | c1 | d1 |
| 1213 | f1 | h1 | g2 | h1 | c1 | d2 |
| 1214 | f1 | h1 | g2 | h1 | c1 | d3 |
| 1215 | f1 | h1 | g2 | h1 | c1 | d5 |
| 1216 | f1 | h1 | g2 | h1 | c1 | d7 |
| 1217 | f1 | h1 | g2 | h1 | c1 | d9 |
| 1218 | f1 | h1 | g2 | h1 | c1 | d11 |
| 1219 | f1 | h1 | g2 | h1 | c1 | d13 |
| 1220 | f1 | h1 | g2 | h1 | c1 | d17 |
| 1221 | f1 | h1 | g2 | h1 | c1 | e3 |
| 1222 | f1 | h1 | g2 | h1 | d1 | d1 |
| 1223 | f1 | h1 | g2 | h1 | d1 | d2 |
| 1224 | f1 | h1 | g2 | h1 | d1 | d3 |
| 1225 | f1 | h1 | g2 | h1 | d1 | d5 |
| 1226 | f1 | h1 | g2 | h1 | d1 | d7 |
| 1227 | f1 | h1 | g2 | h1 | d1 | d9 |
| 1228 | f1 | h1 | g2 | h1 | d1 | d11 |
| 1229 | f1 | h1 | g2 | h1 | d1 | d13 |
| 1230 | f1 | h1 | g2 | h1 | d1 | d17 |
| 1231 | f1 | h1 | g2 | h1 | d1 | e3 |
| 1232 | f1 | h1 | g2 | h1 | d2 | d2 |
| 1233 | f1 | h1 | g2 | h1 | d2 | d3 |
| 1234 | f1 | h1 | g2 | h1 | d2 | d5 |
| 1235 | f1 | h1 | g2 | h1 | d2 | d7 |
| 1236 | f1 | h1 | g2 | h1 | d2 | d9 |
| 1237 | f1 | h1 | g2 | h1 | d2 | d11 |
| 1238 | f1 | h1 | g2 | h1 | d2 | d13 |
| 1239 | f1 | h1 | g2 | h1 | d2 | d17 |
| 1240 | f1 | h1 | g2 | h1 | d2 | e3 |
| 1241 | f1 | h1 | g2 | h1 | d3 | d3 |
| 1242 | f1 | h1 | g2 | h1 | d3 | d5 |
| 1243 | f1 | h1 | g2 | h1 | d3 | d7 |
| 1244 | f1 | h1 | g2 | h1 | d3 | d9 |
| 1245 | f1 | h1 | g2 | h1 | d3 | d11 |
| 1246 | f1 | h1 | g2 | h1 | d3 | d13 |
| 1247 | f1 | h1 | g2 | h1 | d3 | d17 |
| 1248 | f1 | h1 | g2 | h1 | d3 | e3 |
| 1249 | f1 | h1 | g2 | h1 | d5 | d5 |
| 1250 | f1 | h1 | g2 | h1 | d5 | d7 |
| 1251 | f1 | h1 | g2 | h1 | d5 | d9 |
| 1252 | f1 | h1 | g2 | h1 | d5 | d11 |
| 1253 | f1 | h1 | g2 | h1 | d5 | d13 |
| 1254 | f1 | h1 | g2 | h1 | d5 | d17 |
| 1255 | f1 | h1 | g2 | h1 | d5 | e3 |
| 1256 | f1 | h1 | g2 | h1 | d7 | d7 |
| 1257 | f1 | h1 | g2 | h1 | d7 | d9 |
| 1258 | f1 | h1 | g2 | h1 | d7 | d11 |
| 1259 | f1 | h1 | g2 | h1 | d7 | d13 |
| 1260 | f1 | h1 | g2 | h1 | d7 | d17 |
| 1261 | f1 | h1 | g2 | h1 | d7 | e3 |
| 1262 | f1 | h1 | g2 | h1 | d9 | d9 |
| 1263 | f1 | h1 | g2 | h1 | d9 | d11 |
| 1264 | f1 | h1 | g2 | h1 | d9 | d13 |
| 1265 | f1 | h1 | g2 | h1 | d9 | d17 |
| 1266 | f1 | h1 | g2 | h1 | d9 | e3 |
| 1267 | f1 | h1 | g2 | h1 | d11 | d11 |
| 1268 | f1 | h1 | g2 | h1 | d11 | d13 |
| 1269 | f1 | h1 | g2 | h1 | d11 | d17 |
| 1270 | f1 | h1 | g2 | h1 | d11 | e3 |
| 1271 | f1 | h1 | g2 | h1 | d13 | d13 |
| 1272 | f1 | h1 | g2 | h1 | d13 | d17 |
| 1273 | f1 | h1 | g2 | h1 | d13 | e3 |
| 1274 | f1 | h1 | g2 | h1 | d17 | d17 |
| 1275 | f1 | h1 | g2 | h1 | e3 | e3 |
| 1276 | f1 | h1 | g3 | h1 | a1 | a1 |
| 1277 | f1 | h1 | g4 | h1 | a1 | a1 |
| 1278 | f1 | h1 | g1 | h1 | d1 | a1 |
| 1279 | f1 | h1 | g1 | h1 | d1 | a2 |
| 1280 | f1 | h1 | g1 | h1 | d1 | a4 |
| 1281 | f1 | h1 | g1 | h1 | d1 | a5 |
| 1282 | f1 | h1 | g1 | h1 | d1 | a6 |
| 1283 | f1 | h1 | g1 | h1 | d1 | a11 |
| 1284 | f1 | h1 | g1 | h1 | d1 | a15 |
| 1285 | f1 | h1 | g1 | h1 | d1 | b1 |
| 1286 | f1 | h1 | g1 | h1 | d1 | b3 |
| 1287 | f1 | h1 | g1 | h1 | d1 | b4 |
| 1288 | f1 | h1 | g1 | h1 | d1 | b6 |
| 1289 | f1 | h1 | g1 | h1 | d1 | c1 |
| 1290 | f1 | h1 | g1 | h1 | d1 | d1 |
| 1291 | f1 | h1 | g1 | h1 | d1 | d2 |
| 1292 | f1 | h1 | g1 | h1 | d1 | d3 |
| 1293 | f1 | h1 | g1 | h1 | d1 | d5 |
| 1294 | f1 | h1 | g1 | h1 | d1 | d7 |
| 1295 | f1 | h1 | g1 | h1 | d1 | d9 |
| 1296 | f1 | h1 | g1 | h1 | d1 | d11 |
| 1297 | f1 | h1 | g1 | h1 | d1 | d13 |
| 1298 | f1 | h1 | g1 | h1 | d1 | e3 |
| 1299 | f1 | h1 | g1 | h1 | d2 | a1 |
| 1300 | f1 | h1 | g1 | h1 | d2 | a2 |
| 1301 | f1 | h1 | g1 | h1 | d2 | a4 |
| 1302 | f1 | h1 | g1 | h1 | d2 | a5 |
| 1303 | f1 | h1 | g1 | h1 | d2 | a6 |
| 1304 | f1 | h1 | g1 | h1 | d2 | a11 |
| 1305 | f1 | h1 | g1 | h1 | d2 | a15 |
| 1306 | f1 | h1 | g1 | h1 | d2 | b1 |
| 1307 | f1 | h1 | g1 | h1 | d2 | b3 |
| 1308 | f1 | h1 | g1 | h1 | d2 | b4 |
| 1309 | f1 | h1 | g1 | h1 | d2 | b6 |
| 1310 | f1 | h1 | g1 | h1 | d2 | c1 |
| 1311 | f1 | h1 | g1 | h1 | d2 | d2 |
| 1312 | f1 | h1 | g1 | h1 | d2 | d3 |
| 1313 | f1 | h1 | g1 | h1 | d2 | d5 |
| 1314 | f1 | h1 | g1 | h1 | d2 | d7 |
| 1315 | f1 | h1 | g1 | h1 | d2 | d9 |
| 1316 | f1 | h1 | g1 | h1 | d2 | d11 |
| 1317 | f1 | h1 | g1 | h1 | d2 | d13 |
| 1318 | f1 | h1 | g1 | h1 | d2 | e3 |
| 1319 | f1 | h1 | g1 | h1 | d3 | a1 |
| 1320 | f1 | h1 | g1 | h1 | d3 | a2 |
| 1321 | f1 | h1 | g1 | h1 | d3 | a4 |
| 1322 | f1 | h1 | g1 | h1 | d3 | a5 |
| 1323 | f1 | h1 | g1 | h1 | d3 | a6 |
| 1324 | f1 | h1 | g1 | h1 | d3 | a11 |
| 1325 | f1 | h1 | g1 | h1 | d3 | a15 |
| 1326 | f1 | h1 | g1 | h1 | d3 | b1 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 1327 | f1 | h1 | g1 | h1 | d3 | b3 |
| 1328 | f1 | h1 | g1 | h1 | d3 | b4 |
| 1329 | f1 | h1 | g1 | h1 | d3 | b6 |
| 1330 | f1 | h1 | g1 | h1 | d3 | c1 |
| 1331 | f1 | h1 | g1 | h1 | d3 | d3 |
| 1332 | f1 | h1 | g1 | h1 | d3 | d5 |
| 1333 | f1 | h1 | g1 | h1 | d3 | d7 |
| 1334 | f1 | h1 | g1 | h1 | d3 | d9 |
| 1335 | f1 | h1 | g1 | h1 | d3 | d11 |
| 1336 | f1 | h1 | g1 | h1 | d3 | d13 |
| 1337 | f1 | h1 | g1 | h1 | d3 | e3 |
| 1338 | f1 | h1 | g1 | h1 | d4 | a1 |
| 1339 | f1 | h1 | g1 | h1 | d4 | a2 |
| 1340 | f1 | h1 | g1 | h1 | d4 | a4 |
| 1341 | f1 | h1 | g1 | h1 | d4 | a5 |
| 1342 | f1 | h1 | g1 | h1 | d4 | a6 |
| 1343 | f1 | h1 | g1 | h1 | d4 | a11 |
| 1344 | f1 | h1 | g1 | h1 | d4 | a15 |
| 1345 | f1 | h1 | g1 | h1 | d4 | b1 |
| 1346 | f1 | h1 | g1 | h1 | d4 | b3 |
| 1347 | f1 | h1 | g1 | h1 | d4 | b4 |
| 1348 | f1 | h1 | g1 | h1 | d4 | b6 |
| 1349 | f1 | h1 | g1 | h1 | d4 | c1 |
| 1350 | f1 | h1 | g1 | h1 | d4 | d1 |
| 1351 | f1 | h1 | g1 | h1 | d4 | d2 |
| 1352 | f1 | h1 | g1 | h1 | d4 | d3 |
| 1353 | f1 | h1 | g1 | h1 | d4 | d5 |
| 1354 | f1 | h1 | g1 | h1 | d4 | d7 |
| 1355 | f1 | h1 | g1 | h1 | d4 | d9 |
| 1356 | f1 | h1 | g1 | h1 | d4 | d11 |
| 1357 | f1 | h1 | g1 | h1 | d4 | d13 |
| 1358 | f1 | h1 | g1 | h1 | d4 | e3 |
| 1359 | f1 | h1 | g1 | h1 | d5 | a1 |
| 1360 | f1 | h1 | g1 | h1 | d5 | a2 |
| 1361 | f1 | h1 | g1 | h1 | d5 | a4 |
| 1362 | f1 | h1 | g1 | h1 | d5 | a5 |
| 1363 | f1 | h1 | g1 | h1 | d5 | a6 |
| 1364 | f1 | h1 | g1 | h1 | d5 | a11 |
| 1365 | f1 | h1 | g1 | h1 | d5 | a15 |
| 1366 | f1 | h1 | g1 | h1 | d5 | b1 |
| 1367 | f1 | h1 | g1 | h1 | d5 | b3 |
| 1368 | f1 | h1 | g1 | h1 | d5 | b4 |
| 1369 | f1 | h1 | g1 | h1 | d5 | b6 |
| 1370 | f1 | h1 | g1 | h1 | d5 | c1 |
| 1371 | f1 | h1 | g1 | h1 | d5 | d5 |
| 1372 | f1 | h1 | g1 | h1 | d5 | d7 |
| 1373 | f1 | h1 | g1 | h1 | d5 | d9 |
| 1374 | f1 | h1 | g1 | h1 | d5 | d11 |
| 1375 | f1 | h1 | g1 | h1 | d5 | d13 |
| 1376 | f1 | h1 | g1 | h1 | d5 | e3 |
| 1377 | f1 | h1 | g1 | h1 | d6 | a1 |
| 1378 | f1 | h1 | g1 | h1 | d6 | a2 |
| 1379 | f1 | h1 | g1 | h1 | d6 | a4 |
| 1380 | f1 | h1 | g1 | h1 | d6 | a5 |
| 1381 | f1 | h1 | g1 | h1 | d6 | a6 |
| 1382 | f1 | h1 | g1 | h1 | d6 | a11 |
| 1383 | f1 | h1 | g1 | h1 | d6 | a15 |
| 1384 | f1 | h1 | g1 | h1 | d6 | b1 |
| 1385 | f1 | h1 | g1 | h1 | d6 | b3 |
| 1386 | f1 | h1 | g1 | h1 | d6 | b4 |
| 1387 | f1 | h1 | g1 | h1 | d6 | b6 |
| 1388 | f1 | h1 | g1 | h1 | d6 | c1 |
| 1389 | f1 | h1 | g1 | h1 | d6 | d1 |
| 1390 | f1 | h1 | g1 | h1 | d6 | d2 |
| 1391 | f1 | h1 | g1 | h1 | d6 | d3 |
| 1392 | f1 | h1 | g1 | h1 | d6 | d5 |
| 1393 | f1 | h1 | g1 | h1 | d6 | d7 |
| 1394 | f1 | h1 | g1 | h1 | d6 | d9 |
| 1395 | f1 | h1 | g1 | h1 | d6 | d11 |
| 1396 | f1 | h1 | g1 | h1 | d6 | d13 |
| 1397 | f1 | h1 | g1 | h1 | d6 | e3 |
| 1398 | f1 | h1 | g1 | h1 | d7 | a1 |
| 1399 | f1 | h1 | g1 | h1 | d7 | a2 |
| 1400 | f1 | h1 | g1 | h1 | d7 | a4 |
| 1401 | f1 | h1 | g1 | h1 | d7 | a5 |
| 1402 | f1 | h1 | g1 | h1 | d7 | a6 |
| 1403 | f1 | h1 | g1 | h1 | d7 | a11 |
| 1404 | f1 | h1 | g1 | h1 | d7 | a15 |
| 1405 | f1 | h1 | g1 | h1 | d7 | b1 |
| 1406 | f1 | h1 | g1 | h1 | d7 | b3 |
| 1407 | f1 | h1 | g1 | h1 | d7 | b4 |
| 1408 | f1 | h1 | g1 | h1 | d7 | b6 |
| 1409 | f1 | h1 | g1 | h1 | d7 | c1 |
| 1410 | f1 | h1 | g1 | h1 | d7 | d7 |
| 1411 | f1 | h1 | g1 | h1 | d7 | d9 |
| 1412 | f1 | h1 | g1 | h1 | d7 | d11 |
| 1413 | f1 | h1 | g1 | h1 | d7 | d13 |
| 1414 | f1 | h1 | g1 | h1 | d7 | e3 |
| 1415 | f1 | h1 | g1 | h1 | d8 | a1 |
| 1416 | f1 | h1 | g1 | h1 | d8 | a2 |
| 1417 | f1 | h1 | g1 | h1 | d8 | a4 |
| 1418 | f1 | h1 | g1 | h1 | d8 | a5 |
| 1419 | f1 | h1 | g1 | h1 | d8 | a6 |
| 1420 | f1 | h1 | g1 | h1 | d8 | a11 |
| 1421 | f1 | h1 | g1 | h1 | d8 | a15 |
| 1422 | f1 | h1 | g1 | h1 | d8 | b1 |
| 1423 | f1 | h1 | g1 | h1 | d8 | b3 |
| 1424 | f1 | h1 | g1 | h1 | d8 | b4 |
| 1425 | f1 | h1 | g1 | h1 | d8 | b6 |
| 1426 | f1 | h1 | g1 | h1 | d8 | c1 |
| 1427 | f1 | h1 | g1 | h1 | d8 | d1 |
| 1428 | f1 | h1 | g1 | h1 | d8 | d2 |
| 1429 | f1 | h1 | g1 | h1 | d8 | d3 |
| 1430 | f1 | h1 | g1 | h1 | d8 | d5 |
| 1431 | f1 | h1 | g1 | h1 | d8 | d7 |
| 1432 | f1 | h1 | g1 | h1 | d8 | d9 |
| 1433 | f1 | h1 | g1 | h1 | d8 | d11 |
| 1434 | f1 | h1 | g1 | h1 | d8 | d13 |
| 1435 | f1 | h1 | g1 | h1 | d8 | e3 |
| 1436 | f1 | h1 | g1 | h1 | d9 | a1 |
| 1437 | f1 | h1 | g1 | h1 | d9 | a2 |
| 1438 | f1 | h1 | g1 | h1 | d9 | a4 |
| 1439 | f1 | h1 | g1 | h1 | d9 | a5 |
| 1440 | f1 | h1 | g1 | h1 | d9 | a6 |
| 1441 | f1 | h1 | g1 | h1 | d9 | a11 |
| 1442 | f1 | h1 | g1 | h1 | d9 | a15 |
| 1443 | f1 | h1 | g1 | h1 | d9 | b1 |
| 1444 | f1 | h1 | g1 | h1 | d9 | b3 |
| 1445 | f1 | h1 | g1 | h1 | d9 | b4 |
| 1446 | f1 | h1 | g1 | h1 | d9 | b6 |
| 1447 | f1 | h1 | g1 | h1 | d9 | c1 |
| 1448 | f1 | h1 | g1 | h1 | d9 | d9 |
| 1449 | f1 | h1 | g1 | h1 | d9 | d11 |
| 1450 | f1 | h1 | g1 | h1 | d9 | d13 |
| 1451 | f1 | h1 | g1 | h1 | d9 | e3 |
| 1452 | f1 | h1 | g1 | h1 | d10 | a1 |
| 1453 | f1 | h1 | g1 | h1 | d10 | a2 |
| 1454 | f1 | h1 | g1 | h1 | d10 | a4 |
| 1455 | f1 | h1 | g1 | h1 | d10 | a5 |
| 1456 | f1 | h1 | g1 | h1 | d10 | a6 |
| 1457 | f1 | h1 | g1 | h1 | d10 | a11 |
| 1458 | f1 | h1 | g1 | h1 | d10 | a15 |
| 1459 | f1 | h1 | g1 | h1 | d10 | b1 |
| 1460 | f1 | h1 | g1 | h1 | d10 | b3 |
| 1461 | f1 | h1 | g1 | h1 | d10 | b4 |
| 1462 | f1 | h1 | g1 | h1 | d10 | b6 |
| 1463 | f1 | h1 | g1 | h1 | d10 | c1 |
| 1464 | f1 | h1 | g1 | h1 | d10 | d1 |
| 1465 | f1 | h1 | g1 | h1 | d10 | d2 |
| 1466 | f1 | h1 | g1 | h1 | d10 | d3 |
| 1467 | f1 | h1 | g1 | h1 | d10 | d5 |
| 1468 | f1 | h1 | g1 | h1 | d10 | d7 |
| 1469 | f1 | h1 | g1 | h1 | d10 | d9 |
| 1470 | f1 | h1 | g1 | h1 | d10 | d11 |
| 1471 | f1 | h1 | g1 | h1 | d10 | d13 |
| 1472 | f1 | h1 | g1 | h1 | d10 | e3 |
| 1473 | f1 | h1 | g1 | h1 | d11 | a1 |
| 1474 | f1 | h1 | g1 | h1 | d11 | a2 |
| 1475 | f1 | h1 | g1 | h1 | d11 | a4 |
| 1476 | f1 | h1 | g1 | h1 | d11 | a5 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 1477 | f1 | h1 | g1 | h1 | d11 | a6 |
| 1478 | f1 | h1 | g1 | h1 | d11 | a11 |
| 1479 | f1 | h1 | g1 | h1 | d11 | a15 |
| 1480 | f1 | h1 | g1 | h1 | d11 | b1 |
| 1481 | f1 | h1 | g1 | h1 | d11 | b3 |
| 1482 | f1 | h1 | g1 | h1 | d11 | b4 |
| 1483 | f1 | h1 | g1 | h1 | d11 | b6 |
| 1484 | f1 | h1 | g1 | h1 | d11 | c1 |
| 1485 | f1 | h1 | g1 | h1 | d11 | d11 |
| 1486 | f1 | h1 | g1 | h1 | d11 | d13 |
| 1487 | f1 | h1 | g1 | h1 | d11 | e3 |
| 1488 | f1 | h1 | g1 | h1 | d12 | a1 |
| 1489 | f1 | h1 | g1 | h1 | d12 | a2 |
| 1490 | f1 | h1 | g1 | h1 | d12 | a4 |
| 1491 | f1 | h1 | g1 | h1 | d12 | a5 |
| 1492 | f1 | h1 | g1 | h1 | d12 | a6 |
| 1493 | f1 | h1 | g1 | h1 | d12 | a11 |
| 1494 | f1 | h1 | g1 | h1 | d12 | a15 |
| 1495 | f1 | h1 | g1 | h1 | d12 | b1 |
| 1496 | f1 | h1 | g1 | h1 | d12 | b3 |
| 1497 | f1 | h1 | g1 | h1 | d12 | b4 |
| 1498 | f1 | h1 | g1 | h1 | d12 | b6 |
| 1499 | f1 | h1 | g1 | h1 | d12 | c1 |
| 1500 | f1 | h1 | g1 | h1 | d12 | d1 |
| 1501 | f1 | h1 | g1 | h1 | d12 | d2 |
| 1502 | f1 | h1 | g1 | h1 | d12 | d3 |
| 1503 | f1 | h1 | g1 | h1 | d12 | d5 |
| 1504 | f1 | h1 | g1 | h1 | d12 | d7 |
| 1505 | f1 | h1 | g1 | h1 | d12 | d9 |
| 1506 | f1 | h1 | g1 | h1 | d12 | d11 |
| 1507 | f1 | h1 | g1 | h1 | d12 | d13 |
| 1508 | f1 | h1 | g1 | h1 | d12 | e3 |
| 1509 | f1 | h1 | g1 | h1 | d13 | a1 |
| 1510 | f1 | h1 | g1 | h1 | d13 | a2 |
| 1511 | f1 | h1 | g1 | h1 | d13 | a4 |
| 1512 | f1 | h1 | g1 | h1 | d13 | a5 |
| 1513 | f1 | h1 | g1 | h1 | d13 | a6 |
| 1514 | f1 | h1 | g1 | h1 | d13 | a11 |
| 1515 | f1 | h1 | g1 | h1 | d13 | a15 |
| 1516 | f1 | h1 | g1 | h1 | d13 | b1 |
| 1517 | f1 | h1 | g1 | h1 | d13 | b3 |
| 1518 | f1 | h1 | g1 | h1 | d13 | b4 |
| 1519 | f1 | h1 | g1 | h1 | d13 | b6 |
| 1520 | f1 | h1 | g1 | h1 | d13 | c1 |
| 1521 | f1 | h1 | g1 | h1 | d13 | d13 |
| 1522 | f1 | h1 | g1 | h1 | d13 | e3 |
| 1523 | f1 | h1 | g1 | h1 | d14 | a1 |
| 1524 | f1 | h1 | g1 | h1 | d14 | a2 |
| 1525 | f1 | h1 | g1 | h1 | d14 | a4 |
| 1526 | f1 | h1 | g1 | h1 | d14 | a5 |
| 1527 | f1 | h1 | g1 | h1 | d14 | a6 |
| 1528 | f1 | h1 | g1 | h1 | d14 | a11 |
| 1529 | f1 | h1 | g1 | h1 | d14 | a15 |
| 1530 | f1 | h1 | g1 | h1 | d14 | b1 |
| 1531 | f1 | h1 | g1 | h1 | d14 | b3 |
| 1532 | f1 | h1 | g1 | h1 | d14 | b4 |
| 1533 | f1 | h1 | g1 | h1 | d14 | b6 |
| 1534 | f1 | h1 | g1 | h1 | d14 | c1 |
| 1535 | f1 | h1 | g1 | h1 | d14 | d1 |
| 1536 | f1 | h1 | g1 | h1 | d14 | d2 |
| 1537 | f1 | h1 | g1 | h1 | d14 | d3 |
| 1538 | f1 | h1 | g1 | h1 | d14 | d5 |
| 1539 | f1 | h1 | g1 | h1 | d14 | d7 |
| 1540 | f1 | h1 | g1 | h1 | d14 | d9 |
| 1541 | f1 | h1 | g1 | h1 | d14 | d11 |
| 1542 | f1 | h1 | g1 | h1 | d14 | d13 |
| 1543 | f1 | h1 | g1 | h1 | d14 | e3 |
| 1544 | f1 | h1 | g1 | h1 | d15 | a1 |
| 1545 | f1 | h1 | g1 | h1 | d15 | a2 |
| 1546 | f1 | h1 | g1 | h1 | d15 | a4 |
| 1547 | f1 | h1 | g1 | h1 | d15 | a5 |
| 1548 | f1 | h1 | g1 | h1 | d15 | a6 |
| 1549 | f1 | h1 | g1 | h1 | d15 | a11 |
| 1550 | f1 | h1 | g1 | h1 | d15 | a15 |
| 1551 | f1 | h1 | g1 | h1 | d15 | b1 |
| 1552 | f1 | h1 | g1 | h1 | d15 | b3 |
| 1553 | f1 | h1 | g1 | h1 | d15 | b4 |
| 1554 | f1 | h1 | g1 | h1 | d15 | b6 |
| 1555 | f1 | h1 | g1 | h1 | d15 | c1 |
| 1556 | f1 | h1 | g1 | h1 | d15 | d1 |
| 1557 | f1 | h1 | g1 | h1 | d15 | d2 |
| 1558 | f1 | h1 | g1 | h1 | d15 | d3 |
| 1559 | f1 | h1 | g1 | h1 | d15 | d5 |
| 1560 | f1 | h1 | g1 | h1 | d15 | d7 |
| 1561 | f1 | h1 | g1 | h1 | d15 | d9 |
| 1562 | f1 | h1 | g1 | h1 | d15 | d11 |
| 1563 | f1 | h1 | g1 | h1 | d15 | d13 |
| 1564 | f1 | h1 | g1 | h1 | d15 | e3 |
| 1565 | f1 | h1 | g1 | h1 | d16 | a1 |
| 1566 | f1 | h1 | g1 | h1 | d16 | a2 |
| 1567 | f1 | h1 | g1 | h1 | d16 | a4 |
| 1568 | f1 | h1 | g1 | h1 | d16 | a5 |
| 1569 | f1 | h1 | g1 | h1 | d16 | a6 |
| 1570 | f1 | h1 | g1 | h1 | d16 | a11 |
| 1571 | f1 | h1 | g1 | h1 | d16 | a15 |
| 1572 | f1 | h1 | g1 | h1 | d16 | d1 |
| 1573 | f1 | h1 | g1 | h1 | d16 | b3 |
| 1574 | f1 | h1 | g1 | h1 | d16 | b4 |
| 1575 | f1 | h1 | g1 | h1 | d16 | b6 |
| 1576 | f1 | h1 | g1 | h1 | d16 | c1 |
| 1577 | f1 | h1 | g1 | h1 | d16 | d1 |
| 1578 | f1 | h1 | g1 | h1 | d16 | d2 |
| 1579 | f1 | h1 | g1 | h1 | d16 | d3 |
| 1580 | f1 | h1 | g1 | h1 | d16 | d5 |
| 1581 | f1 | h1 | g1 | h1 | d16 | d7 |
| 1582 | f1 | h1 | g1 | h1 | d16 | d9 |
| 1583 | f1 | h1 | g1 | h1 | d16 | d11 |
| 1584 | f1 | h1 | g1 | h1 | d16 | d13 |
| 1585 | f1 | h1 | g1 | h1 | d16 | e3 |
| 1586 | f1 | h1 | g1 | h1 | d17 | a1 |
| 1587 | f1 | h1 | g1 | h1 | d17 | a2 |
| 1588 | f1 | h1 | g1 | h1 | d17 | a4 |
| 1589 | f1 | h1 | g1 | h1 | d17 | a5 |
| 1590 | f1 | h1 | g1 | h1 | d17 | a6 |
| 1591 | f1 | h1 | g1 | h1 | d17 | a11 |
| 1592 | f1 | h1 | g1 | h1 | d17 | a15 |
| 1593 | f1 | h1 | g1 | h1 | d17 | b1 |
| 1594 | f1 | h1 | g1 | h1 | d17 | b3 |
| 1595 | f1 | h1 | g1 | h1 | d17 | b4 |
| 1596 | f1 | h1 | g1 | h1 | d17 | b6 |
| 1597 | f1 | h1 | g1 | h1 | d17 | c1 |
| 1598 | f1 | h1 | g1 | h1 | d17 | d1 |
| 1599 | f1 | h1 | g1 | h1 | d17 | d2 |
| 1600 | f1 | h1 | g1 | h1 | d17 | d3 |
| 1601 | f1 | h1 | g1 | h1 | d17 | d5 |
| 1602 | f1 | h1 | g1 | h1 | d17 | d7 |
| 1603 | f1 | h1 | g1 | h1 | d17 | d9 |
| 1604 | f1 | h1 | g1 | h1 | d17 | d11 |
| 1605 | f1 | h1 | g1 | h1 | d17 | d13 |
| 1606 | f1 | h1 | g1 | h1 | d17 | e3 |
| 1607 | f1 | h1 | g1 | h1 | d18 | a1 |
| 1608 | f1 | h1 | g1 | h1 | d18 | a2 |
| 1609 | f1 | h1 | g1 | h1 | d18 | a4 |
| 1610 | f1 | h1 | g1 | h1 | d18 | a5 |
| 1611 | f1 | h1 | g1 | h1 | d18 | a6 |
| 1612 | f1 | h1 | g1 | h1 | d18 | a11 |
| 1613 | f1 | h1 | g1 | h1 | d18 | a15 |
| 1614 | f1 | h1 | g1 | h1 | d18 | b1 |
| 1615 | f1 | h1 | g1 | h1 | d18 | b3 |
| 1616 | f1 | h1 | g1 | h1 | d18 | b4 |
| 1617 | f1 | h1 | g1 | h1 | d18 | b6 |
| 1618 | f1 | h1 | g1 | h1 | d18 | c1 |
| 1619 | f1 | h1 | g1 | h1 | d18 | d1 |
| 1620 | f1 | h1 | g1 | h1 | d18 | d2 |
| 1621 | f1 | h1 | g1 | h1 | d18 | d3 |
| 1622 | f1 | h1 | g1 | h1 | d18 | d5 |
| 1623 | f1 | h1 | g1 | h1 | d18 | d7 |
| 1624 | f1 | h1 | g1 | h1 | d18 | d9 |
| 1625 | f1 | h1 | g1 | h1 | d18 | d11 |
| 1626 | f1 | h1 | g1 | h1 | d18 | d13 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 1627 | f1 | h1 | g1 | h1 | e1 | a1 |
| 1628 | f1 | h1 | g1 | h1 | e1 | a2 |
| 1629 | f1 | h1 | g1 | h1 | e1 | a3 |
| 1630 | f1 | h1 | g1 | h1 | e1 | a4 |
| 1631 | f1 | h1 | g1 | h1 | e1 | a5 |
| 1632 | f1 | h1 | g1 | h1 | e1 | a6 |
| 1633 | f1 | h1 | g1 | h1 | e1 | a7 |
| 1634 | f1 | h1 | g1 | h1 | e1 | a8 |
| 1635 | f1 | h1 | g1 | h1 | e1 | a9 |
| 1636 | f1 | h1 | g1 | h1 | e1 | a10 |
| 1637 | f1 | h1 | g1 | h1 | e1 | a11 |
| 1638 | f1 | h1 | g1 | h1 | e1 | a12 |
| 1639 | f1 | h1 | g1 | h1 | e1 | a13 |
| 1640 | f1 | h1 | g1 | h1 | e1 | a14 |
| 1641 | f1 | h1 | g1 | h1 | e1 | a15 |
| 1642 | f1 | h1 | g1 | h1 | e1 | b1 |
| 1643 | f1 | h1 | g1 | h1 | e1 | b2 |
| 1644 | f1 | h1 | g1 | h1 | e1 | b3 |
| 1645 | f1 | h1 | g1 | h1 | e1 | b4 |
| 1646 | f1 | h1 | g1 | h1 | e1 | b5 |
| 1647 | f1 | h1 | g1 | h1 | e1 | b6 |
| 1648 | f1 | h1 | g1 | h1 | e1 | b7 |
| 1649 | f1 | h1 | g1 | h1 | e1 | b8 |
| 1650 | f1 | h1 | g1 | h1 | e1 | c1 |
| 1651 | f1 | h1 | g1 | h1 | e1 | c2 |
| 1652 | f1 | h1 | g1 | h1 | e1 | c3 |
| 1653 | f1 | h1 | g1 | h1 | e1 | c4 |
| 1654 | f1 | h1 | g1 | h1 | e1 | c5 |
| 1655 | f1 | h1 | g1 | h1 | e1 | d1 |
| 1656 | f1 | h1 | g1 | h1 | e1 | d2 |
| 1657 | f1 | h1 | g1 | h1 | e1 | d3 |
| 1658 | f1 | h1 | g1 | h1 | e1 | d4 |
| 1659 | f1 | h1 | g1 | h1 | e1 | d5 |
| 1660 | f1 | h1 | g1 | h1 | e1 | d6 |
| 1661 | f1 | h1 | g1 | h1 | e1 | d7 |
| 1662 | f1 | h1 | g1 | h1 | e1 | d8 |
| 1663 | f1 | h1 | g1 | h1 | e1 | d9 |
| 1664 | f1 | h1 | g1 | h1 | e1 | d10 |
| 1665 | f1 | h1 | g1 | h1 | e1 | d11 |
| 1666 | f1 | h1 | g1 | h1 | e1 | d12 |
| 1667 | f1 | h1 | g1 | h1 | e1 | d13 |
| 1668 | f1 | h1 | g1 | h1 | e1 | d14 |
| 1669 | f1 | h1 | g1 | h1 | e1 | d15 |
| 1670 | f1 | h1 | g1 | h1 | e1 | d16 |
| 1671 | f1 | h1 | g1 | h1 | e1 | d17 |
| 1672 | f1 | h1 | g1 | h1 | e1 | d18 |
| 1673 | f1 | h1 | g1 | h1 | e1 | e1 |
| 1674 | f1 | h1 | g1 | h1 | e1 | e2 |
| 1675 | f1 | h1 | g1 | h1 | e1 | e3 |
| 1676 | f1 | h1 | g1 | h1 | e1 | e4 |
| 1677 | f1 | h1 | g1 | h1 | e2 | a1 |
| 1678 | f1 | h1 | g1 | h1 | e2 | a2 |
| 1679 | f1 | h1 | g1 | h1 | e2 | a3 |
| 1680 | f1 | h1 | g1 | h1 | e2 | a4 |
| 1681 | f1 | h1 | g1 | h1 | e2 | a5 |
| 1682 | f1 | h1 | g1 | h1 | e2 | a6 |
| 1683 | f1 | h1 | g1 | h1 | e2 | a7 |
| 1684 | f1 | h1 | g1 | h1 | e2 | a8 |
| 1685 | f1 | h1 | g1 | h1 | e2 | a9 |
| 1686 | f1 | h1 | g1 | h1 | e2 | a10 |
| 1687 | f1 | h1 | g1 | h1 | e2 | a11 |
| 1688 | f1 | h1 | g1 | h1 | e2 | a12 |
| 1689 | f1 | h1 | g1 | h1 | e2 | a13 |
| 1690 | f1 | h1 | g1 | h1 | e2 | a14 |
| 1691 | f1 | h1 | g1 | h1 | e2 | a15 |
| 1692 | f1 | h1 | g1 | h1 | e2 | b1 |
| 1693 | f1 | h1 | g1 | h1 | e2 | b2 |
| 1694 | f1 | h1 | g1 | h1 | e2 | b3 |
| 1695 | f1 | h1 | g1 | h1 | e2 | b4 |
| 1696 | f1 | h1 | g1 | h1 | e2 | b5 |
| 1697 | f1 | h1 | g1 | h1 | e2 | b6 |
| 1698 | f1 | h1 | g1 | h1 | e2 | b7 |
| 1699 | f1 | h1 | g1 | h1 | e2 | b8 |
| 1700 | f1 | h1 | g1 | h1 | e2 | c1 |
| 1701 | f1 | h1 | g1 | h1 | e2 | c2 |
| 1702 | f1 | h1 | g1 | h1 | e2 | c3 |
| 1703 | f1 | h1 | g1 | h1 | e2 | c4 |
| 1704 | f1 | h1 | g1 | h1 | e2 | c5 |
| 1705 | f1 | h1 | g1 | h1 | e2 | d1 |
| 1706 | f1 | h1 | g1 | h1 | e2 | d2 |
| 1707 | f1 | h1 | g1 | h1 | e2 | d3 |
| 1708 | f1 | h1 | g1 | h1 | e2 | d4 |
| 1709 | f1 | h1 | g1 | h1 | e2 | d5 |
| 1710 | f1 | h1 | g1 | h1 | e2 | d6 |
| 1711 | f1 | h1 | g1 | h1 | e2 | d7 |
| 1712 | f1 | h1 | g1 | h1 | e2 | d8 |
| 1713 | f1 | h1 | g1 | h1 | e2 | d9 |
| 1714 | f1 | h1 | g1 | h1 | e2 | d10 |
| 1715 | f1 | h1 | g1 | h1 | e2 | d11 |
| 1716 | f1 | h1 | g1 | h1 | e2 | d12 |
| 1717 | f1 | h1 | g1 | h1 | e2 | d13 |
| 1718 | f1 | h1 | g1 | h1 | e2 | d14 |
| 1719 | f1 | h1 | g1 | h1 | e2 | d15 |
| 1720 | f1 | h1 | g1 | h1 | e2 | d16 |
| 1721 | f1 | h1 | g1 | h1 | e2 | d17 |
| 1722 | f1 | h1 | g1 | h1 | e2 | d18 |
| 1723 | f1 | h1 | g1 | h1 | e2 | e2 |
| 1724 | f1 | h1 | g1 | h1 | e2 | e3 |
| 1725 | f1 | h1 | g1 | h1 | e2 | e4 |
| 1726 | f1 | h1 | g1 | h1 | e3 | a1 |
| 1727 | f1 | h1 | g1 | h1 | e3 | a2 |
| 1728 | f1 | h1 | g1 | h1 | e3 | a3 |
| 1729 | f1 | h1 | g1 | h1 | e3 | a4 |
| 1730 | f1 | h1 | g1 | h1 | e3 | a5 |
| 1731 | f1 | h1 | g1 | h1 | e3 | a6 |
| 1732 | f1 | h1 | g1 | h1 | e3 | a7 |
| 1733 | f1 | h1 | g1 | h1 | e3 | a8 |
| 1734 | f1 | h1 | g1 | h1 | e3 | a9 |
| 1735 | f1 | h1 | g1 | h1 | e3 | a10 |
| 1736 | f1 | h1 | g1 | h1 | e3 | a11 |
| 1737 | f1 | h1 | g1 | h1 | e3 | a12 |
| 1738 | f1 | h1 | g1 | h1 | e3 | a13 |
| 1739 | f1 | h1 | g1 | h1 | e3 | a14 |
| 1740 | f1 | h1 | g1 | h1 | e3 | a15 |
| 1741 | f1 | h1 | g1 | h1 | e3 | b1 |
| 1742 | f1 | h1 | g1 | h1 | e3 | b2 |
| 1743 | f1 | h1 | g1 | h1 | e3 | b3 |
| 1744 | f1 | h1 | g1 | h1 | e3 | b4 |
| 1745 | f1 | h1 | g1 | h1 | e3 | b5 |
| 1746 | f1 | h1 | g1 | h1 | e3 | b6 |
| 1747 | f1 | h1 | g1 | h1 | e3 | b7 |
| 1748 | f1 | h1 | g1 | h1 | e3 | b8 |
| 1749 | f1 | h1 | g1 | h1 | e3 | c1 |
| 1750 | f1 | h1 | g1 | h1 | e3 | c2 |
| 1751 | f1 | h1 | g1 | h1 | e3 | c3 |
| 1752 | f1 | h1 | g1 | h1 | e3 | c3 |
| 1753 | f1 | h1 | g1 | h1 | e3 | c5 |
| 1754 | f1 | h1 | g1 | h1 | e3 | d1 |
| 1755 | f1 | h1 | g1 | h1 | e3 | d2 |
| 1756 | f1 | h1 | g1 | h1 | e3 | d3 |
| 1757 | f1 | h1 | g1 | h1 | e3 | d4 |
| 1758 | f1 | h1 | g1 | h1 | e3 | d5 |
| 1759 | f1 | h1 | g1 | h1 | e3 | d6 |
| 1760 | f1 | h1 | g1 | h1 | e3 | d7 |
| 1761 | f1 | h1 | g1 | h1 | e3 | d8 |
| 1762 | f1 | h1 | g1 | h1 | e3 | d9 |
| 1763 | f1 | h1 | g1 | h1 | e3 | d10 |
| 1764 | f1 | h1 | g1 | h1 | e3 | d11 |
| 1765 | f1 | h1 | g1 | h1 | e3 | d12 |
| 1766 | f1 | h1 | g1 | h1 | e3 | d13 |
| 1767 | f1 | h1 | g1 | h1 | e3 | d14 |
| 1768 | f1 | h1 | g1 | h1 | e3 | d15 |
| 1769 | f1 | h1 | g1 | h1 | e3 | d16 |
| 1770 | f1 | h1 | g1 | h1 | e3 | d17 |
| 1771 | f1 | h1 | g1 | h1 | e3 | d18 |
| 1772 | f1 | h1 | g1 | h1 | e3 | e3 |
| 1773 | f1 | h1 | g1 | h1 | e3 | e4 |
| 1774 | f1 | h1 | g1 | h1 | e4 | a1 |
| 1775 | f1 | h1 | g1 | h1 | e4 | a2 |
| 1776 | f1 | h1 | g1 | h1 | e4 | a3 |

-continued

Compound Combination Table 1

| No. | $Cz^b$ | $L^A$ | $Cz^A$ | $L^B$ | $Ar^A$ | $Ar^B$ |
|---|---|---|---|---|---|---|
| 1777 | f1 | h1 | g1 | h1 | e4 | a4 |
| 1778 | f1 | h1 | g1 | h1 | e4 | a5 |
| 1779 | f1 | h1 | g1 | h1 | e4 | a6 |
| 1780 | f1 | h1 | g1 | h1 | e4 | a7 |
| 1781 | f1 | h1 | g1 | h1 | e4 | a8 |
| 1782 | f1 | h1 | g1 | h1 | e4 | a9 |
| 1783 | f1 | h1 | g1 | h1 | e4 | a10 |
| 1784 | f1 | h1 | g1 | h1 | e4 | a11 |
| 1785 | f1 | h1 | g1 | h1 | e4 | a12 |
| 1786 | f1 | h1 | g1 | h1 | e4 | a13 |
| 1787 | f1 | h1 | g1 | h1 | e4 | a14 |
| 1788 | f1 | h1 | g1 | h1 | e4 | a15 |
| 1789 | f1 | h1 | g1 | h1 | e4 | b1 |
| 1790 | f1 | h1 | g1 | h1 | e4 | b2 |
| 1791 | f1 | h1 | g1 | h1 | e4 | b3 |
| 1792 | f1 | h1 | g1 | h1 | e4 | b4 |
| 1793 | f1 | h1 | g1 | h1 | e4 | b5 |
| 1794 | f1 | h1 | g1 | h1 | e4 | b6 |
| 1795 | f1 | h1 | g1 | h1 | e4 | b7 |
| 1796 | f1 | h1 | g1 | h1 | e4 | b8 |
| 1797 | f1 | h1 | g1 | h1 | e4 | c1 |
| 1798 | f1 | h1 | g1 | h1 | e4 | c2 |
| 1799 | f1 | h1 | g1 | h1 | e4 | c3 |
| 1800 | f1 | h1 | g1 | h1 | e4 | c4 |
| 1801 | f1 | h1 | g1 | h1 | e4 | c5 |
| 1802 | f1 | h1 | g1 | h1 | e4 | d1 |
| 1803 | f1 | h1 | g1 | h1 | e4 | d2 |
| 1804 | f1 | h1 | g1 | h1 | e4 | d3 |
| 1805 | f1 | h1 | g1 | h1 | e4 | d4 |
| 1806 | f1 | h1 | g1 | h1 | e4 | d5 |
| 1807 | f1 | h1 | g1 | h1 | e4 | d6 |
| 1808 | f1 | h1 | g1 | h1 | e4 | d7 |
| 1809 | f1 | h1 | g1 | h1 | e4 | d8 |
| 1810 | f1 | h1 | g1 | h1 | e4 | d9 |
| 1811 | f1 | h1 | g1 | h1 | e4 | d10 |
| 1812 | f1 | h1 | g1 | h1 | e4 | d11 |
| 1813 | f1 | h1 | g1 | h1 | e4 | d12 |
| 1814 | f1 | h1 | g1 | h1 | e4 | d13 |
| 1815 | f1 | h1 | g1 | h1 | e4 | d14 |
| 1816 | f1 | h1 | g1 | h1 | e4 | d15 |
| 1817 | f1 | h1 | g1 | h1 | e4 | d16 |
| 1818 | f1 | h1 | g1 | h1 | e4 | d17 |
| 1819 | f1 | h1 | g1 | h1 | e4 | d18 |
| 1820 | f1 | h1 | g1 | h1 | e4 | e4. |

* * * * *